(12) United States Patent
Takahashi et al.

(10) Patent No.: US 11,965,035 B2
(45) Date of Patent: Apr. 23, 2024

(54) ANTIBODY BINDING TO CHONDROITIN SULFATE PROTEOGLYCAN 5

(71) Applicants: Kyowa Kirin Co., Ltd., Tokyo (JP); KAGOSHIMA UNIVERSITY, Kagoshima (JP)

(72) Inventors: Nobuaki Takahashi, Tokyo (JP); Ryosuke Nakano, Tokyo (JP); Sayaka Maeda, Tokyo (JP); Yuji Ito, Kagoshima (JP)

(73) Assignees: KYOWA KIRIN CO., LTD., Tokyo (JP); KAGOSHIMA UNIVERSITY, Kagoshima (JP)

( * ) Notice: Subject to any disclaimer, the term of this patent is extended or adjusted under 35 U.S.C. 154(b) by 587 days.

(21) Appl. No.: 17/255,692

(22) PCT Filed: Jun. 26, 2019

(86) PCT No.: PCT/JP2019/025450
§ 371 (c)(1),
(2) Date: Dec. 23, 2020

(87) PCT Pub. No.: WO2020/004490
PCT Pub. Date: Jan. 2, 2020

(65) Prior Publication Data
US 2021/0269548 A1    Sep. 2, 2021

(30) Foreign Application Priority Data
Jun. 26, 2018    (JP) ................. 2018-120476

(51) Int. Cl.
*C07K 16/30* (2006.01)
*C12N 5/16* (2006.01)
*G01N 33/50* (2006.01)

(52) U.S. Cl.
CPC ........... *C07K 16/3053* (2013.01); *C12N 5/16* (2013.01); *G01N 33/5058* (2013.01); *C07K 2317/31* (2013.01); *C07K 2317/565* (2013.01); *C07K 2319/33* (2013.01)

(58) Field of Classification Search
CPC combination set(s) only.
See application file for complete search history.

(56) References Cited

U.S. PATENT DOCUMENTS

| 2015/0322149 A1 | 11/2015 | Bohrmann et al. |
| 2018/0057604 A1 | 3/2018 | Liu et al. |
| 2018/0085453 A1 | 3/2018 | Kurihara et al. |
| 2018/0134797 A1 | 5/2018 | Zhang et al. |
| 2019/0276530 A1 | 9/2019 | Bohrmann et al. |

FOREIGN PATENT DOCUMENTS

| CA | 2 623 841 | 4/2007 | |
| JP | 9-194502 | 7/1997 | |
| JP | 2003-79374 | 3/2003 | |
| JP | 2012-62312 | 3/2012 | |
| WO | 2012/023623 | 2/2012 | |
| WO | 2014/033074 | 3/2014 | |
| WO | 2016/081640 | 5/2016 | |
| WO | 2016/081643 | 5/2016 | |
| WO | WO-2016087651 A1 * | 6/2016 | ........... A61K 39/395 |
| WO | 2016/175307 | 11/2016 | |
| WO | WO-2017070170 A1 * | 4/2017 | ................ A61P 7/10 |

OTHER PUBLICATIONS

Kussie PH, Parhami-Seren B, Wysocki LJ, Margolies MN. J Immunol. Jan. 1, 1994;152(1):146-52. PMID: 8254187. (Year: 1994).*
Chen C, Roberts VA, Stevens S, Brown M, Stenzel-Poore MP, Rittenberg MB. EMBO J. Jun. 15, 1995;14(12):2784-94. doi: 10.1002/j.1460-2075.1995.tb07278.x. PMID: 7796805; PMCID: PMC398397. (Year: 1995).*
Sela-Culang I, Kunik V, Ofran Y. The structural basis of antibody-antigen recognition. Front Immunol. Oct. 8, 2013;4:302. doi: 10.3389/fimmu.2013.00302. PMID: 24115948; PMCID: PMC3792396. (Year: 2013).*
Extended European Search Report dated Feb. 15, 2022, in European Patent Application No. 19826585.2.
Yip G.W, et al., "Immunohistochemical Analysis of CSPG5: A Novel Prognostic Factor for Breast Cancer", 13th St. Gallen International Breast Cancer Conference, St. Gallen, Switzerland, 2013, Breast vol. 22, Suppl. 1, Abstract P45, p. S34.
Zhang C. et al., "The X-Linked Intellectual Disability Protein PHF6 Associates with the PAF1 Complex and Regulates Neuronal Migration in the Mammalian Brain", 2013, Neuron, vol. 78, No. 6, , pp. 986-993.
International Search Report dated Aug. 6, 2019 in corresponding International (PCT) Application No. PCT/JP2019/025450, with English translation.
Written Opinion of the International Searching Authority dated Aug. 6, 2019 in corresponding International (PCT) Application No. PCT/JP2019/025450, with English translation.

(Continued)

*Primary Examiner* — Adam Weidner
*Assistant Examiner* — Laura Ann Essex
(74) *Attorney, Agent, or Firm* — WENDEROTH, LIND & PONACK, L.L.P.

(57) ABSTRACT

The invention relates to an antibody which binds to chondroitin sulfate proteoglycan 5 (CSPG5) or an antibody fragment thereof, a hybridoma which produces the antibody or the antibody fragment thereof, a nucleic acid comprising a nucleotide sequence encoding the antibody or the antibody fragment thereof, a transformant cell comprising a vector comprising the nucleic acid, a method for producing the antibody or the antibody fragment thereof, a composition comprising the antibody or the antibody fragment thereof, and a method for detecting or measuring an antigen present in the brain, a method for diagnosing or treating a brain disease, a method for enhancing the property of accumulating in a brain of an antibody, and a method for increasing the amount of an antibody in the brain, each of which using the antibody or the antibody fragment thereof, and the like.

24 Claims, 5 Drawing Sheets

Specification includes a Sequence Listing.

(56) References Cited

OTHER PUBLICATIONS

Rodgers, K. R. and Chou, R. C., "Therapeutic monoclonal antibodies and derivatives: Historical perspectives and future directions", Biotechnology Advances, 2016, vol. 34, pp. 1149-1158.

Pardridge, W. M., "Re-Engineering Biopharmaceuticals for Delivery to Brain with Molecular Trojan Horses", Bioconjugate Chemistry, 2008, vol. 19, No. 7, pp. 1327-1338.

Wang et al., "Monoclonal Antibody Pharmacokinetics and Pharmacodynamics", Clinical Pharmacology & Therapeutics, 2008. vol. 84, No. 5, pp. 548-558.

Garg, A. and Balthasar, J. P., "Investigation of the Influence of FcRn on the Distribution of IgG to the Brain", AAPS Journal. 2009, vol. 11, No. 3, pp. 553-557.

Blennow et al., "Effect of Immunotherapy With Bapineuzumab on Cerebrospinal Fluid Biomarker Levels in Patients With Mild to Moderate Alzheimer Disease", Arch. Neurol., 2012, vol. 69, No. 8, pp. 1002-1010.

Wraith et al., "Enzyme Replacement Therapy for Mucopolysaccharidosis I: A Randomized, Double-Blinded, Placebo-Controlled, Multinational Study of Recombinant Human α-L-Iduronidase (Laronidase)", Journal Pediatrics, 2004, vol. 144, No. 5, pp. 581-588.

Muenzer et al., "A phase II/III clinical study of enzyme replacement therapy with idursulfase in mucopolysaccharidosis II (Hunter syndrome)", Genetics in Medicine, 2006, vol. 8, No. 8, pp. 465-473.

Package insert of intravenous infusion 2.9 mg of Aldurazyme™ (Jul. 2016, 8th edition), with an Annex containing a concise explanation of relevance.

Package insert of intravenous infusion 6 mg of Elaprase™ (Jul. 2016, 6th edition), with an Annex containing a concise explanation of relevance.

Brooks et al., "Significance of immune response to enzyme-replacement therapy for patients with a lysosomal storage disorder", Trends in Molecular Medicine, Oct. 2003, vol. 9, No. 10, pp. 450-453.

Sorrentino, N. C., and Fraldi, A. "Brain Targeting in MPS-IIIA", Pediatric Endocrinolgy Reviews, Jun. 2016, vol. 13, suppl. 1, pp. 630-638.

Couch et al., "Addressing Safety Liabilities of TfR Bispecific Antibodies That Cross the Blood-Brain Barrier", Science Translational Medicine, 2013, vol. 5, issue 183: 183ra57, pp. 1-12.

Yu et al., "Therapeutic bispecific antibodies cross the blood-brain barrier in nonhuman primates", Science Translational Medicine, 2014, vol. 6, issue 261: 261ra154, pp. 1-10.

Niewoehner et al., "Increased Brain Penetration and Potency of a Therapeutic Antibody Using a Monovalent Molecular Shuttle", Neuron, 2014, vol. 81, pp. 49-60.

Yue et al., "Fluorescence-Labeled Immunomicelles: Preparation, in vivo Biodistribution, and Ability to Cross the Blood-Brain Barrier", Macromolecular Bioscience, 2012, vol. 12, pp. 1209-1219.

Pardridge, W. M., and Boado, R., "Reengineering Biopharmaceuticals for Targeted Delivery Across the Blood-Brain Barrier", Methods in Enzymology, 2012, vol. 503, pp. 269-292.

Boado, R. J., and Pardridge, W. M., "Comparison of Blood-Brain Barrier Transport of Glial-Derived Neurotrophic Factor (GDNF) and an IgG-GDNF Fusion Protein in the Rhesus Monkey", Drug Metabolism and Disposition, 2009, vol. 37, No. 12, pp. 2299-2304.

Boado et al., "Drug Targeting of Erythropoietin Across the Primate Blood-Brain Barrier with an IgG Molecular Trojan Horse", Journal Pharmacology Experimental Therapeutics, 2010, vol. 333, No. 3, pp. 961-969.

Boado et al., "IgG-Enzyme Fusion Protein: Pharmacokinetics and Anti-Drug Antibody Response in Rhesus Monkeys", Bioconjugate Chemistry, 2013, vol. 24, pp. 97-104.

Zhang, Y., and Pardridge, W. M., "Delivery of -Galactosidase to Mouse Brain via the Blood-Brain Barrier Transferrin Receptor", Journal Pharmacology Experimental Therapeutics, 2005, vol. 313, No. 3, pp. 1075-1081.

Abulrob et al., "The blood-brain barrier transmigrating single domain antibody: mechanisms of transport and antigenic epitopes in human brain endothelial cells", Journal of Neurochemistry, 2005, vol. 95, pp. 1201-1214.

Farrington et al., "A novel platform for engineering blood-brain barrier-crossing bispecific biologics", FASEB Journal, 2014, vol. 28, pp. 4764-4778.

Webster et al., "Brain penetration, target engagement, and disposition of the blood-brain barrier-crossing bispecific antibody antagonist of metabotropic glutamate receptor type 1", FASEB Journal, 2016, vol. 30, pp. 1927-1940.

Zhang et al., "Mediated efflux of IgG molecules from brain to blood across the blood-brain barrier", Journal of Neuroimmunology, 2001, vol. 114, pp. 168-172.

Cooper et al., "Efflux monoclonal antibodies from rat brain by neonatal Fc receptor, FcRn", Brain Research, 2013, vol. 1534, pp. 13-21.

Watanabe et al., "Neuroglycan C, a Novel Membrane-spanning Chondroitin Sulfate Proteoglycan That Is Restricted to the Brain", Journal of Biological Chemistry, 1995, vol. 270, No. 45, pp. 26876-26882.

Yasuda et al., "Cloning and chromosomal mapping of the human gene of neuroglycan C (NGC), a neural transmembrane chondroitin sulfate proteoglycan with an EGF module", Neuroscience Research, 1998, vol. 32, pp. 313-322.

Aono et al., "Genomic Organization and Expression Pattern of Mouse Neuroglycan C in the Cerebellar Development", Journal Biological Chemistry, 2000, vol. 275, No. 1, pp. 337-342.

Schumacher et al., "Chicken Acidic Leucine-rich EGF-like Domain Containing Brain Protein (CALEB), a Neural Member of the EGF Family of Differentiation Factors, Is Implicated in Neurite Formation", Journal Cell Biology, 1997, vol. 136, No. 4, pp. 895-906.

Inatani et al., "Neuroglycan C, a Neural Tissue-Specific Transmembrane Chondroitin Sulfate Proteoglycan, in Retinal Neural Network Formation", IOVS, 2000, vol. 41, No. 13, pp. 4338-4346.

Jüttner et al., "Impaired presynaptic function and elimination of synapses at premature stages during postnatal development of the cerebellum in the absence of CALEB (CSPG5/neuroglycan C)", European Journal of Neuroscience, 2013, vol. 38, pp. 3270-3280.

Schumacher et al., "CALEB Binds via Its Acidic Stretch to the Fibrinogen-like Domain of Tenascin-C or Tenascin-R and Its Expression Is Dynamically Regulated after Optic Nerve Lesion", Journal Biological Chemistry, 2001, vol. 276, No. 10, pp. 7337-7345.

Schumacher et al., "Regulated binding of the fibrinogen-like domains of tenascin-R and tenascin-C to the neural EGF family member CALEB", J. Neurochem., 2003, vol. 87, pp. 1213-1223.

Kinugasa et al., "Neuroglycan C, a novel member of the neuregulin family", Biochemical Biophysical Research Communications, 2004, vol. 321, pp. 1045-1049.

Aono et al., "Expression and Identification of a New Splice Variant of Neuroglycan C, a Transmembrane Chondroitin Sulfate Proteoglycan, in the Human Brain", Journal Neuroscience Research, 2006, vol. 83, pp. 110-118.

Anderson et al., "Astrocyte scar formation aids central nervous system axon regeneration", Nature, 2016, vol. 532, pp. 195-200, 20 total pages.

Shuo et al., "Ectodomain shedding of neuroglycan C, a brain-specific chondroitin sulfate proteoglycan, by TIMP-2- and TIMP-3-sensitive proteolysis", Journal of Neurochemistry, 2007, vol. 102, pp. 1561-1568.

Takahashi et al., "Strategy for technology development of antibody therapeutics", Folia Pharmacologica Japonica, 2016, vol. 147, pp. 235-240.

The First Office Action issued Dec. 8, 2023 in corresponding Chinese Patent Application No. 201980043858.7, with English language translation.

Oohira, A. et al., "Neuroglycan C, a brain-specific part-time proteoglycan, with a particular multidomain structure", Glycoconjugate Journal, vol. 21, pp. 53-57, 2004.

\* cited by examiner ns between the blood and the interstitial fluid of the brain. The blood-brain barrier has a physical/nonspecific control mechanism due to the intercellular adhesion of the vascular endothelial cells and a substrate-specific efflux mechanism due to efflux transporters, and protects the central nervous system from foreign matters or drugs and plays an important role in maintaining the homeostasis.

ANTIBODY BINDING TO CHONDROITIN SULFATE PROTEOGLYCAN 5

TECHNICAL FIELD

The present invention relates to, for example, an antibody which binds to chondroitin sulfate proteoglycan 5 (CSPG5) or an antibody fragment thereof, a hybridoma which produces the antibody or the antibody fragment thereof, a nucleic acid comprising a nucleotide sequence encoding the antibody or the antibody fragment thereof, a transformant cell comprising a vector comprising the nucleic acid, a method for producing the antibody or the antibody fragment thereof, a composition comprising the antibody or the antibody fragment thereof, and a method for detecting or measuring an antigen present in the brain, a method for diagnosing or treating a brain disease, a method for enhancing the property of accumulating in a brain of an antibody, and a method for increasing the amount of an antibody in the brain, each using the antibody or the antibody fragment thereof, and the like.

BACKGROUND ART

Since the approval of a mouse anti-CD3 antibody, muromonab-CD3 (OKT3) as the first antibody drug by FDA in 1986, many antibody drugs have been developed. In 1994, a chimeric antibody, abciximab, in which a variable region of a mouse antibody and a constant region of a human antibody are linked to reduce the antigenicity of the mouse antibody, was approved.

To further reduce the antigenicity, a humanized antibody technique in which a complementarity determining region (CDR), which plays an important role in binding to an antigen of a variable region of a mouse antibody is grafted into a frame work region (FR) of a human antibody was developed, and a humanized anti-CD20 antibody, dacizumab was approved in 1997.

In addition, a phage display technique using a human antibody sequence library has been used, and a fully human anti-TNF-α antibody, adalimumab was approved in 2002 as the first antibody obtained using the phage display technique. Sixty or more antibody drugs targeting antigens such as CD20, CD52, TNF-α, HER2, and EGFR have already been approved (NPL 1).

In this manner, antibodies have become a widely recognized drug format. Most of the antibody drugs that have been approved so far are those for cancers and immune diseases, which account for about 75% or more of all the antibody drugs.

The importance of biologics such as an antibody is increasing also in the treatment of central nervous system diseases, and it is reported that a monoclonal antibody to amyloid β is studied in Alzheimer's disease and that various types of neurotrophic factors (brain-derived neurotorophic factor BDNF and glial-derived neurotorophic factor GDNF) having a neuroprotective effect exhibit a neuroprotective effect in central nervous system diseases in an animal model (NPL 2).

However, when an antibody is peripherally administered, the amount delivered to the central nervous system is lower than that to the other organs, and the antibody migration ratio (the ratio of the concentration in the cerebrospinal fluid (CSF) to the serum concentration) is reported to be 0.1 to 0.3% (NPLs 3 to 5).

A reason why the drug delivery amount decreases in the central nervous system comprising the brain and the bone marrow is the mechanism called blood-brain barrier (BBB) which limits the transportation of a substance between the blood and the interstitial fluid of the brain. The blood-brain barrier has a physical/nonspecific control mechanism due to the intercellular adhesion of the vascular endothelial cells and a substrate-specific efflux mechanism due to efflux transporters, and protects the central nervous system from foreign matters or drugs and plays an important role in maintaining the homeostasis.

However, due to the existence of the blood-brain barrier, the effective concentration at the time of drug administration is not easily obtained in the central nervous system, and the drug development is difficult. For example, although enzyme replacement therapy is conducted by intravenously administering α-L-iduronidase to Hurler syndrome (mucopolysaccharidosis I) or iduronate-2-sulfatase to Hunter syndrome (mucopolysaccharidosis II), the enzymes do not pass through the blood-brain barrier due to their high molecular weights, and therefore, no efficacy against central nervous system symptoms has been observed (NPLs 6 to 9). Further, it is reported that a side effect such as production of a neutralizing antibody is caused because a certain amount of a recombinant enzyme is continuously administered regularly (NPL 10).

In addition, an attempt to directly administer biologics into the medullary cavity or the brain has also been made to increase the concentration in the brain. For example, a method for administering iduronate-2-sulfatase into the brain of patients with Hunter syndrome (mucopolysaccharidosis II) to prevent the progress of brain disorders of the patients is reported (PTL 1). However, direct administration into the medullary cavity or the brain is highly invasive (NPL 11).

Therefore, various delivery techniques have been studied to increase the concentration of a substance with a high molecular weight such as biologics in the brain. For example, methods in which a complex of a substance with a high molecular weight and a membrane protein which is expressed in brain vascular endothelial cells is formed by binding the substance to the membrane protein, and allowed to pass through the blood-brain barrier through endocytosis are reported.

Most of the reported techniques use receptor-mediated transcytosis (RMT), and the receptor expressed in the brain vascular endothelium to serve as a target comprises, for example, a transferrin receptor, an insulin receptor, an insulin-like growth factor receptor, a low-density lipoprotein receptor family (LDLRf), and the like.

Techniques for passing through the blood-brain barrier via a transferrin receptor by producing a fusion protein of an anti-transferrin receptor antibody and a nerve growth factor are reported. As techniques using an anti-transferrin receptor antibody, bispecific antibodies of an anti-transferrin receptor antibody and an anti-beta secretase (BACE1) antibody (PTLs 2 and 3 and NPLs 12 and 13), and fusion antibodies obtained by fusing a monovalent anti-transferrin receptor antibody to the carboxyl-terminal side of an anti-amyloid β antibody (PTL 4 and NPL 14) are reported.

It is reported that, regarding the brain delivery using a bispecific antibody of an anti-transferrin receptor antibody and an anti-BACE1 antibody, the amount of the antibody incorporated in the brain increases by about 4 times the amount of the control when the antibody is administered to a mouse at 20 mg/kg body weight (NPL 13).

Further, a technique for allowing a drug to pass through the blood-brain barrier by encapsulating the drug with a liposome having an anti-transferrin receptor antibody on its surface is reported. It is reported that the amount incorporated in the brain of a rat increases by about 2 to 5 times by a fusion body of an anti-rat transferrin receptor antibody and an immunomicelle (NPL 15).

Further, techniques for passing through the blood-brain barrier via an insulin receptor by producing a fusion protein of a neurotrophic factor, an enzyme, or an anti-amyloid antibody fused to the carboxyl-terminal side of an anti-insulin receptor antibody are reported (NPLs 16 to 19).

It is reported that in a rhesus monkey, the amount incorporated in the brain 2 hours after administering a fusion antibody of a labeled anti-human insulin receptor antibody and GDNF is about 15 times as compared with that of GDNF (NPL 17).

However, a transferrin receptor and an insulin receptor are expressed not only in the brain vascular endothelial cells but also in the whole body comprising the liver and the like, and therefore, a drug is delivered also to the liver and the like as the amount of the drug delivered to the central nervous system increases in these techniques (NPL 20). Further, because the antigen is expressed in the whole body, the half-life of the antibody in the blood is short (NPL 12).

In addition, it is reported that an antibody (Fc5) to TMEM30A, which is an antigen expressed in the brain vascular endothelial membrane, shows an RMT-like activity (PTL 5 and NPLs 21 and 22). Fc5 is an antibody of a variable domain of a heavy chain of a heavy chain antibody (hereinafter VHH) of a single domain derived from llama, and it is demonstrated in an in vitro BBB model and in a rat in vivo model that the amount of a fusion body of Fc5 and human Fc delivered to the brain increases as compared with that of the control IgG.

It is reported that the CSF exposure of a fusion body of a Fc5-derived single chain antibody (scFv) and a metabotropic glutamate receptor type I (mGluRI) antibody increases as compared with that of a fusion body of a control single chain antibody and a mGluRI antibody in a rat model, but the increase in the amount is around 5 times (NPL 23).

It is also reported that an IgG antibody is rapidly discharged from the brain to the circulating blood by a neonatal Fc receptor (FcRn) (NPLs 24 and 25), and for example, the half-life of IgG in the brain after the administration into the brain is as short as 48 minutes in a rat (NPL 24).

CSPG5 is a transmembrane chondroitin sulfate proteoglycan and is present exclusively in central nervous system tissues (NPLs 26, 27, and 28). In immunohistochemical staining, staining of neuropils, neurons (nerve cells) such as dendrites and nerve fibers, and/or astrocytes is confirmed (NPLs 28, 29, 30, and 36). The expression of CSPG5 in a rat central nervous system is observed from the embryonic stage, and reaches a peak at week 3 after birth, and is reduced to about half of the peak level at the adult stage (NPLs 26 and 30).

Further, from an experiment using CSPG5 knockout mice, CSPG5 is required for maturation of a cerebellar γ-aminobutyric acid (GABA)-gated synapse, but the Purkinje cell dendritic tree is not affected (NPL 31). CSPG5 exists in a proteoglycan form in central nervous system tissues during development, and exists in a non-proteoglycan form in mature central nervous system tissues (NPLs 28 and 30).

CSPG5 has a 120 kDa core protein. The core protein is divided into five different structures such as an N-terminal domain to which a chondroitin sulfate chain binds, an acidic amino acid cluster, a cysteine-rich domain comprising an epidermal growth factor (EGF)-like module, a transmembrane segment, and a cytoplasmic domain (NPLs 26 and 27).

The extracellular domain of CSPG5 binds to tenascin-C and tenascin-R through an acidic amino acid cluster (NPLs 29, 32, and 33), and interacts with an ErbB3 fusion protein (NPL 34). Further, several antibodies which bind to CSPG5 are reported (PTL 6 and NPLs 26 and 35).

CITATION LIST

Patent Literature

PTL 1: WO 2012/023623
PTL 2: WO 2016/081640
PTL 3: WO 2016/081643
PTL 4: WO 2014/033074
PTL 5: Canadian Patent No. 2623841
PTL 6: WO 2016/175307

Non Patent Literature

NPL 1: Kyla R R. and Richard C C., Biotechnol Adv, pii: S0734-9750 (16), 30091-X, 2016
NPL 2: Pardridge W M., Bioconjugate Chem., 19, 1327-1338, 2008
NPL 3: Wang W., et al., Clin. pharmacol. Ther., 84, 548-558, 2008
NPL 4: Garg A., et al., AAPSJ., 11, 553-557, 2009
NPL 5: Kaj B., et al., Arch. Neurol., 69 (8), 1002-1010, 2012
NPL 6: Wraith J E. et al., J. Pediatr. 144 (5), 581-588, 2004
NPL 7: Muenzer J. et al., Genet Med. 8 (8), 465-473, 2006
NPL 8: Package insert of intravenous infusion 2.9 mg of Aldurazyme (registered trademark) (July, 2016, 8th edition)
NPL 9: Package insert of intravenous infusion 6 mg of Elaprase (registered trademark) (July, 2016, 6th edition)
NPL 10: Brooks, D. A. et al., Trends Mol. Med. 9, 450-453, 2003
NPL 11: Sorrentino N C. et al., Pediatr Endocrinol Rev. 1, 630-638, 2016
NPL 12: Couch J A., et al., Science Translational Medicine, 5, 183ra57, 2013
NPL 13: Yu Y J., et al., Science Translational Medicine, 6, 261ra154, 2014
NPL 14: Niewoehner J., et al., Neuron. 81, 49-60, 2014
NPL 15: Jun Y, et al., Macromol. Biosci. 12, 1209-1219, 2012
NPL 16: Pardridge W M. and Boado R J., Methods in Enzymology, 503, 269-292,
NPL 17: Boado R J., et al., Drug Metab. Dispos., 37 (12), 2299-2304, 2009
NPL 18: Boado R J., et al., J. Pharmacol. Exp. Ther., 333 (3), 961-969, 2010
NPL 19: Boado R J., et al., Bioconjugate Chem., 1, 97-104, 2012
NPL 20: Yun Zhang. et al., J. Pharmacol. Exp. Ther., 313 (3), 1075-1081, 2005
NPL 21: Abulrob A., et al., J. Neuyrochem., 95 (4), 1201-1214, 2005
NPL 22: Farrington G K., et al., FASEB J., 28, 4764-4778, 2014
NPL 23: Webster C I., et al., FASEB J., 30, 1927-1940, 2016
NPL 24: Zhang Y, et al., J. Neuroimmunol., 114 (1-2), 168-172, 2001
NPL 25: Philip R C., et al., Brain Research, 1534, 13-21, 2013
NPL 26: Watanabe E., et al., J. Biol. Chem., 270, 26876-26882, 1995
NPL 27: Yasuda Y., et al., Neurosci. Res., 32, 313-322, 1998

NPL 28: Aono S., et al., J. Biol. Chem., 275, 337-342, 2000
NPL 29: Schumacher S., et al., J. Cell Biol., 136, 895-906, 1997
NPL 30: Inatani M., et al., Invest. Ophthalmol. Vis. Sci., 41, 4338-46, 2000
NPL 31: Juttner R., et al., Eur. J. Neurosci., 38, 3270-3280, 2013
NPL 32: Schumacher S., et al., J. Biol. Chem., 276, 7337-7345, 2001
NPL 33: Schumacher S. & Stube E. M., J. Neurochem., 87, 1213-1223, 2003
NPL 34: Kinugasa Y, et al., Biochem. Bioph. Res. Co., 321, 1045-1049, 2004
NPL 35: Aono S., et al., J. Neurosci. Res., 83, 110-118, 2006
NPL 36: Mark A., et al., Nature, 532, 195-200, 2016

SUMMARY OF INVENTION

Technical Problem

The invention relates to, for example, a CSPG5-binding molecule which binds to CSPG5 and methods using the molecule, and the like. Specifically, an object is to provide an antibody which binds to CSPG5 or an antibody fragment thereof, a hybridoma which produces the antibody or the antibody fragment thereof, a nucleic acid comprising a nucleotide sequence encoding the antibody or the antibody fragment thereof, a transformant cell comprising a vector comprising the nucleic acid, a method for producing the antibody or the antibody fragment thereof, a composition comprising the antibody or the antibody fragment thereof, and a method for detecting or measuring an antigen present in the brain, a method for diagnosing or treating a brain disease, a method for enhancing a property of accumulating in a brain of an antibody, and a method for increasing the amount of an antibody in the brain, each using the antibody or the antibody fragment thereof, and the like.

Solution to Problem

As a means for solving the problems, the invention provides a CSPG5-binding molecule which binds to CSPG5 and methods using the molecule, specifically, an antibody which binds to CSPG5 or an antibody fragment thereof.

That is, the invention relates to the following (1) to (23).
(1) An antibody which binds to chondroitin sulfate proteoglycan 5 (CSPG5) or an antibody fragment thereof
(2) The antibody or the antibody fragment thereof according to (1), wherein the antibody has a property of accumulating in a brain.
(3) The antibody or the antibody fragment thereof according to (2), wherein the antibody has affinity for neurons and/or astrocytes.
(4) The antibody or the antibody fragment thereof according to any one of (1) to (3), wherein the antibody is selected from the group consisting of the following (a) to (s):
(a) an antibody in which the amino acid sequences of complementarity determining regions (CDRs) 1 to 3 of a variable domain of a heavy chain (VH) comprise the amino acid sequences represented by SEQ ID NOS: 3, 4, and 5, respectively, and in which the amino acid sequences of CDR1 to CDR3 of a variable domain of a light chain (VL) comprise the amino acid sequences represented by SEQ ID NOS: 8, 9, and 10, respectively;
(b) an antibody in which the amino acid sequences of CDR1 to CDR3 of VH comprise the amino acid sequences represented by SEQ ID NOS: 13, 14, and 15, respectively, and in which the amino acid sequences of CDR1 to CDR3 of VL comprise the amino acid sequences represented by SEQ ID NOS: 18, 19, and 20, respectively;
(c) an antibody in which the amino acid sequences of CDR1 to CDR3 of VH comprise the amino acid sequences represented by SEQ ID NOS: 23, 24, and 25, respectively, and in which the amino acid sequences of CDR1 to CDR3 of VL comprise the amino acid sequences represented by SEQ ID NOS: 28, 29, and 30, respectively;
(d) an antibody in which the amino acid sequences of CDR1 to CDR3 of VH comprise the amino acid sequences represented by SEQ ID NOS: 33, 34, and 35, respectively, and in which the amino acid sequences of CDR1 to CDR3 of VL comprise the amino acid sequences represented by SEQ ID NOS: 38, 39, and 40, respectively;
(e) an antibody in which the amino acid sequences of CDR1 to CDR3 of VH comprise the amino acid sequences represented by SEQ ID NOS: 43, 44, and 45, respectively, and in which the amino acid sequences of CDR1 to CDR3 of VL comprise the amino acid sequences represented by SEQ ID NOS: 48, 49, and 50, respectively;
(f) an antibody in which the amino acid sequences of CDR1 to CDR3 of VH comprise the amino acid sequences represented by SEQ ID NOS: 53, 54, and 55, respectively, and in which the amino acid sequences of CDR1 to CDR3 of VL comprise the amino acid sequences represented by SEQ ID NOS: 58, 59, and 60, respectively;
(g) an antibody in which the amino acid sequences of CDR1 to CDR3 of VH comprise the amino acid sequences represented by SEQ ID NOS: 63, 64, and 65, respectively, and in which the amino acid sequences of CDR1 to CDR3 of VL comprise the amino acid sequences represented by SEQ ID NOS: 68, 69, and 70, respectively;
(h) an antibody in which the amino acid sequences of CDR1 to CDR3 of VH comprise the amino acid sequences represented by SEQ ID NOS: 73, 74, and 75, respectively, and in which the amino acid sequences of CDR1 to CDR3 of VL comprise the amino acid sequences represented by SEQ ID NOS: 78, 79, and 80, respectively;
(i) an antibody in which the amino acid sequences of CDR1 to CDR3 of VH comprise the amino acid sequences represented by SEQ ID NOS: 83, 84, and 85, respectively, and in which the amino acid sequences of CDR1 to CDR3 of VL comprise the amino acid sequences represented by SEQ ID NOS: 88, 89, and 90, respectively;
(j) an antibody in which the amino acid sequences of CDR1 to CDR3 of VH comprise the amino acid sequences represented by SEQ ID NOS: 93, 94, and 95, respectively, and in which the amino acid sequences of CDR1 to CDR3 of VL comprise the amino acid sequences represented by SEQ ID NOS: 98, 99, and 100, respectively;
(k) an antibody in which the amino acid sequences of CDR1 to CDR3 of VH comprise the amino acid sequences represented by SEQ ID NOS: 103, 104, and, 105, respectively, and in which the amino acid sequences of CDR1 to CDR3 of VL comprise the amino acid sequences represented by SEQ ID NOS: 108, 109, and 110, respectively;
(l) an antibody in which the amino acid sequences of CDR1 to CDR3 of VH comprise the amino acid sequences represented by SEQ ID NOS: 113, 114, and 115, respectively, and in which the amino acid sequences of CDR1 to CDR3 of VL comprise the amino acid sequences represented by SEQ ID NOS: 118, 119, and 120, respectively;
(m) an antibody in which the amino acid sequences of CDR1 to CDR3 of VH comprise the amino acid sequences represented by SEQ ID NOS: 123, 124, and 125, respectively, and in which the amino acid sequences of CDR1 to CDR3 of VL comprise the amino acid sequences represented by SEQ ID NOS: 128, 129, and 130, respectively;
(n) an antibody in which the amino acid sequences of CDR1 to CDR3 of VH comprise the amino acid sequences represented by SEQ ID NOS: 133, 134, and 135, respectively, and in which the amino acid sequences of CDR1 to CDR3 of VL comprise the amino acid sequences represented by SEQ ID NOS: 138, 139, and 140, respectively;
(o) an antibody in which the amino acid sequences of CDR1 to CDR3 of VH comprise the amino acid sequences represented by SEQ ID NOS: 143, 144, and 145, respectively, and in which the amino acid sequences of CDR1 to CDR3 of VL comprise the amino acid sequences represented by SEQ ID NOS: 148, 149, and 150, respectively;
(p) an antibody which competes for binding to CSPG5 with at least one of the antibodies described in (a) to (o);
(q) an antibody which binds to an epitope comprising an epitope to which any one of the antibodies described in (a) to (o) binds;
(r) an antibody which binds to the same epitope as an epitope to which any one of the antibodies described in (a) to (o) binds; and
(s) an antibody which comprises an amino acid sequence having 85% or more homology with the amino acid sequence of any one of the antibodies described in (a) to (o).
(5) The antibody or the antibody fragment thereof according to any one of (1) to (4), wherein the antibody is selected from the group consisting of the following (A) to (P):
(A) an antibody in which the amino acid sequence of VH comprises the amino acid sequence represented by SEQ ID NO: 2 and in which the amino acid sequence of VL comprises the amino acid sequence represented by SEQ ID NO: 7;
(B) an antibody in which the amino acid sequence of VH comprises the amino acid sequence represented by SEQ ID NO: 12 and in which the amino acid sequence of VL comprises the amino acid sequence represented by SEQ ID NO: 17;
(C) an antibody in which the amino acid sequence of VH comprises the amino acid sequence represented by SEQ ID NO: 22 and in which the amino acid sequence of VL comprises the amino acid sequence represented by SEQ ID NO: 27;
(D) an antibody in which the amino acid sequence of VH comprises the amino acid sequence represented by SEQ ID NO: 32 and in which the amino acid sequence of VL comprises the amino acid sequence represented by SEQ ID NO: 37;
(E) an antibody in which the amino acid sequence of VH comprises the amino acid sequence represented by SEQ ID NO: 42 and in which the amino acid sequence of VL comprises the amino acid sequence represented by SEQ ID NO: 47;
(F) an antibody in which the amino acid sequence of VH comprises the amino acid sequence represented by SEQ ID NO: 52 and in which the amino acid sequence of VL comprises the amino acid sequence represented by SEQ ID NO: 57;
(G) an antibody in which the amino acid sequence of VH comprises the amino acid sequence represented by SEQ ID NO: 62 and in which the amino acid sequence of VL comprises the amino acid sequence represented by SEQ ID NO: 67;
(H) an antibody in which the amino acid sequence of VH comprises the amino acid sequence represented by SEQ ID NO: 72 and in which the amino acid sequence of VL comprises the amino acid sequence represented by SEQ ID NO: 77;
(I) an antibody in which the amino acid sequence of VH comprises the amino acid sequence represented by SEQ ID NO: 82 and in which the amino acid sequence of VL comprises the amino acid sequence represented by SEQ ID NO: 87;
(J) an antibody in which the amino acid sequence of VH comprises the amino acid sequence represented by SEQ ID NO: 92 and in which the amino acid sequence of VL comprises the amino acid sequence represented by SEQ ID NO: 97;
(K) an antibody in which the amino acid sequence of VH comprises the amino acid sequence represented by SEQ ID NO: 102 and in which the amino acid sequence of VL comprises the amino acid sequence represented by SEQ ID NO: 107;
(L) an antibody in which the amino acid sequence of VH comprises the amino acid sequence represented by SEQ ID NO: 112 and in which the amino acid sequence of VL comprises the amino acid sequence represented by SEQ ID NO: 117;
(M) an antibody in which the amino acid sequence of VH comprises the amino acid sequence represented by SEQ ID NO: 122 and in which the amino acid sequence of VL comprises the amino acid sequence represented by SEQ ID NO: 127;
(N) an antibody in which the amino acid sequence of VH comprises the amino acid sequence represented by SEQ ID NO: 132 and in which the amino acid sequence of VL comprises the amino acid sequence represented by SEQ ID NO: 137;
(O) an antibody in which the amino acid sequence of VH comprises the amino acid sequence represented by SEQ ID NO: 142 and in which the amino acid sequence of VL comprises the amino acid sequence represented by SEQ ID NO: 147; and
(P) an antibody which comprises an amino acid sequence having 85% or more homology with the amino acid sequence of any one of the antibodies described in (A) to (0).
(6) The antibody or the antibody fragment thereof according to any one of (1) to (5), wherein the antibody or the antibody fragment thereof is a bispecific antibody.
(7) The bispecific antibody according to (6), wherein the bispecific antibody binds to CSPG5 and an antigen present in a brain.
(8) The bispecific antibody according to (6) or (7), wherein the bispecific antibody comprises an antigen-binding site which binds to CSPG5 and an antigen-binding site which binds to an antigen present in a brain.
(9) The antibody fragment according to any one of (1) to (8), wherein the antibody fragment is selected from the group consisting of Fab, Fab', F(ab')2, a single chain antibody (scFv), a dimerized V region (diabody), a disulfide-stabilized V region (dsFv), a variable domain of a heavy chain of a heavy chain antibody (VHH), and a peptide comprising CDR.
(10) The antibody and the antibody fragment thereof according to any one of (1) to (9), wherein the antibody is a genetically recombinant antibody.
(11) The antibody and the antibody fragment thereof according to any one of (1) to (10), wherein the antibody is selected from the group consisting of a mouse antibody, a rat antibody, a rabbit antibody, an alpaca antibody, a camel antibody, a llama antibody, a chimeric antibody, a humanized antibody, and a human antibody.
(12) A fusion antibody or a fusion antibody fragment thereof, which is obtained by binding at least one selected from the group consisting of the following (i) to (iii) to the antibody or the antibody fragment thereof which binds to CSPG5 according to any one of (1) to (11):
(a) a hydrophilic polymer;
(b) an amphipathic polymer; and
(c) a functional molecule.
(13) A hybridoma which produces the antibody, the antibody fragment thereof, the fusion antibody, or the fusion antibody fragment thereof according to any one of (1) to (12).
(14) A nucleic acid, comprising a nucleotide sequence encoding the antibody, the antibody fragment thereof, the fusion antibody, or the fusion antibody fragment thereof according to any one of (1) to (12).
(15) A transformant cell, comprising a vector comprising the nucleic acid according to (14).
(16) A method for producing the antibody, the antibody fragment thereof, the fusion antibody, or the fusion antibody fragment thereof according to any one of (1) to (12), comprising:
culturing the hybridoma according to (13) or the transformant cell according to (15), and
collecting the antibody, the antibody fragment thereof, the fusion antibody, or the fusion antibody fragment thereof according to any one of (1) to (12) from a culture solution.
(17) A composition, comprising the antibody, the antibody fragment thereof, the fusion antibody, or the fusion antibody fragment thereof according to any one of (1) to (12).
(18) The composition according to (17), which is a composition for detecting or measuring an antigen present in a brain.
(19) The composition according to (17), which is a composition for diagnosing or treating a brain disease.
(20) A method for detecting or measuring an antigen present in a brain using the antibody, the antibody fragment thereof, the fusion antibody, or the fusion antibody fragment thereof according to any one of (1) to (12) or the composition according to (17).
(21) A method for diagnosing or treating a brain disease using the antibody, the antibody fragment thereof, the fusion antibody, or the fusion antibody fragment thereof according to any one of (1) to (12) or the composition according to (17).
(22) A method for enhancing the property of accumulating in a brain of an antibody, an antibody fragment thereof, a fusion antibody, or a fusion antibody fragment thereof using the antibody, the antibody fragment thereof, the fusion antibody, or the fusion antibody fragment thereof according to any one of (1) to (12) or the composition according to (17).
(23) A method for increasing the amount of an antibody, the amount of an antibody fragment thereof, the amount of a fusion antibody, or the amount of a fusion antibody fragment thereof in a brain using the antibody, the antibody fragment thereof, the fusion antibody, or the fusion antibody fragment thereof according to any one of (1) to (12) or the composition according to (17).

Advantageous Effects of Invention

The CSPG5-binding molecule of the invention not only enhances the property of accumulating in a brain of the binding molecule itself by specifically binding to CSPG5, but also can be applied to the treatment of a brain disease by modifying the CSPG5-binding molecule with another target molecule and transporting and retaining the target molecule in the brain. As a specific CSPG5-binding molecule of the invention, an antibody or an antibody fragment thereof is exemplified. The antibody or the antibody fragment thereof of the invention is an antibody or an antibody fragment thereof having a property of accumulating in a brain by binding to CSPG5 in the brain. Therefore, the antibody or the antibody fragment thereof of the invention can be used as a composition for detecting or measuring an antigen present in the brain (CSPG5, or CSPG5 and another antigen present in the brain), a composition for diagnosing a brain disease, and a pharmaceutical composition for treating a brain disease.

BRIEF DESCRIPTION OF DRAWINGS

FIG. 1(A) shows the antibody concentration in serum 3 days after administering the antibody. The vertical axis represents the antibody concentration (ng/mL), and the horizontal axis represents the administered antibodies. FIG. 1(B) shows the antibody concentration in a brain tissue 3 days after administering the antibody. The vertical axis represents the antibody concentration (ng/g brain), and the horizontal axis represents the administered antibodies. FIG. 1(C) shows the antibody concentration in serum 9 days after administering the antibody. The vertical axis represents the antibody concentration (ng/mL), and the horizontal axis represents the administered antibodies. FIG. 1(D) shows the antibody concentration in a brain tissue 9 days after administering the antibody. The vertical axis represents the antibody concentration (ng/g brain), and the horizontal axis represents the administered antibodies.

FIG. 2(A) shows the antibody concentration in serum 7 days after administering the antibody. The vertical axis represents the antibody concentration (ng/mL), and the horizontal axis represents the administered antibodies. FIG. 2(B) shows the antibody concentration in a brain tissue 7 days after administering the antibody. The vertical axis represents the antibody elution amount (ng/g brain), and the horizontal axis represents the administered antibodies. The antibody concentration is expressed as a value obtained by conversion from the molar concentration using the molecular weight (150 kDa) of a monoclonal antibody.

FIGS. 3(A) and (C) each show the antibody concentration in serum 7 days after administering the antibody. The vertical axis represents the antibody concentration (ng/mL), and the horizontal axis represents the administered antibodies. FIGS. 3(B) and (D) each show the antibody concentration in a brain tissue 7 days after administering the antibody. The vertical axis represents the antibody elution amount (ng/g brain), and the horizontal axis represents the administered antibodies. The antibody concentration is expressed as a value obtained by conversion from the molar concentration using the molecular weight (150 kDa) of a monoclonal antibody.

FIG. 4(A) shows the imaging images of the brain 9 days after administering the antibody. FIG. 4(B) shows the ratio of a value of the fluorescence amount in the brain corrected by the fluorescence intensity of the administered antibody to the anti-AVM antibody. The vertical axis represents the ratio to the anti-AVM antibody, and the horizontal axis represents the administered antibodies.

DESCRIPTION OF EMBODIMENTS

Figure 1:
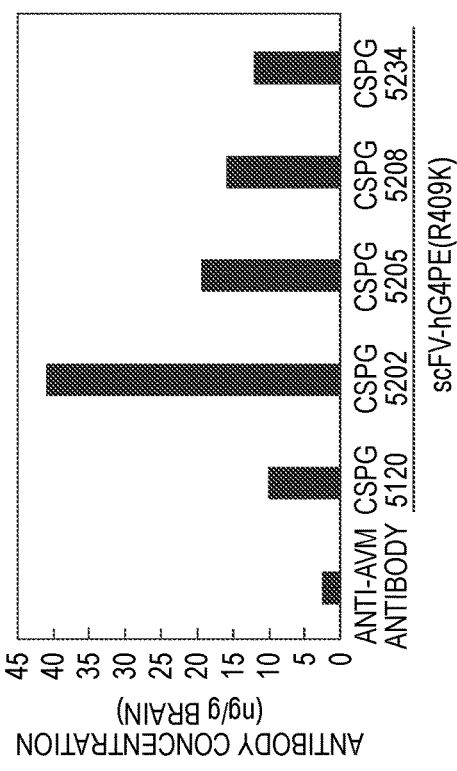
FIG. 1 shows the results of measuring the concentration of each antibody in a tissue.
Figure 1:
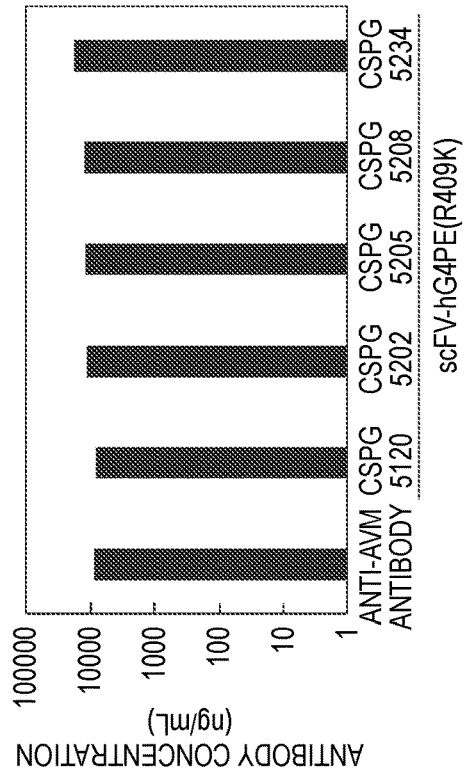
Figure 1:
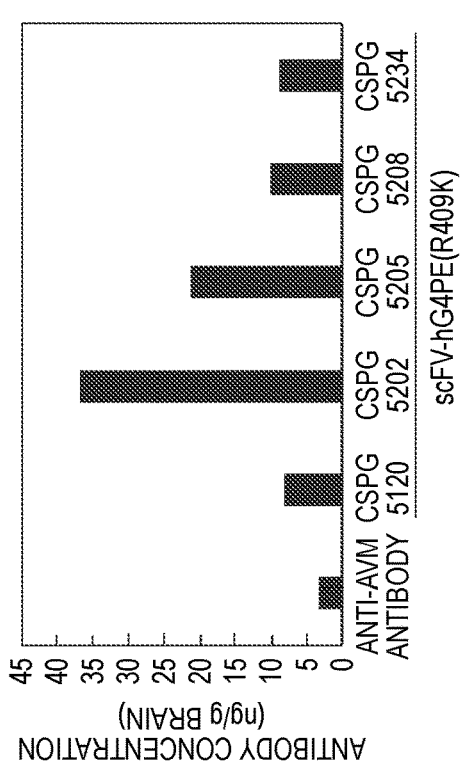
Figure 1:
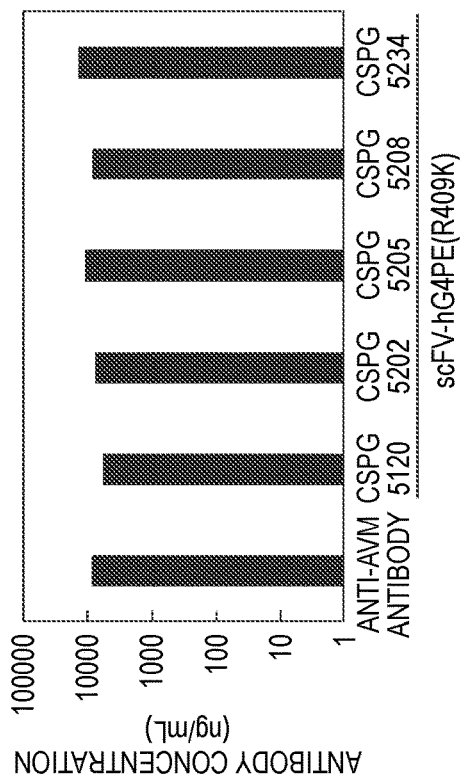

The invention relates to an antigen-binding molecule which binds to CSPG5. More specifically, the invention relates to an antibody which binds to CSPG5 or an antibody fragment thereof.

The CSPG5-binding molecule of the invention may be in any molecular form as long as the molecule specifically binds to CSPG5 and the resulting molecule is retained in the brain, and may be any molecule such as a protein, a nucleic acid, or a low molecular weight compound/high molecular weight compound obtained by organic synthesis. Specifically, the CSPG5-binding molecule may be any of a recombinant protein, an antibody, an aptamer, a low molecular weight compound obtained by low molecular weight screening, and the like, but preferably, an antibody and an antibody fragment thereof are exemplified. The CSPG5-binding molecule is preferably a molecule which binds to the extracellular domain of CSPG5.

CSPG5 is a transmembrane chondroitin sulfate proteoglycan. For example, the full length of human CSPG5 comprising a signal sequence is composed of 539 amino acids, and CSPG5 mainly exists in central nervous system tissues and plays a role in maturation of a cerebellar γ-aminobutyric acid-gated synapse in the process of development of central nervous tissues and intermolecular interaction, and the like.

The animal species of CSPG5 to which the CSPG5-binding molecule of the invention binds are a mouse, a rat, a rhesus monkey, and/or a human, and the like, but are not particularly limited to these species, and an appropriate animal species can be selected according to the use of the antibody. For example, when the antibody of the invention is used for medical purposes for humans, the antibody is preferably an antibody which binds to at least human CSPG5.

In the invention, as human CSPG5, a polypeptide which comprises the amino acid sequence represented by SEQ ID NO: 160 or the amino acid sequence of NCBI accession No. NP_006565.2, a polypeptide which is composed of an amino acid sequence in which one or more amino acids are deleted, substituted, or added in the amino acid sequence represented by SEQ ID NO: 160 or the amino acid sequence of NCBI accession No. NP_006565.2, and which has the function of human CSPG5, a polypeptide which is composed of an amino acid sequence having 60% or more, preferably 80% or more, more preferably 90% or more, and most preferably 95% or more homology with the amino acid sequence represented by SEQ ID NO: 160 or the amino acid sequence of NCBI accession No. NP_006565.2, and which has the function of human CSPG5, or the like is exemplified.

The polypeptide which has an amino acid sequence in which one or more amino acids are deleted, substituted, or added in the amino acid sequence represented by SEQ ID NO: 160 or the amino acid sequence represented by NCBI accession No. NP_006565.2 can be obtained by, for example, introducing a site-specific mutation into a DNA encoding a polypeptide comprising the amino acid sequence of SEQ ID NO: 160 using a site-directed mutagenesis method [Molecular Cloning, A Laboratory Manual, Second Edition, Cold Spring Harbor Laboratory Press (1989), Current Protocols in Molecular Biology, John Wiley & Sons (1987-1997), Nucleic acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985)] or the like.

The number of amino acids that are deleted, substituted, or added is not particularly limited, but is preferably one to several tens, for example, 1 to 20, more preferably one to several, for example, 1 to 5 amino acids.

The same applies to the amino acid sequence of mouse CSPG5 [SEQ ID NO: 162 or NCBI accession No. NP_038912.3] and the amino acid sequence of rhesus monkey CSPG5 [SEQ ID NO: 164 or NCBI accession No. AFE76329.1].

In the invention, as a gene encoding human CSPG5, the nucleotide sequence represented by SEQ ID NO: 159 or the nucleotide sequence of NCBI accession No. NM_006574.3 is exemplified. A gene which is composed of a nucleotide sequence in which one or more nucleotides are deleted, substituted, or added in the nucleotide sequence represented by SEQ ID NO: 159 or the nucleotide sequence of NCBI accession No. NM_006574.3, and which comprises a DNA encoding a polypeptide having the function of CSPG5, a gene which is composed of a nucleotide sequence having at least 60% or more homology, preferably a nucleotide sequence having 80% or more homology, and more preferably a nucleotide sequence having 95% or more homology with the nucleotide sequence represented by SEQ ID NO: 159 or the nucleotide sequence of NCBI accession No. NM_006574.3, and which comprises a DNA encoding a polypeptide having the function of CSPG5, or a gene which is composed of a DNA that hybridizes with a DNA comprising the nucleotide sequence represented by SEQ ID NO: 159 or the nucleotide sequence of NCBI accession No. NM_006574.3 under stringent conditions, and which encodes a polypeptide having the function of CSPG5, or the like is also comprised in the gene encoding CSPG5 in the invention.

The DNA that hybridizes under stringent conditions refers to a hybridizable DNA obtained by a colony hybridization method, a plaque hybridization method, a southern blot hybridization method, a DNA microarray method, or the like using a DNA comprising the nucleotide sequence represented by SEQ ID NO: 159 or the nucleotide sequence of NCBI accession No. NM_006574.3 as a probe.

Specifically, a DNA that can be identified by performing a hybridization method [Molecular Cloning, A Laboratory Manual, Second Edition, Cold Spring Harbor Laboratory Press (1989), Current Protocols in Molecular Biology, John Wiley & Sons (1987-1997), DNA Cloning 1: Core Techniques, A Practical Approach, Second Edition, Oxford University (1995)] at 65° C. in the presence of 0.7 to 1.0 mol/L sodium chloride using a filter or a microscope slide on which a DNA derived from a hybridized colony or plaque, or a PCR product or an oligo DNA having the sequence is immobilized, and thereafter washing the filter or the microscope slide under the condition of 65° C. using a saline sodium citrate (SSC) solution having a concentration of 0.1 to 2 times (a composition of the SSC solution having a concentration of 1 time is composed of 150 mmol/L sodium chloride and 15 mmol/L sodium citrate) can be exemplified.

As the hybridizable DNA, a DNA having at least 60% or more homology, preferably a DNA having 80% or more homology, and more preferably a DNA having 95% or more homology with the nucleotide sequence represented by SEQ ID NO: 159 or the nucleotide sequence of NCBI accession No. NM_006574.3 can be exemplified.

The same applies to the nucleotide sequence of mouse CSPG5 [SEQ ID NO: 161 or NCBI accession No. NM_013884.3] and the nucleotide sequence of rhesus monkey CSPG5 [SEQ ID NO: 163 or NCBI accession No. XM 015131074.1].

Examples of the function of CSPG5 comprise involvement in the maturation of a cerebellar γ-aminobutyric acid-gated synapse in the process of development of central nervous tissues and intermolecular interaction as described above, and the like.

A gene polymorphism is often observed in a nucleotide sequence of a gene encoding a protein of a eukaryote. A gene in which a small-scale mutation has occurred in a nucleotide sequence due to such a polymorphism in a gene used in the invention is also comprised in the gene encoding CSPG5 in the invention.

The numerical value of homology in the invention may be a numerical value calculated using a homology search program known to those skilled in the art unless otherwise specified, however, with respect to a nucleotide sequence, a numerical value calculated using a default parameter in BLAST [J. Mol. Biol., 215, 403 (1990)], and the like are exemplified, and with respect to an amino acid sequence, a numerical value calculated using a default parameter in BLAST2 [Nucleic Acids Res., 25, 3389 (1997), Genome Res., 7, 649 (1997), ncbi.nlm.nih.gov], and the like are exemplified.

As for the default parameters, G (Cost to open gap) is 5 in the case of a nucleotide sequence and 11 in the case of an amino acid sequence, -E (Cost to extend gap) is 2 in the case of a nucleotide sequence and 1 in the case of an amino acid sequence, -q (Penalty for nucleotide mismatch) is -3, -r (reward for nucleotide match) is 1, -e (expect value) is 10, -W (wordsize) is 11 in the case of a nucleotide sequence and 3 in the case of an amino acid sequence, -y [Dropoff (X) for blast extensions in bits] is 20 in the case of blastn and 7 in the case of programs other than blastn, -X (X dropoff value for gapped alignment in bits) is 15, and -Z (final X dropoff value for gapped alignment in bits) is 50 in the case of blastn and 25 in the case of programs other than blastn (ncbi.nlm.nih.gov).

A polypeptide comprising a partial sequence of the amino acid sequence of any of the above-mentioned various types of CSPG5 can be produced by a method known to those skilled in the art. Specifically, the polypeptide can be produced by deleting a part of a DNA encoding the amino acid sequence of any of the above-mentioned various types of CSPG5 and culturing a transformant transfected with an expression vector comprising the resulting DNA. In addition, a polypeptide having an amino acid sequence in which one or more amino acids are deleted, substituted, or added in the amino acid sequence of any of various types of CSPG5 can be obtained in the same manner as described above.

Further, a polypeptide composed of the amino acid sequence of any of various types of CSPG5, or a polypeptide having an amino acid sequence in which one or more amino acids are deleted, substituted, or added in the amino acid sequence of any of various types of CSPG5 can also be produced by a chemical synthesis method such as a fluorenylmethyloxycarbonyl (Fmoc) method or a t-butyloxycarbonyl (tBoc) method.

In the invention, the extracellular domain of human CSPG5 refers to the amino acid sequence from position 31 to position 423 in the amino acid sequence represented by SEQ ID NO: 160 or NCBI accession No. NP_006565.2.

The extracellular domain of mouse CSPG5 refers to the amino acid sequence from position 31 to position 423 in the amino acid sequence represented by SEQ ID NO: 162 or NCBI accession No. NP_038912.3.

The extracellular domain of rhesus monkey CSPG5 refers to the amino acid sequence from position 31 to position 414 in the amino acid sequence represented by SEQ ID NO: 164 or NCBI accession No. AFE76329.1.

It can be confirmed that the antibody of the invention binds to the extracellular domain of CSPG5 by measuring the affinity of the antibody of the invention for CSPG5-expressing cells or a recombinant CSPG5 protein using an enzyme-linked immunosorbent assay (ELISA), flow cytometry, a surface plasmon resonance method, or the like. Further, it can also be confirmed using known immunological detection methods [Monoclonal Antibodies-Principles and practice, Third edition, Academic Press (1996), Antibodies-A Laboratory Manual, Cold Spring Harbor Laboratory (1988), Manual for monoclonal antibody experiments, Kodansha scientific books (1987)], and the like in combination.

The CSPG5-binding molecule of the invention is a molecule having a property of accumulating in a brain by specifically binding to CSPG5 in the brain, and for example, the antibody of the invention is an antibody having a property of accumulating in a brain by binding to CSPG5 in the brain. Further, the antibody of the invention is an antibody having a property of accumulating in a brain by penetrating through the blood-brain barrier in the brain from the periphery, migrating into the brain, and binding to CSPG5 in the brain, when administrating the antibody at the periphery of an animal. The antibody of the invention is preferably an antibody having an excellent property of accumulating in a brain or an antibody having an enhanced property of accumulating in a brain.

In the invention, the "property of accumulating in a brain" refers to a property in which when a target subject is administered to a test animal, the target subject is retained in the brain. That is, it means that the concentration in the brain (or the amount in the brain) of the target subject increases or that the target subject exists at a fixed concentration to such an extent that it can be detected due to at least any one cause selected from an increase in migration into the brain, an increase in accumulation in the brain, a decrease in migration from the inside to the outside of the brain, a decrease in efflux from the inside to the outside of the brain, and a decrease in decomposition in the brain.

In the invention, the "having an excellent property of accumulating in a brain", "having a high property of accumulating in a brain", or "having an enhanced property of accumulating in a brain" means that when a target subject is administered to a test animal, the concentration in the brain (or the amount in the brain) of the target subject after the elapse of the same number of days from the administration increases as compared with that of the control, or the target subject exists at a fixed concentration (amount) to such an extent that it can be detected for a long time in the brain.

Such a phenomenon occurs due to at least any one cause of an increase in migration of the target subject into the brain, an increase in accumulation in the brain, a decrease in migration from the inside to the outside of the brain, a decrease in efflux from the inside to the outside of the brain, and a decrease in decomposition in the brain as compared with the control.

In the invention, the "having an excellent property of accumulating in a brain", "having a high property of accumulating in a brain", or "having an enhanced property of accumulating in a brain" comprises, for example, that when the target subject is administered to a test animal, the concentration (amount) in the brain of the target subject 1 to 10 days after the administration, preferably 2 to 10 days, 3 to 10 days, and more preferably 4 to 10 days after the administration is higher as compared with that of the control, or the concentration in the brain (or the amount in the brain) of the target subject reaches its peak on day 4 or later after the administration, preferably on day 5 or later, day 6 or later, day 7 or later, day 8 or later, day 9 or later, and more preferably on day 10 or later after the administration, and the like.

The antibody having an excellent property of accumulating in a brain, the antibody having a high property of accumulating in a brain, or the antibody having an enhanced property of accumulating in a brain may be any antibody as long as the antibody is an antibody whose antibody concentration (antibody amount) in the brain is higher than that of a control antibody or an antibody having a characteristic capable of existing in the brain for a long time.

For example, an antibody having a characteristic that the migration ability into the brain and/or the accumulation ability in the brain is higher than that of a control antibody, a characteristic that the migration ability from the inside to the outside of the brain, the efflux ability, and/or the decomposition ability in the brain is lower than that of a control antibody, and a characteristic that the migration ability into the brain and/or the accumulation ability in the brain is higher than the migration ability from the inside to the outside of the brain, the efflux ability, and/or the decomposition ability in the brain, or the like is exemplified.

Therefore, as the antibody or the antibody fragment thereof of the invention, when the antibody or the antibody fragment thereof is administered to an animal, an antibody or an antibody fragment thereof whose antibody concentration (or antibody amount) in the brain after the elapse of the same number of days from the administration is higher than that of a control antibody or an antibody or an antibody fragment thereof capable of existing in the brain for a long time, or the like is exemplified.

The change in the antibody concentration (or the antibody amount) in the brain may be any change, and for example, a case where after the antibody concentration in the brain has once reached its peak during the measurement period, the antibody concentration gradually decreases, a case where after the antibody concentration in the brain has reached its peak, the antibody concentration is continuously maintained, or a case where the antibody concentration in the brain continues to increase after administering the antibody, or the like is exemplified.

As the antibody or the antibody fragment thereof of the invention, for example, an antibody whose antibody concentration or antibody amount in the brain is higher than that of a control antibody on day 3 or day 9 after the administration to a mouse, an antibody whose antibody concentration or antibody amount in the brain is maintained or increases during a period from day 3 to day 9 after the administration to a mouse, or an antibody whose existence in the brain can be clearly confirmed even on day 9 or later after the administration to a mouse, or the like is exemplified, but it is not limited thereto.

The control antibody may be any antibody as long as the control antibody is an antibody of the same type or subclass as that of the test antibody, but for example, an anti-avermectin (AVM) antibody or the like can be used.

In the invention, as the "in the brain", for example, in the brain parenchyma, in the cerebral ventricle, in the cerebrospinal fluid, or the like is exemplified, but it is not limited thereto.

In immunohistochemical staining of CSPG5, for example, staining of neuropils, neurons (nerve cells) such as dendrites and nerve fibers, and/or astrocytes is confirmed (NPLs 28, 29, and 30). Therefore, as one aspect of the CSPG5-binding molecule of the invention, a molecule which has affinity for neurons and/or astrocytes by specifically binding to CSPG5 on neurons and/or astrocytes, thereby having a property of accumulating in a brain is exemplified. As one aspect of the antibody of the invention, for example, an antibody which has affinity for neurons and/or astrocytes by binding to CSPG5 on neurons and/or astrocytes, thereby having a property of accumulating in a brain is exemplified.

In the invention, as a method for administering an antibody to an animal, for example, intravenous administration, intraventricular administration, intraperitoneal administration, subcutaneous administration, intradermal administration, intranasal administration, intrathecal administration, or the like is exemplified, but it is not limited thereto.

In the invention, as a method for measuring the property of accumulating in a brain of an antibody, for example, a method in which a brain tissue is collected several days after administering an antibody to an animal, followed by homogenization and centrifugation, and then, the antibody concentration in the resulting supernatant is measured, and the antibody amount per unit brain weight is calculated, a method in which the existence of an antibody is detected by a known immunological method using a collected brain tissue, a method in which a labeled antibody is administered to an animal and the existence of the antibody is detected over time using an in vivo imaging system, or the like is exemplified.

As the antibody of the invention, an antibody selected from the group consisting of the following (a) to (s) is exemplified. Among these, the antibody (e) is preferred from the viewpoint of the property of accumulating in a brain and internalization ability of the antibody.

(a) an antibody in which the amino acid sequences of CDR1 to CDR3 of VH comprise the amino acid sequences represented by SEQ ID NOS: 3, 4, and 5, respectively, and in which the amino acid sequences of CDR1 to CDR3 of VL comprise the amino acid sequences represented by SEQ ID NOS: 8, 9, and 10, respectively (b) an antibody in which the amino acid sequences of CDR1 to CDR3 of VH comprise the amino acid sequences represented by SEQ ID NOS: 13, 14, and 15, respectively, and in which the amino acid sequences of CDR1 to CDR3 of VL comprise the amino acid sequences represented by SEQ ID NOS: 18, 19, and 20, respectively (c) an antibody in which the amino acid sequences of CDR1 to CDR3 of VH comprise the amino acid sequences represented by SEQ ID NOS: 23, 24, and 25, respectively, and in which the amino acid sequences of CDR1 to CDR3 of VL comprise the amino acid sequences represented by SEQ ID NOS: 28, 29, and 30, respectively (d) an antibody in which the amino acid sequences of CDR1 to CDR3 of VH comprise the amino acid sequences represented by SEQ ID NOS: 33, 34, and 35, respectively, and in which the amino acid sequences of CDR1 to CDR3 of VL comprise the amino acid sequences represented by SEQ ID NOS: 38, 39, and 40, respectively (e) an antibody in which the amino acid sequences of CDR1 to CDR3 of VH comprise the amino acid sequences represented by SEQ ID NOS: 43, 44, and 45, respectively, and in which the amino acid sequences of CDR1 to CDR3 of VL comprise the amino acid sequences represented by SEQ ID NOS: 48, 49, and 50, respectively (f) an antibody in which the amino acid sequences of CDR1 to CDR3 of VH comprise the amino acid sequences represented by SEQ ID NOS: 53, 54, and 55, respectively, and in which the amino acid sequences of CDR1 to CDR3 of VL comprise the amino acid sequences represented by SEQ ID NOS: 58, 59, and 60, respectively (g) an antibody in which the amino acid sequences of CDR1 to CDR3 of VH comprise the amino acid sequences represented by SEQ ID NOS: 63, 64, and 65, respectively, and in which the amino acid sequences of CDR1 to CDR3 of VL comprise the amino acid sequences represented by SEQ ID NOS: 68, 69, and 70, respectively (h) an antibody in which the amino acid sequences of CDR1 to CDR3 of VH comprise the amino acid sequences represented by SEQ ID NOS: 73, 74, and 75, respectively, and in which the amino acid sequences of CDR1 to CDR3 of VL comprise the amino acid sequences represented by SEQ ID NOS: 78, 79, and 80, respectively (i) an antibody in which the amino acid sequences of CDR1 to CDR3 of VH comprise the amino acid sequences represented by SEQ ID NOS: 83, 84, and 85, respectively, and in which the amino acid sequences of CDR1 to CDR3 of VL comprise the amino acid sequences represented by SEQ ID NOS: 88, 89, and 90, respectively (j) an antibody in which the amino acid sequences of CDR1 to CDR3 of VH comprise the amino acid sequences represented by SEQ ID NOS: 93, 94, and 95, respectively, and in which the amino acid sequences of CDR1 to CDR3 of VL comprise the amino acid sequences represented by SEQ ID NOS: 98, 99, and 100, respectively (k) an antibody in which the amino acid sequences of CDR1 to CDR3 of VH comprise the amino acid sequences represented by SEQ ID NOS: 103, 104, and, 105, respectively, and in which the amino acid sequences of CDR1 to CDR3 of VL comprise the amino acid sequences represented by SEQ ID NOS: 108, 109, and 110, respectively (l) an antibody in which the amino acid sequences of CDR1 to CDR3 of VH comprise the amino acid sequences represented by SEQ ID NOS: 113, 114, and 115, respectively, and in which the amino acid sequences of CDR1 to CDR3 of VL comprise the amino acid sequences represented by SEQ ID NOS: 118, 119, and 120, respectively (m) an antibody in which the amino acid sequences of CDR1 to CDR3 of VH comprise the amino acid sequences represented by SEQ ID NOS: 123, 124, and 125, respectively, and in which the amino acid sequences of CDR1 to CDR3 of VL comprise the amino acid sequences represented by SEQ ID NOS: 128, 129, and 130, respectively (n) an antibody in which the amino acid sequences of CDR1 to CDR3 of VH comprise the amino acid sequences represented by SEQ ID NOS: 133, 134, and 135, respectively, and in which the amino acid sequences of CDR1 to CDR3 of VL comprise the amino acid sequences represented by SEQ ID NOS: 138, 139, and 140, respectively (o) an antibody in which the amino acid sequences of CDR1 to CDR3 of VH comprise the amino acid sequences represented by SEQ ID NOS: 143, 144, and 145, respectively, and in which the amino acid sequences of CDR1 to CDR3 of VL comprise the amino acid sequences represented by SEQ ID NOS: 148, 149, and 150, respectively (p) an antibody which competes for binding to CSPG5 with at least one of the antibodies described in (a) to (o)

(q) an antibody which binds to an epitope comprising an epitope to which any one of the antibodies described in (a) to (o) binds (r) an antibody which binds to the same epitope as an epitope to which any one of the antibodies described in (a) to (o) binds (s) an antibody which comprises an amino acid sequence having 85% or more homology with the amino acid sequence of any one of the antibodies described in (a) to (o).

As the antibody of the invention, an antibody which comprises the amino acid sequences of CDR1 to CDR3 of VH and CDR1 to CDR3 of VL of an antibody having 85% or more, preferably 90% or more homology with the amino acid sequences of CDR1 to CDR3 of VH and CDR1 to CDR3 of VL of any one of the antibodies described in (a) to (o) is comprised. The 90% or more homology is more preferably 91%, 92%, 93%, 94%, 95%, 96%, 97%, 98%, or 99% homology, or the like.

In the invention, as one aspect of the antibodies described in (a) to (o), a CSPG5115 antibody, a CSPG5120 antibody, a CSPG5168 antibody, a CSPG5201 antibody, a CSPG5202 antibody, a CSPG5205 antibody, a CSPG5206 antibody, a CSPG5207 antibody, a CSPG5208 antibody, a CSPG5214 antibody, a CSPG5219 antibody, a CSPG5222 antibody, a CSPG5227 antibody, a CSPG5230 antibody, and a CSPG5234 antibody, each of which is a human anti-CSPG5 monoclonal antibody, and the like are exemplified. Among these, a CSPG5202 antibody is preferred from the viewpoint of the property of accumulating in a brain and internalization ability of the antibody.

In the invention, the antibody (p) refers to a second antibody which inhibits binding of a first antibody to CSPG5 when any one of the antibodies described in (a) to (o) is defined as the first antibody.

In the invention, the antibody (q) refers to a second antibody which binds to a second epitope comprising a first epitope when any one of the antibodies described in (a) to (o) is defined as a first antibody, and an epitope to which the first antibody binds is defined as the first epitope.

Further, the antibody (r) of the invention refers to a second antibody which binds to a first epitope when any one of the antibodies described in (a) to (o) is defined as a first antibody, and an epitope to which the first antibody binds is defined as the first epitope.

In addition, as the antibody of the invention, specifically, an antibody selected from the group consisting of the following (A) to (P) is also exemplified. Among these, the antibody (E) is preferred from the viewpoint of the property of accumulating in a brain and internalization ability of the antibody.

(A) an antibody in which the amino acid sequence of VH comprises the amino acid sequence represented by SEQ ID NO: 2 and in which the amino acid sequence of VL comprises the amino acid sequence represented by SEQ ID NO: 7

(B) an antibody in which the amino acid sequence of VH comprises the amino acid sequence represented by SEQ ID NO: 12 and in which the amino acid sequence of VL comprises the amino acid sequence represented by SEQ ID NO: 17

(C) an antibody in which the amino acid sequence of VH comprises the amino acid sequence represented by SEQ ID NO: 22 and in which the amino acid sequence of VL comprises the amino acid sequence represented by SEQ ID NO: 27

(D) an antibody in which the amino acid sequence of VH comprises the amino acid sequence represented by SEQ ID NO: 32 and in which the amino acid sequence of VL comprises the amino acid sequence represented by SEQ ID NO: 37

(E) an antibody in which the amino acid sequence of VH comprises the amino acid sequence represented by SEQ ID NO: 42 and in which the amino acid sequence of VL comprises the amino acid sequence represented by SEQ ID NO: 47

(F) an antibody in which the amino acid sequence of VH comprises the amino acid sequence represented by SEQ ID NO: 52 and in which the amino acid sequence of VL comprises the amino acid sequence represented by SEQ ID NO: 57

(G) an antibody in which the amino acid sequence of VH comprises the amino acid sequence represented by SEQ ID NO: 62 and in which the amino acid sequence of VL comprises the amino acid sequence represented by SEQ ID NO: 67

(H) an antibody in which the amino acid sequence of VH comprises the amino acid sequence represented by SEQ ID NO: 72 and in which the amino acid sequence of VL comprises the amino acid sequence represented by SEQ ID NO: 77

(I) an antibody in which the amino acid sequence of VH comprises the amino acid sequence represented by SEQ ID NO: 82 and in which the amino acid sequence of VL comprises the amino acid sequence represented by SEQ ID NO: 87

(J) an antibody in which the amino acid sequence of VH comprises the amino acid sequence represented by SEQ ID NO: 92 and in which the amino acid sequence of VL comprises the amino acid sequence represented by SEQ ID NO: 97

(K) an antibody in which the amino acid sequence of VH comprises the amino acid sequence represented by SEQ ID NO: 102 and in which the amino acid sequence of VL comprises the amino acid sequence represented by SEQ ID NO: 107

(L) an antibody in which the amino acid sequence of VH comprises the amino acid sequence represented by SEQ ID NO: 112 and in which the amino acid sequence of VL comprises the amino acid sequence represented by SEQ ID NO: 117

(M) an antibody in which the amino acid sequence of VH comprises the amino acid sequence represented by SEQ ID NO: 122 and in which the amino acid sequence of VL comprises the amino acid sequence represented by SEQ ID NO: 127

(N) an antibody in which the amino acid sequence of VH comprises the amino acid sequence represented by SEQ ID NO: 132 and in which the amino acid sequence of VL comprises the amino acid sequence represented by SEQ ID NO: 137

(O) an antibody in which the amino acid sequence of VH comprises the amino acid sequence represented by SEQ ID NO: 142 and in which the amino acid sequence of VL comprises the amino acid sequence represented by SEQ ID NO: 147

(P) an antibody which comprises an amino acid sequence having 85% or more homology with the amino acid sequence of any one of the antibodies described in (A) to (O)

As the antibody of the invention, an antibody which comprises the amino acid sequences of VH and VL of an antibody having 85% or more, preferably 90% or more homology with the amino acid sequences of VH and VL of any one of the antibodies described in (A) to (O) is comprised. The 90% or more homology is more preferably 91%, 92%, 93%, 94%, 95%, 96%, 97%, 98%, or 99% homology, or the like.

In the invention, as one aspect of the antibodies described in (A) to (0), a CSPG5115 antibody, a CSPG5120 antibody, a CSPG5168 antibody, a CSPG5201 antibody, a CSPG5202 antibody, a CSPG5205 antibody, a CSPG5206 antibody, a CSPG5207 antibody, a CSPG5208 antibody, a CSPG5214 antibody, a CSPG5219 antibody, a CSPG5222 antibody, a CSPG5227 antibody, a CSPG5230 antibody, and a CSPG5234 antibody, each of which is a human anti-CSPG5 monoclonal antibody, and the like are exemplified. Among these, a CSPG5202 antibody is preferred from the viewpoint of the property of accumulating in a brain and internalization ability of the antibody.

In the invention, the EU index refers to the position of an amino acid residue according to Sequences of Proteins of Immunological Interest, Fifth edition (1991). The positions of the amino acid residues shown below all indicate the positions of the amino acid residues according to the EU index unless otherwise specified.

An antibody molecule is also called an immunoglobulin (Ig), and its basic structure is a tetramer having two polypeptides called heavy chains (H chains) and two polypeptides called light chains (L chains).

Further, each H chain is composed of respective domains of a variable domain of an H chain (also referred to as VH) and a constant domain of an H chain (also referred to as CH) from the N-terminal side, and each L chain is composed of respective domains of a variable domain of an L chain (also referred to as VL) and a constant domain of an L chain (also referred to as CL) from the N-terminal side.

As the CH, α, δ, ε, γ, and μ chains are known for each subclass. The CH is further composed of respective domains of a CH1 domain, a hinge domain, a CH2 domain, and a CH3 domain from the N-terminal side.

The domain refers to a functional structural unit which constitutes each polypeptide of an antibody molecule. Further, the CH2 domain and the CH3 domain are collectively referred to as an Fc (Fragment, crystallizable) region or simply Fc. As the CL, a $C_\lambda$ chain and a $C_\kappa$ chain are known.

The subclasses of an antibody in which the CH is α, δ, ε, γ, and μ chains are referred to as IgA, IgD, IgE, IgG, and IgM, respectively. There sometimes exist isotypes for a subclass of each antibody depending on the animal. In a human, there are IgA1 and IgA2 isotypes for IgA, and there are IgG1, IgG2, IgG3, and IgG4 isotypes for IgG.

In the invention, the CH1 domain, the hinge domain, the CH2 domain, the CH3 domain, and the Fc region can be specified by numbers of amino acid residues from the N-terminus according to the EU index.

Specifically, CH1 is specified as the amino acid sequence at positions 118 to 215 according to the EU index, the hinge is specified as the amino acid sequence at positions 216 to 230 according to the EU index, CH2 is specified as the amino acid sequence at positions 231 to 340 according to the EU index, CH3 is specified as the amino acid sequence at positions 341 to 447 according to the EU index, and the Fc region is specified as the amino acid sequence at positions 231 to 447 according to the EU index.

As the antibody of the invention, a polyclonal antibody, a monoclonal antibody, and an oligoclonal antibody are all comprised. The polyclonal antibody refers to a group of antibody molecules secreted by antibody-producing cells of different clones. The monoclonal antibody is an antibody secreted by antibody-producing cells of a single clone, and refers to an antibody, which recognizes only one epitope (also referred to as an antigenic determinant), and in which the amino acid sequence (primary sequence) constituting the monoclonal antibody is uniform. The oligoclonal antibody refers to a group of antibody molecules in which a plurality of different monoclonal antibodies are mixed.

As the monoclonal antibody in the invention, an antibody produced by a hybridoma or a genetically recombinant antibody produced by a transformant transformed with an expression vector comprising an antibody gene is exemplified.

As the epitope, a single amino acid sequence, a conformation composed of an amino acid sequence, an amino acid sequence modified after translation, and a conformation composed of an amino acid sequence modified after translation, each of which the monoclonal antibody recognizes and binds to, and the like are exemplified.

As the amino acid sequence modified after translation, an O-linked glycan in which a glycan is attached to Tyr and Ser having an OH substituent, an N-linked glycan in which a glycan is attached to Gln and Asn having an $NH_2$ substituent, and a tyrosine-sulfated amino acid sequence in which a sulfuric acid molecule is attached to Tyr having an OH substituent are exemplified.

The epitope of CSPG5 to which the antibody of the invention binds can be identified by performing an antibody binding test using a deletion variant in which some domains of CSPG5 are deleted, a mutant in which some domains of CSPG5 are substituted with domains derived from another protein, a partial peptide fragment of CSPG5, or the like. Further, the antibody binding test can also be performed using cells expressing the deletion variant or the mutant.

Alternatively, the epitope of CSPG5 to which the antibody of the invention binds can also be identified by adding the antibody of the invention to peptide fragments of CSPG5 obtained by digestion using a protease and performing epitope mapping using known mass spectrometry.

As the antibody of the invention, genetically recombinant antibodies such as a mouse antibody, a rat antibody, a hamster antibody, a rabbit antibody, a llama antibody, a camel antibody, an alpaca antibody, a chimeric antibody, a humanized antibody (also referred to as a "CDR-grafted antibody"), and a human antibody produced by a genetic recombination technique are also comprised.

In the invention, the chimeric antibody refers to an antibody in which VH and VL are derived from an animal species different from that of CH and CL. An antibody composed of VH and VL of an antibody of an animal other than a human (a non-human animal) and CH and CL of a human antibody is called a human chimeric antibody, and an antibody composed of VH and VL of an antibody of an animal other than a mouse and CH and CL of a mouse antibody is called a mouse chimeric antibody. Other chimeric antibodies are also named in the same manner.

As the non-human animal, any animal such as a mouse, a rat, a hamster, a rabbit, a llama, a camel, or an alpaca can be used as long as it is an animal capable of producing a hybridoma or an antibody phage library.

The hybridoma refers to a cell which is obtained by cell fusion of a B cell obtained by immunizing a non-human animal with an antigen and a myeloma cell derived from a mouse or the like and which produces a monoclonal antibody having a desired antigen specificity.

An antibody phage library refers to a library produced by cloning a gene of an immunoglobulin variable region into a phage and expressing an antigen-binding molecule on its surface. As the phage used, M13 phage or the like is exemplified, but it is not particularly limited.

The antigen-binding molecule which is displayed on a phage may be in any form, but is preferably an antibody fragment such as scFv, Fab, or VHH.

In the invention, the antibody phage library may be any library of an immune library, a naive library, and a synthetic library.

The immune library refers to an antibody phage library constructed based on an antibody gene derived from lymphocytes of an animal immunized with an antigen or a patient. The naive library refers to an antibody phage library constructed based on an antibody gene derived from lymphocytes of a normal animal or a healthy human. The synthetic library refers to a library in which CDR of a V gene in a genomic DNA or a reconstructed functional V gene is substituted with an oligonucleotide encoding a random amino acid sequence of an appropriate length.

As a method for producing a chimeric antibody, a method for producing a human chimeric antibody will be described below. Other chimeric antibodies can also be produced in the same manner.

The human chimeric antibody can be produced by obtaining cDNAs encoding VH and VL from a hybridoma derived from a non-human animal cell which produces a monoclonal antibody, inserting each of the cDNAs into an expression vector for animal cells having DNAs encoding CH and CL of a human antibody, thereby constructing a human chimeric antibody expression vector, and then introducing the vector into an animal cell and expressing the antibody.

Further, the human chimeric antibody can also be produced by cloning genes encoding VH and VL from an antibody phage library derived from a non-human animal, inserting each of the genes into an expression vector for animal cells having DNAs encoding CH and CL of a human antibody, thereby constructing a human chimeric antibody expression vector, and then introducing the vector into an animal cell and expressing the antibody.

The humanized antibody refers to an antibody in which the amino acid sequences of CDRs of VH and VL of a non-human animal antibody are grafted into the corresponding CDRs of VH and VL of a human antibody. A region other than the CDRs of VH and VL is called FR.

The humanized antibody can be produced by constructing a cDNA encoding the amino acid sequence of VH composed of the amino acid sequence of CDR of VH of a non-human animal antibody and the amino acid sequence of FR of VH of an arbitrary human antibody, and a cDNA encoding the amino acid sequence of VL composed of the amino acid sequence of CDR of VL of a non-human animal antibody and the amino acid sequence of FR of VL of an arbitrary human antibody, inserting each of the cDNAs into an expression vector for animal cells having DNAs encoding CH and CL of a human antibody, thereby constructing a humanized antibody expression vector, and then introducing the vector into an animal cell and expressing the antibody.

The human antibody originally refers to an antibody that naturally exists in the human body, but also comprises antibodies obtained from a human antibody phage library or a human antibody-producing transgenic animal, and the like.

The human antibody can be obtained by immunizing a mouse having a human immunoglobulin gene (Tomizuka K. et al., Proc Natl Acad Sci USA. 97, 722-7, 2000.) with a desired antigen. In addition, the human antibody can be obtained without immunization by selecting a human antibody having a desired binding activity using a phage display library obtained by amplifying an antibody gene from human-derived B cells (Winter G. et al., Annu Rev Immunol. 12: 433-55. 1994).

Further, the human antibody can be obtained by producing cells which produce a human antibody having a desired binding activity by immortalizing human B cells using an EB virus (Rosen A. et al., Nature 267, 52-54. 1977).

The human antibody phage library is a library of phages in which an antibody fragment such as Fab, scFv, or VHH is expressed on the surface thereof by inserting an antibody gene prepared from lymphocytes of a human (a healthy human or a patient) into a phage gene. It is possible to collect a phage that expresses an antibody fragment having a desired antigen-binding activity from the library using a binding activity to a substrate onto which an antigen is immobilized as an index. The antibody fragment can also be further converted into a human antibody molecule composed of two complete H chains and two complete L chains using a genetic engineering technique.

The human antibody-producing transgenic animal refers to an animal in which a human antibody gene is incorporated into the chromosome of a host animal. Specifically, a human antibody-producing transgenic animal can be produced by introducing a human antibody gene into a mouse ES cell, implanting the ES cell into an early embryo of another mouse and then allowing the embryo to develop into an animal.

The production of the human antibody from the human antibody-producing transgenic animal can be performed by culturing a human antibody-producing hybridoma obtained by a general hybridoma production method to be performed using a mammal other than a human so as to produce and accumulate the human antibody in the culture, and purifying the antibody from the culture.

The antibody of the invention comprises a heavy chain antibody composed only of a heavy chain. The heavy chain antibody refers to an antibody obtained from an animal of the family Camelidae such as a llama, a camel, and an alpaca or a genetically recombinant antibody produced based on the antibody.

In the invention, the antibody fragment is a fragment of an antibody and refers to a fragment having an antigen-binding activity. Examples thereof comprise Fab, Fab', F(ab')$_2$, scFv, a diabody, dsFv, a peptide comprising a plurality of CDRs, VHH, and the like. Further, the antibody fragment of the invention also comprises any antibody fragment as long as the antibody fragment comprises a partial fragment of an antibody and has a CSPG5 binding activity, such as an antibody fragment obtained by fusing the full length or a part of a constant region or Fc of an antibody to the antibody fragment or an antibody fragment comprising a constant region or Fc.

The Fab is an antibody fragment, which has a molecular weight of about 50,000 and has an antigen-binding activity, and in which about a half of an H chain at the N-terminal side and the entire L chain are bound through a disulfide bond (S—S bond) among the fragments obtained by treating an IgG antibody with a protease papain (cleaved at an amino acid residue at position 224 in the H chain).

The F(ab')$_2$ is an antibody fragment, which has a molecular weight of about 100,000 and has an antigen-binding activity, and is slightly larger than a molecule obtained by binding Fabs through an S—S bond in the hinge region among the fragments obtained by treating IgG with a protease pepsin (cleaved at an amino acid residue at position 234 in the H chain).

The Fab' is an antibody fragment, which has a molecular weight of about 50,000 and has an antigen-binding activity, and in which an S—S bond in the hinge region of the above F(ab')$_2$ is cleaved.

The scFv is a VH-P-VL or VL-P-VH polypeptide in which one VH and one VL are linked using an appropriate peptide linker (P) such as a linker peptide obtained by connecting an arbitrary number of linkers (G4S) composed of four Gly residues and one Ser residue, and is an antibody fragment having an antigen-binding activity.

The diabody is an antibody fragment in which scFvs having the same or different antigen-binding specificities form a dimer, and is an antibody fragment having a divalent antigen-binding activity to the same antigen or antigen-binding activities specific for different antigens.

The dsFv is an antibody fragment, which is obtained by binding polypeptides in which one amino acid residue in each of VH and VL is substituted with a cysteine residue through an S—S bond between the cysteine residues, and which has an antigen-binding activity.

The peptide comprising CDR is configured to comprise at least one or more regions of CDRs of VH or VL, and is an antibody fragment having an antigen-binding activity. In a peptide comprising a plurality of CDRs, the CDRs can be bound directly or through an appropriate peptide linker. As the peptide comprising CDR of the invention, a peptide comprising six CDRs derived from the antibody of the invention is preferably exemplified.

The peptide comprising CDR can be produced by constructing DNAs encoding CDRs of VH and VL of the antibody of the invention, inserting the DNAs into an expression vector for a prokaryote or an expression vector for a eukaryote, and then introducing the expression vector into a prokaryote or a eukaryote and expressing the peptide. In addition, the peptide comprising CDR can also be produced by a chemical synthesis method such as an Fmoc method or a tBoc method.

The VHH is a variable domain of a heavy chain antibody and is also called a nanobody. The antibody fragment of the invention comprises any antibody fragment as long as the antibody fragment comprises any of the antibody fragments described above or a partial fragment thereof and has a CSPG5 binding activity.

In the invention, an antibody having one antigen-binding site or an antibody fragment thereof is called a monovalent antibody. Examples of the format of a monovalent antibody comprise the formats of an antibody having one antigen-binding site or an antibody fragment thereof described in WO 2014/054804, WO 2011/090754, WO 2007/048037, WO 2012/116927, and the like, and other formats.

In the invention, an antibody of one molecule which binds to three or more different antigens or epitopes or an antibody fragment thereof is called a multispecific antibody. In addition, in the invention, an antibody of one molecule which binds to two different antigens or epitopes or an antibody fragment thereof is called a bispecific antibody.

Examples of the formats of a multispecific antibody or a bispecific antibody comprise the formats described in WO 2009/131239, WO 2014/054804, WO 01/077342, US Patent Application Publication No. 2007/0071675, WO 2007/024715, Wu et al., [Nature Biotechnology, 2007, 25(11), pp. 1290-1297], Labrijn et al., [PNAS 2013, vol. 110, no. 13, pp. 5145-5150], Jong et al., [see 10.1371/j ournal.pbio.1002344 on the website: dx.doi.org], Kontermann et al., [mAbs 2012, vol. 4, issue 2, pp. 182-197], Spiess et al., [Molecular Immunology 67 (2015) 95-106], Ridgway et al., [Protein engineering, 1996 vol. 9, no. 7, pp. 617-621], WO 2009/080251, WO 2010/151792, WO 2014/033074, and the like, and other formats.

Specific examples of the bispecific antibody comprise the bispecific antibodies described below, and the like.
  (1) A bispecific antibody in which amino acid modifications S354C/T366W are introduced into CH3 of one heavy chain (heavy chain A) of the two heavy chains of an antibody and amino acid modifications Y349C/T366S/L368A/Y407V are introduced into CH3 of the other heavy chain (heavy chain B).
  (2) A bispecific antibody in which an antibody fragment is fused to the C-terminus of an antibody.
  (3) A bispecific antibody in which an antibody fragment is fused to the N-terminus of an antibody.

The bispecific antibody described in (1) may be a bispecific antibody in which the antigen-binding site comprising VH of the heavy chain A binds to CSPG5 and in which the antigen-binding site comprising VH of the heavy chain B binds to an antigen present in the brain or a bispecific antibody in which the antigen-binding sites bind the other way around.

Examples of the bispecific antibody described in (2) comprise a bispecific antibody in which an antibody fragment is bound to the C-terminus of one of the two heavy chains constituting an antibody, a bispecific antibody in which an antibody fragment is bound to the C-termini of both two heavy chains constituting an antibody, a bispecific antibody in which an antibody fragment is bound to the C-terminus of one of the two light chains constituting an antibody, a bispecific antibody in which an antibody fragment is bound to the C-termini of both two light chains constituting an antibody, a bispecific antibody in which an antibody fragment is bound to each of the C-termini of the two light chains and the C-termini of the two heavy chains constituting an antibody, and the like. Note that an appropriate linker may be present between the C-terminus of the antibody and the antibody fragment.

The antibody fragment comprised in the bispecific antibody described in (2) is preferably scFv, Fab, VHH, or the like, but is not particularly limited thereto.

The bispecific antibody described in (2) may be a bispecific antibody in which the antigen-binding site at the N-terminus binds to CSPG5 and in which the antigen-binding site at the C-terminus binds to an antigen present in the brain or a bispecific antibody in which the antigen-binding sites bind the other way around.

The bispecific antibody described in (3) refers to a bispecific antibody in which an antibody fragment is bound to the N-terminus of at least any one of the two heavy chains or the two light chains constituting an antibody. Further, an appropriate linker may be present between the N-terminus of the heavy chain and/or the light chain of the antibody and the antibody fragment. The antibody fragment comprised in the bispecific antibody described in (3) is preferably scFv, Fab, VHH, or the like, but is not particularly limited thereto.

Further, examples of the bispecific antibody described in (3) comprise a bispecific antibody having a structure of $VH_1$-CH1-$VH_2$-CH1-Hinge-CH2-CH3 from the N-terminus of a heavy chain, a bispecific antibody, which has the heavy chain structure described above, and in which $VH_1$ and $VH_2$ each form an antigen-binding site together with VL, and the like. The VLs with which $VH_1$ and $VH_2$ form antigen-binding sites may have the same amino acid sequence or different amino acid sequences.

In the invention, the multispecific antibody or the bispecific antibody may be any antibody as long as the antibody is a multispecific antibody or a bispecific antibody which binds to CSPG5. Among such antibodies, a multispecific antibody or a bispecific antibody which binds to CSPG5 and an antigen present in the brain is preferred, and a multispecific antibody or a bispecific antibody comprising an antigen-binding site which binds to CSPG5 and an antigen-binding site which binds to an antigen present in the brain is more preferred.

In the invention, examples of the antigen present in the brain comprise a protein, a glycan, a lipid, and the like, and the antigen is preferably a protein among these.

Examples of the protein present in the brain comprise Prion, 5T4, AFP, ADAM10, ADAM12, ADAM17, AFP, AXL, BCAM, BSG, C5, C5R, CA9, CA72-4, CADM3, CCL11, CCL2, CCR1, CCR4, CCR5, CCR6, CD2, CD3E, CD4, CD5, CD6, CD8, CD11, CD18, CD19, CD20, CD22, CD24, CD25, CD29, CD30, CD32B, CD33, CD37, CD38, CD40, CD40LG, CD44, CD47, CD52, CD55SC1, CD56, CD66E, CD71, CD72, CD74, CD79a, CD79b, CD80, CD86, CD95, CD98, CD137, CD147, CD138, CD168, CD200, CD248, CD254, CD257, CDH2, CDH3, CEA, CEACAM1, CEACAM5, CEACAM6, CEACAM8, Claudin3, Claudin4, CSF-1, CSF2RA, CSPG-4, CSPG5, CTLA4, CRF-1, Cripto, CXCR4, CXCR5, DJ-1, DLL4, DR4, DR5, ED-B, EFNA2, EGFR, EGFRvIII, ETBR, ENPP3, EPCAM, EphA2, EphA4, EPOR, ERBB2, ERBB3, ERBB4, FAPα, FAS, FcγRI, FCER2, FGFR1, FGFR2, FGFR3, FGFR4, FLT1, FOLH1, FOLR1, GDF2, GFR, GLP1R, glypican-3, GPNMB, GRP78, HAPLN4, HB-EGF, HGF, HLA-DRβ, HMGB1, ICAM1, ICAM5, IFNA1, IFNB, IgE, IgE-Fc, IGF1R, IL10, IL12B, IL13, IL15, IL17A, IL1A, IL1B, IL2RA, IL4, IL5, IL5RA, IL6, IL6R, IL9, IL2Rα, IL2Rβ, IL2Rγ, INSR, ITGA2, ITGA2B2, ITGB3, ITGA4, ITGB7, ITGA5, ITGAL, ITGAV, ITGB3, ITGB2, KDR, L1CAM, LAG3, LRP3, mesothelin, MAG, MMP14, MMP15, MOG, MST1R, MSTN, MUC1, MUC4, MUC16, MUC5AC, myostatin, NECTIN4, NCAN, NGF, NMDAR, NOTCH, NRG1, NRP, OX40, OX40L, P2Y6, PAR1, PDGFA, PDGFB, PDGFRA, PDGFRB, PD1, PDL1, PLP1, PSCA, PTPRZ, RET, RGMA, SLAM7, SLC44A4, TAG-72, TCR, TGFB1, TGFB2, TGFBR, TIMP2, TLR9, TNF, TNFR, TNFRSF10A, TNFRSF10B, TNFRSF12A, TNFSF13, TNFSF14, TNFSF2, TNFSF7, TREM2, TRAILR2, TRKA, TRKB, TRKC, Transferrin, VEGF, VEGFR, VLA-4, CGRP, alpha-synuclein, TDP-43, Tau, FUS, Amyloid-beta (Aβ), APP, BACE1, Presenilin, LINGO-1, Nogo, Troy, polyQ, an androgen receptor, huntingtin, ataxin 1, ataxin 2, Phospho-Tau, Phospho-alpha-synuclein, and the like, but the protein is not limited to these proteins.

Examples of the glycan present in the brain comprise Lewis-x, Lewis-y, CD15, and the like, but the glycan is not limited to these glycans.

Examples of the lipid present in the brain comprise GD1a, GD2, GD3, GM1, GM2, GM3, phosphatidylserine, and the like, but the lipid is not limited to these lipids.

The antibody or the antibody fragment thereof of the invention also comprises an antibody comprising any amino acid modified after translation. Examples of the modification after translation comprise deletion of a lysine residue at the C-terminus of an H chain (lysine clipping), conversion of a glutamine residue at the N-terminus of a polypeptide into pyroglutamine (pyroGlu), and the like [Beck et al, Analytical Chemistry, 85, 715-736 (2013)].

In the antibody or the antibody fragment thereof of the invention, an amino acid modification of the Fc region may be performed. As the amino acid modification of the Fc region, for example, an amino acid modification for stabilizing the antibody or regulating the half-life in the blood, or the like is exemplified. Specific examples of the amino acid modification of the Fc region comprise those in WO 2006/033386, WO 2006/075668, WO 2011/122011, WO 2009/125825, and the like.

The antibody or the antibody fragment thereof of the invention also comprises a fusion antibody or a fusion antibody fragment thereof modified by binding a desired molecule to the antibody or the antibody fragment thereof. A method for modifying an antibody is not particularly limited, and any method can be used as long as the method can modify a desired amino acid residue and glycan.

For example, chemical modification using a chemical reaction [Introduction to Antibody Engineering, Chijinshokan Co., Ltd. (1994), Kolb et al., Angew Chem Int Ed Engl. 40. 2004-21, 2001], modification by a genetic engineering technique in which a recombinant protein expression vector is introduced into an appropriate host cell for expression using a genetic recombination technique, and the like are exemplified.

In the invention, when the antibody or the antibody fragment thereof is modified with another molecule by chemical modification, as the modification site, a constant region of the antibody or the antibody fragment is exemplified, and in particular, a Cys residue at the C-terminus or the S—S bond site is preferred. It is also possible to introduce a residue that can be chemically modified later at an arbitrary position of the antibody or the antibody fragment in advance by a genetic engineering technique.

Further, when the antibody or the antibody fragment thereof is directly modified with another molecule by a genetic engineering technique, as the modification site, the N-terminus or the C-terminus of a light chain or a heavy chain of the antibody or the antibody fragment is exemplified.

In the invention, examples of the molecule for modifying the antibody or the antibody fragment thereof comprise a hydrophilic polymer, an amphipathic polymer, a functional molecule, and the like.

Examples of the hydrophilic polymer and the amphipathic polymer comprise a polyoxyalkylene, a molecule comprising a polyol or a polysaccharide, and the like.

Examples of the polyoxyalkylene comprise polyethylene glycol (PEG) composed of a linear or branched chain, polypropylene glycol, polypropylene ethylene glycol, and the like.

Examples of the molecule comprising a polyol or a polysaccharide comprise linear or branched polysaccharides, in which glucose is polymerized, such as amylose, dextran, pullulan, and glycogen, and the like. Further, the molecule is not limited to a homopolysaccharide, but may be a heteropolysaccharide.

The molecular weight of the molecule comprising a hydrophilic polymer or an amphipathic polymer is not particularly limited but is preferably 100 Da or more, and is preferably, for example, 100 Da to 100 kDa.

Examples of the functional molecule comprise an antigen-binding molecule, a fragment of an antigen-binding molecule, a drug, a bioactive peptide, a bioactive protein, a nucleic acid, a radiolabeling compound, a glycan, a lipid, a fluorescent compound, and the like. A molecule with bispecificity as a result of modification with a functional molecule such as an antigen-binding molecule is a bispecific antibody.

Examples of the antigen-binding molecule comprise an antibody, a receptor, a ligand, and the like.

The fragment of an antigen-binding molecule may be any as long as the fragment is a fragment of the antigen-binding molecule and has an antigen-binding activity.

Examples of the drug comprise anticancer agents such as an alkylating agent, a nitrosourea agent, an antimetabolite, an antiviral agent, an antibiotic, a plant alkaloid, a topoisomerase inhibitor, a tubulin polymerization inhibitor, a hormonal therapy agent, a hormone antagonist, an aromatase inhibitor, a P-glycoprotein inhibitor, a platinum complex derivative, an M-phase inhibitor, and a kinase inhibitor [Clinical oncology, Japanese Journal of Cancer and Chemotherapy (1996)], anti-inflammatory agents such as a steroidal agent, a nonsteroidal agent, an immunomodulatory agent, an immunosuppressive agent, and an antihistamine agent [Inflammation and anti-inflammatory therapy, Ishiyaku Publishers, Inc. (1982)], and the like.

More specific examples thereof comprise mertansine, emtansine, amifostine (Ethyol), cisplatin, dacarbazine (DTIC), dactinomycin, mechlorethamine (nitrogen mustard), streptozocin, cyclophosphamide, ifosfamide, carmustine (BCNU), lomustine (CCNU), doxorubicin (Adriamycin), epirubicin, gemcitabine (Gemzar), daunorubicin, procarbazine, mitomycin, cytarabine, etoposide, 5-fluorouracil, fluorouracil, vinblastine, vincristine, bleomycin, daunomycin, peplomycin, estramustine, paclitaxel (Taxol), docetaxel (Taxotere), Aldesleukin, asparaginase, busulfan, carboplatin, oxaliplatin, nedaplatin, cladribine, camptothecin, 10-hydroxy-7-ethyl-camptothecin (SN38), floxuridine, fludarabine, hydroxyurea, idarubicin, mesna, irinotecan (CPT-11), nogitecan, mitoxantrone, topotecan, leuprolide, megestrol, melphalan, mercaptopurine, hydroxycarbamide, plicamycin, mitotane, pegaspargase, pentostatin, pipobroman, streptozocin, tamoxifen, goserelin, leuprorelin, flutamide, teniposide, testolactone, thioguanine, thiotepa, uracil mustard, vinorelbine, chlorambucil, hydrocortisone, prednisolone, methylprednisolone, vindesine, nimustine, semustine, capecitabine, Tomudex, azacitidine, UFT, oxaloplatin, gefitinib (Iressa), imatinib (STI571), erlotinib, an FMS-like tyrosine kinase 3 (Flt3) inhibitor, a vascular endothelial growth factor receptor (VEGFR) inhibitor, a fibroblast growth factor receptor (FGFR) inhibitor, an epidermal growth factor receptor (EGFR) inhibitor such as Tarceva, radicicol, 17-allylamino-17-demethoxygeldanamycin, rapamycin, amsacrine, all-trans retinoic acid, thalidomide, lenalidomide, anastrozole, fadrozole, letrozole, exemestane, bucillamine, azathioprine, mizoribine, cyclosporine, rapamycin, hydrocortisone, bexarotene (Targretin), tamoxifen, dexamethasone, a progestin, an estrogen, anastrozole (Arimidex), Leuplin, aspirin, indomethacin, celecoxib, azathioprine, penicillamine, gold thiomalate, chlorpheniramine maleate, chlorpheniramine, clemastine, tretinoin, arsenic, bortezomib, allopurinol, calicheamicin, ibritumomab tiuxetan, targretin, ozogamine, clarithromycin, leucovorin, ketoconazole, aminoglutethimide, suramin, methotrexate, maytansinoid, and the like, and may also comprise derivatives thereof.

Examples of a method for binding the drug and the antibody or the antibody fragment thereof comprise a method for binding the drug and an amino group of the antibody through glutaraldehyde, a method for binding an amino group of the drug and a carboxyl group of the antibody through water-soluble carbodiimide, and the like in addition to the above-mentioned method.

Examples of the bioactive peptide or the bioactive protein comprise interferon (IFN)-α, IFN-β, IFN-γ, interleukin (IL)-2, IL-12, IL-15, IL-18, IL-21, IL-23, a granulocyte colony stimulating factor (G-CSF), a granulocyte/macrophage colony stimulating factor (GM-CSF), a macrophage colony stimulating factor (M-CSF), a cytokine or a growth factor which activates immunocompetent cells such as NK cells, macrophages, or neutrophils, proteases such as hydrase, lyase, and isomerase, enzymes such as acid sphingomyelinase and glucocerebrosidase, toxins comprising bacterial toxins and phytotoxins such as ricin, diphtheria toxin, or ONTAK, and the like, an antimicrobial peptide having a cell membrane damaging activity, a peptide having cell membrane affinity or cell membrane permeability, derivatives thereof, and the like.

The nucleic acid may be any molecule as long as it is a molecule in which a nucleotide or a molecule having a function equivalent to that of the nucleotide is polymerized, and examples thereof comprise a siRNA, a microRNA, an antisense RNA/DNA, a DNA aptamer, and the like.

The radiolabeling compound may be any as long as it is a nuclide to be used for diagnostic or therapeutic purposes, and examples thereof comprise $^3$H, $^{14}$C, $^{32}$P, $^{33}$P, $^{35}$S, $^{51}$Cr, $^{57}$CO, $^{18}$F, $^{153}$Gd, $^{159}$Gd, $^{64}$Cu, $^{68}$Ge, $^{166}$Ho, $^{115}$In, $^{113}$In, $^{112}$In, $^{111}$In, $^{131}$I, $^{125}$I, $^{123}$I, $^{121}$I, $^{140}$La, $^{177}$Lu, $^{54}$Mn, $^{99}$Mo, $^{103}$Pd, $^{142}$Pr, $^{149}$Pm, $^{186}$Re, $^{188}$Re, $^{211}$At, $^{105}$Rh, $^{97}$Ru, $^{153}$Sm, $^{47}$Sc, $^{75}$Se, $^{85}$Sr, $^{99}$Tc, $^{201}$Ti, $^{113}$Sn, $^{117}$Sn, $^{133}$Xe, $^{169}$Yb, $^{175}$Yb, $^{90}$Y, $^{65}$Zn, and the like, or compounds comprising any of the nuclides.

The radiolabeling compound can be directly bound to the antibody by a chloramine T method or the like. In addition, a substance that chelates the radiolabeling compound may be bound to the antibody. Examples of the chelating agent comprise 1,4,7,10-tetraazacyclododecane tetraacetic acid (DOTA), 1-[2-(4-aminophenyl)ethyl]-1,4,7,10-tetraazacyclododecane tetraacetic acid (PA-DOTA), 1,4,7,10-tetraazacyclotridecane tetraacetic acid (TRITA), diethylenetriaminepentaacetic acid (DTPA), and the like, and an antibody modified with the chelating agent and a modified antibody labeled with the radiolabeling compound through the chelating agent are also comprised in the antibody of the invention.

Examples of the glycan comprise a monosaccharide, a disaccharide, an oligosaccharide, and the like, and more specific examples thereof comprise fucose, mannose, glucose, allose, altose, gulose, idose, galactose, talose, ribose, arabinose, xylose, lyxose, erythose, erythrose, threose, cellobiose, maltose, isomaltose, lactose, lipoarabinomannan, Lewis X trisaccharide, sialyl-Lewis X tetrasaccharide, and the like. Further, the glycan may be a natural product comprising a glycan known as an immunoadjuvant, and examples thereof comprise β(1→3) glucan (lentinan or schizophyllan), α-galactosylceramide (KRN7000), and the like.

Examples of the lipid comprise a simple lipid (neutral lipid), which is an ester of a fatty acid and any of various types of alcohols or an analogue thereof. Examples thereof comprise a fat (for example, triacylglycerol), a wax (for example, a fatty acid ester of a higher alcohol), a sterol ester, a cholesterol ester, a fatty acid ester or the like of a vitamin, a complex lipid having a polar group such as phosphoric acid, a saccharide, sulfuric acid, or an amine in addition to a fatty acid and an alcohol, for example, a phospholipid (for example, a glycerophospholipid, a sphingophospholipid, or the like) and a glycolipid (for example, a glyceroglycolipid, a sphingoglycolipid, or the like), a derived lipid which refers to a lipid-soluble compound among compounds produced by hydrolysis of a simple lipid or a complex lipid such as a fatty acid, a higher alcohol, a lipid-soluble vitamin, a steroid, a carbohydrate, and the like.

Examples of the fluorescent compound comprise fluorescent dyes comprising fluorescein series such as fluorescein isothiocyanate (FITC), rhodamine series such as rhodamine isothiocyanate (RITC), Cy3, Cy5, eosine series, Alexa Fluor series, NBD series, and the like, a light-emitting substance such as an acridinium ester or lophine, fluorescent proteins such as green fluorescent protein (GFP), and the like.

To the antibody or the antibody fragment thereof of the invention, the hydrophilic polymer, the amphipathic polymer, or the functional molecule can be bound directly or through an appropriate linker. Examples of the linker comprise an ester, a disulfide, a hydrazone, a dipeptide, and the like.

When a fusion antibody or a fusion antibody fragment is produced by modifying the antibody or the antibody fragment thereof of the invention by a genetic engineering technique, a fusion antibody or a fusion antibody fragment can be produced by linking a cDNA encoding a protein to a cDNA encoding an antibody, thereby constructing a DNA encoding the fusion antibody or the fusion antibody fragment, inserting the DNA into an expression vector for a prokaryote or a eukaryote, introducing the expression vector into a prokaryote or a eukaryote, and expressing the fusion antibody or the fusion antibody fragment.

The composition of the invention may be any as long as the composition comprises the antibody or the antibody fragment thereof of the invention. The composition may comprise an appropriate carrier or an additive such as a stabilizing agent in addition to the antibody or the antibody fragment thereof.

Examples of the composition of the invention comprise a composition for detection or measurement comprising the antibody or the antibody fragment thereof of the invention, and the like. Examples of the composition of the invention comprise a pharmaceutical composition (therapeutic agent) comprising the antibody or the antibody fragment thereof of the invention as an active ingredient, and the like, and the composition is formulated into a desired dosage form together with a pharmacologically acceptable carrier.

In the invention, the composition for detection or measurement may be any composition as long as the composition comprises the antibody or the antibody fragment thereof of the invention and can detect or measure an antigen to which the antibody or the antibody fragment thereof of the invention specifically binds. As the antigen to which the antibody or the antibody fragment thereof of the invention specifically binds, CSPG5, or CSPG5 and an antigen present in the brain, or the like is exemplified.

The antibody or the antibody fragment thereof of the invention has a property of binding to CSPG5 in the brain and being accumulated in the brain when it is administered to an animal. Therefore, by using the composition for detection or measurement comprising the antibody or the antibody fragment thereof, the antibody can be maintained in the brain, or the antibody concentration in the brain can be improved, so that CSPG5 or CSPG5 and an antigen present in the brain can be detected or measured for a long time, and/or CSPG5 or CSPG5 and an antigen present in the brain can also be detected or measured with high sensitivity.

For example, when the composition for detection or measurement is a composition comprising a bispecific antibody which binds to CSPG5 and an antigen present in the brain, CSPG5 and the antigen present in the brain, to which the bispecific antibody binds, can be detected or measured for a long time, and/or CSPG5 and the antigen present in the brain can be detected or measured with high sensitivity.

Further, for example, when the composition for detection or measurement is a composition comprising a fusion antibody or a fusion antibody fragment thereof which is labeled with a radiolabeling compound or a fluorescent dye and which binds to CSPG5, CSPG5 can be detected or measured for a long time, and/or CSPG5 can be detected or measured with high sensitivity.

The pharmaceutical composition (therapeutic agent) comprising the antibody or the antibody fragment thereof of the invention may be a therapeutic agent for any disease as long as the antigen to which the antibody or the antibody fragment thereof of the invention specifically binds is expressed in the disease but is preferably a therapeutic agent for a brain disease.

Examples of the brain disease comprise Alzheimer's disease, a prodromal stage of Alzheimer's disease, Huntington disease, Parkinson's disease, a brain tumor, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, a cerebrovascular disorder, epilepsy, migraine, a hyperactivity disorder, Creutzfeldt-Jakob disease, corticobasal degeneration, a lysosomal storage disease, depression, dystonia, and the like.

The antibody or the antibody fragment thereof of the invention has a property of binding to CSPG5 in the brain and being accumulated in the brain when it is administered to an animal. Therefore, by using the therapeutic agent comprising the antibody or the antibody fragment thereof, the antibody or the antibody fragment thereof can be maintained in the brain for a long time, and the antibody concentration in the brain can be improved, so that a therapeutic effect on the above-mentioned diseases can be exhibited.

For example, when the therapeutic agent is a therapeutic agent comprising a fusion antibody of an anti-CSPG5 antibody of the invention, by delivering a fused molecule into the brain, a therapeutic effect of the molecule can be exhibited. Specifically, when the therapeutic agent is a therapeutic agent comprising a fusion antibody in which a drug, an enzyme, or the like is fused to an anti-CSPG5 antibody, a therapeutic effect of the drug or the enzyme can be exhibited, and when the therapeutic agent is a therapeutic agent comprising a bispecific antibody which binds to CSPG5 and an antigen present in the brain, a therapeutic effect on a brain disease associated with the antigen, which is present in the brain, and to which the bispecific antibody binds, can be exhibited.

Further, for example, when the therapeutic agent is a fusion antibody or a fusion antibody fragment which is modified with a low molecular weight drug and which binds to CSPG5, a therapeutic effect on a brain disease targeted by the low molecular weight drug can be exhibited. At that time, the therapeutic effect is preferably higher when the therapeutic agent of the invention is used as compared with a case when the low molecular weight drug is used alone.

The therapeutic agent comprising the antibody or the antibody fragment thereof of the invention may be a therapeutic agent comprising only the antibody or the antibody fragment thereof as an active ingredient, however, in general, the therapeutic agent is desirably provided as a pharmaceutical preparation produced by mixing with one or more pharmacologically acceptable carriers using an arbitrary method known in the technical field of pharmaceutics.

As the route of administration, it is preferred to use the most effective route for the treatment, and examples thereof comprise oral administration or parenteral administration such as intraoral, intra-airway, intrarectal, subcutaneous, intradermal, intramuscular, intraventricular, intrathecal, intranasal, intraperitoneal, or intravenous administration, and intravenous or intraventricular administration or the like is particularly preferably exemplified. Examples of the dosage form comprise a spray, a capsule, a tablet, a powder, a granule, a syrup, an emulsion, a suppository, an injection, an ointment, a tape, and the like.

The dose or the frequency of administration varies depending on an intended therapeutic effect, an administration method, a treatment duration, an age, a body weight, or the like, but is generally 10 µg/kg to 20 mg/kg per day for an adult.

Further, the invention also comprises a method for retaining an antibody in the brain, a method for enhancing the property of accumulating in a brain of an antibody, and a method for increasing the antibody concentration (or the antibody amount) in the brain, each using the antibody or the antibody fragment thereof of the invention.

Further, the invention also relates to a peptide which binds to CSPG5, a nucleic acid comprising a nucleotide sequence encoding the peptide, a transformant cell comprising a vector comprising the nucleic acid, a method for producing the peptide comprising culturing the transformant cell and collecting the peptide from the culture solution, a composition comprising the peptide, or a method for detecting or measuring an antigen present in the brain, a method for diagnosing or treating a brain disease, a method for enhancing the property of accumulating in a brain of a peptide, or a method for increasing the amount of the peptide in the brain, each using the peptide or the composition.

The peptide of the invention comprises a fusion peptide in which a peptide is modified.

As for the definitions of various terms related to the peptide which binds to CSPG5 and the like, the same ones as the definitions of the terms described for the antibody which binds to CSPG5 and the like described above are used unless otherwise specified.

Hereinafter, the method for producing the antibody or the antibody fragment thereof of the invention, the method for treating a disease, the method for diagnosing a disease, and the like will be specifically described.

1. Method for Producing Antibody
(1) Preparation of Antigen

CSPG5 to serve as an antigen or CSPG5-expressing cells can be obtained by introducing an expression vector comprising a cDNA encoding the full length of CSPG5 or a partial length thereof into E. coli, yeast, an insect cell, an animal cell, or the like. In addition, CSPG5 can also be obtained by purifying CSPG5 from various types of animal cell lines, animal cells, animal tissues, and the like in which CSPG5 is expressed in a large amount.

Further, the animal cell lines, the animal cells, the animal tissues, and the like can also be used as they are as an antigen. In addition, a synthetic peptide having a partial sequence of CSPG5 is prepared using a chemical synthesis method such as an Fmoc method or a tBoc method and can also be used as an antigen.

A known tag such as FLAG or His may be added to the C-terminus or the N-terminus of CSPG5 or a synthetic peptide having a partial sequence of CSPG5.

CSPG5 used in the invention can be produced using the method or the like described in Molecular Cloning, A Laboratory Manual, Second Edition, Cold Spring Harbor Laboratory Press (1989), Current Protocols In Molecular Biology, John Wiley & Sons (1987-1997) or the like, by, for example, expressing a DNA encoding CSPG5 in a host cell by the following method.

First, a recombinant vector is produced by inserting a full-length cDNA comprising a region encoding CSPG5 downstream of a promoter in an appropriate expression vector. A DNA fragment that has been prepared based on the full-length cDNA and has an appropriate length and comprises a region encoding a polypeptide may be used in place of the full-length cDNA. Subsequently, by introducing the obtained recombinant vector into a host cell suitable for the expression vector, a transformant which produces the polypeptide can be obtained.

As the expression vector, any vector can be used as long as it can replicate autonomously or can be integrated into a chromosome in a host cell to be used and comprises a suitable promoter at a position capable of transcribing a DNA encoding the polypeptide. As the host cell, any cell such as a microorganism belonging to the genus *Escherichia* such as *E. coli*, yeast, an insect cell, an animal cell, or the like, can be used as long as a target gene can be expressed.

In the case where a prokaryote such as *E. coli* is used as the host cell, the expression vector is preferably a vector that can replicate autonomously in the prokaryote and also comprises a promoter, a ribosomal binding sequence, a DNA comprising a region encoding human CSPG5, and a transcription termination sequence. In addition, although the transcription termination sequence is not essentially needed for the expression vector, the transcription termination sequence is preferably located immediately downstream of a structural gene. Further, the recombinant vector may comprise a gene that controls the promoter.

As the expression vector, it is preferred to use a plasmid in which a distance between a Shine-Dalgarno sequence (also referred to as an SD sequence) that is a ribosomal binding sequence and a start codon is adjusted to an appropriate length (for example, 6 to 18 nucleotides).

In addition, in the nucleotide sequence of the DNA encoding CSPG5, a nucleotide can be substituted so that a codon becomes optimum for expression in a host, and as a result, the production rate of target CSPG5 can be improved.

As the expression vector, any vector can be used as long as it can exhibit its function in a host cell to be used, and examples thereof comprise pBTrp2, pBTac1, pBTac2 (hereinabove manufactured by Roche Diagnostics K.K.), pKK233-2 (manufactured by Pharmacia Corporation), pSE280 (manufactured by Invitrogen, Inc.), pGEMEX-1 (manufactured by Promega Corporation), pQE-8 (manufactured by QIAGEN, Inc.), pKYP10 (JP-A-S58-110600), pKYP200 [Agricultural Biological Chemistry, 48, 669 (1984)], pLSA1 [Agric. Biol. Chem., 53, 277 (1989)], pGEL1 [Proc. Natl. Acad. Sci. USA, 82, 4306 (1985)], pBluescript II SK (−) (manufactured by Stratagene Corporation), pTrs30 [prepared from *E. coli* JM109/pTrS30 (FERM BP-5407)], pTrs32 [prepared from *E. coli* JM109/pTrS32 (FERM BP-5408)], pGHA2 [prepared from *E. coli* IGHA2 (FERM BP-400), JP-A-S60-221091], pGKA2 [prepared from *E. coli* IGKA2 (FERM BP-6798), JP-A-S60-221091], pTerm2 (U.S. Pat. Nos. 4,686,191, 4,939,094, and U.S. Pat. No. 160,735), pSupex, pUB110, pTP5, pC194, pEG400 [J. Bacteriol., 172, 2392 (1990)], pGEX (manufactured by Pharmacia Corporation), pET System (manufactured by Novagen, Inc.), pME18SFL3, and the like.

As the promoter, any promoter may be used as long as it can exhibit its function in a host cell to be used. For example, a promoter derived from *E. coli*, a phage, or the like such as a trp promoter (Ptrp), a lac promoter, a PL promoter, a PR promoter, or a T7 promoter is exemplified. Further, for example, an artificially designed and modified promoter such as a tandem promoter in which two Ptrp's are linked in series, a tac promoter, a lacT7 promoter, or a let I promoter, or the like is exemplified.

Examples of the host cell comprise *E. coli* XL1-Blue, *E. coli* XL2-Blue, *E. coli* DH1, *E. coli* MC1000, *E. coli* KY3276, *E. coli* W1485, *E. coli* JM109, *E. coli* HB 101, *E. coli* No. 49, *E. coli* W3110, *E. coli* NY49, *E. coli* DH5α, and the like.

As a method for introducing a recombinant vector into a host cell, any method can be used as long as it is a method for introducing a DNA into a host cell to be used, and for example, a method using calcium ions [Proc. Natl. Acad.

Sci. USA, 69, 2110 (1972), Gene, 17, 107 (1982), and Molecular & General Genetics, 168, 111 (1979)] is exemplified.

When an animal cell is used as a host, as the expression vector, any vector can be used as long as it can exhibit its function in the animal cell, and examples thereof comprise pcDNAI, pCDM8 (manufactured by Funakoshi Co., Ltd.), pAGE107 [JP-A-H3-22979; Cytotechnology, 3, 133 (1990)], pAS3-3 (JP-A-H2-227075), pCDM8 [Nature, 329, 840 (1987)], pcDNAI/Amp (manufactured by Invitrogen, Inc.), pcDNA3.1 (manufactured by Invitrogen, Inc.), pREP4 (manufactured by Invitrogen, Inc.), pAGE103 [J. Biochemistry, 101, 1307 (1987)], pAGE210, pME18SFL3, pKANTEX93 (WO 97/10354), N5KG1val (U.S. Pat. No. 6,001,358), INPEP4 (manufactured by Biogen-IDEC, Inc.), pCI (manufactured by Promega Corporation), a transposon vector (WO 2010/143698), and the like.

As the promoter, any promoter can be used as long as it can exhibit its function in an animal cell, and examples thereof comprise a cytomegalovirus (CMV) immediate early (IE) gene promoter, an SV40 early promoter, a retrovirus promoter, a metallothionein promoter, a heat-shock promoter, an SRα promoter, and a Moloney murine leukemia virus promoter or enhancer. In addition, a human CMV IE gene enhancer may be used together with the promoter.

Examples of the host cell comprise a human leukemia cell Namalwa cell, a monkey cell COS cell, a Chinese hamster ovary cell CHO cell [Journal of Experimental Medicine, 108, 945 (1958); Proc. Natl. Acad. Sci. USA, 60, 1275 (1968); Genetics, 55, 513 (1968); Chromosoma, 41, 129 (1973); Methods in Cell Science, 18, 115 (1996); Radiation Research, 148, 260 (1997); Proc. Natl. Acad. Sci. USA, 77, 4216 (1980); Proc. Natl. Acad. Sci. USA, 60, 1275 (1968); Cell, 6, 121 (1975); Molecular Cell Genetics, Appendix I, II (pp. 883-900)]; a dihydrofolate reductase gene (dhfr)-deficient CHO cell (CHO/DG44 cell) [Proc. Natl. Acad. Sci. USA, 77, 4216 (1980)], CHO-K1 (ATCC CCL-61), DUkXB11 (ATCC CCL-9096), Pro-5 (ATCC CCL-1781), CHO-S (Life Technologies, Cat #11619), Pro-3, a rat myeloma cell YB2/3HL.P2.G11.16Ag.20 (or also called YB2/0), a mouse myeloma cell NS0, a mouse myeloma cell 5P2/0-Ag14, a Syrian hamster cell BHK or HBT5637 (JP-A-S63-000299), and the like.

As a method for introducing an expression vector into a host cell, any method can be used as long as it is a method for introducing a DNA into an animal cell. Examples thereof comprise an electroporation method [Cytotechnology, 3, 133 (1990)], a calcium phosphate method (JP-A-H2-227075), a lipofection method [Proc. Natl. Acad. Sci. USA, 84, 7413 (1987)], and the like.

CSPG5 can be produced by culturing a transformant derived from a microorganism, an animal cell, or the like having an expression vector incorporating a DNA encoding CSPG5 obtained as described above in a culture medium so as to produce and accumulate the CSPG5 in a culture solution, and then collecting the CSPG5 from the culture solution. A method for culturing the transformant in a culture medium can be carried out according to a conventional method used for culturing a host.

In the case of being expressed in a cell derived from a eukaryote, CSPG5 to which a sugar or a glycan is added can be obtained.

When culturing a microorganism transformed with an expression vector using an inducible promoter, an inducer may be added to a culture medium as needed. For example, when a microorganism transformed with an expression vector using a lac promoter is cultured, isopropyl-β-D-thiogalactopyranoside or the like may be added to a culture medium, and when a microorganism transformed with an expression vector using a trp promoter is cultured, indoleacrylic acid or the like may be added to a culture medium.

Examples of the culture medium in which the transformant obtained using an animal cell as a host is cultured comprise RPMI 1640 medium [The Journal of the American Medical Association, 199, 519 (1967)], Eagle's MEM medium [Science, 122, 501 (1952)], Dulbecco's modified MEM medium [Virology, 8, 396 (1959)], Medium 199 [Proc. Soc. Exp. Biol. Med., 73, 1 (1950)], Iscove's modified Dulbecco's medium (IMDM), which are generally used, or a culture medium in which fetal bovine serum (FBS) or the like is added to any of these culture media, and the like. The culture is usually carried out for 1 to 7 days under the conditions of pH 6 to 8 and 30 to 40° C. in the presence of 5% $CO_2$, or the like. In addition, during the culture, an antibiotic such as kanamycin or penicillin may be added to the culture medium as needed.

As a method for expressing a gene encoding CSPG5, for example, a method such as secretory production or fusion protein expression [Molecular Cloning, A Laboratory Manual, Second Edition, Cold Spring Harbor Laboratory Press (1989)] is exemplified in addition to direct expression.

Examples of a method for producing CSPG5 comprise a method for producing CSPG5 in a host cell, a method for secreting CSPG5 out of a host cell, and a method for producing CSPG5 on an outer membrane of a host cell, and an appropriate method can be selected by changing a host cell to be used or the structure of CSPG5 to be produced.

When CSPG5 is produced in a host cell or on an outer membrane of a host cell, CSPG5 can be actively secreted out of the host cell using the method of Paulson et al. [J. Biol. Chem., 264, 17619 (1989)], the method of Lowe et al. [Proc. Natl. Acad. Sci., USA, 86, 8227 (1989), Genes Develop., 4, 1288 (1990)], or the method described in JP-A-H05-336963, WO 94/23021, or the like. In addition, the amount of production of CSPG5 can also be increased by utilizing a gene amplification system using a dihydrofolate reductase gene or the like (JP-A-H2-227075).

The obtained CSPG5 can be isolated and purified, for example, as follows. When CSPG5 is expressed in cells in a dissolved state, the cells are collected by centrifugation after completion of the culture, suspended in an aqueous buffer solution, followed by homogenization of the cells using an ultrasonic homogenizer, a French press, a Manton Gaulin homogenizer, a Dyno mill, or the like, whereby a cell-free extract solution is obtained. It is possible to obtain a purified preparation from a supernatant obtained by centrifugation of the cell-free extract solution using methods such as conventional protein isolation and purification methods, that is, a solvent extraction method, a salting-out method using ammonium sulfate or the like, a desalting method, a precipitation method using an organic solvent, anion exchange chromatography using a resin such as diethylaminoethyl (DEAE)-Sepharose or DIAION HPA-75 (manufactured by Mitsubishi Chemical Corporation), cation exchange chromatography using a resin such as S-Sepharose FF (manufactured by Pharmacia Corporation), hydrophobic chromatography using a resin such as Butyl Sepharose or Phenyl Sepharose, a gel filtration method using a molecular sieve, affinity chromatography, chromatofocusing, electrophoresis such isoelectric focusing electrophoresis, and the like alone or in combination.

When CSPG5 is expressed in cells by forming an insoluble body, the cells are collected and then homogenized in the same manner as described above, followed by centrifugation, whereby the insoluble body of the CSPG5 is collected as a precipitated fraction. The collected insoluble body of the CSPG5 is solubilized with a protein denaturing agent. The CSPG5 is returned to a normal conformation by diluting or dialyzing the solubilized solution, and thereafter, a purified preparation of a polypeptide can be obtained by the same isolation and purification methods as described above.

When CSPG5 or a derivative such as a sugar-modified body thereof is extracellularly secreted, the CSPG5 or the derivative such as a sugar-modified body thereof can be collected in a culture supernatant. The culture is subjected to a treatment using a method such as centrifugation in the same manner as described above, thereby obtaining a soluble fraction, and then, by using the same isolation and purification methods as described above, a purified preparation can be obtained from the soluble fraction.

In addition, CSPG5 used in the invention can also be produced using a chemical synthesis method such an Fmoc method or a tBoc method. Further, chemical synthesis can also be carried out using a peptide synthesizer manufactured by Advanced Chemtech, Inc., PerkinElmer, Inc., Pharmacia Corporation, Protein Technology Instrument, Inc., Synthecell-Vega Biomolecules Corporation, Perceptive, Inc., Shimadzu Corporation, or the like.

(2) Immunization of Animal and Preparation of Antibody-Producing Cells for Fusion An animal such as a mouse, a rat, a rabbit, or a hamster at 3 to 20 weeks of age is immunized with the antigen obtained in (1), and antibody-producing cells in the spleen, the lymph node, or the peripheral blood of the animal are collected. In addition, an animal such as a llama, an alpaca, or a camel can also be used as the animal to be immunized.

The immunization is carried out by subcutaneously, intravenously, or intraperitoneally administering an antigen to an animal, for example, together with an appropriate adjuvant such as a Freund's complete adjuvant, an aluminum hydroxide gel, or *Bordetella pertussis* vaccine. When the antigen is a partial peptide, a conjugate of the antigen with a carrier protein such as bovine serum albumin (BSA) or Keyhole Limpet hemocyanin (KLH) is produced and used as an immunogen.

When a mouse or a rat is immunized, the administration of the antigen is carried out 5 to 10 times every 1 to 2 weeks after the first administration. On day 3 to 7 after each administration, the blood is collected from a venous plexus of the fundus, and the antibody titer of the serum thereof is measured using an enzyme immunoassay method [Antibodies—A Laboratory Manual, Cold Spring Harbor Laboratory (1988)] or the like. An animal whose serum shows a sufficient antibody titer against the antigen used for the immunization is used as a supply source for the antibody-producing cells for fusion.

On day 3 to 7 after the final administration of the antigen, a tissue comprising the antibody-producing cells such as the spleen is extracted from the immunized animal, and the antibody-producing cells are collected. When spleen cells are used, the spleen is shredded and loosened, followed by centrifugation, and then, erythrocytes are removed, whereby the antibody-producing cells for fusion are obtained.

Other animals to be immunized can also be immunized in the same manner, and antibody-producing cells can be obtained. Appropriate conditions for the interval of immunizations and the period between the final immunization and the extraction of the tissue can be selected in accordance with an animal species to be immunized.

(3) Preparation of Myeloma Cells

As myeloma cells, an established cell line obtained from a mouse is used, and for example, an 8-azaguanine resistant mouse (BALB/c derived) myeloma cell line P3-X63Ag8-U1 (P3-U1) [Current Topics in Microbiology and Immunology, 18, 1 (1978)], P3-NS1/1-Ag41 (NS-1) [European J. Immunology, 6, 511 (1976)], SP2/0-Ag14 (SP-2) [Nature, 276, 269 (1978)], P3-X63-Ag8653 (653) [J. Immunology, 123, 1548 (1979)], P3-X63-Ag8 (X63) [Nature, 256, 495 (1975)], or the like is used.

The myeloma cells are subcultured in a normal culture medium [RPMI 1640 medium supplemented with glutamine, 2-mercaptoethanol, gentamicin, FBS, and 8-azaguanine], and then subcultured in a normal culture medium 3 to 4 days before cell fusion, and $2\times10^7$ or more cells are ensured on the day of the fusion.

(4) Cell Fusion and Preparation of Monoclonal Antibody-Producing Hybridoma

The antibody-producing cells for fusion obtained in (2) and the myeloma cells obtained in (3) are thoroughly washed with Minimum Essential Medium (MEM) or phosphate buffered saline (PBS: 1.83 g of disodium phosphate, 0.21 g of monopotassium phosphate, 7.65 g of sodium chloride, 1 L of distilled water, pH 7.2), and mixed so that the cell count becomes as follows: the antibody-producing cells for fusion:the myeloma cells=5:1 to 10:1, followed by centrifugation, and then, the supernatant is removed.

After the precipitated cell aggregate is well loosened, a mixed solution of polyethylene glycol 1000 (PEG-1000), MEM medium, and dimethylsulfoxide is added thereto while stirring at 37° C. Further, 1 to 2 mL of MEM medium is added thereto several times every 1 to 2 minutes, and then, MEM medium is added thereto so that the total amount becomes 50 mL.

After centrifugation, the supernatant is removed. The precipitated cell aggregate is gently loosened, and then, the cells are gently suspended in HAT medium [a normal culture medium supplemented with hypoxanthine, thymidine, and aminopterin]. The resulting suspension is cultured in a 5% $CO_2$ incubator at 37° C. for 7 to 14 days.

After the culture, a portion of the culture supernatant is withdrawn, and a cell aggregate that reacts with CSPG5 but does not react with an antigen other than CSPG5 is selected by a hybridoma selection method such as the below-mentioned binding assay. Subsequently, cloning is performed by a limiting dilution method, and a cell in which a high antibody titer is stably observed is selected as a monoclonal antibody-producing hybridoma.

(5) Preparation of Purified Monoclonal Antibody

The monoclonal antibody-producing hybridoma obtained in (4) is intraperitoneally injected into a mouse or a nude mouse at 8 to 10 weeks of age having been subjected to a pristane treatment [0.5 mL of 2,6,10,14-tetramethylpentadecane (pristane) is intraperitoneally administered, followed by breeding for 2 weeks]. In 10 to 21 days, the hybridoma is converted into an ascites tumor.

The ascites is collected from this mouse, followed by centrifugation to remove solids, and then, salting out is carried out with 40 to 50% ammonium sulfate. Thereafter, purification is carried out by a caprylic acid precipitation method, a DEAE-Sepharose column, a protein A column, or a gel filtration column, and then, an IgG or IgM fraction is collected, whereby a purified monoclonal antibody is prepared.

Further, after culturing the monoclonal antibody-producing hybridoma obtained in (4) in RPMI 1640 medium supplemented with 10% FBS, or the like, the supernatant is removed by centrifugation, and the residue is suspended in Hybridoma-SFM medium, and then cultured for 3 to 7 days.

The obtained cell suspension is centrifuged, and purification by a protein A column or a protein G column is carried out from the obtained supernatant, and then an IgG fraction is collected, and thus, a purified monoclonal antibody can also be obtained. Note that 5% Daigo's GF21 can also be added to the Hybridoma-SFM medium.

The determination of the subclass of the antibody is carried out by an enzyme immunoassay method using a subclass typing kit. The quantitative determination of the amount of a protein can be carried out by a Lowry method or by calculation from an absorbance at 280 nm.

(6) Selection of Antibody

The selection of an antibody is carried out by measuring the affinity of the antibody for the CSPG5-expressing cells using flow cytometry or the like as shown below. The CSPG5-expressing cells may be any cells as long as CSPG5 is expressed on the cell surface, and examples thereof comprise animal cells, an animal cell line, the CSPG5 forced expression cell line obtained in (1), and the like.

After dispensing the CSPG5-expressing cells in a plate such as a 96-well plate, a test substance such as serum, a culture supernatant of a hybridoma, or a purified antibody is dispensed therein as the first antibody and allowed to react. The cells after the reaction are thoroughly washed with PBS comprising 1 to 10% BSA (hereinafter referred to as BSA-PBS) or the like, and an anti-immunoglobulin antibody labeled with a fluorescent reagent or the like is then dispensed therein as the second antibody and allowed to react. After thoroughly washing with BSA-PBS or the like, the fluorescence amount of the labeled antibody is measured using a flow cytometer, whereby an antibody which specifically reacts with the CSPG5-expressing cells is selected.

Further, the selection of an antibody can also be carried out by measuring the affinity of a monoclonal antibody for the CSPG5-expressing cells, a CSPG5 protein, or the like using ELISA or surface plasmon resonance described below. The CSPG5 protein may be a protein composed of some domains of CSPG5 or a protein to which a tag such as GST is added.

In ELISA, after dispensing the CSPG5-expressing cells or the CSPG5 protein in a plate such as a 96-well plate, the wells are blocked with BSA-PBS, and a test substance such as serum, a culture supernatant of a hybridoma, or a purified antibody is dispensed therein as the first antibody and allowed to react. Subsequently, after thoroughly washing with PBS or the like, an anti-immunoglobulin antibody labeled with a fluorescent reagent or the like is dispensed therein as the second antibody and allowed to react.

Then, after thoroughly washing with PBS or the like, a coloring reagent is added. At the end, a coloring reaction is stopped with a reaction stopping solution, and the absorbance in each well is measured with a microplate reader, whereby an antibody which specifically reacts with the CSPG5-expressing cells or the CSPG5 protein is selected.

In the surface plasmon resonance, by using a known protocol, the affinity of an antibody which binds to CSPG5 can be measured by immobilizing the antibody on an appropriate sensor chip and using the CSPG5 protein as an analyte.

By using the affinity of the antibody obtained, an antibody having desired affinity for the CSPG5 protein can be selected. Further, the affinity of an antibody which binds to CSPG5 can also be measured by immobilizing the CSPG5 protein on a sensor chip and using the antibody as an analyte.

In addition, an antibody which binds to CSPG5 competitively with the antibody of the invention can be obtained by adding a test antibody to an assay system using flow cytometry or ELISA described above to cause a reaction. That is, by screening an antibody which inhibits binding of the antibody of the invention to CSPG5 when the test antibody is added, an antibody that competes with the antibody of the invention for binding to the amino acid sequence of CSPG5 or the conformation thereof can be obtained.

Further, an antibody which binds to an epitope comprising an epitope to which the antibody of the invention binds can be obtained by identifying the epitope for an antibody obtained by the screening method described above by a known method, producing a synthetic peptide comprising the identified epitope, a synthetic peptide which is made to mimic the conformation of the epitope, or the like, and then performing immunization therewith.

Further, an antibody which binds to the same epitope as the epitope to which the antibody of the invention binds can be obtained by identifying the epitope for an antibody obtained by the screening method described above, producing a partial synthetic peptide of the identified epitope, a synthetic peptide which is made to mimic the conformation of the epitope, or the like, and then performing immunization therewith.

(7) Acquisition of Antibody by Phage Display Method
(7-1) Method for Producing Antibody Phage Library In the invention, as an antibody phage library, an immune library, a naive library, and a synthetic library can be used. The production methods for the respective libraries will be described below.

Lymphocytes derived from an animal immunized in the same manner as described in the above (1) or a patient are collected for an immune library, and lymphocytes derived from a normal animal or a healthy human are collected for a naive library, and RNA is extracted from the lymphocytes, and cDNAs are synthesized by a reverse transcription reaction.

An antibody gene fragment amplified by PCR using each cDNA as a template is inserted into a phagemid vector, and E. coli is transformed by the phagemid vector. When the obtained transformant is infected with a helper phage, an antibody phage library of the antibody gene can be obtained.

Further, with respect to the synthetic library, CDR of a V gene in a genomic DNA or a reconstructed functional V gene is substituted with an oligonucleotide encoding a random amino acid sequence of an appropriate length, and E. coli is transformed with a phagemid vector into which the V gene has been inserted. When the obtained transformant is infected with a helper phage, an antibody phage library can be obtained.

As the cDNAs derived from lymphocytes and the antibody phage library, commercially available ones can also be used.

As the phagemid vector, pCANTAB 5E (Amersham Pharmacia Biotech, Inc.), pUC118/pUC119 vector (TaKaRa, Inc.), pBlueScript II Phagemid Vector (Agilent Technologies, Inc.), pKSTV-02 (Miyazaki et al, J. Biochem. 158(3), 205-215, 2015), and the like can be used.

As the helper phage, M13KO7 helper phage (Invitrogen, Inc.), VCSM13 Interference Resistant Helper Phage (Agilent Technologies, Inc.), R408 Interference Resistant Helper Phage (Agilent Technologies, Inc.), and the like can be used.

In the phage display, a phage vector can also be used. There are a peptide phage library in which a filamentous phage g3p is used as a displayed molecule (manufactured by New England Biolabs, Inc. or the like), a method in which g7p, g8p, or g9p is used as a displayed molecule, and the like.

Further, phage display using T7 phage can also be used. As a display system on T7 phage, there are T7 Select vector (Novagen, Inc.) and the like.

(7-2) Selection of Antibody Phage Clone

The selection of an antibody phage clone from the antibody phage library produced in (7-1) can be carried out using the ELISA method shown below.

CSPG5 is immobilized on an immuno tube, and the tube is blocked with a blocking buffer. The antibody phage library produced in (7-1) is added to each well of the tube and allowed to react. Subsequently, the wells are washed, and a fluorescently labeled anti-phage antibody is added and allowed to react. Thereafter, the wells are washed again, and a coloring solution is added. Thereafter, a coloring reaction is stopped with a reaction stopping solution, and the absorbance in each well is measured with a microplate reader. In this manner, an antibody phage clone which binds to CSPG5 is selected.

2. Production of Genetically Recombinant Antibody

As production examples of a genetically recombinant antibody, production methods for a human chimeric antibody and a humanized antibody will be described below. A genetically recombinant mouse antibody, rat antibody, rabbit antibody, hamster antibody, camel antibody, llama antibody, alpaca antibody, and human antibody, various types of chimeric antibodies, a heavy chain antibody, and the like can also be produced in the same manner.

(1) Construction of Expression Vector for Genetically Recombinant Antibody

An expression vector for a genetically recombinant antibody is an expression vector for animal cells into which DNAs encoding CH and CL of a human antibody are incorporated, and can be constructed by cloning each of the DNAs encoding CH and CL of a human antibody into an expression vector for animal cells.

As a constant region (C region) of a human antibody, CH and CL of an arbitrary human antibody can be used. For example, CH of γ1 subclass and CL of κ class of a human antibody, or the like are used. As the DNA encoding CH or CL of a human antibody, a cDNA is used, but a chromosomal DNA composed of an exon and an intron can also be used.

As the expression vector for animal cells, any vector can be used as long as it can incorporate a gene encoding a C region of a human antibody and express the gene. For example, pAGE107 [Cytotechnol., 3, 133 (1990)], pAGE103 [J. Biochem., 101, 1307 (1987)], pHSG274 [Gene, 27, 223 (1984)], pKCR [Proc. Natl. Acad. Sci. USA, 78, 1527 (1981)], pSG1bd2-4 [Cytotechnol., 4, 173 (1990)], pSE1UK1Sed1-3 [Cytotechnol., 13, 79 (1993)], or the like is used.

As the promoter and the enhancer in the expression vector for animal cells, an SV40 early promoter [J. Biochem., 101, 1307 (1987)], Moloney murine leukemia virus LTR [Biochem. Biophys. Res. Commun., 149, 960 (1987)], or an immunoglobulin H chain promoter [Cell, 41, 479 (1985)] and enhancer [Cell, 33, 717 (1983)], and the like are exemplified.

As the expression vector for a genetically recombinant antibody, an expression vector for a genetically recombinant antibody of a type (tandem-type) in which the antibody H chain and L chain are present on the same vector [J. Immunol. Methods, 167, 271 (1994)] is used from the viewpoints of ease of construction of the expression vector for a genetically recombinant antibody, ease of introduction into an animal cell, balancing of the expression levels of the antibody H chain and L chain in the animal cell, and the like, however, a type in which the antibody H chain and L chain are present on separate vectors can also be used. As the tandem-type expression vector for a genetically recombinant antibody, pKANTEX93 (WO 97/10354), pEE18 [Hybridoma, 17, 559 (1998)], or the like is used.

(2) Acquisition of cDNA Encoding Variable Region (V Region) of Antibody Derived from Animal Other Than Human and Analysis of Amino Acid Sequence Acquisition of cDNAs encoding VH and VL of a non-human antibody and an analysis of an amino acid sequence can be carried out as follows.

(2-1) When Antibody is Obtained by Hybridoma Method mRNA is extracted from hybridoma cells which produce a non-human antibody, and cDNAs are synthesized. The synthesized cDNAs are each cloned into a vector such as a phage or a plasmid, thereby producing a cDNA library.

A recombinant phage or a recombinant plasmid comprising each cDNA encoding VH or VL is isolated from the library using a DNA encoding a C region domain or a V region domain of a non-human antibody as a probe. Each entire nucleotide sequence of the target VH or VL of the non-human antibody on the recombinant phage or the recombinant plasmid is determined, and each entire amino acid sequence of VH or VL is deduced from the nucleotide sequence.

As an animal other than a human for producing hybridoma cells which produce a non-human antibody, a mouse, a rat, a hamster, a rabbit, a llama, a camel, an alpaca, or the like is used, but any animal can be used as long as it can produce hybridoma cells.

For the preparation of the total RNA from hybridoma cells, a guanidine thiocyanate-cesium trifluoroacetate method [Methods in Enzymol., 154, 3 (1987)], or a kit such as RNeasy Kit (manufactured by QIAGEN, Inc.), or the like is used.

In the preparation of mRNA from the total RNA, an oligo(dT)-immobilized cellulose column method [Molecular Cloning, A Laboratory Manual, Second Edition, Cold Spring Harbor Laboratory Press (1989)], or a kit such as Oligo-dT30<Super> mRNA Purification (registered trademark) Kit (manufactured by Takara Bio, Inc.), or the like is used. Further, mRNA can also be prepared from hybridoma cells using a kit such as Fast Track mRNA Isolation (registered trademark) Kit (manufactured by Invitrogen, Inc.), or QuickPrep mRNA Purification (registered trademark) Kit (manufactured by Pharmacia Corporation).

In the synthesis of the cDNAs and the production of the cDNA library, a known method [Molecular Cloning, A Laboratory Manual, Second Edition, Cold Spring Harbor Laboratory Press (1989), Current Protocols in Molecular Biology, Supplement 1, John Wiley & Sons (1987-1997)], or a kit such as SuperScript Plasmid System for cDNA Synthesis and Plasmid Cloning (manufactured by Invitrogen, Inc.) or ZAP-cDNA Synthesis (registered trademark) Kit (manufactured by Stratagene Corporation), or the like is used.

When the cDNA library is produced, as the vector into which a cDNA synthesized using mRNA extracted from hybridoma cells as a template is incorporated, any vector can be used as long as it is a vector capable of incorporating the cDNA. For example, ZAP ExPress [Strategies, 5, 58 (1992)], pBluescript II SK (+) [Nucleic Acids Research, 17, 9494 (1989)], λZAPII (manufactured by Stratagene Corporation), λgt 10, λgt 11 [DNA Cloning: A Practical Approach, I, 49 (1985)], Lambda BlueMid (manufactured by Clontech Laboratories, Inc.), XExCell, pT7T3-18U (manufactured by Pharmacia Corporation), pCD2 [Mol. Cell. Biol., 3, 280 (1983)], pUC18 [Gene, 33, 103 (1985)], or the like is used.

As the *E. coli* into which the cDNA library constructed by a phage or a plasmid vector is introduced, any *E. coli* can be used as long as it can introduce, express, and maintain the cDNA library. For example, XL1-Blue MRF' [Strategies, 5, 81 (1992)], C600 [Genetics, 39, 440 (1954)], Y1088, Y1090 [Science, 222, 778 (1983)], NM522 [J. Mol. Biol., 166, 1 (1983)], K802 [J. Mol. Biol., 16, 118 (1966)], JM105 [Gene, 38, 275 (1985)], or the like is used.

In the selection of the cDNA clone encoding VH or VL of a non-human antibody from the cDNA library, a colony hybridization method using an isotope- or fluorescence-labeled probe, or a plaque hybridization method [Molecular Cloning, A Laboratory Manual, Second Edition, Cold Spring Harbor Laboratory Press (1989)], or the like is used.

In addition, the cDNA encoding VH or VL can also be prepared by preparing a primer and performing a polymerase chain reaction (PCR) method [Molecular Cloning, A Laboratory Manual, Second Edition, Cold Spring Harbor Laboratory Press (1989), Current Protocols in Molecular Biology, Supplement 1, John Wiley & Sons (1987-1997)] using the cDNA synthesized from mRNA or the cDNA library as a template.

The selected cDNA is cleaved with an appropriate restriction enzyme or the like, and then cloned into a plasmid such as pBluescript SK (−) (manufactured by Stratagene Corporation), and the nucleotide sequence of the cDNA is determined by a commonly used nucleotide sequence analysis method or the like. In the nucleotide sequence analysis method, for example, after performing a reaction such as a dideoxy method [Proc. Natl. Acad. Sci. USA, 74, 5463 (1977)], an automatic nucleotide sequence analyzer such as ABI Prism 3700 (manufactured by PE Biosystems, Inc.) or an A.L.F. DNA sequencer (manufactured by Pharmacia Corporation), or the like is used.

(2-2) When Antibody is Obtained by Phage Display Method

Each entire nucleotide sequence of VH or VL is determined from the plasmid vector of the selected phage clone using a DNA encoding the vector region or the V region domain as a probe, and then, each entire amino acid sequence of VH or VL can be deduced from the nucleotide sequence.

In either the hybridoma method or the phage display method, by deducing the entire amino acid sequences of VH and VL from the determined nucleotide sequences and comparing with the entire amino acid sequences of VH and VL of a known antibody [Sequences of Proteins of Immunological Interest, US Dept. Health and Human Services (1991)], respectively, it is confirmed whether the obtained cDNAs encode the complete amino acid sequences of VH and VL of an antibody comprising a secretion signal sequence.

With respect to the complete amino acid sequences of VH and VL of the antibody comprising a secretion signal sequence, by comparison with the entire amino acid sequences of VH and VL of a known antibody [Sequences of Proteins of Immunological Interest, US Dept. Health and Human Services (1991)], the length of the secretion signal sequence and the N-terminal amino acid sequence can be deduced, and further, the subgroup to which these belong can be found.

In addition, the amino acid sequences of CDRs of VH and VL can also be found out by comparison with the amino acid sequences of VH and VL of a known antibody [Sequences of Proteins of Immunological Interest, US Dept. Health and Human Services (1991)].

Further, by using the obtained complete amino acid sequences of VH and VL, it is possible to confirm whether the complete amino acid sequences of VH and VL are new by, for example, carrying out a homology search by a BLAST method [J. Mol. Biol., 215, 403 (1990)] or the like with respect to an arbitrary database such as SWISS-PROT or PIR-Protein.

(3) Construction of Human Chimeric Antibody Expression Vector

By cloning each cDNA encoding VH or VL of a non-human antibody upstream of each gene encoding CH or CL of a human antibody in the expression vector for a genetically recombinant antibody obtained in (1), a human chimeric antibody expression vector can be constructed.

In order to ligate the cDNA encoding VH or VL of a non-human antibody at the 3' end side to CH or CL of a human antibody at the 5' end side, cDNAs of VH and VL designed so that the nucleotide sequence of a ligation region encodes an appropriate amino acid and becomes an appropriate restriction enzyme recognition sequence are produced.

The produced cDNAs of VH and VL are each cloned upstream of each gene encoding CH or CL of a human antibody in the expression vector for a genetically recombinant antibody obtained in (1) so that the cDNAs are expressed in an appropriate form, whereby a human chimeric antibody expression vector is constructed.

In addition, each cDNA encoding VH or VL of a non-human antibody is amplified by a PCR method using a synthetic DNA comprising an appropriate restriction enzyme recognition sequence at both ends, and can also be cloned into the expression vector for a genetically recombinant antibody obtained in (1).

(4) Construction of cDNA Encoding V Region of Humanized Antibody

A cDNA encoding VH or VL of a humanized antibody can be constructed as follows.

Each amino acid sequence of FR of VH or VL of a human antibody for grafting the amino acid sequence of CDR of VH or VL of a non-human antibody is selected. As the amino acid sequence of FR to be selected, any amino acid sequence can be used as long as it is derived from a human antibody.

For example, an amino acid sequence of FR of a human antibody registered in a database such as Protein Data Bank, or a common amino acid sequence in each subgroup of FR of a human antibody [Sequences of Proteins of Immunological Interest, US Dept. Health and Human Services (1991)], or the like is used. In order to suppress a decrease in the binding activity of an antibody, an amino acid sequence of FR with the highest possible homology (at least 60% or more) with the amino acid sequence of FR of VH or VL of the original antibody is selected.

Subsequently, each of the amino acid sequences of the CDRs of the original antibody is grafted into the selected amino acid sequence of FR of VH or VL of a human antibody, and each amino acid sequence of VH or VL of a humanized antibody is designed. By converting the designed amino acid sequence into a DNA sequence in consideration of the usage frequency of codons found in the nucleotide sequence of the antibody gene [Sequences of Proteins of Immunological Interest, US Dept. Health and Human Services (1991)], each DNA sequence encoding the amino acid sequence of VH or VL of a humanized antibody is designed.

Based on the designed DNA sequences, several synthetic DNAs having a length of around 100 nucleotides are synthesized, and a PCR reaction is carried out using the DNAs. In this case, in consideration of the reaction efficiency of the PCR reaction and the synthesizable length of DNA, 6 synthetic DNAs are preferably designed for each of the VH and VL.

Further, by introducing an appropriate restriction enzyme recognition sequence at the 5' or 3' end of the synthetic DNA located at both ends, a cDNA encoding VH or VL of a humanized antibody can be easily cloned into the expression vector for a genetically recombinant antibody obtained in (1).

After the PCR reaction, the amplified products are each cloned into a plasmid such as pBluescript SK (−) (manufactured by Stratagene Corporation), and the nucleotide sequences are determined in the same manner as described in (2), and a plasmid having the DNA sequence encoding the amino acid sequence of VH or VL of a desired humanized antibody is obtained.

Alternatively, the full length of VH and the full length of VL each synthesized as a single long chain DNA based on the designed DNA sequences can also be used in place of the PCR amplified products. Further, by introducing an appropriate restriction enzyme recognition sequence at both ends of the synthesized long chain DNA, the cDNA encoding VH or VL of the humanized antibody can be easily cloned into the expression vector for a genetically recombinant antibody obtained in (1).

(5) Modification of Amino Acid Sequence of V Region of Humanized Antibody

The antigen-binding activity of a humanized antibody prepared merely by grafting only the CDRs of VH and VL of a non-human antibody into FRs of VH and VL of a human antibody is decreased as compared with that of the original non-human antibody [BIO/TECHNOLOGY, 9, 266 (1991)].

In the humanized antibody, the lowered antigen-binding activity can be increased by identifying an amino acid residue directly involved in the binding to an antigen, an amino acid residue interacting with an amino acid residue of CDR, and an amino acid residue maintaining the conformation of the antibody and indirectly involved in the binding to an antigen in the amino acid sequences of FRs of VH and VL of a human antibody, and substituting such an amino acid residue with an amino acid residue of the original non-human antibody.

In order to identify such an amino acid residue of FR involved in the antigen-binding activity, the conformation of the antibody can be constructed and analyzed using X-ray crystallography [J. Mol. Biol., 112, 535 (1977)], or computer modeling [Protein Engineering, 7, 1501 (1994)], or the like. Further, a humanized antibody having a necessary antigen-binding activity can be obtained by producing several types of variants for each antibody, and repeatedly examining the correlation with the antigen-binding activity thereof through trial and error.

The amino acid residues of FRs of VH and VL of a human antibody can be modified by carrying out the PCR reaction described in (4) using a synthetic DNA for modification. With respect to the amplification product after the PCR reaction, the nucleotide sequence is determined to confirm whether the intended modification has been carried out by the method described in (2).

(6) Construction of Humanized Antibody Expression Vector

A humanized antibody expression vector can be constructed by cloning each cDNA encoding VH or VL of a constructed genetically recombinant antibody upstream of each gene encoding CH or CL of a human antibody in the expression vector for a genetically recombinant antibody obtained in (1).

For example, the cloning is carried out upstream of each gene encoding CH or CL of a human antibody in the expression vector for a genetically recombinant antibody obtained in (1) by introducing an appropriate restriction enzyme recognition sequence at the 5' or 3' end of the synthetic DNA located at both ends among the synthetic DNAs used when constructing VH or VL of any of the humanized antibodies obtained in (4) and (5) so that the cDNA is expressed in an appropriate form.

(7) Transient Expression of Genetically Recombinant Antibody

By transiently expressing genetically recombinant antibodies using any of the genetically recombinant antibody expression vectors obtained in (3) and (6), or a modified expression vector thereof, the antigen-binding activities of many types of human chimeric antibodies and humanized antibodies produced can be efficiently evaluated.

As a host cell into which the expression vector is introduced, any cell can be used as long as it is a host cell capable of expressing a genetically recombinant antibody, but for example, a COS-7 cell [American Type Culture Collection (ATCC) number: CRL1651] is used [Methods in Nucleic Acids Res., CRC Press, 283 (1991)].

In the introduction of the expression vector into a COS-7 cell, a DEAE-dextran method [Methods in Nucleic Acids Res., CRC Press (1991)], a lipofection method [Proc. Natl. Acad. Sci. USA, 84, 7413 (1987)], or the like is used.

After the introduction of the expression vector, the expression level and the antigen-binding activity of the genetically recombinant antibody in a culture supernatant are measured using an enzyme immunoassay method [Monoclonal Antibodies-Principles and practice, Third Edition, Academic Press (1996), Antibodies-A Laboratory Manual, Cold Spring Harbor Laboratory (1988), Monoclonal Antibody Experimental Manual, Kodansha scientific books (1987)], or the like.

(8) Acquisition of Transformant Stably Expressing Genetically Recombinant Antibody and Preparation of Genetically Recombinant Antibody A transformant that stably expresses a genetically recombinant antibody can be obtained by introducing any of the genetically recombinant antibody expression vectors obtained in (3) and (6) into an appropriate host cell.

In the introduction of the expression vector into a host cell, an electroporation method [JP-A-H2-257891, Cytotechnology, 3, 133 (1990)], or the like is used.

As the host cell into which the genetically recombinant antibody expression vector is introduced, any cell can be used as long as it is a host cell capable of expressing a genetically recombinant antibody. For example, CHO-K1 (ATCC CCL-61), DUKXB11 (ATCC CCL-9096), Pro-5 (ATCC CCL-1781), CHO-S (Life Technologies, Cat #11619), a rat myeloma cell YB2/3HL.P2.G11.16Ag.20 (ATCC No. CRL1662, also called YB2/0), a mouse myeloma cell NS0, a mouse myeloma cell SP2/0-Ag14 (ATCC No. CRL1581), a mouse P3X63-Ag8.653 cell (ATCC No. CRL1580), a dhfr-deficient CHO cell (CHO/DG44 cell) [Proc. Natl. Acad. Sci. USA, 77, 4216 (1980)], or the like is used.

In addition, a host cell in which the activity of a protein such as an enzyme involved in the intracellular synthesis of sugar nucleotide GDP-fucose, a protein such as an enzyme involved in glycan modification such that the 1-position of fucose is α-linked to the 6-position of N-acetylglucosamine at the reducing terminus of an N-glycoside-linked complex glycan, a protein involved in the intracellular transport of sugar nucleotide GDP-fucose to the Golgi body, or the like is decreased or lost, for example, an α1,6-fucosyltransferase gene-deficient CHO cell (WO 2005/035586 and WO 02/31140), Lec13 having acquired lectin resistance [Somatic Cell and Molecular genetics, 12, 55 (1986)], or the like can also be used.

After introduction of the expression vector, a transformant that stably expresses a genetically recombinant antibody is selected by culturing the transformant in a medium for animal cell culture comprising a drug such as G418 sulfate (hereinafter referred to as G418) (JP-A-H2-257891).

As the medium for animal cell culture, RPMI 1640 medium (manufactured by Invitrogen, Inc.), GIT medium (manufactured by Nippon Pharmaceutical Co., Ltd.), EX-CELL 301 medium (manufactured by JRH Biosciences, Inc.), IMDM medium (manufactured by Invitrogen, Inc.) or Hybridoma-SFM (manufactured by Invitrogen, Inc.), or a medium in which any of various additives such as FBS is added to any of these media, or the like is used. By culturing the obtained transformant in the medium, a genetically recombinant antibody is expressed and accumulated in the culture supernatant. The expression level and the antigen-binding activity of the genetically recombinant antibody in the culture supernatant can be measured by an ELISA method or the like. In addition, the expression level of the genetically recombinant antibody produced by the transformant can be increased using a dhfr gene amplification system (JP-A-H2-257891) or the like.

The genetically recombinant antibody is purified using a protein A column from the culture supernatant of the transformant [Monoclonal Antibodies—Principles and practice, Third edition, Academic Press (1996), Antibodies—A Laboratory Manual, Cold Spring Harbor Laboratory (1988)]. In addition, methods used for purifying a protein such as gel filtration, ion exchange chromatography, and ultrafiltration can also be combined.

The molecular weight of an H chain, an L chain, or the entire antibody molecule of a purified genetically recombinant antibody can be measured using polyacrylamide gel electrophoresis [Nature, 227, 680 (1970)], or Western blotting [Monoclonal Antibodies—Principles and Practice, Third Edition, Academic Press (1996), Antibodies—A Laboratory Manual, Cold Spring Harbor Laboratory (1988)], or the like.

(9) Method for Producing Antibody Fragment

The antibody fragment of the invention can be produced according to a known method. The antibody fragment of the invention may be produced by cleaving an antibody produced according to the method described in the above (1) to (8) using an enzyme or the like or may be produced by a genetic engineering technique after preparing a nucleotide sequence encoding a desired antibody fragment.

(10) Method for Producing Monovalent Antibody

In the invention, a monovalent antibody can be produced by the method described in WO 2014/054804, WO 2011/090754, WO 2007/048037, WO 2012/116927, or the like, or another method.

(11) Method for Producing Bispecific Antibody or Multispecific Antibody

The bispecific antibody or the multispecific antibody of the invention can be produced according to the method for producing the antibody described above. For example, the bispecific antibody or the multispecific antibody can be produced using the method described in WO 2009/131239, WO 2014/054804, WO 01/077342, US Patent Application Publication No. 2007/0071675, WO 2007/024715, Wu et al., [Nature Biotechnology, 2007, 25(11), pp. 1290-1297], Labrijn et al., [PNAS 2013, vol. 110, no. 13, pp. 5145-5150], Jong et al., [see 10.1371/j ournal.pbio.1002344 on the website: dx.doi.org], Kontermann et al., [mAbs 2012, vol. 4, issue 2, pp. 182-197], Spiess et al., [Molecular Immunology 67 (2015) 95-106], Ridgway et al., [Protein engineering, 1996 vol. 9 no. 7 pp. 617-621], WO 2009/080251, WO 2010/151792, WO 2014/033074, or the like.

For example, an expression vector for a bispecific antibody in which scFv that binds to CSPG5 is fused to the C-terminus of an IgG antibody which binds to an antigen present in the brain can be produced by the method described below, and the bispecific antibody can be produced according to the method for expressing an antibody and the method for purifying an antibody described above. In addition, a bispecific antibody in which an antibody fragment is fused to the C-terminus of an antibody can also be produced in the same manner.

The gene fragment of a CH1-Hinge-CH2-CH3-linker region is amplified by a PCR method using a synthetic gene of a heavy chain constant region of an IgG antibody which binds to an antigen present in the brain as a template. Subsequently, by using the nucleotide sequence of an antibody which binds to CSPG5 as a template, the nucleotide sequence of a scFv region in which VH and VL of the antibody are linked with an appropriate linker is prepared using a PCR method or the like. The two regions are linked by a PCR method or the like, and the obtained gene fragment is inserted into an appropriate vector such as a pCI vector.

Further, each of the gene fragments of the light chain domains (VL and CL) of an IgG antibody which binds to an antigen present in the brain and the gene fragment of VH of the antibody is amplified by a PCR method using an appropriate template and is inserted at an appropriate position of the vector.

In addition, the bispecific antibody of the invention can also be produced by binding an antigen-binding site comprising an antibody fragment to an IgG antibody by a chemical method.

3. Evaluation of Activity of Antibody or Antibody Fragment Thereof

In the invention, the activity of an antibody or an antibody fragment thereof can be evaluated as follows.

(1) Binding Activity to CSPG5

The binding activity of the antibody or the antibody fragment thereof of the invention to CSPG5 is measured using flow cytometry, ELISA, or surface plasmon resonance detection described in the above 1-(6), or the like. Further, the binding activity can also be measured using a fluorescent antibody method [Cancer Immunol. Immunother., 36, 373 (1993)].

Also when the antibody or the antibody fragment thereof of the invention is a monovalent antibody which binds to CSPG5, the binding activity of the monovalent antibody to CSPG5 can be measured in the same manner. Also when the antibody or the antibody fragment thereof of the invention is a bispecific antibody or a multispecific antibody which binds to CSPG5 and an antigen present in the brain, the binding activity of the bispecific antibody or the multispecific antibody to CSPG5 or the antigen present in the brain can be measured in the same manner.

(2) Measurement Method for the Property of Accumulating in a Brain

The property of accumulating in a brain of the antibody or the antibody fragment thereof of the invention can be measured by the method described below.

A method in which a brain tissue is collected several days after administering the antibody or the antibody fragment thereof to an animal, the brain tissue is homogenized and centrifuged, and then, the concentration of the antibody or the antibody fragment thereof in the resulting supernatant is measured, and the amount of the antibody or the antibody fragment thereof per unit brain weight is calculated, a method in which the presence of the antibody or the antibody fragment thereof is detected by a known immunological method using the collected brain tissue, or the like is exemplified. Further, a method in which the antibody or the antibody fragment thereof labeled with a pharmacologically acceptable label is administered to an animal and the presence of the antibody or the antibody fragment thereof is detected over time by an in vivo imaging system, or the like is exemplified.

As the animal used for the property of accumulating in a brain, a suitable animal according to the use of the antibody or the antibody fragment thereof of the invention can be selected.

(3) Measurement Method for Antibody-Dependent Cellular Cytotoxicity Activity (ADCC) and Complement-Dependent Cytotoxicity Activity (CDC)

The CDC or ADCC of the antibody or the antibody fragment thereof of the invention to human CSPG5-expressing cells or cells expressing CSPG5 and an antigen present in the brain can be measured by a known measurement method [Cancer Immunol. Immunother., 36, 373 (1993); Current protocols in Immunology, Chapter 7. Immunologic studies in humans, Editor, John E, Coligan et al., John Wiley & Sons, Inc., (1993)].

4. Method for Controlling Effector Activity of Antibody or Antibody Fragment

As a method for controlling the effector activity of the antibody or the antibody fragment thereof of the invention, a method for controlling the amount of α1,6-fucose (also called a core fucose) which binds to N-acetylglucosamine (GlcNAc) present at the reducing terminus of the N-linked complex glycan which binds to asparagine (Asn) at position 297 in the Fc region of the antibody or the antibody fragment thereof comprising Fc (WO 2005/035586, WO 2002/31140, WO 00/61739), a method for controlling by modifying an amino acid residue in the Fc region of the antibody or the antibody fragment thereof, and the like are known. The effector activity of the antibody or the antibody fragment thereof of the invention can be controlled using any of the methods.

The effector activity refers to an antibody-dependent activity that is caused through the Fc region of the antibody or the antibody fragment thereof, and ADCC, CDC, antibody-dependent phagocytosis (ADP) that is caused by phagocytes such as macrophages or dendritic cells, and the like are known.

As the measurement method for the effector activity, for example, the target cells, human peripheral blood mononuclear cells (PBMCs) as the effector, and a target cell-specific antibody or an antibody fragment thereof are mixed, followed by incubation for about 4 hours, and thereafter, released lactate dehydrogenase (LDH) can be measured as an index of cytotoxicity. In addition, the effector activity can also be measured by a $^{51}$Cr-release method, a flow cytometry method, or the like.

The effector activity of the antibody or the antibody fragment comprising Fc can be increased or decreased by controlling the content of the core fucose in the N-linked complex glycan of Fc of the antibody. As a method for decreasing the content of fucose which binds to the N-linked complex glycan bound to Fc of the antibody or the antibody fragment thereof, an antibody or an antibody fragment thereof to which fucose is not bound can be obtained by expressing the antibody or the antibody fragment thereof using CHO cells deficient in the α1,6-fucosyltransferase gene. The antibody or the antibody fragment thereof to which fucose is not bound has high ADCC.

On the other hand, as a method for increasing the content of fucose which binds to the N-linked complex glycan bound to Fc of the antibody or the antibody fragment thereof, an antibody or an antibody fragment thereof to which fucose is bound can be obtained by expressing the antibody or the antibody fragment thereof using a host cell into which the α1,6-fucosyltransferase gene has been introduced. The antibody or the antibody fragment thereof to which fucose is bound has lower ADCC than the antibody or the antibody fragment thereof to which fucose is not bound.

Further, by modifying an amino acid residue in the Fc region of the antibody or the antibody fragment thereof, the ADCC or CDC can be increased or decreased. For example, the CDC of the antibody or the antibody fragment thereof can be increased using the amino acid sequence of the Fc region described in US Patent Application Publication No. 2007/0148165.

Further, the ADCC or CDC can be increased or decreased by performing the amino acid modification described in U.S. Pat. Nos. 6,737,056, 7,297,775, or U.S. Pat. No. 7,317,091.

Further, the antibody or the antibody fragment thereof of the invention also comprises an antibody or an antibody fragment thereof whose half-life in the blood is controlled by controlling the reactivity with an Fc receptor, for example through the amino acid modification described in JP-A-2013-165716, JP-A-2012-021004, or the like in accordance with the amino acid modification or the glycan modification in the constant region comprised in the antibody or the antibody fragment thereof described above.

Further, by combing and using the above-mentioned methods for one antibody or an antibody fragment thereof, an antibody or an antibody fragment thereof whose effector activity or half-life in the blood is controlled can be obtained.

5. Method for Treating Disease Using Antibody or Antibody Fragment Thereof of Invention The antibody or the antibody fragment thereof of the invention can be used for treating a brain disease of an animal in which CSPG5 is expressed in the brain.

Examples of the brain disease comprise Alzheimer's disease, a prodromal stage of Alzheimer's disease, Huntington disease, Parkinson's disease, a brain tumor, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, a cerebrovascular disorder, epilepsy, migraine, a hyperactivity disorder, Creutzfeldt-Jakob disease, corticobasal degeneration, a lysosomal storage disease, depression, dystonia, and the like.

The brain disease that can be treated with the antibody or the antibody fragment thereof of the invention differs depending on the antigen to which the antibody or the antibody fragment thereof of the invention binds, the type of the molecule which modifies the antibody or the antibody fragment thereof in the fusion antibody or the fusion antibody fragment thereof of the invention, or the like.

The therapeutic agent comprising the antibody or the antibody fragment thereof of the invention may be a therapeutic agent comprising only the antibody or the antibody fragment thereof as an active ingredient, however, in general, the therapeutic agent is provided as a pharmaceutical preparation produced by mixing with one or more pharmacologically acceptable carriers using a method known in the technical field of pharmaceutics.

Examples of the route of administration comprise oral administration or parenteral administration such as intraoral, intra-airway, intrarectal, subcutaneous, intramuscular, intraventricular, intraperitoneal administration, intradermal administration, intranasal administration, intrathecal administration, or intravenous administration. Examples of the dosage form comprise a spray, a capsule, a tablet, a powder, a granule, a syrup, an emulsion, a suppository, an injection, an ointment, a tape, and the like.

Examples of a formulation suitable for oral administration comprise an emulsion, a syrup, a capsule, a tablet, a powder, a granule, and the like.

A liquid preparation such as an emulsion or a syrup is produced using water, a saccharide such as sucrose, sorbitol, or fructose, a glycol such as polyethylene glycol or propylene glycol, an oil such as sesame oil, olive oil, or soybean oil, a preservative such as a p-hydroxybenzoic acid ester, a flavor such as strawberry flavor or peppermint, or the like as an additive.

A capsule, a tablet, a powder, a granule, or the like is produced using an excipient such as lactose, glucose, sucrose, or mannitol, a disintegrating agent such as starch or sodium alginate, a lubricant such as magnesium stearate or talc, a binder such as polyvinyl alcohol, hydroxypropyl cellulose, or gelatin, a surfactant such as a fatty acid ester, a plasticizer such as glycerin, or the like as an additive.

Examples of a formulation suitable for parenteral administration comprise an injection, a suppository, a spray, and the like. An injection is produced using a carrier composed of a salt solution, a glucose solution, or a mixture of both solutions, or the like. A suppository is produced using a carrier such as cacao butter, a hydrogenated fat, or carboxylic acid.

A spray is produced using a carrier which does not stimulate the buccal or airway mucous membrane of a recipient and disperses the antibody or the antibody fragment thereof of the invention as fine particles so as to facilitate absorption thereof, or the like. As the carrier, for example, lactose, glycerin, or the like is used. In addition, the spray can also be produced as an aerosol or a dry powder. Further, a component exemplified as the additive for the formulation suitable for oral administration can also be added to the above-mentioned parenteral preparation.

6. Method for Detecting or Measuring Antigen Present in Brain or Method for Diagnosing Disease Using Antibody or Antibody Fragment Thereof of Invention By using the antibody or the antibody fragment thereof of the invention, CSPG5 or CSPG5 and an antigen present in the brain can be detected or measured. Further, by detecting or measuring CSPG5 or CSPG5 and an antigen present in the brain, a brain disease of an animal in which CSPG5 is expressed in the brain can be diagnosed.

Examples of the brain disease comprise Alzheimer's disease, a prodromal stage of Alzheimer's disease, Huntington disease, Parkinson's disease, a brain tumor, multiple sclerosis, muscular dystrophy, amyotrophic lateral sclerosis, multiple system atrophy, progressive supranuclear palsy, nigrostriatal degeneration, olivopontocerebellar atrophy, bulbospinal muscular atrophy, spinocerebellar degeneration, a cerebrovascular disorder, epilepsy, migraine, a hyperactivity disorder, Creutzfeldt-Jakob disease, corticobasal degeneration, a lysosomal storage disease, depression, dystonia, and the like, however, the brain disease that can be diagnosed with the antibody or the antibody fragment thereof of the invention differs depending on the antigen to which the antibody or the antibody fragment thereof of the invention binds, the type of the molecule which modifies the antibody or the antibody fragment thereof in the fusion antibody or the fusion antibody fragment thereof of the invention, and the like.

The brain disease of an animal in which CSPG5 is expressed in the brain can be diagnosed, for example, by detecting or measuring CSPG5 present in the brain of a patient or a diseased animal by an immunological method. Further, the brain disease can be diagnosed by detecting CSPG5 that is expressed or present in cells in the brain of a patient or a diseased animal using an immunological method such as flow cytometry.

When a monovalent antibody which binds to CSPG5 is used as the antibody or the antibody fragment thereof of the invention, CSPG5 in the brain can be measured in the same manner as described above. When a bispecific antibody or a multispecific antibody which binds to CSPG5 and an antigen present in the brain is used as the antibody or the antibody fragment thereof of the invention, CSPG5 in the brain or the antigen present in the brain can be detected or measured in the same manner as described above.

The immunological method is a method for detecting or measuring the amount of an antibody or the amount of an antigen using a labeled antigen or antibody, or the like. For example, a radioactive material labeled immune antibody method, an enzyme immunoassay method, a fluorescence immunoassay method, a luminescence immunoassay method, a Western blotting method, a physicochemical method, or the like is used.

In the radioactive material labeled immune antibody method, for example, the antibody or the antibody fragment thereof of the invention is allowed to react with an antigen or cells expressing an antigen, or the like, and then, an anti-immunoglobulin antibody or an antibody fragment thereof subjected to radiolabeling is further allowed to react therewith, followed by measurement with a scintillation counter or the like.

In the enzyme immunoassay method, for example, the antibody or the antibody fragment thereof of the invention is allowed to react with an antigen or cells expressing an antigen, or the like, and then, an anti-immunoglobulin antibody or an antibody fragment thereof subjected to labeling with an enzyme or the like is further allowed to react therewith, followed by adding a substrate and measuring the absorbance of the reaction solution with an absorptiometer. For example, a sandwich ELISA method or the like is used. As a labeling substance used in the enzyme immunoassay method, a known [Enzyme Immunoassay Method, Igaku-Shoin Ltd. (1987)] enzyme label can be used.

For example, an alkaline phosphatase label, a peroxidase label, a luciferase label, a biotin label, or the like is used. The sandwich ELISA method is a method in which after an antibody is bound to a solid phase, an antigen to be detected or measured is trapped, and then, a second antibody is allowed to react with the trapped antigen.

In the ELISA method, two types of antibodies which recognize the antigen desired to be detected or measured and which have different antigen recognition sites are prepared, and among these, a first antibody is adsorbed on a plate (for example, a 96-well plate) in advance, and subsequently, a second antibody is labeled with a fluorescent substance such as FITC, an enzyme such as peroxidase, or biotin, or the like beforehand.

With the plate on which the first antibody is adsorbed, cells or a homogenate thereof, tissues or a homogenate thereof, a cell culture supernatant, serum, pleural effusion, ascites, intraocular fluid, or the like separated from the living body is allowed to react, and thereafter the second antibody is allowed to react, followed by a detection reaction according to the labeling substance. From a calibration curve created by serially diluting the antigen at a known concentration, the antigen concentration in the test sample is calculated.

As the antibody used in the sandwich ELISA method, either a polyclonal antibody or a monoclonal antibody may be used. Further, an antibody fragment such as Fab, Fab' or $F(ab)_2$ may be used in place of the antibody. The combination of the two types of antibodies used in the sandwich ELISA method may be a combination of monoclonal antibodies or antibody fragments thereof which recognize different epitopes or may be a combination of a polyclonal antibody and a monoclonal antibody or antibody fragments thereof.

In the fluorescence immunoassay method, measurement is carried out by the method described in the documents [Monoclonal Antibodies-Principles and practice, Third edition, Academic Press (1996), Manual for monoclonal antibody experiments, Kodansha scientific books (1987)] or the like. As the labeling substance used in the fluorescence immunoassay method, a known [Fluorescent Antibody Method, Soft Science, Inc. (1983)] fluorescent label can be used. For example, FITC, RITC, or the like is used.

In the luminescence immunoassay method, measurement is carried out by the method described in the document [Bioluminescence and Chemiluminescence, Clinical Test 42, Hirokawa-Shoten Ltd. (1998)] or the like. As the labeling substance used in the luminescence immunoassay method, a known luminescent label is exemplified, and an acridinium ester, lophine, or the like is used.

In the Western blotting method, after fractionating an antigen, cells expressing an antigen, or the like by SDS (sodium dodecyl sulfate)-PAGE (polyacrylamide gel) [Antibodies—A Laboratory Manual Cold Spring Harbor Laboratory (1988)], the gel is blotted on a polyvinylidene fluoride (PVDF) membrane or a nitrocellulose membrane, an antibody or an antibody fragment thereof that recognizes the antigen is allowed to react with the membrane, and further, an anti-mouse IgG antibody or a binding fragment subjected to labeling with a fluorescent substance such as FITC, labeling with an enzyme such as peroxidase, biotin labeling or the like is allowed to react therewith, followed by visualizing the label, whereby measurement is carried out. An example is shown below.

Cells or tissues expressing a polypeptide having the amino acid sequence of CSPG5 are lysed, and 0.1 to 30 µg as a protein amount per lane is subjected to electrophoresis by the SDS-PAGE method under reducing conditions. The electrophoresed proteins are transferred to a PVDF membrane and allowed to react with BSA-PBS at room temperature for 30 minutes to perform a blocking operation.

Here, the antibody or the antibody fragment thereof of the invention is allowed to react, and the membrane is washed with PBS comprising 0.05 to 0.1% polyoxyethylene sorbitan monolaurate (Tween 20) (hereinafter referred to as Tween-PBS) and allowed to react with a goat anti-mouse IgG labeled with peroxidase at room temperature for 2 hours.

By washing with Tween-PBS and detecting a band to which the antibody or the antibody fragment thereof of the invention is bound using ECL Western Blotting Detection Reagents (manufactured by Amersham, Inc.) or the like, the polypeptide having the amino acid sequence of CSPG5 is detected.

As the antibody or the antibody fragment thereof used for detection by Western blotting, an antibody or an antibody fragment thereof capable of binding to a polypeptide which does not retain the natural conformation is used.

The physicochemical method is carried out, for example, by binding CSPG5, which is the antigen, to the antibody or the antibody fragment thereof of the invention to form an aggregate and detecting the aggregate. As another physicochemical method, a capillary tube method, a one-dimensional immunodiffusion method, an immunoturbidimetric method, a latex immunoturbidimetric method [Outline of Clinical Examination Method, KANEHARA & Co., LTD. (1998)], or the like can also be used.

In the latex immunoturbidimetric method, when a carrier such as a polystyrene latex having a particle size of about 0.1 to 1 µm sensitized with an antibody or an antigen is used to cause the antigen-antibody reaction with a corresponding antigen or antibody, the scattered light is increased in a reaction solution, and the transmitted light is decreased. The antigen concentration or the like in a test sample is measured by detecting this change as an absorbance or an integrating sphere turbidity.

For the detection or measurement of cells expressing CSPG5, a known immunological detection method can be used, but particularly, an immunoprecipitation method, an immunocytochemical staining method, an immunohistochemical staining method, a fluorescent antibody staining method, or the like is preferably used.

In the immunoprecipitation method, after allowing cells or the like expressing CSPG5 to react with the antibody or the antibody fragment thereof of the invention, a carrier having a specific binding ability to an immunoglobulin such as Protein G-Sepharose is added thereto to precipitate an antigen-antibody complex. Alternatively, the method can also be carried out by the following method.

The antibody or the antibody fragment thereof of the invention described above is immobilized on a 96-well plate for ELISA, followed by blocking with BSA-PBS. When the antibody is, for example, in an unpurified state such as a hybridoma culture supernatant, anti-mouse immunoglobulin, anti-rat immunoglobulin, protein A, protein G, or the like is immobilized on a 96-well plate for ELISA in advance, followed by blocking with BSA-PBS, and thereafter, the hybridoma culture supernatant is dispensed and bound thereto.

Subsequently, BSA-PBS is discarded, and the plate is thoroughly washed with PBS, and then, a lysate solution of cells or tissues expressing human CSPG5 is allowed to react therewith. From the plate after being thoroughly washed, an immunoprecipitate is extracted with a sample buffer for SDS-PAGE, and then detected by the above-mentioned Western blotting.

The immunocytostaining method or the immunohistochemical staining method is a method in which cells or tissues expressing an antigen, or the like are treated with a surfactant or methanol, or the like for enhancing the permeability of the antibody in some cases, and then are allowed to react with the antibody of the invention, and further allowed to react with an anti-immunoglobulin antibody or a binding fragment thereof fluorescently labeled with FITC or the like, labeled with an enzyme such as peroxidase, or labeled with biotin, or the like, and thereafter the label is visualized, and then observed with a microscope.

In addition, detection can be carried out by a fluorescent antibody staining method in which a fluorescently labeled antibody is allowed to react with a cell and analyzed with a flow cytometer [Monoclonal Antibodies—Principles and Practice, Third edition, Academic Press (1996), Monoclonal Antibody Experimental Manual, Kodansha scientific books (1987)]. In particular, the antibody or the antibody fragment thereof of the invention enables detection of a cell which expresses the detection target while retaining the natural conformation by a fluorescent antibody staining method.

In addition, when the FMAT 8100 HTS system (manufactured by Applied Biosystems, Inc.) or the like is used in the fluorescent antibody staining method, the amount of an antigen or the amount of an antibody can be measured without separating the formed antibody-antigen complex from a free antibody or antigen that is not involved in the formation of the antibody-antigen complex.

Hereinafter, the invention will be more specifically described by way of Examples, however, the invention is not limited to the following Examples.

EXAMPLES

[Example 1] Acquisition of Anti-CSPG5 Antibody (1) Acquisition of Antibody Using Human Antibody Phage Libraries A VH gene fragment and a VL gene fragment were amplified from human PBMC-derived cDNAs by PCR. Each of the VH gene fragment and the VL gene fragment was inserted into a phagemid vector pCANTAB 5E (manufactured by Amersham Pharmacia Biotech, Inc.), and plasmids were obtained by transforming *E. coli* TG1 (manufactured by Lucigen Corporation). The obtained plasmids were infected with M13K07 Helper Phage (manufactured by Invitrogen, Inc.), whereby human antibody M13 phage libraries of the VH gene and the VL gene were obtained.

In addition, a synthetic human antibody M13 phage library in which random mutations were introduced into CDR3 was produced in the same manner.

By using the human antibody M13 phage libraries, anti-CSPG5 monoclonal antibodies were obtained using the phage display method described below. Human CSPG5-FLAG_Fc or mouse CSPG5-FLAG_Fc of Example 4 described below was immobilized on a MAXISORP STARTUBE (manufactured by NUNC, Inc.), followed by blocking using SuperBlock Blocking Buffer (manufactured by Thermo Fisher Scientific, Inc.).

The human antibody M13 phage library was allowed to react with the tube at room temperature for 1 hour, and washing was carried out with PBS or PBS comprising 0.1% Tween 20 (hereinafter referred to as PBS-T), and thereafter, the phage was eluted with a 0.1 mol/L glycine-hydrochloride buffer solution (Gly-HCl) (pH 2.2). The eluate was neutralized by adding a trishydroxymethylaminomethane hydrochloride buffer solution (Tris-HCl) (pH 8.5) thereto. TG1 competent cells were infected with the eluted phage, and the phage was amplified. Thereafter, the phage was allowed to react with human CSPG5-FLAG_Fc or mouse CSPG5-FLAG_Fc immobilized on the MAXISORP STARTUBE again, followed by washing and elution.

This procedure was repeated to concentrate phages displaying scFv which specifically binds to human CSPG5-FLAG_Fc and mouse CSPG5-FLAG_Fc. The concentrated phages were monocloned, and clones having affinity for human CSPG5-FLAG_Fc and mouse CSPG5-FLAG_Fc were selected by ELISA.

In the ELISA, human CSPG5-FLAG_Fc and mouse CSPG5-FLAG_Fc were immobilized on MAXISORP (manufactured by NUNC, Inc.), followed by blocking using SuperBlock Blocking Buffer (manufactured by Thermo Fisher Scientific, Inc.). As a negative control, a plate on which Fc was immobilized was also prepared.

To each well, each phage clone was added and allowed to react at room temperature for 30 minutes, and thereafter, each well was washed with PBS-T. Subsequently, a solution obtained by diluting an anti-M13 antibody (manufactured by GE Healthcare, Inc.) labeled with horseradish peroxidase with PBS-T comprising 10% Block Ace (manufactured by Dainippon Pharmaceutical Co., Ltd.) was added to each well and incubated at room temperature for 30 minutes. After the microplate was washed 3 times with PBS-T, a 3,3',5,5'-tetramethylbenzidine (TMB) chromogenic substrate solution (manufactured by DAKO, Inc.) was added thereto, followed by incubation at room temperature. The coloring reaction was stopped by adding a 0.5 mol/L sulfuric acid to each well, and an absorbance at a wavelength of 450 nm (reference wavelength: 570 nm) was measured using a microplate reader.

A sequence analysis was carried out for clones bound to human CSPG5-FLAG_Fc and mouse CSPG5-FLAG_Fc, and the following 15 types of clones were obtained as the anti-CSPG5 antibody phagemid vectors: pCANTAB_CSPG5115, pCANTAB_CSPG5120, pCANTAB_CSPG5168, pCANTAB_CSPG5201, pCANTAB_CSPG5202, pCANTAB_CSPG5205, pCANTAB_CSPG5206, pCANTAB_CSPG5207, pCANTAB_CSPG5208, pCANTAB_CSPG5214, pCANTAB_CSPG5219, pCANTAB_CSPG5222, pCANTAB_CSPG5227, pCANTAB_CSPG5230, and pCANTAB_CSPG5234.

The nucleotide sequences encoding VH and VL of various types of anti-CSPG5 antibodies, and the amino acid sequences deduced from the nucleotide sequences are shown in Table 1.

|  | Clone Name | | | | | | | |
| --- | --- | --- | --- | --- | --- | --- | --- | --- |
|  | CSPG 5115 | CSPG 5120 | CSPG 5168 | CSPG 5201 | CSPG 5202 | CSPG 5205 | CSPG 5206 | CSPG 5207 |
| Nucleotide sequence encoding VH (excluding signal sequence) | SEQ ID NO: 1 | SEQ ID NO: 11 | SEQ ID NO: 21 | SEQ ID NO: 31 | SEQ ID NO: 41 | SEQ ID NO: 51 | SEQ ID NO: 61 | SEQ ID NO: 71 |
| Amino acid sequence of VH (excluding signal sequence) | SEQ ID NO: 2 | SEQ ID NO: 12 | SEQ ID NO: 22 | SEQ ID NO: 32 | SEQ ID NO: 42 | SEQ ID NO: 52 | SEQ ID NO: 62 | SEQ ID NO: 72 |

-continued

| | | | | | | | | |
|---|---|---|---|---|---|---|---|---|
| Amino acid sequence of HCDR1 | SEQ ID NO: 3 | SEQ ID NO: 13 | SEQ ID NO: 23 | SEQ ID NO: 33 | SEQ ID NO: 43 | SEQ ID NO: 53 | SEQ ID NO: 63 | SEQ ID NO: 73 |
| Amino acid sequence of HCDR2 | SEQ ID NO: 4 | SEQ ID NO: 14 | SEQ ID NO: 24 | SEQ ID NO: 34 | SEQ ID NO: 44 | SEQ ID NO: 54 | SEQ ID NO: 64 | SEQ ID NO: 74 |
| Amino acid sequence of HCDR3 | SEQ ID NO: 5 | SEQ ID NO: 15 | SEQ ID NO: 25 | SEQ ID NO: 35 | SEQ ID NO: 45 | SEQ ID NO: 55 | SEQ ID NO: 65 | SEQ ID NO: 75 |
| Nucleotide sequence encoding VL (excluding signal sequence) | SEQ ID NO: 6 | SEQ ID NO: 16 | SEQ ID NO: 26 | SEQ ID NO: 36 | SEQ ID NO: 46 | SEQ ID NO: 56 | SEQ ID NO: 66 | SEQ ID NO: 76 |
| Amino acid sequence of VL (excluding signal sequence) | SEQ ID NO: 7 | SEQ ID NO: 17 | SEQ ID NO: 27 | SEQ ID NO: 37 | SEQ ID NO: 47 | SEQ ID NO: 57 | SEQ ID NO: 67 | SEQ ID NO: 77 |
| Amino acid sequence of LCDR1 | SEQ ID NO: 8 | SEQ ID NO: 18 | SEQ ID NO: 28 | SEQ ID NO: 38 | SEQ ID NO: 48 | SEQ ID NO: 58 | SEQ ID NO: 68 | SEQ ID NO: 78 |
| Amino acid sequence of LCDR2 | SEQ ID NO: 9 | SEQ ID NO: 19 | SEQ ID NO: 29 | SEQ ID NO: 39 | SEQ ID NO: 49 | SEQ ID NO: 59 | SEQ ID NO: 69 | SEQ ID NO: 79 |
| Amino acid sequence of LCDR3 | SEQ ID NO: 10 | SEQ ID NO: 20 | SEQ ID NO: 30 | SEQ ID NO: 40 | SEQ ID NO: 50 | SEQ ID NO: 60 | SEQ ID NO: 70 | SEQ ID NO: 80 |

| | Clone Name | | | | | | |
|---|---|---|---|---|---|---|---|
| Clone Name | CSPG 5208 | CSPG 5214 | CSPG 5219 | CSPG 5222 | CSPG 5227 | CSPG 5230 | CSPG 5234 |
| Nucleotide sequence encoding VH (excluding signal sequence) | SEQ ID NO: 81 | SEQ ID NO: 91 | SEQ ID NO: 101 | SEQ ID NO: 111 | SEQ ID NO: 121 | SEQ ID NO: 131 | SEQ ID NO: 141 |
| Amino acid sequence of VH (excluding signal sequence) | SEQ ID NO: 82 | SEQ ID NO: 92 | SEQ ID NO: 102 | SEQ ID NO: 112 | SEQ ID NO: 122 | SEQ ID NO: 132 | SEQ ID NO: 142 |
| Amino acid sequence of HCDR1 | SEQ ID NO: 83 | SEQ ID NO: 93 | SEQ ID NO: 103 | SEQ ID NO: 113 | SEQ ID NO: 123 | SEQ ID NO: 133 | SEQ ID NO: 143 |
| Amino acid sequence of HCDR2 | SEQ ID NO: 84 | SEQ ID NO: 94 | SEQ ID NO: 104 | SEQ ID NO: 114 | SEQ ID NO: 124 | SEQ ID NO: 134 | SEQ ID NO: 144 |
| Amino acid sequence of HCDR3 | SEQ ID NO: 85 | SEQ ID NO: 95 | SEQ ID NO: 105 | SEQ ID NO: 115 | SEQ ID NO: 125 | SEQ ID NO: 135 | SEQ ID NO: 145 |
| Nucleotide sequence encoding VL (excluding signal sequence) | SEQ ID NO: 86 | SEQ ID NO: 96 | SEQ ID NO: 106 | SEQ ID NO: 116 | SEQ ID NO: 126 | SEQ ID NO: 136 | SEQ ID NO: 146 |
| Amino acid sequence of VL (excluding signal sequence) | SEQ ID NO: 87 | SEQ ID NO: 97 | SEQ ID NO: 107 | SEQ ID NO: 117 | SEQ ID NO: 127 | SEQ ID NO: 137 | SEQ ID NO: 147 |
| Amino acid sequence of LCDR1 | SEQ ID NO: 88 | SEQ ID NO: 98 | SEQ ID NO: 108 | SEQ ID NO: 118 | SEQ ID NO: 128 | SEQ ID NO: 138 | SEQ ID NO: 148 |
| Amino acid sequence of LCDR2 | SEQ ID NO: 89 | SEQ ID NO: 99 | SEQ ID NO: 109 | SEQ ID NO: 119 | SEQ ID NO: 129 | SEQ ID NO: 139 | SEQ ID NO: 149 |
| Amino acid sequence of LCDR3 | SEQ ID NO: 90 | SEQ ID NO: 100 | SEQ ID NO: 110 | SEQ ID NO: 120 | SEQ ID NO: 130 | SEQ ID NO: 140 | SEQ ID NO: 150 |

[Example 2] Production of Antibody (1) Construction of CSPG5 scFv-hG4PE(R409K) Expression Vector An expression vector was constructed for producing a scFv-Fc antibody in which each anti-CSPG5 scFv antibody was bound to the Fc region of a human IgG4 antibody comprising amino acid residue substitutions of S228P, L235E, and R409K according to the EU numbering (hereinafter sometimes abbreviated as "IgG4 variant").

The gene fragment of the scFv region was amplified by PCR using the phagemid vector pCANTAB_CSPG5115 as a template. The gene fragment of the Hinge-CH2-CH3 region was amplified by PCR using a synthetic gene of the heavy chain constant region as a template. The obtained gene fragments were inserted into a pCI vector (manufactured by Promega, Inc.), whereby a pCI_CSPG5115 scFv-hG4PE(R409K) vector was produced.

Antibody expression vectors in which the gene fragment of the scFv region of each of the various types of anti-CSPG5 antibodies shown in Table 1 was introduced were produced in the same manner and named pCI_CSPG5120 scFv-hG4PE(R409K) vector, pCI_CSPG5168 scFv-hG4PE(R409K) vector, pCI_CSPG5201 scFv-hG4PE(R409K) vector, pCI_CSPG5202 scFv-hG4PE(R409K) vector, pCI_CSPG5205 scFv-hG4PE(R409K) vector, pCI_CSPG5206 scFv-hG4PE(R409K) vector, pCI_CSPG5207 scFv-hG4PE(R409K) vector, pCI C SPG5208 scFv-hG4PE(R409K) vector, pCI_CSPG5214 scFv-hG4PE(R409K) vector, pCI C SPG5219 scFv-hG4PE(R409K) vector, pCI_CSPG5222 scFv-hG4PE(R409K) vector, pCI_CSPG5227 scFv-hG4PE(R409K) vector, pCI_CSPG5230 scFv-hG4PE(R409K) vector, and pCI_CSPG5234 scFv-hG4PE(R409K) vector, respectively.

(2) Construction of pCI_CSPG5202-hKG4PE(R409K) Vector and pCI_AVM-hLG4PE(R409K)-CSPG5202scFv Vector An expression vector was constructed for producing an anti-CSPG5202-IgG4 antibody in which the antibody variable regions of an anti-CSPG5202 scFv antibody were bound to CL and CH of the human IgG4 variant, respectively, and an anti-AVM-IgG4-CSPG5 dscFv antibody in which two anti-CSPG5202 scFv antibodies were bound to the C-terminal side of an anti-AVM-IgG4 antibody. The gene fragments of VL and VH were amplified by PCR using the phagemid vector pCANTAB_CSPG5202 as a template. The gene fragments of CL and CH were amplified by PCR using a synthetic gene as a template. The obtained gene fragments were inserted into a pCI vector (manufactured by Promega, Inc.), whereby a pCI_CSPG5202-hKG4PE(R409K) vector was produced.

The gene fragments of VL and VH were amplified by PCR using a variable region of an anti-AVM antibody as a template, the gene fragment of the scFV region of CSPG5202 was amplified by PCR using the phagemid vector pCANTAB_CSPG5202 as a template, and the gene fragments of CL and the CH1-Hinge-CH2-CH3-linker region were amplified by PCR using a synthetic gene as a template.

The obtained gene fragments were inserted into a pCI vector (manufactured by Promega, Inc.), whereby a pCI_AVM-hLG4PE(R409K)-CSPG5202scFv vector was produced. The names of the antibody expression vectors, the nucleotide sequences encoding the light chain or the heavy chain, and the amino acid sequences deduced from the nucleotide sequences are shown in Table 2.

TABLE 2

| Name of antibody expression vector | pCI_CSPG5202-hKG4PE(R409K) | pCI_AVM-hLG4PE(R409K)-CSPG5202scFv |
|---|---|---|
| Nucleotide sequence encoding light chain (excluding signal sequence) | SEQ ID NO: 151 | SEQ ID NO: 155 |
| Amino acid sequence of light chain (excluding signal sequence) | SEQ ID NO: 152 | SEQ ID NO: 156 |
| Nucleotide sequence encoding heavy chain (excluding signal sequence) | SEQ ID NO: 153 | SEQ ID NO: 157 |

TABLE 2-continued

| Name of antibody expression vector | pCI_CSPG5202-hKG4PE(R409K) | pCI_AVM-hLG4PE(R409K)-CSPG5202scFv |
|---|---|---|
| Amino acid sequence of heavy chain (excluding signal sequence) | SEQ ID NO: 154 | SEQ ID NO: 158 |

(3) Construction of Anti-Avermectin Antibody Expression Vector and pCI_AVM-hLG4PE(R409K)_AVMscFv5 Vector As a negative control antibody, a chimeric anti-Avermectin (AVM) antibody was produced. An SD rat was immunized with AVM, and an anti-AVM antibody-producing hybridoma was established by a conventional method. The gene fragments of the VL and VH regions were amplified by PCR using a variable region derived from the hybridoma as a template. A synthesized nucleotide sequence encoding the lambda chain constant region of human IgG and the amplified variable region were inserted into an N5KG4PE vector (described in WO 2002/088186), whereby an expression vector N5LG4PE_AVM was produced.

The gene fragments of CL and the CH1-Hinge-CH2-CH3-linker region were amplified by PCR using a synthetic gene as a template. Further, the gene fragments of the VH region and the VL region of AVM were amplified by PCR using N5LG4PE_AVM as a template. The obtained gene fragments were inserted into a pCI vector (manufactured by Promega, Inc.), whereby a pCI_AVM-hLG4PE(R409K)-AVMscFv5 vector was produced.

(4) Preparation of Antibody

The antibody expression plasmid vector was introduced into Expi293F cells (manufactured by Thermo Fisher Scientific, Inc.) using Expi293 (trademark) Expression System (manufactured by Thermo Fisher Scientific, Inc.), and the cells were cultured to express the antibody in a transient expression system. The culture supernatant was collected 3 to 4 days after the introduction of the vector and filtered through a membrane filter having a pore size of 0.22 μm (manufactured by Merck Millipore Corporation). The antibody protein in this culture supernatant was subjected to affinity purification using a Protein A resin (Mab Select SuRe, manufactured by GE Healthcare Biosciences, Inc.). As the washing solution, a phosphate buffer solution was used. The protein adsorbed on the Protein A was eluted with a 20 mmol/L sodium citrate and 50 mmol/L NaCl buffer solution (pH 3.4) and collected in a tube comprising 1 mol/L Tris-HCl (pH 8.0). Subsequently, the solvent in the eluate was replaced with PBS by ultrafiltration using Amicon Ultra (manufactured by Merck Millipore Corporation) and a NAP column (manufactured by GE Healthcare Biosciences, Inc.). The obtained solution was sterilized by filtration through a membrane filter having a pore size of 0.22 μm (manufactured by Merck Millipore Corporation). An absorbance at 280 nm of the antibody solution was measured, and the concentration of the purified antibody was calculated.

Anti-CSPG5 scFv-Fc antibodies obtained by expressing the vectors produced in Example 2(1) were named CSPG5115 scFv-hG4PE(R409K), CSPG5120 scFv-hG4PE(R409K), CSPG5168 scFv-hG4PE(R409K), CSPG5201 scFv-hG4PE(R409K), CSPG5202 scFv-hG4PE(R409K), CSPG5205 scFv-hG4PE(R409K), CSPG5206 scFv-hG4PE(R409K), CSPG5207 scFv-hG4PE(R409K), CSPG5208 scFv-hG4PE(R409K), CSPG5214 scFv-hG4PE(R409K), CSPG5219 scFv-hG4PE(R409K), CSPG5222 scFv-hG4PE(R409K), CSPG5227 scFv-hG4PE(R409K), CSPG5230 scFv-hG4PE(R409K), and CSPG5234 scFv-hG4PE(R409K), respectively.

An anti-CSPG5-IgG4 antibody obtained by expressing the pCI_CSPG5202-hKG4PE(R409K) vector produced in Example 2(2) was named CSPG5202 IgG4PE(R409K), and an anti-AVM-IgG4-CSPG5 dscFv bispecific antibody obtained by expressing the pCI_AVM-hLG4PE(R409K)-CSPG5202scFv vector produced in Example 2(2) was named AVM IgG4PE(R409K) CSPG5202 dscFv. Further, an anti-AVM-IgG4 antibody obtained by expressing the N5LG4PE_AVM produced in Example 2(3) and an anti-AVM-IgG4 AVM dscFv bispecific antibody obtained by expressing the pCI_AVM-hLG4PE(R409K)_AVMscFv5 vector produced in Example 2(3) were named anti-AVM antibody and AVM IgG4PE(R409K)_AVM dscFv5, respectively.

[Example 3] Analysis of Reactivity with CSPG5-Expressing Cells

The nucleotide sequence encoding human CSPG5 is represented by SEQ ID NO: 159, an amino acid sequence deduced from the nucleotide sequence is represented by SEQ ID NO: 160, the nucleotide sequence encoding mouse CSPG5 is represented by SEQ ID NO: 161, an amino acid sequence deduced from the nucleotide sequence is represented by SEQ ID NO: 162, the nucleotide sequence encoding monkey CSPG5 is represented by SEQ ID NO: 163, and an amino acid sequence deduced from the nucleotide sequence is represented by SEQ ID NO: 164.

The full-length gene sequences of human CSPG5, mouse CSPG5, and monkey CSPG5 were synthesized, and the gene sequences were each inserted into the BamHI-NotI site of a pEF6/V5-His (manufactured by Thermo Fisher Scientific, Inc.) vector, whereby the following plasmid vectors for membrane expression of the respective types of CSPG5: pEF6_human CSPG5, pEF6_mouse CSPG5, and pEF6_monkey CSPG5 were produced.

The respective types of membrane CSPG5 antigen expression vectors were each introduced into Expi293F cells using FreeStyle (trademark) 293 Expression System (manufactured by Thermo Fisher Scientific, Inc.), and the cells were cultured to express the membrane antigens in a transient expression system. By using the cells, the reactivity of the antibodies produced in Example 2 with the CSPG5-expressing cells was analyzed by a fluorescence activated cell sorting (FACS) method according to the following procedure.

Expi293F cells, human CSPG5/Expi293F cells, mouse CSPG5/Expi293F cells, and monkey CSPG5/Expi293F cells were separately suspended in Staining Buffer (SB) of PBS comprising 0.1% $NaN_3$ and 1% FBS and dispensed in a round-bottom 96-well plate (manufactured by Becton, Dickinson and Company). After centrifugation (2000 rpm, 4° C., 2 minutes), the supernatant was removed, and to the resulting pellet, 10 μg/mL of each antibody obtained in Example 2 was added to suspend the pellet, and the resulting suspension was left to stand for 30 minutes at ice temperature. After further centrifugation (2000 rpm, 4° C., 2 minutes), the supernatant was removed, and the resulting pellet was washed with SB, and thereafter, 1 μg/mL of an RPE fluorescently labeled goat anti-human antibody (manufactured by Southern Biotech, Inc.) was added thereto, and the resultant was incubated for 30 minutes at ice temperature. After washing with SB, the cells were suspended in SB, and the fluorescence intensity of each cell was measured using a flow cytometer FACS CANTO II (manufactured by Becton, Dickinson and Company). Note that as a negative control, 10 μg/mL of the anti-AVM antibody was used.

The detection results were analyzed, and a mean fluorescence intensity (MFI) was calculated using a geometric mean. Further, with respect to the MFI when the concentration of each antibody was 10 μg/mL, the ratio of the MFI (mean fluorescence intensity ratio) between the human CSPG5/Expi293F cells and the Expi293F cells (parent cell line) was calculated. Also for the monkey CSPG5/Expi293F cells and the mouse CSPG5/Expi293F cells, the mean fluorescence intensity ratio relative to the Expi293F cells (parent cell line) was calculated by the same procedure, and the results are shown in Table 3.

TABLE 3

| | Mean fluorescence intensity ratio | | |
|---|---|---|---|
| | Human CSPG5-expressing cells/parent cell line | Monkey CSPG5-expressing cells/parent cell line | Mouse CSPG5-expressing cells/parent cell line |
| Anti-AVM antibody | 0.93 | 1.00 | 0.94 |
| CSPG5115 scFv-hG4PE(R409K) | 3.24 | 3.56 | 3.44 |
| CSPG5120 scFv-hG4PE(R409K) | 18.48 | 8.01 | 20.37 |
| CSPG5168 scFv-hG4PE(R409K) | 5.46 | 3.36 | 5.81 |
| CSPG5201 scFv-hG4PE(R409K) | 2.41 | 1.73 | 2.95 |
| CSPG5202 scFv-hG4PE(R409K) | 6.16 | 3.69 | 5.39 |
| CSPG5205 scFv-hG4PE(R409K) | 28.50 | 9.58 | 30.14 |
| CSPG5206 scFv-hG4PE(R409K) | 4.31 | 3.40 | 4.50 |
| CSPG5207 scFv-hG4PE(R409K) | 4.23 | 3.87 | 4.19 |
| CSPG5208 scFv-hG4PE(R409K) | 16.85 | 6.96 | 16.55 |
| CSPG5214 scFv-hG4PE(R409K) | 2.15 | 4.03 | 2.28 |
| CSPG5219 scFv-hG4PE(R409K) | 4.75 | 5.74 | 4.87 |
| CSPG5222 scFv-hG4PE(R409K) | 2.52 | 2.82 | 2.94 |
| CSPG5227 scFv-hG4PE(R409K) | 5.29 | 4.09 | 10.01 |
| CSPG5230 scFv-hG4PE(R409K) | 3.35 | 4.45 | 3.56 |
| CSPG5234 scFv-hG4PE(R409K) | 14.10 | 10.43 | 14.32 |

As shown in Table 3, in the case of all the anti-CSPG5 antibodies, the mean fluorescence intensity ratio was increased as compared with that of the anti-AVM antibody that is the negative control, and the anti-CSPG5 antibodies showed reactivity with the human CSPG5/Expi293F cells, the mouse CSPG5/Expi293F cells, and the monkey CSPG5/Expi293F cells. Therefore, it was revealed that the anti-CSPG5 antibodies recognize and bind to all human CSPG5, mouse CSPG5, and monkey CSPG5. Further, also with respect to CSPG5202 IgG4PE(R409K), CSPG5202 scFv-hG4PE(R409K), and AVM IgG4PE(R409K) CSPG5202 dscFv, reactivity with the Expi293F cells, the human CSPG5/Expi293F cells, the monkey CSPG5/Expi293F cells, and the mouse CSPG5/Expi293F cells was analyzed by the same procedure, and as a result, the mean fluorescence intensity ratio was increased as compared with that of the anti-AVM antibody that is the negative control, and it was revealed that the antibodies react with the human CSPG5/Expi293F cells, the mouse CSPG5/Expi293F cells, and the monkey CSPG5/Expi293F cells.

[Example 4] Production of Soluble CSPG5 Antigen (1) Production of Extracellular Domain Protein of CSPG5 to Which FLAG_Fc is Bound As a soluble antigen of human CSPG5 or mouse CSPG5, an extracellular domain protein of CSPG5 to which FLAG_Fc was added at the C-terminus was produced by the method described below. A synthetic gene of the extracellular domain of human or mouse CSPG5 and a synthetic gene of FLAG_Fc were inserted into a pCI vector (manufactured by Promega, Inc.), whereby the following plasmid vectors for expressing the extracellular domains of human and mouse CSPG5 to which FLAG_Fc was added at the C-terminal side: pCI-human CSPG5-FLAG_Fc and pCI-mouse CSPG5-FLAG_Fc were produced.

The nucleotide sequence of human CSPG5-FLAG_Fc is represented by SEQ ID NO: 165, an amino acid sequence deduced from the nucleotide sequence is represented by SEQ ID NO: 166, the nucleotide sequence of mouse CSPG5-FLAG_Fc is represented by SEQ ID NO: 167, and an amino acid sequence deduced from the nucleotide sequence is represented by SEQ ID NO: 168.

The pCI-human CSPG5-FLAG_Fc and the pCI-mouse CSPG5-FLAG_Fc were separately introduced into Expi293F cells using Expi293 (trademark) Expression System (manufactured by Thermo Fisher Scientific, Inc.), and the cells were cultured to express the proteins in a transient expression system, and the proteins were purified in the same manner as in Example 2. The concentrations of the purified human and mouse CSPG5-FLAG_Fc proteins in the solutions were determined based on the absorbance at 280 nm.

(2) Production of Extracellular Domain Protein of CSPG5 to Which GST is Bound

As a soluble antigen of human CSPG5 or mouse CSPG5, an extracellular domain protein of CSPG5 to which GST was added at the C-terminus was produced by the method described below. A synthetic gene of the extracellular domain of human or mouse CSPG5 and a synthetic gene of GST were inserted into a pCI vector (manufactured by Promega, Inc.), whereby the following plasmid vectors for expressing the extracellular domains of human and mouse CSPG5 to which GST was added at the C-terminal side: pCI-human CSPG5-GST and pCI-mouse CSPG5-GST were produced.

The nucleotide sequence of human CSPG5-GST is represented by SEQ ID NO: 169, an amino acid sequence deduced from the nucleotide sequence is represented by SEQ ID NO: 170, the nucleotide sequence of mouse CSPG5-GST is represented by SEQ ID NO: 171, and an amino acid sequence deduced from the nucleotide sequence is represented by SEQ ID NO: 172.

pCI-human CSPG5-GST and pCI-mouse CSPG5-GST were separately introduced into Expi293F cells using Expi293 (trademark) Expression System (manufactured by Thermo Fisher Scientific, Inc.), and the cells were cultured to express the proteins in a transient expression system. The culture supernatant was collected 3 to 4 days after the introduction of the vector and filtered through a membrane filter having a pore size of 0.22 μm (manufactured by Merck Millipore Corporation).

The protein in this culture supernatant was subjected to affinity purification using a Glutathione Sepharose 4B (manufactured by GE Healthcare Biosciences, Inc.). As the washing solution, a phosphate buffer solution was used. The protein adsorbed on the Glutathione Sepharose 4B was eluted with 50 mmol/L Tris-HCl and 10 mmol/L reduced glutathione (pH 8.0).

Subsequently, the solvent in the solution was replaced with PBS by ultrafiltration using Amicon Ultra (manufactured by Merck Millipore Corporation) and a NAP column (manufactured by GE Healthcare Biosciences, Inc.). The obtained solution was sterilized by filtration through a membrane filter having a pore size of 0.22 μm (manufactured by Merck Millipore Corporation). The concentrations of the purified human and mouse CSPG5-GST proteins in the solutions were determined based on the absorbance at 280 nm.

[Example 5] Evaluation of Affinity for CSPG5 by Surface Plasmon Resonance Detection The affinity of the anti-CSPG5 antibodies, the CSPG5202 IgG4PE(R409K), and the AVM IgG4PE(R409K) CSPG5202 dscFv produced in Example 2 for human CSPG5 and mouse CSPG5 was measured using Biacore T-100 (GE Healthcare).

Each of the antibodies was immobilized on a CM5 sensor chip using a Human antibody Capture kit, and the binding ability was evaluated using human CSPG5-GST and mouse CSPG5-GST produced in Example 4 as analytes. The obtained sensorgram was analyzed with BIA evaluation software, and the dissociation constant ($K_D$ value) was calculated.

All the antibodies had a dissociation constant for human CSPG5 of $1\times10^{-8}$ mol/L or less, and the 16 types of antibodies except for CSPG5214 scFv-hG4PE(R409K) had a dissociation constant of $1\times10^{-9}$ mol/L or less. From these results, it was demonstrated that all the antibodies are antibodies having high affinity for human CSPG5.

In addition, all the antibodies had a dissociation constant for mouse CSPG5 of $1\times10^{-8}$ mol/L or less. From these results, it was demonstrated that all the antibodies are antibodies having high affinity not only for human CSPG5, but also for mouse CSPG5.

[Example 6] Evaluation of Migration Ability into Mouse Brain (1) Measurement of Antibody Amount Each of the antibodies was administered to a mouse through the tail vein (i.v.) at 9 mg/kg body weight, and after 3 days and 9 days, the blood was collected. On the same day as the blood collection, whole body perfusion was performed under anesthesia, and thereafter, a brain tissue was collected and the weight thereof was measured.

Further, a buffer solution was added to the collected brain tissue, and the brain tissue was homogenized, followed by centrifugation, and an antibody solution eluted in the supernatant was collected. The volume thereof was measured, and also the antibody concentration was measured using AlphaLISA (manufactured by PerkinElmer, Inc.). The antibody amount per unit brain weight was calculated. Note that the standard curve was created using the antibody attached to the kit.

The antibody concentration in the serum 3 days after administering the antibody is shown in FIG. 1(A), the antibody amount per unit brain weight in the brain tissue is shown in FIG. 1(B), the antibody concentration in the serum 9 days after administering the antibody is shown in FIG. 1(C), and the antibody amount per unit brain weight in the brain tissue is shown in FIG. 1(D).

As shown in FIGS. 1(A) and (C), there was no difference in serum concentration of the anti-CSPG5 scFv-Fc antibody 3 days and 9 days after administering the antibody as compared with that of the negative control (anti-AVM-IgG4 antibody). On the other hand, as shown in FIG. 1(B), it was demonstrated that the antibody amount in the brain of the anti-CSPG5 scFv-Fc antibody is increased by about 4 to 17 times as compared with that of the negative control. Further, as shown in FIG. 1(D), it was demonstrated that in the case of the anti-CSPG5 scFv-Fc antibody: CSPG5202 scFvhG4PE(R409K), even 9 days after administering the antibody, the antibody amount in the brain is increased by about 10 times as compared with that of the negative control.

Subsequently, a test method carried out under conditions different from those described above and the results will be shown. Each of the antibodies was administered to a mouse through the tail vein (i.v.) at 35 nmol/kg body weight, and after 7 days, the blood was collected. On the same day as the blood collection, whole body perfusion was performed under anesthesia, and thereafter, a brain tissue was collected and the weight thereof was measured. Further, a buffer solution was added to the collected brain tissue, and the brain tissue was homogenized, followed by centrifugation, and an antibody solution eluted in the supernatant was collected. The volume thereof was measured, and also the antibody concentration was measured using AlphaLISA (manufactured by PerkinElmer, Inc.), and the antibody amount per unit brain weight was calculated. The antibody concentration was expressed as a value obtained by conversion from the molar concentration using the molecular weight (150 kDa) of a monoclonal antibody. Note that the standard curve was created using each antibody.

Figure 2:
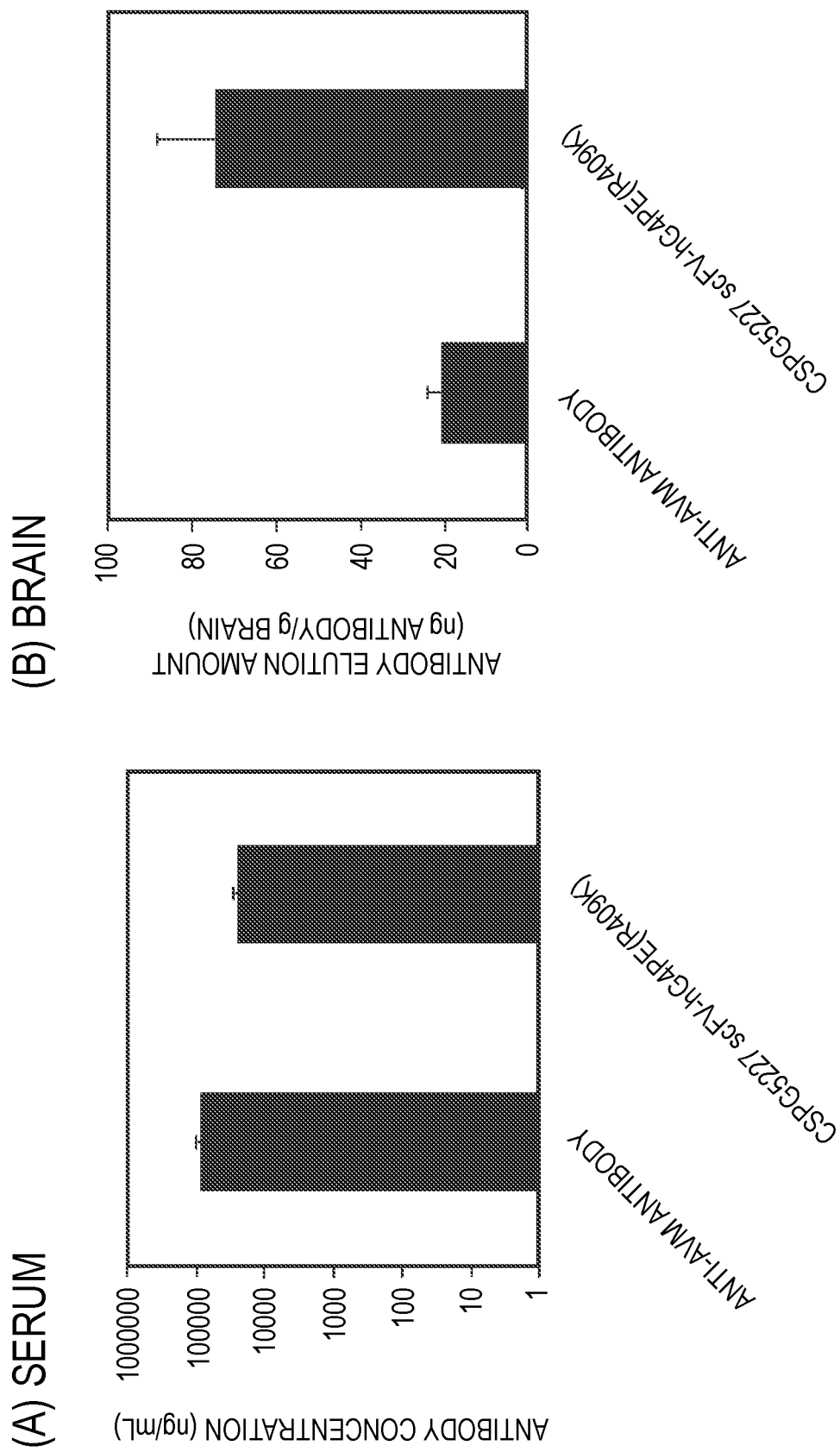
FIG. 2 shows the results of measuring the concentration of each antibody in a tissue.

The antibody concentration in the serum of the anti-CSPG5 scFv-Fc antibody: CSPG5227 scFv-hG4PE(R409K) is shown in FIG. 2(A), and the antibody amount per unit brain weight in the brain tissue thereof is shown in FIG. 2(B). It was demonstrated that the antibody amount in the brain is increased as compared with that of the negative control (anti-AVM-IgG4 antibody).

Further, the antibody concentrations in the serum of the anti-CSPG5 scFv-Fc antibody: CSPG5202 scFv-hG4PE(R409K) and the anti-CSPG5-IgG4 antibody: CSPG5202 IgG4PE(R409K) are shown in FIG. 3(A), and the antibody amounts per unit brain weight in the brain tissue thereof are shown in FIG. 3(B).

Figure 3:
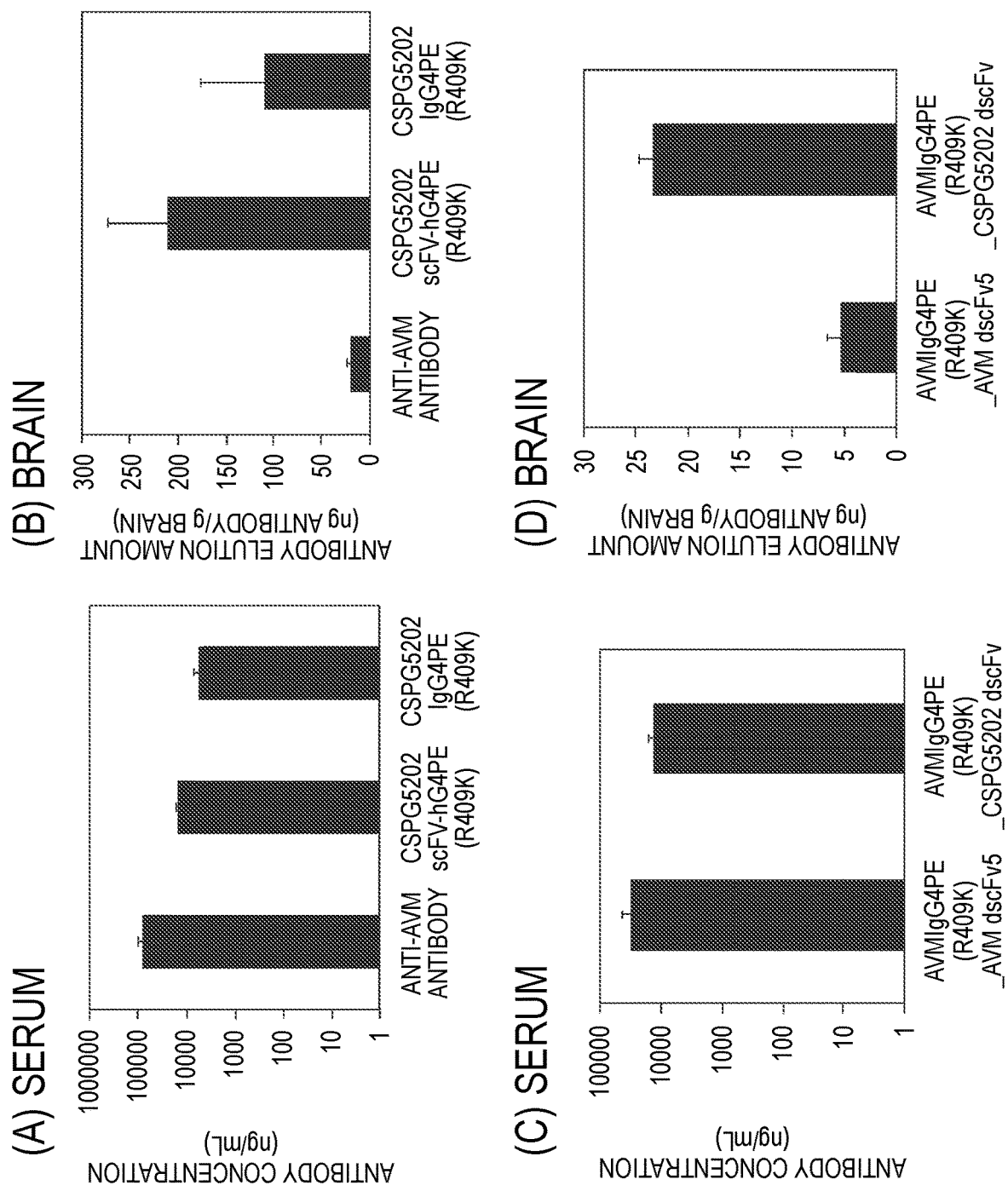
FIG. 3 shows show the results of measuring the concentration of each antibody in a tissue.

As shown in FIG. 3(B), it was demonstrated that the antibody amount in the brain is increased by about 10 times in the case of the anti-CSPG5 scFv-Fc antibody: CSPG5202 scFv-hG4PE(R409K), and increased by about 5 times in the case of the anti-CSPG5-IgG4 antibody: CSPG5202 IgG4PE(R409K) as compared with that of the negative control (anti-AVM-IgG4 antibody).

Further, the antibody concentrations in the serum of the anti-AVM-IgG4 AVM dscFv bispecific antibody: AVM IgG4PE(R409K)_AVM dscFv5 and the anti-AVM-IgG4-CSPG5 dscFv bispecific antibody: AVM IgG4PE(R409K) CSPG5202 dscFv are shown in FIG. 3(C), and the antibody amounts in the brain tissue per unit brain weight thereof are shown in FIG. 3(D).

As shown in FIG. 3(D), it was demonstrated that the antibody amount in the brain of the anti-AVM-IgG4-CSPG5 dscFv bispecific antibody: AVM IgG4PE(R409K) CSPG5202 dscFv is increased as compared with that of AVM IgG4PE(R409K)_AVM dscFv5 that is the negative control of the bispecific antibody. Accordingly, it was demonstrated that the bispecific antibody which binds to CSPG5 can increase the antibody amount in the brain as compared with the bispecific antibody which does not bind to CSPG5.

(2) Imaging Analysis

The anti-CSPG5 scFv-Fc antibodies and the negative control (anti-AVM-IgG4 antibody) were labeled using Alexa FluorR 488 Protein Labeling Kit (manufactured by Molecular Probes, Inc.). Each of the labeled antibodies was administered to a mouse through the tail vein (i.v.) at 9 mg/kg body weight, and after 9 days, the blood was collected.

Figure 4:
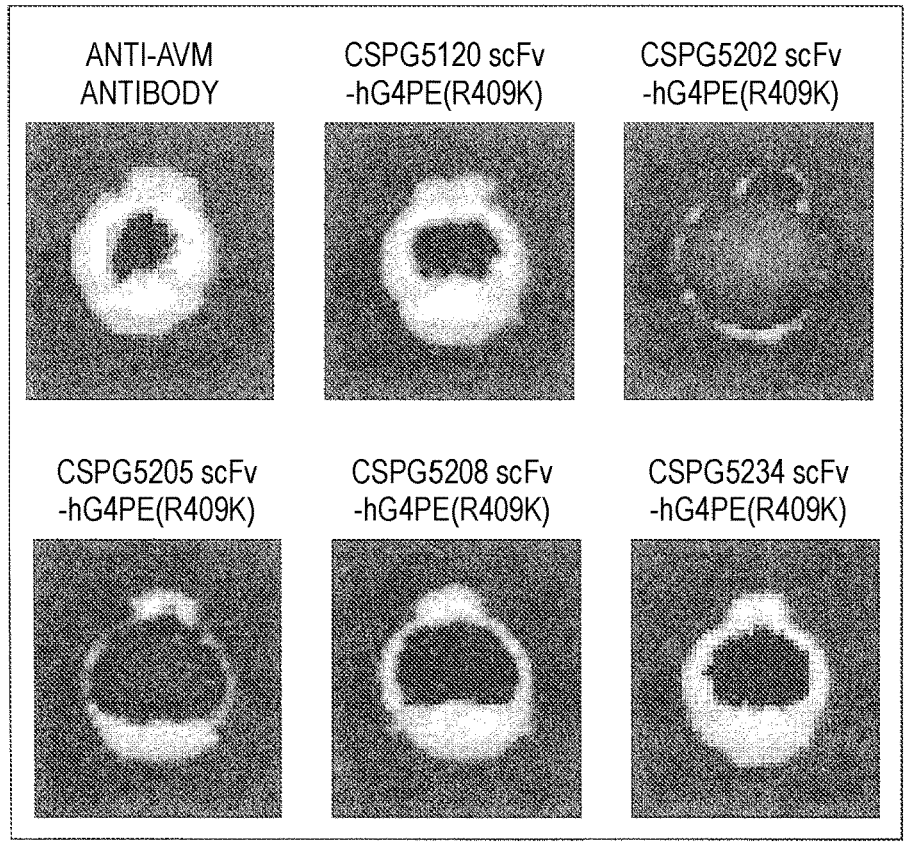
FIG. 4 shows the results of imaging evaluation of the migration ability into a mouse brain of each antibody.
Figure 4:
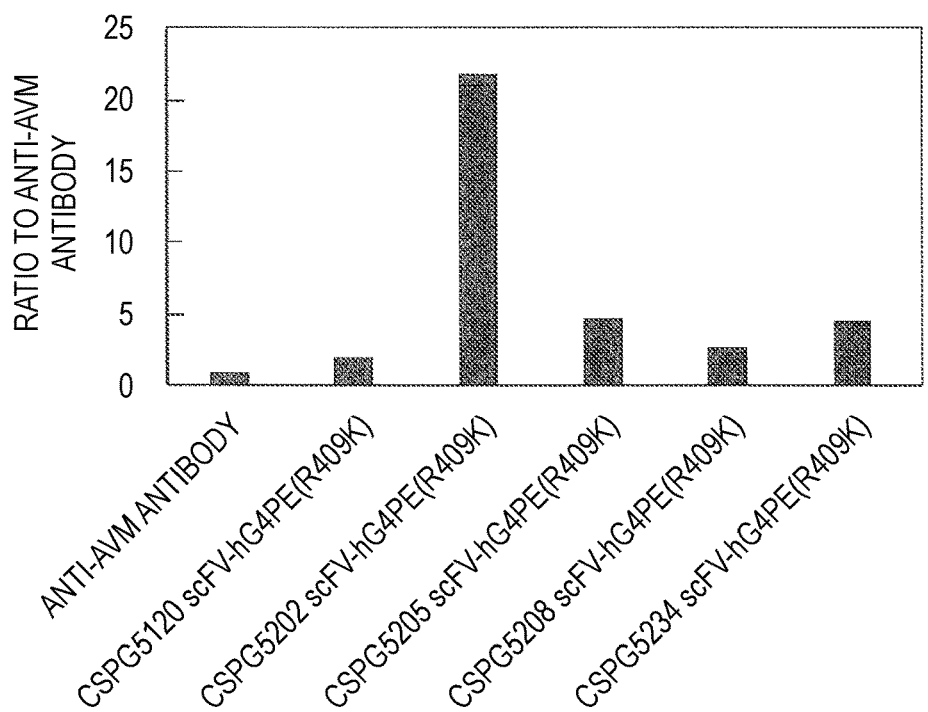

After the blood was collected, whole body perfusion was performed under anesthesia, and thereafter, a brain tissue was collected, and the fluorescence intensity was measured using IVIS Spectrum (manufactured by PerkinElmer, Inc.). Imaging images of the brain 9 days after administering the antibody are shown in FIG. 4(A). The ratio of a value of the fluorescence amount in the brain corrected by the fluorescence intensity of the administered antibody to the negative control is shown in FIG. 4(B).

As shown in FIG. 4(B), it was demonstrated that the antibody amount in the brain of any of the anti-CSPG5 scFv-Fc antibodies can be increased by several times as compared with that of the negative control. Above all, the antibody amount in the brain of the anti-CSPG5 scFv-Fc antibody: CSPG5202 scFv-hG4PE(R409K) is increased by about 20 times as shown in FIG. 4(B), and it was demonstrated that the distribution of the antibody spreads over the entire area of the brain as shown in FIG. 4(A).

[Example 7] Evaluation of Antibody Internalization pEF6_human CSPG5 produced in Example 3 was introduced into mouse connective tissue-derived fibroblast cells L929 [American Type Culture Collection (ATCC) No. CCL-1] using HilyMax (manufactured by Dojindo Laboratories). The transfected cells were selected using an antibiotic Blasticidin (manufactured by Invitrogen, Inc.), followed by cloning by a limiting dilution method, whereby L929 cells expressing CSPG5 on the cell surface (hereinafter abbreviated as human CSPG5/L929 #09) was produced.

The internalization ability of the antibodies produced in Example 2 was analyzed by the method shown below. In a 96-well plate, human CSPG5/L929 #09 or human abdominal neuroblastoma IMR-32 [The European Collection of Authenticated Cell Cultures (ECACC) No. 86041809] was seeded at $5 \times 10^3$ cells/well and adhered thereto overnight at 37° C.

The antibody diluted so that the final concentration was within a range of 1 μg/mL to 100 fg/mL and a saporin-labeled anti-IgG antibody [Hum-ZAP (manufactured by Advanced Targeting Systems, Inc.)] diluted so that the final concentration was 1 μg/mL were added thereto. After 48 hours in the case of the human CSPG5/L929 #09, and after 72 hours in the case of the IMR-32, viable cells were detected using Cell Proliferation Kit II (XTT assay) (manufactured by Roche Diagnostics, Inc.). An XTT labeling reagent and an electron coupling reagent were mixed, and the resulting mixture was added at 50 μL/well. After a reaction was carried out for 4 hours, an absorbance at a wavelength of 490 nm (reference wavelength: 630 nm) was measured. The data for the hCSPG5/L929 #09 are shown in FIG. 5, and the data for the IMR-32 are shown in FIG. 6.

Figure 5:
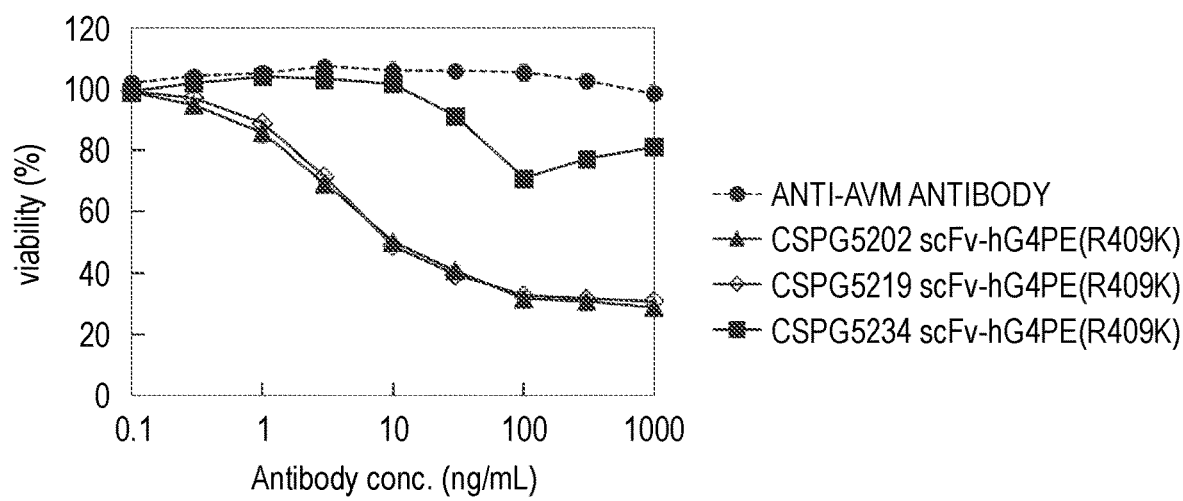
FIG. 5 shows the results of an internalization analysis of CSPG5202 scFv-hG4PE(R409K), CSPG5219 scFv-hG4PE(R409K), and CSPG5234 scFv-hG4PE(R409K) in hCSPG5/L929 #09. The horizontal axis represents the antibody concentration (ng/mL), and the vertical axis represents the viability (%) of cells. The dotted line graph shows the anti-AVM antibody that is a negative control, and the solid line graphs show samples. The black triangle marker (▲) shows the data of CSPG5202 scFv-hG4PE(R409K), the lozenge marker (◇) shows the data of CSPG5219 scFv-hG4PE(R409K), and the black square marker (■) shows the data of CSPG5234 scFv-hG4PE(R409K).

As shown in FIG. 5, it was demonstrated that CSPG5202 scFv-hG4PE(R409K), CSPG5219 scFv-hG4PE(R409K), and CSPG5234 scFv-hG4PE(R409K) markedly induce cell death in L929 cells made to forcibly express CSPG5 in an antibody concentration-dependent manner as compared with the negative control antibody.

Figure 6:
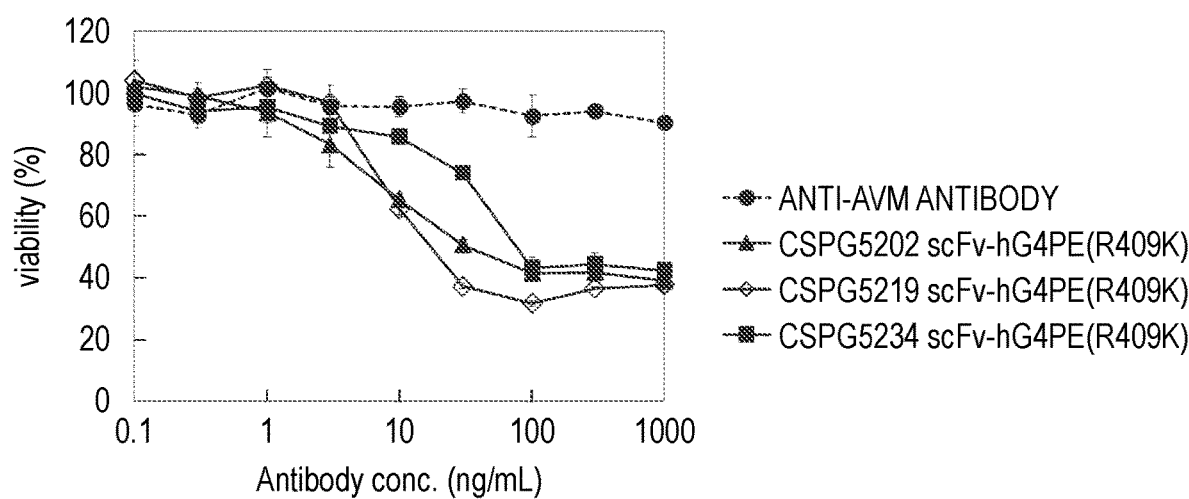
FIG. 6 shows the results of an internalization analysis of CSPG5202 scFv-hG4PE(R409K), CSPG5219 scFv-hG4PE(R409K), and CSPG5234 scFv-hG4PE(R409K) in IMR-32. The horizontal axis represents the antibody concentration (ng/mL), and the vertical axis represents the viability (%) of cells. The dotted line graph shows the anti-AVM antibody that is a negative control, and the solid line graphs show samples. The black triangle marker (▲) shows the data of CSPG5202 scFv-hG4PE(R409K), the lozenge marker (◇) shows the data of CSPG5219 scFv-hG4PE(R409K), and the black square marker (■) shows the data of CSPG5234 scFv-hG4PE(R409K).

Further, as shown in FIG. 6, also in the IMR-32 cells that originally express CSPG5, CSPG5202 scFv-hG4PE(R409K), CSPG5219 scFv-hG4PE(R409K), and CSPG5234 scFv-hG4PE(R409K) markedly induce cell death in an antibody concentration-dependent manner as compared with the negative control antibody.

In this manner, it was confirmed that the CSPG5-binding antibody binds to CSPG5 expressed on the cell membrane and is internalized in both the forced expression cell line and the cell line.

The invention has been explained in detail using the specific aspects, but it is obvious for those skilled in the art that various changes and modifications can be made without departing from the spirit and scope of the invention. The present application is based on a Japanese Patent Application filed on Jun. 26, 2018 (Patent Application No. 2018-120476), which is incorporated by reference in its entirety.

SEQUENCE LISTING FREE TEXT

SEQ ID NO: 1-Description of artificial sequence: nucleotide sequence encoding VH of CSPG5115 excluding signal sequence
SEQ ID NO: 2-Description of artificial sequence: amino acid sequence of VH of CSPG5115 excluding signal sequence
SEQ ID NO: 3-Description of artificial sequence: amino acid sequence of HCDR1 of CSPG5115
SEQ ID NO: 4-Description of artificial sequence: amino acid sequence of HCDR2 of CSPG5115
SEQ ID NO: 5-Description of artificial sequence: amino acid sequence of HCDR3 of CSPG5115
SEQ ID NO: 6-Description of artificial sequence: nucleotide sequence encoding VL of CSPG5115 excluding signal sequence
SEQ ID NO: 7-Description of artificial sequence: amino acid sequence of VL of CSPG5115 excluding signal sequence
SEQ ID NO: 8-Description of artificial sequence: amino acid sequence of LCDR1 of CSPG5115
SEQ ID NO: 9-Description of artificial sequence: amino acid sequence of LCDR2 of CSPG5115
SEQ ID NO: 10-Description of artificial sequence: amino acid sequence of LCDR3 of CSPG5115
SEQ ID NO: 11-Description of artificial sequence: nucleotide sequence encoding VH of CSPG5120 excluding signal sequence
SEQ ID NO: 12-Description of artificial sequence: amino acid sequence of VH of CSPG5120 excluding signal sequence
SEQ ID NO: 13-Description of artificial sequence: amino acid sequence of HCDR1 of CSPG5120
SEQ ID NO: 14-Description of artificial sequence: amino acid sequence of HCDR2 of CSPG5120
SEQ ID NO: 15-Description of artificial sequence: amino acid sequence of HCDR3 of CSPG5120
SEQ ID NO: 16-Description of artificial sequence: nucleotide sequence encoding VL of CSPG5120 excluding signal sequence
SEQ ID NO: 17-Description of artificial sequence: amino acid sequence of VL of CSPG5120 excluding signal sequence
SEQ ID NO: 18-Description of artificial sequence: amino acid sequence of LCDR1 of CSPG5120
SEQ ID NO: 19-Description of artificial sequence: amino acid sequence of LCDR2 of CSPG5120
SEQ ID NO: 20-Description of artificial sequence: amino acid sequence of LCDR3 of CSPG5120
SEQ ID NO: 21-Description of artificial sequence: nucleotide sequence encoding VH of CSPG5168 excluding signal sequence
SEQ ID NO: 22-Description of artificial sequence: amino acid sequence of VH of CSPG5168 excluding signal sequence
SEQ ID NO: 23-Description of artificial sequence: amino acid sequence of HCDR1 of CSPG5168
SEQ ID NO: 24-Description of artificial sequence: amino acid sequence of HCDR2 of CSPG5168
SEQ ID NO: 25-Description of artificial sequence: amino acid sequence of HCDR3 of CSPG5168
SEQ ID NO: 26-Description of artificial sequence: nucleotide sequence encoding VL of CSPG5168 excluding signal sequence
SEQ ID NO: 27-Description of artificial sequence: amino acid sequence of VL of CSPG5168 excluding signal sequence
SEQ ID NO: 28-Description of artificial sequence: amino acid sequence of LCDR1 of CSPG5168
SEQ ID NO: 29-Description of artificial sequence: amino acid sequence of LCDR2 of CSPG5168
SEQ ID NO: 30-Description of artificial sequence: amino acid sequence of LCDR3 of CSPG5168
SEQ ID NO: 31-Description of artificial sequence: nucleotide sequence encoding VH of CSPG5201 excluding signal sequence
SEQ ID NO: 32-Description of artificial sequence: amino acid sequence of VH of CSPG5201 excluding signal sequence
SEQ ID NO: 33-Description of artificial sequence: amino acid sequence of HCDR1 of CSPG5201
SEQ ID NO: 34-Description of artificial sequence: amino acid sequence of HCDR2 of CSPG5201
SEQ ID NO: 35-Description of artificial sequence: amino acid sequence of HCDR3 of CSPG5201
SEQ ID NO: 36-Description of artificial sequence: nucleotide sequence encoding VL of CSPG5201 excluding signal sequence
SEQ ID NO: 37-Description of artificial sequence: amino acid sequence of VL of CSPG5201 excluding signal sequence
SEQ ID NO: 38-Description of artificial sequence: amino acid sequence of LCDR1 of CSPG5201
SEQ ID NO: 39-Description of artificial sequence: amino acid sequence of LCDR2 of CSPG5201
SEQ ID NO: 40-Description of artificial sequence: amino acid sequence of LCDR3 of CSPG5201
SEQ ID NO: 41-Description of artificial sequence: nucleotide sequence encoding VH of CSPG5202 excluding signal sequence
SEQ ID NO: 42-Description of artificial sequence: amino acid sequence of VH of CSPG5202 excluding signal sequence
SEQ ID NO: 43-Description of artificial sequence: amino acid sequence of HCDR1 of CSPG5202 SEQ ID NO: 44-Description of artificial sequence: amino acid sequence of HCDR2 of CSPG5202
SEQ ID NO: 45-Description of artificial sequence: amino acid sequence of HCDR3 of CSPG5202
SEQ ID NO: 46-Description of artificial sequence: nucleotide sequence encoding VL of CSPG5202 excluding signal sequence
SEQ ID NO: 47-Description of artificial sequence: amino acid sequence of VL of CSPG5202 excluding signal sequence
SEQ ID NO: 48-Description of artificial sequence: amino acid sequence of LCDR1 of CSPG5202 SEQ ID NO: 49-Description of artificial sequence: amino acid sequence of LCDR2 of CSPG5202
SEQ ID NO: 50-Description of artificial sequence: amino acid sequence of LCDR3 of CSPG5202
SEQ ID NO: 51-Description of artificial sequence: nucleotide sequence encoding VH of CSPG5205 excluding signal sequence SEQ ID NO: 52-Description of artificial sequence: amino acid sequence of VH of CSPG5205 excluding signal sequence
SEQ ID NO: 53-Description of artificial sequence: amino acid sequence of HCDR1 of CSPG5205
SEQ ID NO: 54-Description of artificial sequence: amino acid sequence of HCDR2 of CSPG5205
SEQ ID NO: 55-Description of artificial sequence: amino acid sequence of HCDR3 of CSPG5205
SEQ ID NO: 56-Description of artificial sequence: nucleotide sequence encoding VL of CSPG5205 excluding signal sequence
SEQ ID NO: 57-Description of artificial sequence: amino acid sequence of VL of CSPG5205 excluding signal sequence
SEQ ID NO: 58-Description of artificial sequence: amino acid sequence of LCDR1 of CSPG5205
SEQ ID NO: 59-Description of artificial sequence: amino acid sequence of LCDR2 of CSPG5205
SEQ ID NO: 60-Description of artificial sequence: amino acid sequence of LCDR3 of CSPG5205
SEQ ID NO: 61-Description of artificial sequence: nucleotide sequence encoding VH of CSPG5206 excluding signal sequence
SEQ ID NO: 62-Description of artificial sequence: amino acid sequence of VH of CSPG5206 excluding signal sequence
SEQ ID NO: 63-Description of artificial sequence: amino acid sequence of HCDR1 of CSPG5206
SEQ ID NO: 64-Description of artificial sequence: amino acid sequence of HCDR2 of CSPG5206
SEQ ID NO: 65-Description of artificial sequence: amino acid sequence of HCDR3 of CSPG5206
SEQ ID NO: 66-Description of artificial sequence: nucleotide sequence encoding VL of CSPG5206 excluding signal sequence
SEQ ID NO: 67-Description of artificial sequence: amino acid sequence of VL of CSPG5206 excluding signal sequence
SEQ ID NO: 68-Description of artificial sequence: amino acid sequence of LCDR1 of CSPG5206
SEQ ID NO: 69-Description of artificial sequence: amino acid sequence of LCDR2 of CSPG5206
SEQ ID NO: 70-Description of artificial sequence: amino acid sequence of LCDR3 of CSPG5206
SEQ ID NO: 71-Description of artificial sequence: nucleotide sequence encoding VH of CSPG5207 excluding signal sequence
SEQ ID NO: 72-Description of artificial sequence: amino acid sequence of VH of CSPG5207 excluding signal sequence
SEQ ID NO: 73-Description of artificial sequence: amino acid sequence of HCDR1 of CSPG5207
SEQ ID NO: 74-Description of artificial sequence: amino acid sequence of HCDR2 of CSPG5207
SEQ ID NO: 75-Description of artificial sequence: amino acid sequence of HCDR3 of CSPG5207
SEQ ID NO: 76-Description of artificial sequence: nucleotide sequence encoding VL of CSPG5207 excluding signal sequence
SEQ ID NO: 77-Description of artificial sequence: amino acid sequence of VL of CSPG5207 excluding signal sequence
SEQ ID NO: 78-Description of artificial sequence: amino acid sequence of LCDR1 of CSPG5207
SEQ ID NO: 79-Description of artificial sequence: amino acid sequence of LCDR2 of CSPG5207
SEQ ID NO: 80-Description of artificial sequence: amino acid sequence of LCDR3 of CSPG5207
SEQ ID NO: 81-Description of artificial sequence: nucleotide sequence encoding VH of CSPG5208 excluding signal sequence
SEQ ID NO: 82-Description of artificial sequence: amino acid sequence of VH of CSPG5208 excluding signal sequence
SEQ ID NO: 83-Description of artificial sequence: amino acid sequence of HCDR1 of CSPG5208
SEQ ID NO: 84-Description of artificial sequence: amino acid sequence of HCDR2 of CSPG5208
SEQ ID NO: 85-Description of artificial sequence: amino acid sequence of HCDR3 of CSPG5208
SEQ ID NO: 86-Description of artificial sequence: nucleotide sequence encoding VL of CSPG5208 excluding signal sequence
SEQ ID NO: 87-Description of artificial sequence: amino acid sequence of VL of CSPG5208 excluding signal sequence
SEQ ID NO: 88-Description of artificial sequence: amino acid sequence of LCDR1 of CSPG5208
SEQ ID NO: 89-Description of artificial sequence: amino acid sequence of LCDR2 of CSPG5208
SEQ ID NO: 90-Description of artificial sequence: amino acid sequence of LCDR3 of CSPG5208
SEQ ID NO: 91-Description of artificial sequence: nucleotide sequence encoding VH of CSPG5214 excluding signal sequence
SEQ ID NO: 92-Description of artificial sequence: amino acid sequence of VH of CSPG5214 excluding signal sequence
SEQ ID NO: 93-Description of artificial sequence: amino acid sequence of HCDR1 of CSPG5214
SEQ ID NO: 94-Description of artificial sequence: amino acid sequence of HCDR2 of CSPG5214
SEQ ID NO: 95-Description of artificial sequence: amino acid sequence of HCDR3 of CSPG5214
SEQ ID NO: 96-Description of artificial sequence: nucleotide sequence encoding VL of CSPG5214 excluding signal sequence
SEQ ID NO: 97-Description of artificial sequence: amino acid sequence of VL of CSPG5214 excluding signal sequence
SEQ ID NO: 98-Description of artificial sequence: amino acid sequence of LCDR1 of CSPG5214
SEQ ID NO: 99-Description of artificial sequence: amino acid sequence of LCDR2 of CSPG5214
SEQ ID NO: 100-Description of artificial sequence: amino acid sequence of LCDR3 of CSPG5214
SEQ ID NO: 101-Description of artificial sequence: nucleotide sequence encoding VH of CSPG5219 excluding signal sequence
SEQ ID NO: 102-Description of artificial sequence: amino acid sequence of VH of CSPG5219 excluding signal sequence
SEQ ID NO: 103-Description of artificial sequence: amino acid sequence of HCDR1 of CSPG5219
SEQ ID NO: 104-Description of artificial sequence: amino acid sequence of HCDR2 of CSPG5219
SEQ ID NO: 105-Description of artificial sequence: amino acid sequence of HCDR3 of CSPG5219
SEQ ID NO: 106-Description of artificial sequence: nucleotide sequence encoding VL of CSPG5219 excluding signal sequence SEQ ID NO: 107-Description of artificial sequence: amino acid sequence of VL of CSPG5219 excluding signal sequence SEQ ID NO: 108-Description of artificial sequence: amino acid sequence of LCDR1 of CSPG5219

SEQ ID NO: 109-Description of artificial sequence: amino acid sequence of LCDR2 of CSPG5219

SEQ ID NO: 110-Description of artificial sequence: amino acid sequence of LCDR3 of CSPG5219

SEQ ID NO: 111-Description of artificial sequence: nucleotide sequence encoding VH of CSPG5222 excluding signal sequence SEQ ID NO: 112-Description of artificial sequence: amino acid sequence of VH of CSPG5222 excluding signal sequence SEQ ID NO: 113-Description of artificial sequence: amino acid sequence of HCDR1 of CSPG5222

SEQ ID NO: 114-Description of artificial sequence: amino acid sequence of HCDR2 of CSPG5222

SEQ ID NO: 115-Description of artificial sequence: amino acid sequence of HCDR3 of CSPG5222

SEQ ID NO: 116-Description of artificial sequence: nucleotide sequence encoding VL of CSPG5222 excluding signal sequence SEQ ID NO: 117-Description of artificial sequence: amino acid sequence of VL of CSPG5222 excluding signal sequence SEQ ID NO: 118-Description of artificial sequence: amino acid sequence of LCDR1 of CSPG5222

SEQ ID NO: 119-Description of artificial sequence: amino acid sequence of LCDR2 of CSPG5222

SEQ ID NO: 120-Description of artificial sequence: amino acid sequence of LCDR3 of CSPG5222

SEQ ID NO: 121-Description of artificial sequence: nucleotide sequence encoding VH of CSPG5227 excluding signal sequence SEQ ID NO: 122-Description of artificial sequence: amino acid sequence of VH of CSPG5227 excluding signal sequence SEQ ID NO: 123-Description of artificial sequence: amino acid sequence of HCDR1 of CSPG5227

SEQ ID NO: 124-Description of artificial sequence: amino acid sequence of HCDR2 of CSPG5227

SEQ ID NO: 125-Description of artificial sequence: amino acid sequence of HCDR3 of CSPG5227

SEQ ID NO: 126-Description of artificial sequence: nucleotide sequence encoding VL of CSPG5227 excluding signal sequence SEQ ID NO: 127-Description of artificial sequence: amino acid sequence of VL of CSPG5227 excluding signal sequence SEQ ID NO: 128-Description of artificial sequence: amino acid sequence of LCDR1 of CSPG5227

SEQ ID NO: 129-Description of artificial sequence: amino acid sequence of LCDR2 of CSPG5227

SEQ ID NO: 130-Description of artificial sequence: amino acid sequence of LCDR3 of CSPG5227

SEQ ID NO: 131-Description of artificial sequence: nucleotide sequence encoding VH of CSPG5230 excluding signal sequence SEQ ID NO: 132-Description of artificial sequence: amino acid sequence of VH of CSPG5230 excluding signal sequence SEQ ID NO: 133-Description of artificial sequence: amino acid sequence of HCDR1 of CSPG5230

SEQ ID NO: 134-Description of artificial sequence: amino acid sequence of HCDR2 of CSPG5230

SEQ ID NO: 135-Description of artificial sequence: amino acid sequence of HCDR3 of CSPG5230

SEQ ID NO: 136-Description of artificial sequence: nucleotide sequence encoding VL of CSPG5230 excluding signal sequence SEQ ID NO: 137-Description of artificial sequence: amino acid sequence of VL of CSPG5230 excluding signal sequence SEQ ID NO: 138-Description of artificial sequence: amino acid sequence of LCDR1 of CSPG5230

SEQ ID NO: 139-Description of artificial sequence: amino acid sequence of LCDR2 of CSPG5230

SEQ ID NO: 140-Description of artificial sequence: amino acid sequence of LCDR3 of CSPG5230

SEQ ID NO: 141-Description of artificial sequence: nucleotide sequence encoding VH of CSPG5234 excluding signal sequence SEQ ID NO: 142-Description of artificial sequence: amino acid sequence of VH of CSPG5234 excluding signal sequence SEQ ID NO: 143-Description of artificial sequence: amino acid sequence of HCDR1 of CSPG5234

SEQ ID NO: 144-Description of artificial sequence: amino acid sequence of HCDR2 of CSPG5234

SEQ ID NO: 145-Description of artificial sequence: amino acid sequence of HCDR3 of CSPG5234

SEQ ID NO: 146-Description of artificial sequence: nucleotide sequence encoding VL of CSPG5234 excluding signal sequence SEQ ID NO: 147-Description of artificial sequence: amino acid sequence of VL of CSPG5234 excluding signal sequence SEQ ID NO: 148-Description of artificial sequence: amino acid sequence of LCDR1 of CSPG5234

SEQ ID NO: 149-Description of artificial sequence: amino acid sequence of LCDR2 of CSPG5234

SEQ ID NO: 150-Description of artificial sequence: amino acid sequence of LCDR3 of CSPG5234

SEQ ID NO: 151-Description of artificial sequence: nucleotide sequence encoding light chain (excluding signal sequence) of pCI_CSPG5202-hKG4PE(R409K)

SEQ ID NO: 152-Description of artificial sequence: amino acid sequence of light chain (excluding signal sequence) of pCI_CSPG5202-hKG4PE(R409K)

SEQ ID NO: 153-Description of artificial sequence: nucleotide sequence encoding heavy chain (excluding signal sequence) of pCI_CSPG5202-hKG4PE(R409K)

SEQ ID NO: 154-Description of artificial sequence: amino acid sequence of heavy chain (excluding signal sequence) of pCI_CSPG5202-hKG4PE(R409K)

SEQ ID NO: 155-Description of artificial sequence: nucleotide sequence encoding light chain (excluding signal sequence) of pCI_AVM-hLG4PE(R409K)-CSPG5202scFv SEQ ID NO: 156-Description of artificial sequence: amino acid sequence of light chain (excluding signal sequence) of pCI_AVM-hLG4PE(R409K)-CSPG5202scFv SEQ ID NO: 157-Description of artificial sequence: nucleotide sequence encoding heavy chain (excluding signal sequence) of pCI_AVM-hLG4PE(R409K)-CSPG5202scFv SEQ ID NO: 158-Description of artificial sequence: amino acid sequence of heavy chain (excluding signal sequence) of pCI_AVM-hLG4PE(R409K)-CSPG5202scFv SEQ ID NO: 159-Description of artificial sequence: nucleotide sequence encoding human CSPG5 (comprising signal sequence)

SEQ ID NO: 160-Description of artificial sequence: amino acid sequence of human CSPG5 (comprising signal sequence)

SEQ ID NO: 161-Description of artificial sequence: nucleotide sequence encoding mouse CSPG5 (comprising signal sequence)

SEQ ID NO: 162-Description of artificial sequence: amino acid sequence of mouse CSPG5 (comprising signal sequence)

SEQ ID NO: 163-Description of artificial sequence: nucleotide sequence encoding monkey CSPG5 (comprising signal sequence)

SEQ ID NO: 164-Description of artificial sequence: amino acid sequence of monkey CSPG5 (comprising signal sequence)

SEQ ID NO: 165—Description of artificial sequence: nucleotide sequence encoding human CSPG5-FLAG_Fc (comprising signal sequence)

SEQ ID NO: 166-Description of artificial sequence: amino acid sequence of human CSPG5-FLAG_Fc (comprising signal sequence) SEQ ID NO: 167-Description of artificial sequence: nucleotide sequence encoding mouse CSPG5-FLAG_Fc (comprising signal sequence)

SEQ ID NO: 168-Description of artificial sequence: amino acid sequence of mouse CSPG5-FLAG_Fc (comprising signal sequence)

SEQ ID NO: 169-Description of artificial sequence: nucleotide sequence encoding human CSPG5-GST (comprising signal sequence)

SEQ ID NO: 170-Description of artificial sequence: amino acid sequence of human CSPG5-GST (comprising signal sequence)

SEQ ID NO: 171-Description of artificial sequence: nucleotide sequence encoding mouse CSPG5-GST (comprising signal sequence) SEQ ID NO: 172-Description of artificial sequence: amino acid sequence of mouse CSPG5-GST (comprising signal sequence)

The invention claimed is:

1. An antibody or an antibody fragment thereof which binds to chondroitin sulfate proteoglycan 5 (CSPG5), wherein the antibody or fragment thereof is selected from the group consisting of the following (a) to (o):

(a) an antibody or fragment thereof in which the amino acid sequences of complementarity determining regions (CDRs) 1 to 3 of a variable domain of a heavy chain (VH) comprise the amino acid sequences represented by SEQ ID NOS: 3, 4, and 5, respectively, and in which the amino acid sequences of CDR1 to CDR3 of a variable domain of a light chain (VL) comprise the amino acid sequences represented by SEQ ID NOS: 8, 9, and 10, respectively;

(b) an antibody or fragment thereof in which the amino acid sequences of CDR1 to CDR3 of VH comprise the amino acid sequences represented by SEQ ID NOS: 13, 14, and 15, respectively, and in which the amino acid sequences of CDR1 to CDR3 of VL comprise the amino acid sequences represented by SEQ ID NOS: 18, 19, and 20, respectively;

(c) an antibody or fragment thereof in which the amino acid sequences of CDR1 to CDR3 of VH comprise the amino acid sequences represented by SEQ ID NOS: 23, 24, and 25, respectively, and in which the amino acid sequences of CDR1 to CDR3 of VL comprise the amino acid sequences represented by SEQ ID NOS: 28, 29, and 30, respectively;

(d) an antibody or fragment thereof in which the amino acid sequences of CDR1 to CDR3 of VH comprise the amino acid sequences represented by SEQ ID NOS: 33, 34, and 35, respectively, and in which the amino acid sequences of CDR1 to CDR3 of VL comprise the amino acid sequences represented by SEQ ID NOS: 38, 39, and 40, respectively;

(e) an antibody or fragment thereof in which the amino acid sequences of CDR1 to CDR3 of VH comprise the amino acid sequences represented by SEQ ID NOS: 43, 44, and 45, respectively, and in which the amino acid sequences of CDR1 to CDR3 of VL comprise the amino acid sequences represented by SEQ ID NOS: 48, 49, and 50, respectively;

(f) an antibody or fragment thereof in which the amino acid sequences of CDR1 to CDR3 of VH comprise the amino acid sequences represented by SEQ ID NOS: 53, 54, and 55, respectively, and in which the amino acid sequences of CDR1 to CDR3 of VL comprise the amino acid sequences represented by SEQ ID NOS: 58, 59, and 60, respectively;

(g) an antibody or fragment thereof in which the amino acid sequences of CDR1 to CDR3 of VH comprise the amino acid sequences represented by SEQ ID NOS: 63, 64, and 65, respectively, and in which the amino acid sequences of CDR1 to CDR3 of VL comprise the amino acid sequences represented by SEQ ID NOS: 68, 69, and 70, respectively;

(h) an antibody or fragment thereof in which the amino acid sequences of CDR1 to CDR3 of VH comprise the amino acid sequences represented by SEQ ID NOS: 73, 74, and 75, respectively, and in which the amino acid sequences of CDR1 to CDR3 of VL comprise the amino acid sequences represented by SEQ ID NOS: 78, 79, and 80, respectively;

(i) an antibody or fragment thereof in which the amino acid sequences of CDR1 to CDR3 of VH comprise the amino acid sequences represented by SEQ ID NOS: 83, 84, and 85, respectively, and in which the amino acid sequences of CDR1 to CDR3 of VL comprise the amino acid sequences represented by SEQ ID NOS: 88, 89, and 90, respectively;

(j) an antibody or fragment thereof in which the amino acid sequences of CDR1 to CDR3 of VH comprise the amino acid sequences represented by SEQ ID NOS: 93, 94, and 95, respectively, and in which the amino acid sequences of CDR1 to CDR3 of VL comprise the amino acid sequences represented by SEQ ID NOS: 98, 99, and 100, respectively;

(k) an antibody or fragment thereof in which the amino acid sequences of CDR1 to CDR3 of VH comprise the amino acid sequences represented by SEQ ID NOS: 103, 104, and, 105, respectively, and in which the amino acid sequences of CDR1 to CDR3 of VL comprise the amino acid sequences represented by SEQ ID NOS: 108, 109, and 110, respectively;

(l) an antibody or fragment thereof in which the amino acid sequences of CDR1 to CDR3 of VH comprise the amino acid sequences represented by SEQ ID NOS: 113, 114, and 115, respectively, and in which the amino acid sequences of CDR1 to CDR3 of VL comprise the amino acid sequences represented by SEQ ID NOS: 118, 119, and 120, respectively;

(m) an antibody or fragment thereof in which the amino acid sequences of CDR1 to CDR3 of VH comprise the amino acid sequences represented by SEQ ID NOS: 123, 124, and 125, respectively, and in which the amino acid sequences of CDR1 to CDR3 of VL comprise the amino acid sequences represented by SEQ ID NOS: 128, 129, and 130, respectively;

(n) an antibody or fragment thereof in which the amino acid sequences of CDR1 to CDR3 of VH comprise the amino acid sequences represented by SEQ ID NOS: 133, 134, and 135, respectively, and in which the amino acid sequences of CDR1 to CDR3 of VL comprise the amino acid sequences represented by SEQ ID NOS: 138, 139, and 140, respectively; and (o) an antibody or fragment thereof in which the amino acid sequences of CDR1 to CDR3 of VH comprise the amino acid sequences represented by SEQ ID NOS: 143, 144, and 145, respectively, and in which the amino acid sequences of CDR1 to CDR3 of VL comprise the amino acid sequences represented by SEQ ID NOS: 148, 149, and 150, respectively.

2. The antibody or the antibody fragment thereof according to claim 1, wherein the antibody or fragment thereof is selected from the group consisting of the following (A) to (O):
  (A) an antibody or fragment thereof in which the amino acid sequence of VH comprises the amino acid sequence represented by SEQ ID NO: 2 and in which the amino acid sequence of VL comprises the amino acid sequence represented by SEQ ID NO: 7;
  (B) an antibody or fragment thereof in which the amino acid sequence of VH comprises the amino acid sequence represented by SEQ ID NO: 12 and in which the amino acid sequence of VL comprises the amino acid sequence represented by SEQ ID NO: 17;
  (C) an antibody or fragment thereof in which the amino acid sequence of VH comprises the amino acid sequence represented by SEQ ID NO: 22 and in which the amino acid sequence of VL comprises the amino acid sequence represented by SEQ ID NO: 27;
  (D) an antibody or fragment thereof in which the amino acid sequence of VH comprises the amino acid sequence represented by SEQ ID NO: 32 and in which the amino acid sequence of VL comprises the amino acid sequence represented by SEQ ID NO: 37;
  (E) an antibody or fragment thereof in which the amino acid sequence of VH comprises the amino acid sequence represented by SEQ ID NO: 42 and in which the amino acid sequence of VL comprises the amino acid sequence represented by SEQ ID NO: 47;
  (F) an antibody or fragment thereof in which the amino acid sequence of VH comprises the amino acid sequence represented by SEQ ID NO: 52 and in which the amino acid sequence of VL comprises the amino acid sequence represented by SEQ ID NO: 57;
  (G) an antibody or fragment thereof in which the amino acid sequence of VH comprises the amino acid sequence represented by SEQ ID NO: 62 and in which the amino acid sequence of VL comprises the amino acid sequence represented by SEQ ID NO: 67;
  (H) an antibody or fragment thereof in which the amino acid sequence of VH comprises the amino acid sequence represented by SEQ ID NO: 72 and in which the amino acid sequence of VL comprises the amino acid sequence represented by SEQ ID NO: 77;
  (I) an antibody or fragment thereof in which the amino acid sequence of VH comprises the amino acid sequence represented by SEQ ID NO: 82 and in which the amino acid sequence of VL comprises the amino acid sequence represented by SEQ ID NO: 87;
  (J) an antibody or fragment thereof in which the amino acid sequence of VH comprises the amino acid sequence represented by SEQ ID NO: 92 and in which the amino acid sequence of VL comprises the amino acid sequence represented by SEQ ID NO: 97;
  (K) an antibody or fragment thereof in which the amino acid sequence of VH comprises the amino acid sequence represented by SEQ ID NO: 102 and in which the amino acid sequence of VL comprises the amino acid sequence represented by SEQ ID NO: 107;
  (L) an antibody or fragment thereof in which the amino acid sequence of VH comprises the amino acid sequence represented by SEQ ID NO: 112 and in which the amino acid sequence of VL comprises the amino acid sequence represented by SEQ ID NO: 117;
  (M) an antibody or fragment thereof in which the amino acid sequence of VH comprises the amino acid sequence represented by SEQ ID NO: 122 and in which the amino acid sequence of VL comprises the amino acid sequence represented by SEQ ID NO: 127;
  (N) an antibody or fragment thereof in which the amino acid sequence of VH comprises the amino acid sequence represented by SEQ ID NO: 132 and in which the amino acid sequence of VL comprises the amino acid sequence represented by SEQ ID NO: 137; and
  (O) an antibody or fragment thereof in which the amino acid sequence of VH comprises the amino acid sequence represented by SEQ ID NO: 142 and in which the amino acid sequence of VL comprises the amino acid sequence represented by SEQ ID NO: 147.

3. The antibody or the antibody fragment thereof according to claim 1, wherein the antibody or the antibody fragment thereof is a bispecific antibody.

4. The antibody or the antibody fragment thereof according to claim 1, wherein the antibody or the antibody fragment thereof is a bispecific antibody, and wherein the bispecific antibody binds to CSPG5 and to an antigen present in a brain.

5. The antibody fragment according to claim 1, wherein the antibody fragment is selected from the group consisting of Fab, Fab', F(ab')$_2$, a single chain antibody (scFv), a dimerized V region (diabody), and a disulfide-stabilized V region (dsFv).

6. The antibody or the antibody fragment thereof according to claim 1, wherein the antibody is a genetically recombinant antibody.

7. The antibody or the antibody fragment thereof according to claim 1, wherein the antibody is selected from the group consisting of a mouse antibody, a chimeric antibody, a humanized antibody, and a human antibody.

8. A fusion antibody or a fusion antibody fragment thereof, in which at least one selected from the group consisting of the following (i) to (iii) is linked to the antibody or the antibody fragment thereof which binds to CSPG5 according to claim 1:
  (i) a hydrophilic polymer;
  (ii) an amphipathic polymer; and
  (iii) a functional molecule.

9. A nucleic acid comprising a nucleotide sequence encoding the fusion antibody or the fusion antibody fragment thereof according to claim 8.

10. A transformant cell comprising a vector comprising the nucleic acid according to claim 9.

11. A method for producing the fusion antibody or the fusion antibody fragment thereof according to claim 8, comprising:
  culturing a transformant cell comprising a vector comprising a nucleic acid encoding the fusion antibody or the fusion antibody fragment thereof, and
  collecting the antibody or the antibody fragment thereof from a culture solution.

12. A pharmaceutical composition comprising the fusion antibody or the fusion antibody fragment thereof according to claim 8 and a pharmacologically acceptable carrier.

13. A method for detecting or measuring an antigen present in a brain, comprising:
  contacting brain cells or tissue with the fusion antibody or the fusion antibody fragment thereof according to claim 8 under conditions permitting binding of said antibody or antibody fragment to CSPG5, and
  detecting or measuring binding of said antibody or antibody fragment to CSPG5.

14. A method for diagnosing or treating a brain disease, comprising:

administering the fusion antibody or the fusion antibody fragment thereof according to claim 8 at a periphery of the subject.

15. A method for enhancing the property of accumulating of a fusion antibody or a fusion antibody fragment thereof in a brain of a subject, comprising:
    administering the fusion antibody or the fusion antibody fragment thereof according to claim 8 at a periphery of the subject.

16. A hybridoma which produces the antibody or the antibody fragment thereof according to claim 1.

17. A nucleic acid comprising a nucleotide sequence encoding the antibody or the antibody fragment thereof according to claim 1.

18. A transformant cell comprising a vector comprising the nucleic acid according to claim 17.

19. A method for producing the antibody or the antibody fragment thereof according to claim 1, comprising:
    culturing either (i) a hybridoma which produces the antibody or the antibody fragment thereof or (ii) a transformant cell comprising a vector comprising a nucleic acid encoding the antibody or the antibody fragment thereof, and
    collecting the antibody or the antibody fragment thereof from a culture solution.

20. A pharmaceutical composition comprising the antibody or the antibody fragment thereof according to claim 1 and a pharmacologically acceptable carrier.

21. A method for detecting or measuring an antigen present in a brain, comprising:
    contacting brain cells or tissue with an the antibody or the antibody fragment thereof according to claim 1 under conditions permitting binding of said antibody or antibody fragment to CSPG5, and
    detecting or measuring binding of said antibody or antibody fragment to CSPG5.

22. A method for diagnosing or treating a brain disease, comprising:
    administering the antibody or the antibody fragment thereof according to claim 1 at a periphery of the subject.

23. A method for enhancing the property of accumulating an antibody or an antibody fragment thereof in a brain of a subject, comprising:
    administering the antibody or the antibody fragment thereof according to claim 1 at a periphery of the subject.

24. A method for producing a fusion antibody or a fusion antibody fragment thereof, comprising:
    (a) culturing either (i) a hybridoma which produces the antibody or the antibody fragment thereof of claim 1 or (ii) a transformant cell comprising a vector comprising a nucleic acid encoding the antibody or the antibody fragment thereof of claim 1,
    (b) collecting the antibody or the antibody fragment thereof from a culture solution, and
    (c) linking at least one selected from the group consisting of the following (i) to (iii) to the antibody or the antibody fragment thereof collected in (b):
    (i) a hydrophilic polymer;
    (ii) an amphipathic polymer; and
    (iii) a functional molecule.

\* \* \* \* \*

SEQUENCE LISTING

```
<160> NUMBER OF SEQ ID NOS: 172

<210> SEQ ID NO 1
<211> LENGTH: 375
<212> TYPE: DNA
<213> ORGANISM: Artificial Sequence
<220> FEATURE:
<223> OTHER INFORMATION: Description of the artificial sequence: base
      sequence of VH of CSPG5115 excluding signal sequence

<400> SEQUENCE: 1
gaggtccagc tggtgcagtc tggggctgag gtgaagaagc ctggggcctc actgaaggtc      60
tcctgcaagg cttctggata cagcttcact gactatatta tacattgggt gcgccaggcc     120
cccggacaaa gtcttgagtg gatgggatgg atcaacggtg cagtggtgt cccaaaatat      180 tcagacaagt tccagggcag agtcaccatt accagagaca catccgcgaa cacagcctac     240
atggagattc gtagcctggg atctgaagac acggctgtgt attactgtgc gagagggggg     300
gtttgtagtg gcgataagtg ctactactac ggtatggacg tctggggcca agggaccacg     360
gtcaccgtct cctca                                                      375

<210> SEQ ID NO 2
<211> LENGTH: 125
<212> TYPE: PRT
<213> ORGANISM: Artificial Sequence
<220> FEATURE:
<223> OTHER INFORMATION: Description of the artificial sequence: amino
      acid sequence of VH of CSPG5115 excluding signal sequence

<400> SEQUENCE: 2

Glu Val Gln Leu Val Gln Ser Gly Ala Glu Val Lys Lys Pro Gly Ala
1               5                   10                  15

Ser Leu Lys Val Ser Cys Lys Ala Ser Gly Tyr Ser Phe Thr Asp Tyr
            20                  25                  30

Ile Ile His Trp Val Arg Gln Ala Pro Gly Gln Ser Leu Glu Trp Met
        35                  40                  45

Gly Trp Ile Asn Gly Gly Ser Gly Val Pro Lys Tyr Ser Asp Lys Phe
    50                  55                  60

Gln Gly Arg Val Thr Ile Thr Arg Asp Thr Ser Ala Asn Thr Ala Tyr
65                  70                  75                  80
```

```
Met Glu Ile Arg Ser Leu Gly Ser Glu Asp Thr Ala Val Tyr Tyr Cys
                85                  90                  95

Ala Arg Gly Gly Val Cys Ser Gly Asp Lys Cys Tyr Tyr Tyr Gly Met
            100                 105                 110

Asp Val Trp Gly Gln Gly Thr Thr Val Thr Val Ser Ser
        115                 120                 125

<210> SEQ ID NO 3
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5115

<400> SEQUENCE: 3

Asp Tyr Ile Ile His
1               5

<210> SEQ ID NO 4
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5115

<400> SEQUENCE: 4

Trp Ile Asn Gly Gly Ser Gly Val Pro Lys Tyr Ser Asp Lys Phe Gln
1               5                   10                  15

Gly

<210> SEQ ID NO 5
<211> LENGTH: 16
<212> TYPE: PRT
<213> ORGANISM: Artificial Sequence
<220> FEATURE:
<223> OTHER INFORMATION: Description of the artificial sequence: amino
      acid sequence of HCDR3 of CSPG5115

<400> SEQUENCE: 5

Gly Gly Val Cys Ser Gly Asp Lys Cys Tyr Tyr Tyr Gly Met Asp Val
1               5                   10                  15

<210> SEQ ID NO 6
<211> LENGTH: 315
<212> TYPE: DNA
<213> ORGANISM: Artificial Sequence
<220> FEATURE:
<223> OTHER INFORMATION: Description of the artificial sequence: base
      sequence of VL of CSPG5115 excluding signal sequence

<400> SEQUENCE: 6
cagtctgtgt tgactcagcc accctcagtg tccgtgtccc caggacagac agccagcatc      60
acctgttctg gagataaatt gggggataaa tatagttggt ggtatcaaca gaagcctggc     120
cagtcccctc tattggtcat ccatcaagat aacaagcggc cctcagggat ccctgagcga     180
ttctctggct ccaactctgg gaacacagcc actctgacca tctcgggac ccaggctatg     240 gatgaggctg actattactg ccaggcgtgg gaccgcggcg tggtattcgg cggagggacc     300
aagctgaccg tccta                                                     315

<210> SEQ ID NO 7
```

-continued

```
<211> LENGTH: 105
<212> TYPE: PRT
<213> ORGANISM: Artificial Sequence
<220> FEATURE:
<223> OTHER INFORMATION: Description of the artificial sequence: amino
      acid sequence of VL of CSPG5115 excluding signal sequence

<400> SEQUENCE: 7

Gln Ser Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ser
            20                  25                  30

Trp Trp Tyr Gln Gln Lys Pro Gly Gln Ser Pro Leu Leu Val Ile His
        35                  40                  45

Gln Asp Asn Lys Arg Pro Ser Gly Ile Pro Glu Arg Phe Ser Gly Ser
    50                  55                  60

Asn Ser Gly Asn Thr Ala Thr Leu Thr Ile Val Gly Thr Gln Ala Met
65                  70                  75                  80

Asp Glu Ala Asp Tyr Tyr Cys Gln Ala Trp Asp Arg Gly Val Val Phe
                85                  90                  95

Gly Gly Gly Thr Lys Leu Thr Val Leu
            100                 105

<210> SEQ ID NO 8
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR1 of CSPG5115

<400> SEQUENCE: 8

Ser Gly Asp Lys Leu Gly Asp Lys Tyr Ser Trp
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5115

<400> SEQUENCE: 9

Gln Asp Asn Lys Arg Pro Ser
1               5

<210> SEQ ID NO 10
<211> LENGTH: 8
<212> TYPE: PRT
<213> ORGANISM: Artificial Sequence
<220> FEATURE:
<223> OTHER INFORMATION: Description of the artificial sequence: amino
      acid sequence of LCDR3 of CSPG5115

<400> SEQUENCE: 10

Gln Ala Trp Asp Arg Gly Val Val
1               5

<210> SEQ ID NO 11
<211> LENGTH: 345
<212> TYPE: DNA
<213> ORGANISM: Artificial Sequence
<220> FEATURE:
<223> OTHER INFORMATION: Description of the artificial sequence: base
``` sequence of VH of CSPG5120 excluding signal sequence

<400> SEQUENCE: 11

```
gaggtgcagc tggtgcagtc tgggggaggc ttggtccagc ctggggggtc cctcagactc    60
tcctgtgcag cctctggatt cacctttagt aactactgga tgacctgggt ccgccaggct   120
ccaggggagg ggccggagtg ggtggccaac ataaatcaag atggaagtca gaaatactat   180
gtggactctg tgaagggccg attcaccatc tccagagaca cgccaagaa ctcactgaat   240
ctgcaaatga acaacctgag agccgaggac acggccctat attactgtgc gaaaagtaat   300
gccatggacg tctggggcca agggaccctg gtcaccgtct cctca                   345
```

<210> SEQ ID NO 12
<211> LENGTH: 115
<212> TYPE: PRT
<213> ORGANISM: Artificial Sequence
<220> FEATURE:
<223> OTHER INFORMATION: Description of the artificial sequence: amino acid sequence of VH of CSPG5120 excluding signal sequence

<400> SEQUENCE: 12

Glu Val Gln Leu Val Gln Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Thr Trp Val Arg Gln Ala Pro Gly Glu Gly Pro Glu Trp Val
        35                  40                  45

Ala Asn Ile Asn Gln Asp Gly Ser Gln Lys Tyr Tyr Val Asp Ser Val
    50                  55                  60

Lys Gly Arg Phe Thr Ile Ser Arg Asp Asn Ala Lys Asn Ser Leu Asn
65                  70                  75                  80

Leu Gln Met Asn Asn Leu Arg Ala Glu Asp Thr Ala Leu Tyr Tyr Cys
                85                  90                  95

Ala Lys Ser Asn Ala Met Asp Val Trp Gly Gln Gly Thr Leu Val Thr
            100                 105                 110

Val Ser Ser
        115

<210> SEQ ID NO 13
<211> LENGTH: 5
<212> TYPE: PRT
<213> ORGANISM: Artificial Sequence
<220> FEATURE:
<223> OTHER INFORMATION: Description of the artificial sequence: amino acid sequence of HCDR1 of CSPG5120

<400> SEQUENCE: 13

Asn Tyr Trp Met Thr
1               5

<210> SEQ ID NO 14
<211> LENGTH: 17
<212> TYPE: PRT
<213> ORGANISM: Artificial Sequence
<220> FEATURE:
<223> OTHER INFORMATION: Description of the artificial sequence: amino acid sequence of HCDR2 of CSPG5120

<400> SEQUENCE: 14

Asn Ile Asn Gln Asp Gly Ser Gln Lys Tyr Tyr Val Asp Ser Val Lys
1               5                   10                  15

Gly

<210> SEQ ID NO 15
<211> LENGTH: 6
<212> TYPE: PRT
<213> ORGANISM: Artificial Sequence
<220> FEATURE:
<223> OTHER INFORMATION: Description of the artificial sequence: amino
      acid sequence of HCDR3 of CSPG5120

<400> SEQUENCE: 15

Ser Asn Ala Met Asp Val
1               5

<210> SEQ ID NO 16
<211> LENGTH: 336
<212> TYPE: DNA
<213> ORGANISM: Artificial Sequence
<220> FEATURE:
<223> OTHER INFORMATION: Description of the artificial sequence: base
      sequence of VL of CSPG5120 excluding signal sequence

<400> SEQUENCE: 16
gatattgtga tgactcagtc tccactctcc ctgcccgtca ctcctggaga gccggcctcc      60
atctcctgca ggtccagtga gagcctcctg catagtaatg gatacaacta cttgaattgg     120
tacctgcaga agccagggca gtctccacaa ctcctgatct atttgggttc gcatcgggcc     180
tccggggtcc ctgacaggct cagtggcagt ggatcagaca cagatttcac attgaaaatc     240
agcagagtgg aggctgagga tgttggcatt tattactgta tgcaaggtcg acagactccc     300
atcactttcg gcggagggac caagctggag atcaaa                              336

<210> SEQ ID NO 17
<211> LENGTH: 112
<212> TYPE: PRT
<213> ORGANISM: Artificial Sequence
<220> FEATURE:
<223> OTHER INFORMATION: Description of the artificial sequence: amino
      acid sequence of VL of CSPG5120 excluding signal sequence

<400> SEQUENCE: 17

Asp Ile Val Met Thr Gln Ser Pro Leu Ser Leu Pro Val Thr Pro Gly
1               5                   10                  15

Glu Pro Ala Ser Ile Ser Cys Arg Ser Ser Glu Ser Leu Leu His Ser
            20                  25                  30

Asn Gly Tyr Asn Tyr Leu Asn Trp Tyr Leu Gln Lys Pro Gly Gln Ser
        35                  40                  45

Pro Gln Leu Leu Ile Tyr Leu Gly Ser His Arg Ala Ser Gly Val Pro
    50                  55                  60

Asp Arg Leu Ser Gly Ser Gly Ser Asp Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Arg Gln Thr Pro Ile Thr Phe Gly Gly Gly Thr Lys Leu Glu Ile Lys
            100                 105                 110

<210> SEQ ID NO 18
<211> LENGTH: 16
<212> TYPE: PRT
<213> ORGANISM: Artificial Sequence
<220> FEATURE:
<223> OTHER INFORMATION: Description of the artificial sequence: amino
      acid sequence of LCDR1 of CSPG5120

```
<400> SEQUENCE: 18

Arg Ser Ser Glu Ser Leu Leu His Ser Asn Gly Tyr Asn Tyr Leu Asn
1               5                   10                  15

<210> SEQ ID NO 19
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5120

<400> SEQUENCE: 19

Leu Gly Ser His Arg Ala Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CSPG5120

<400> SEQUENCE: 20

Met Gln Gly Arg Gln Thr Pro Ile Thr
1               5

<210> SEQ ID NO 21
<211> LENGTH: 351
<212> TYPE: DNA
<213> ORGANISM: Artificial Sequence
<220> FEATURE:
<223> OTHER INFORMATION: Description of the artificial sequence: base
      sequence of VH of CSPG5168 excluding signal sequence

<400> SEQUENCE: 21
gaggtgcagc tggtggagac tgggggagcc ttggttcagc ctggagggtc actgagactc      60
tcctgtgcag gctctggatt tatcttcagt aaatatgaaa tgacctgggt ccgccaggct     120
ccagggaagg ggctggagtg gtctcaact atcggtagtc ttggtctgaa gacctttac      180 acagactccg taagggccg gttcaccacc tccagagaca attccaggga cactttattt     240
ctgcaaatgg acaacctgag agtcgaggac acggccatat atttctgtgt gaaaggcggc     300
atacgtcggg cagattactg gggcaaggga accctggtga ccgtctcctc a              351

<210> SEQ ID NO 22
<211> LENGTH: 117
<212> TYPE: PRT
<213> ORGANISM: Artificial Sequence
<220> FEATURE:
<223> OTHER INFORMATION: Description of the artificial sequence: amino
      acid sequence of VH of CSPG5168 excluding signal sequence

<400> SEQUENCE: 22

Glu Val Gln Leu Val Glu Thr Gly Gly Ala Leu Val Gln Pro Gly Gly
1               5                   10                  15

Ser Leu Arg Leu Ser Cys Ala Gly Ser Gly Phe Ile Phe Ser Lys Tyr
            20                  25                  30

Glu Met Thr Trp Val Arg Gln Ala Pro Gly Lys Gly Leu Glu Trp Val
        35                  40                  45

Ser Thr Ile Gly Ser Leu Gly Leu Lys Thr Phe Tyr Thr Asp Ser Val
    50                  55                  60
```

```
Lys Gly Arg Phe Thr Thr Ser Arg Asp Asn Ser Arg Asp Thr Leu Phe
 65                  70                  75                  80

Leu Gln Met Asp Asn Leu Arg Val Glu Asp Thr Ala Ile Tyr Phe Cys
                 85                  90                  95

Val Lys Gly Gly Ile Arg Arg Ala Asp Tyr Trp Gly Lys Gly Thr Leu
            100                 105                 110

Val Thr Val Ser Ser
        115

<210> SEQ ID NO 23
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5168

<400> SEQUENCE: 23

Lys Tyr Glu Met Thr
1               5

<210> SEQ ID NO 24
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5168

<400> SEQUENCE: 24

Thr Ile Gly Ser Leu Gly Leu Lys Thr Phe Tyr Thr Asp Ser Val Lys
1               5                   10                  15

Gly

<210> SEQ ID NO 25
<211> LENGTH: 8
<212> TYPE: PRT
<213> ORGANISM: Artificial Sequence
<220> FEATURE:
<223> OTHER INFORMATION: Description of the artificial sequence: amino
      acid sequence of HCDR3 of CSPG5168

<400> SEQUENCE: 25

Gly Gly Ile Arg Arg Ala Asp Tyr
1               5

<210> SEQ ID NO 26
<211> LENGTH: 321
<212> TYPE: DNA
<213> ORGANISM: Artificial Sequence
<220> FEATURE:
<223> OTHER INFORMATION: Description of the artificial sequence: base
      sequence of VL of CSPG5168 excluding signal sequence

<400> SEQUENCE: 26
gaaatagtga tgacacagtc tccagccacc ctgtctttgt ctccagggga aagagccacc      60
ctctcctgca gggccagtca gagtgttagc agctacttag cctggtacca acagaaacct     120
ggccaggctc ccaggctcct catctatgat gcatccaaca gggccactgg catcccagcc     180
aggttcagtg gcagtgggtc tgggacagac ttcactctca ccatcagcag cctagagcct     240
gaagattttg cagtttatta ctgtcagcag cgtagcaact ggcctctcac tttcggcgga     300
gggaccaagg tggaaatcaa a                                                321
```

<210> SEQ ID NO 27
<211> LENGTH: 107
<212> TYPE: PRT
<213> ORGANISM: Artificial Sequence
<220> FEATURE:
<223> OTHER INFORMATION: Description of the artificial sequence: amino
      acid sequence of VL of CSPG5168 excluding signal sequence

<400> SEQUENCE: 27

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Leu
                85                  90                  95

Thr Phe Gly Gly Gly Thr Lys Val Glu Ile Lys
            100                 105

<210> SEQ ID NO 28
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR1 of CSPG5168

<400> SEQUENCE: 28

Arg Ala Ser Gln Ser Val Ser Ser Tyr Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5168

<400> SEQUENCE: 29

Asp Ala Ser Asn Arg Ala Thr
1               5

<210> SEQ ID NO 30
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CSPG5168

<400> SEQUENCE: 30

Gln Gln Arg Ser Asn Trp Pro Leu Thr
1               5

<210> SEQ ID NO 31
<211> LENGTH: 348
<212> TYPE: DNA

<213> ORGANISM: Artificial Sequence
<220> FEATURE:
<223> OTHER INFORMATION: Description of the artificial sequence: base sequence of VH of CSPG5201 excluding signal sequence

<400> SEQUENCE: 31

```
gaagtccaac tgctggaatc gggtggtggt ctggtgcaac cgggcggctc gctgcgtctg    60
tcatgtgctg cgtcgggctt tacctttagc tcttatgcaa tgtcctgggt cgtcaggca    120 ccgggtaaag gtctggaatg ggttagcgca attagtggct ccggcggtag cacctattac    180
gccgattctg ttaaaggtcg ttttaccatc tcacgcgaca actcgaaaaa tacgctgtat    240
ctgcagatga acagtctgcg cgcagaagat accgctgtct attactgcgc aaaaaagtgg    300
aatcttttcg actactgggg ccaaggtacg ctggttacgg ttagcagc                 348
```

<210> SEQ ID NO 32
<211> LENGTH: 116
<212> TYPE: PRT
<213> ORGANISM: Artificial Sequence
<220> FEATURE:
<223> OTHER INFORMATION: Description of the artificial sequence: amino acid sequence of VH of CSPG5201 excluding signal sequence

<400> SEQUENCE: 32

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Trp Asn Leu Phe Asp Tyr Trp Gly Gln Gly Thr Leu Val
            100                 105                 110

Thr Val Ser Ser
        115
```

<210> SEQ ID NO 33
<211> LENGTH: 5
<212> TYPE: PRT
<213> ORGANISM: Artificial Sequence
<220> FEATURE:
<223> OTHER INFORMATION: Description of the artificial sequence: amino acid sequence of HCDR1 of CSPG5201

<400> SEQUENCE: 33

```
Ser Tyr Ala Met Ser
1               5
```

<210> SEQ ID NO 34
<211> LENGTH: 17
<212> TYPE: PRT
<213> ORGANISM: Artificial Sequence
<220> FEATURE:
<223> OTHER INFORMATION: Description of the artificial sequence: amino acid sequence of HCDR2 of CSPG5201

<400> SEQUENCE: 34

```
Ala Ile Ser Gly Ser Gly Gly Ser Thr Tyr Tyr Ala Asp Ser Val Lys
1               5                   10                  15

Gly
```

<210> SEQ ID NO 35
<211> LENGTH: 7
<212> TYPE: PRT
<213> ORGANISM: Artificial Sequence
<220> FEATURE:
<223> OTHER INFORMATION: Description of the artificial sequence: amino
      acid sequence of HCDR3 of CSPG5201

<400> SEQUENCE: 35

```
Lys Trp Asn Leu Phe Asp Tyr
1               5
```

<210> SEQ ID NO 36
<211> LENGTH: 333
<212> TYPE: DNA
<213> ORGANISM: Artificial Sequence
<220> FEATURE:
<223> OTHER INFORMATION: Description of the artificial sequence: base
      sequence of VL of CSPG5201 excluding signal sequence

<400> SEQUENCE: 36

```
caatcggctc tgacccaacc ggcaagtgtc tctggttctc cgggtcaatc aatcacgatc      60
tcctgtacgg gtacctctac ggatgtcaac ggctataatt acgtcagctg gtatcagcaa     120
tacgcgggta agccccgaa actgattatc tttgatgtta gtaaacgtcc gtcgggcgtt      180
agcaaccgct tcagtggctc caaatcaggt gacaccgcct ctctgacgat ttccggtctg     240
caggcagaag atgaagctga ctatcattgc agctcttacc gtaggctgcg gttgcctgtc     300
ctgtttggtg gtggcacgaa actgaccgtt ctg                                  333
```

<210> SEQ ID NO 37
<211> LENGTH: 111
<212> TYPE: PRT
<213> ORGANISM: Artificial Sequence
<220> FEATURE:
<223> OTHER INFORMATION: Description of the artificial sequence: amino
      acid sequence of VL of CSPG5201 excluding signal sequence

<400> SEQUENCE: 37

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Thr Asp Val Asn Gly Tyr
            20                  25                  30

Asn Tyr Val Ser Trp Tyr Gln Gln Tyr Ala Gly Lys Ala Pro Lys Leu
        35                  40                  45

Ile Ile Phe Asp Val Ser Lys Arg Pro Ser Gly Val Ser Asn Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr His Cys Ser Ser Tyr Arg Arg Leu
                85                  90                  95

Arg Leu Pro Val Leu Phe Gly Gly Gly Thr Lys Leu Thr Val Leu
            100                 105                 110
```

<210> SEQ ID NO 38
<211> LENGTH: 14
<212> TYPE: PRT
<213> ORGANISM: Artificial Sequence

```
<220> FEATURE:
<223> OTHER INFORMATION: Description of the artificial sequence: amino
      acid sequence of LCDR1 of CSPG5201

<400> SEQUENCE: 38

Thr Gly Thr Ser Thr Asp Val Asn Gly Tyr Asn Tyr Val Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5201

<400> SEQUENCE: 39

Asp Val Ser Lys Arg Pro Ser
1               5

<210> SEQ ID NO 40
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR3 of CSPG5201

<400> SEQUENCE: 40

Ser Ser Tyr Arg Arg Leu Arg Leu Pro Val Leu
1               5                   10

<210> SEQ ID NO 41
<211> LENGTH: 354
<212> TYPE: DNA
<213> ORGANISM: Artificial Sequence
<220> FEATURE:
<223> OTHER INFORMATION: Description of the artificial sequence: base
      sequence of VH of CSPG5202 excluding signal sequence

<400> SEQUENCE: 41
gaagtccaac tgctggaatc gggtggtggt ctggtgcaac cgggcggctc gctgcgtctg      60
tcatgtgctg cgtcgggctt tacctttagc tcttatgcaa tgtcctgggt gcgtcaggca     120
ccgggtaaag gtctggaatg ggttagcgca attagtggct ccggcggtag cacctattac     180
gccgattctg ttaaaggtcg ttttaccatc tcacgcgaca actcgaaaaa tacgctgtat     240
ctgcagatga acagtctgcg cgcagaagat accgctgtct attactgcgc aaaaattagt     300
aagacgcagg ggttcgacta ctggggccaa ggtacgctgg ttacggttag cagc           354

<210> SEQ ID NO 42
<211> LENGTH: 118
<212> TYPE: PRT
<213> ORGANISM: Artificial Sequence
<220> FEATURE:
<223> OTHER INFORMATION: Description of the artificial sequence: amino
      acid sequence of VH of CSPG5202 excluding signal sequence

<400> SEQUENCE: 42

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45
```

```
Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ile Ser Lys Thr Gln Gly Phe Asp Tyr Trp Gly Gln Gly Thr
            100                 105                 110

Leu Val Thr Val Ser Ser
            115
```

<210> SEQ ID NO 43
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5202

<400> SEQUENCE: 43

```
Ser Tyr Ala Met Ser
1               5
```

<210> SEQ ID NO 44
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5202

<400> SEQUENCE: 44

```
Ala Ile Ser Gly Ser Gly Gly Ser Thr Tyr Tyr Ala Asp Ser Val Lys
1               5                   10                  15

Gly
```

<210> SEQ ID NO 45
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CSPG5202

<400> SEQUENCE: 45

```
Ile Ser Lys Thr Gln Gly Phe Asp Tyr
1               5
```

<210> SEQ ID NO 46
<211> LENGTH: 339
<212> TYPE: DNA
<213> ORGANISM: Artificial Sequence
<220> FEATURE:
<223> OTHER INFORMATION: Description of the artificial sequence: base
      sequence of VL of CSPG5202 excluding signal sequence

<400> SEQUENCE: 46

```
gacatcgtca tgacgcaaag tccggattca ctggctgtta gtctgggcga acgtgctacg      60
atcaactgta atcctctca aagtgtgctg tatagctcta acaataaaaa ctatctggca     120
tggtaccagc aaaaaccggg tcagccgccg aaactgctga tttactgggc atctacccgt    180
gaatccggtg tcccggatcg cttttcaggc tcgggtagcg gcacggactt cacccctgacg   240
```

```
atcagttccc tgcaagcgga agatgtggcc gtttattact gtcaacaaag tcggacgcgg    300
aggcctacgt tcggtcaagg caccaaagtg gaaatcaaa                           339
```

<210> SEQ ID NO 47
<211> LENGTH: 113
<212> TYPE: PRT
<213> ORGANISM: Artificial Sequence
<220> FEATURE:
<223> OTHER INFORMATION: Description of the artificial sequence: amino acid sequence of VL of CSPG5202 excluding signal sequence

<400> SEQUENCE: 47

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Arg Thr Arg Arg Pro Thr Phe Gly Gln Gly Thr Lys Val Glu Ile
            100                 105                 110

Lys
```

<210> SEQ ID NO 48
<211> LENGTH: 17
<212> TYPE: PRT
<213> ORGANISM: Artificial Sequence
<220> FEATURE:
<223> OTHER INFORMATION: Description of the artificial sequence: amino acid sequence of LCDR1 of CSPG5202

<400> SEQUENCE: 48

```
Lys Ser Ser Gln Ser Val Leu Tyr Ser Ser Asn Asn Lys Asn Tyr Leu
1               5                   10                  15

Ala
```

<210> SEQ ID NO 49
<211> LENGTH: 7
<212> TYPE: PRT
<213> ORGANISM: Artificial Sequence
<220> FEATURE:
<223> OTHER INFORMATION: Description of the artificial sequence: amino acid sequence of LCDR2 of CSPG5202

<400> SEQUENCE: 49

```
Trp Ala Ser Thr Arg Glu Ser
1               5
```

<210> SEQ ID NO 50
<211> LENGTH: 9
<212> TYPE: PRT
<213> ORGANISM: Artificial Sequence
<220> FEATURE:
<223> OTHER INFORMATION: Description of the artificial sequence: amino acid sequence of LCDR3 of CSPG5202

<400> SEQUENCE: 50

Gln Gln Ser Arg Thr Arg Arg Pro Thr
1               5

<210> SEQ ID NO 51
<211> LENGTH: 354
<212> TYPE: DNA
<213> ORGANISM: Artificial Sequence
<220> FEATURE:
<223> OTHER INFORMATION: Description of the artificial sequence: base
      sequence of VH of CSPG5205 excluding signal sequence

<400> SEQUENCE: 51

```
gaagtccaac tgctggaatc gggtggtggt ctggtgcaac cgggcggctc gctgcgtctg      60
tcatgtgctg cgtcgggctt tacctttagc tcttatgcaa tgtcctgggt gcgtcaggca     120
ccgggtaaag gtctggaatg ggttagcgca attagtggct ccggcggtag caccttattac   180 gccgattctg ttaaaggtcg ttttaccatc tcacgcgaca actcgaaaaa tacgctgtat    240
ctgcagatga acagtctgcg cgcagaagat accgctgtct attactgcgc aaaaactaag    300
ccgaataatg ctttcgacta ctggggccaa ggtacgctgg ttacggttag cagc          354
```

<210> SEQ ID NO 52
<211> LENGTH: 118
<212> TYPE: PRT
<213> ORGANISM: Artificial Sequence
<220> FEATURE:
<223> OTHER INFORMATION: Description of the artificial sequence: amino
      acid sequence of VH of CSPG5205 excluding signal sequence

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Lys Pro Asn Asn Ala Phe Asp Tyr Trp Gly Gln Gly Thr
            100                 105                 110

Leu Val Thr Val Ser Ser
        115

<210> SEQ ID NO 53
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5205

<400> SEQUENCE: 53

Ser Tyr Ala Met Ser
1               5

<210> SEQ ID NO 54
<211> LENGTH: 17
<212> TYPE: PRT

```
<213> ORGANISM: Artificial Sequence
<220> FEATURE:
<223> OTHER INFORMATION: Description of the artificial sequence: amino
      acid sequence of HCDR2 of CSPG5205

<400> SEQUENCE: 54

Ala Ile Ser Gly Ser Gly Gly Ser Thr Tyr Tyr Ala Asp Ser Val Lys
1               5                   10                  15

Gly

<210> SEQ ID NO 55
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CSPG5205

<400> SEQUENCE: 55

Thr Lys Pro Asn Asn Ala Phe Asp Tyr
1               5

<210> SEQ ID NO 56
<211> LENGTH: 339
<212> TYPE: DNA
<213> ORGANISM: Artificial Sequence
<220> FEATURE:
<223> OTHER INFORMATION: Description of the artificial sequence: base
      sequence of VL of CSPG5205 excluding signal sequence

<400> SEQUENCE: 56
gacatcgtca tgacgcaaag tccggattca ctggctgtta gtctgggcga acgtgctacg      60
atcaactgta atcctctca aagtgtgctg tatagctcta acaataaaaa ctatctggca     120
tggtaccagc aaaaaccggg tcagccgccg aaactgctga tttactgggc atctacccgt     180
gaatccggtg tcccggatcg cttttcaggc tcgggtagcg gcacggactt caccctgacg     240
atcagttccc tgcaagcgga agatgtggcc gtttattact gtcaacaaac ggcgactcag     300
ccgcttacgt tcggtcaagg caccaaagtg gaaatcaaa                             339

<210> SEQ ID NO 57
<211> LENGTH: 113
<212> TYPE: PRT
<213> ORGANISM: Artificial Sequence
<220> FEATURE:
<223> OTHER INFORMATION: Description of the artificial sequence: amino
      acid sequence of VL of CSPG5205 excluding signal sequence

<400> SEQUENCE: 57

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Thr Ala Thr Gln Pro Leu Thr Phe Gly Gln Gly Thr Lys Val Glu Ile
```

Lys

<210> SEQ ID NO 58
<211> LENGTH: 17
<212> TYPE: PRT
<213> ORGANISM: Artificial Sequence
<220> FEATURE:
<223> OTHER INFORMATION: Description of the artificial sequence: amino
      acid sequence of LCDR1 of CSPG5205

<400> SEQUENCE: 58

Lys Ser Ser Gln Ser Val Leu Tyr Ser Ser Asn Asn Lys Asn Tyr Leu
1               5                   10                  15

Ala

<210> SEQ ID NO 59
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5205

<400> SEQUENCE: 59

Trp Ala Ser Thr Arg Glu Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CSPG5205

<400> SEQUENCE: 60

Gln Gln Thr Ala Thr Gln Pro Leu Thr
1               5

<210> SEQ ID NO 61
<211> LENGTH: 351
<212> TYPE: DNA
<213> ORGANISM: Artificial Sequence
<220> FEATURE:
<223> OTHER INFORMATION: Description of the artificial sequence: base
      sequence of VH of CSPG5206 excluding signal sequence

<400> SEQUENCE: 61
gaagtccaac tgctggaatc gggtggtggt ctggtgcaac cgggcggctc gctgcgtctg      60
tcatgtgctg cgtcgggctt tacctttagc tcttatgcaa tgtcctgggt gcgtcaggca     120
ccgggtaaag gtctggaatg ggttagcgca attagtggct ccggcggtag cacctattac     180
gccgattctg ttaaaggtcg ttttaccatc tcacgcgaca actcgaaaaa tacgctgtat     240
ctgcagatga acagtctgcg cgcagaagat accgctgtct attactgcgc aaaaaagcgg     300
tcgctggcgt tcgactactg gggccaaggt acgctggtta cggttagcag c              351

<210> SEQ ID NO 62
<211> LENGTH: 117
<212> TYPE: PRT
<213> ORGANISM: Artificial Sequence
<220> FEATURE:
<223> OTHER INFORMATION: Description of the artificial sequence: amino
      acid sequence of VH of CSPG5206 excluding signal sequence

<400> SEQUENCE: 62

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Lys Arg Ser Leu Ala Phe Asp Tyr Trp Gly Gln Gly Thr Leu
            100                 105                 110

Val Thr Val Ser Ser
        115

<210> SEQ ID NO 63
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5206

<400> SEQUENCE: 63

Ser Tyr Ala Met Ser
1               5

<210> SEQ ID NO 64
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5206

<400> SEQUENCE: 64

Ala Ile Ser Gly Ser Gly Gly Ser Thr Tyr Tyr Ala Asp Ser Val Lys
1               5                   10                  15

Gly

<210> SEQ ID NO 65
<211> LENGTH: 8
<212> TYPE: PRT
<213> ORGANISM: Artificial Sequence
<220> FEATURE:
<223> OTHER INFORMATION: Description of the artificial sequence: amino
      acid sequence of HCDR3 of CSPG5206

<400> SEQUENCE: 65

Lys Arg Ser Leu Ala Phe Asp Tyr
1               5

<210> SEQ ID NO 66
<211> LENGTH: 333
<212> TYPE: DNA
<213> ORGANISM: Artificial Sequence
<220> FEATURE:
<223> OTHER INFORMATION: Description of the artificial sequence: base
      sequence of VL of CSPG5206 excluding signal sequence

<400> SEQUENCE: 66

```
caatcggctc tgacccaacc ggcaagtgtc tctggttctc cgggtcaatc aatcacgatc    60
tcctgtacgg gtacctctac ggatgtcaac ggctataatt acgtcagctg gtatcagcaa   120
tacgcgggta aagccccgaa actgattatc tttgatgtta gtaaacgtcc gtcgggcgtt   180
agcaaccgct tcagtggctc caaatcaggt gacaccgcct ctctgacgat ttccggtctg   240
caggcagaag atgaagctga ctatcattgc agctcttaca atcgtaagag gccgccggtc   300
ctgtttggtg gtggcacgaa actgaccgtt ctg                                333
```

<210> SEQ ID NO 67
<211> LENGTH: 111
<212> TYPE: PRT
<213> ORGANISM: Artificial Sequence
<220> FEATURE:
<223> OTHER INFORMATION: Description of the artificial sequence: amino acid sequence of VL of CSPG5206 excluding signal sequence

<400> SEQUENCE: 67

```
Gln Ser Ala Leu Thr Gln Pro Ala Ser Val Ser Gly Ser Pro Gly Gln
1               5                   10                  15

Ser Ile Thr Ile Ser Cys Thr Gly Thr Ser Thr Asp Val Asn Gly Tyr
            20                  25                  30

Asn Tyr Val Ser Trp Tyr Gln Gln Tyr Ala Gly Lys Ala Pro Lys Leu
        35                  40                  45

Ile Ile Phe Asp Val Ser Lys Arg Pro Ser Gly Val Ser Asn Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr His Cys Ser Ser Tyr Asn Arg Lys
                85                  90                  95

Arg Pro Pro Val Leu Phe Gly Gly Gly Thr Lys Leu Thr Val Leu
            100                 105                 110
```

<210> SEQ ID NO 68
<211> LENGTH: 14
<212> TYPE: PRT
<213> ORGANISM: Artificial Sequence
<220> FEATURE:
<223> OTHER INFORMATION: Description of the artificial sequence: amino acid sequence of LCDR1 of CSPG5206

<400> SEQUENCE: 68

```
Thr Gly Thr Ser Thr Asp Val Asn Gly Tyr Asn Tyr Val Ser
1               5                   10
```

<210> SEQ ID NO 69
<211> LENGTH: 7
<212> TYPE: PRT
<213> ORGANISM: Artificial Sequence
<220> FEATURE:
<223> OTHER INFORMATION: Description of the artificial sequence: amino acid sequence of LCDR2 of CSPG5206

<400> SEQUENCE: 69

```
Asp Val Ser Lys Arg Pro Ser
1               5
```

<210> SEQ ID NO 70
<211> LENGTH: 11
<212> TYPE: PRT

<213> ORGANISM: Artificial Sequence
<220> FEATURE:
<223> OTHER INFORMATION: Description of the artificial sequence: amino
      acid sequence of LCDR3 of CSPG5206

<400> SEQUENCE: 70

Ser Ser Tyr Asn Arg Lys Arg Pro Pro Val Leu
1               5                   10

<210> SEQ ID NO 71
<211> LENGTH: 354
<212> TYPE: DNA
<213> ORGANISM: Artificial Sequence
<220> FEATURE:
<223> OTHER INFORMATION: Description of the artificial sequence: base
      sequence of VH of CSPG5207 excluding signal sequence

<400> SEQUENCE: 71
gaagtccaac tgctggaatc gggtggtggt ctggtgcaac cgggcggctc gctgcgtctg     60
tcatgtgctg cgtcgggctt tacctttagc tcttatgcaa tgtcctgggt gcgtcaggca    120
ccgggtaaag gtctggaatg ggttagcgca attagtggct ccggcggtag cacctattac    180
gccgattctg ttaaaggtcg ttttaccatc tcacgcgaca actcgaaaaa tacgctgtat    240
ctgcagatga acagtctgcg cgcagaagat accgctgtct attactgcgc aaaatgggct    300
cggacttcgc ctttcgacta ctggggccaa ggtacgctgg ttacggttag cagc          354

<210> SEQ ID NO 72
<211> LENGTH: 118
<212> TYPE: PRT
<213> ORGANISM: Artificial Sequence
<220> FEATURE:
<223> OTHER INFORMATION: Description of the artificial sequence: amino
      acid sequence of VH of CSPG5207 excluding signal sequence

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Ala Arg Thr Ser Pro Phe Asp Tyr Trp Gly Gln Gly Thr
            100                 105                 110

Leu Val Thr Val Ser Ser
        115

<210> SEQ ID NO 73
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5207

<400> SEQUENCE: 73

Ser Tyr Ala Met Ser
1               5

<210> SEQ ID NO 74
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5207

<400> SEQUENCE: 74

Ala Ile Ser Gly Ser Gly Gly Ser Thr Tyr Tyr Ala Asp Ser Val Lys
1               5                   10                  15

Gly

<210> SEQ ID NO 75
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CSPG5207

<400> SEQUENCE: 75

Trp Ala Arg Thr Ser Pro Phe Asp Tyr
1               5

<210> SEQ ID NO 76
<211> LENGTH: 333
<212> TYPE: DNA
<213> ORGANISM: Artificial Sequence
<220> FEATURE:
<223> OTHER INFORMATION: Description of the artificial sequence: base
      sequence of VL of CSPG5207 excluding signal sequence

<400> SEQUENCE: 76
caatcggctc tgacccaacc ggcaagtgtc tctggttctc cgggtcaatc aatcacgatc      60
tcctgtacgg gtacctctac ggatgtcaac ggctataatt acgtcagctg gtatcagcaa     120
tacgcgggta agccccgaa actgattatc tttgatgtta gtaaacgtcc gtcgggcgtt      180
agcaaccgct tcagtggctc caaatcaggt gacaccgcct ctctgacgat ttccggtctg     240
caggcagaag atgaagctga ctatcattgc agctcttaca cgccgagtag ggcgcgggtc     300
ctgtttggtg gtggcacgaa actgaccgtt ctg                                  333

<210> SEQ ID NO 77
<211> LENGTH: 111
<212> TYPE: PRT
<213> ORGANISM: Artificial Sequence
<220> FEATURE:
<223> OTHER INFORMATION: Description of the artificial sequence: amino
      acid sequence of VL of CSPG5207 excluding signal sequence

<400> SEQUENCE: 77

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Thr Asp Val Asn Gly Tyr
                20                  25                  30

Asn Tyr Val Ser Trp Tyr Gln Gln Tyr Ala Gly Lys Ala Pro Lys Leu
            35                  40                  45

Ile Ile Phe Asp Val Ser Lys Arg Pro Ser Gly Val Ser Asn Arg Phe
        50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr His Cys Ser Ser Tyr Thr Pro Ser
                85                  90                  95

Arg Ala Arg Val Leu Phe Gly Gly Gly Thr Lys Leu Thr Val Leu
            100                 105                 110

<210> SEQ ID NO 78
<211> LENGTH: 14
<212> TYPE: PRT
<213> ORGANISM: Artificial Sequence
<220> FEATURE:
<223> OTHER INFORMATION: Description of the artificial sequence: amino
      acid sequence of LCDR1 of CSPG5207

<400> SEQUENCE: 78

Thr Gly Thr Ser Thr Asp Val Asn Gly Tyr Asn Tyr Val Ser
1               5                   10

<210> SEQ ID NO 79
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5207

<400> SEQUENCE: 79

Asp Val Ser Lys Arg Pro Ser
1               5

<210> SEQ ID NO 80
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR3 of CSPG5207

<400> SEQUENCE: 80

Ser Ser Tyr Thr Pro Ser Arg Ala Arg Val Leu
1               5                   10

<210> SEQ ID NO 81
<211> LENGTH: 354
<212> TYPE: DNA
<213> ORGANISM: Artificial Sequence
<220> FEATURE:
<223> OTHER INFORMATION: Description of the artificial sequence: base
      sequence of VH of CSPG5208 excluding signal sequence

<400> SEQUENCE: 81
gaagtccaac tgctggaatc gggtggtggt ctggtgcaac cgggcggctc gctgcgtctg      60
tcatgtgctg cgtcgggctt acctttagc tcttatgcaa tgtcctgggt cgtcaggca      120 ccgggtaaag gtctggaatg ggttagcgca attagtggct ccggcggtag cacctattac      180
gccgattctg ttaaaggtcg ttttaccatc tcacgcgaca actcgaaaaa tacgctgtat      240
ctgcagatga acagtctgcg cgcagaagat accgctgtct attactgcgc aaaatatacg      300
agggagggga gtttcgacta ctggggccaa ggtacgctgg ttacggttag cagc            354

<210> SEQ ID NO 82
<211> LENGTH: 118
<212> TYPE: PRT
<213> ORGANISM: Artificial Sequence -continued

```
<220> FEATURE:
<223> OTHER INFORMATION: Description of the artificial sequence: amino
      acid sequence of VH of CSPG5208 excluding signal sequence

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Tyr Thr Arg Glu Gly Ser Phe Asp Tyr Trp Gly Gln Gly Thr
            100                 105                 110

Leu Val Thr Val Ser Ser
        115

<210> SEQ ID NO 83
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5208

<400> SEQUENCE: 83

Ser Tyr Ala Met Ser
1               5

<210> SEQ ID NO 84
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5208

<400> SEQUENCE: 84

Ala Ile Ser Gly Ser Gly Gly Ser Thr Tyr Tyr Ala Asp Ser Val Lys
1               5                   10                  15

Gly

<210> SEQ ID NO 85
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CSPG5208

<400> SEQUENCE: 85

Tyr Thr Arg Glu Gly Ser Phe Asp Tyr
1               5

<210> SEQ ID NO 86
<211> LENGTH: 339
<212> TYPE: DNA
<213> ORGANISM: Artificial Sequence
```

```
<220> FEATURE:
<223> OTHER INFORMATION: Description of the artificial sequence: base
      sequence of VL of CSPG5208 excluding signal sequence

<400> SEQUENCE: 86
gacatcgtca tgacgcaaag tccggattca ctggctgtta gtctgggcga acgtgctacg    60
atcaactgta atcctctca aagtgtgctg tatagctcta acaataaaaa ctatctggca   120
tggtaccagc aaaaaccggg tcagccgccg aaactgctga tttactgggc atctacccgt   180
gaatccggtg tcccggatcg cttttcaggc tcgggtagcg gcacggactt caccctgacg   240
atcagttccc tgcaagcgga agatgtggcc gtttattact gtcaacaagc gctggagcgg   300
gcgccgacgt tcggtcaagg caccaaagtg gaaatcaaa                          339

<210> SEQ ID NO 87
<211> LENGTH: 113
<212> TYPE: PRT
<213> ORGANISM: Artificial Sequence
<220> FEATURE:
<223> OTHER INFORMATION: Description of the artificial sequence: amino
      acid sequence of VL of CSPG5208 excluding signal sequence

<400> SEQUENCE: 87

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ala Leu Glu Arg Ala Pro Thr Phe Gly Gln Gly Thr Lys Val Glu Ile
            100                 105                 110

Lys

<210> SEQ ID NO 88
<211> LENGTH: 17
<212> TYPE: PRT
<213> ORGANISM: Artificial Sequence
<220> FEATURE:
<223> OTHER INFORMATION: Description of the artificial sequence: amino
      acid sequence of LCDR1 of CSPG5208

<400> SEQUENCE: 88

Lys Ser Ser Gln Ser Val Leu Tyr Ser Ser Asn Asn Lys Asn Tyr Leu
1               5                   10                  15

Ala

<210> SEQ ID NO 89
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5208

<400> SEQUENCE: 89
```

Trp Ala Ser Thr Arg Glu Ser
1               5

<210> SEQ ID NO 90
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CSPG5208

<400> SEQUENCE: 90

Gln Gln Ala Leu Glu Arg Ala Pro Thr
1               5

<210> SEQ ID NO 91
<211> LENGTH: 354
<212> TYPE: DNA
<213> ORGANISM: Artificial Sequence
<220> FEATURE:
<223> OTHER INFORMATION: Description of the artificial sequence: base
      sequence of VH of CSPG5214 excluding signal sequence

<400> SEQUENCE: 91
gaagtccaac tgctggaatc gggtggtggt ctggtgcaac cgggcggctc gctgcgtctg      60
tcatgtgctg cgtcgggctt tacctttagc tcttatgcaa tgtcctgggt cgtcaggca     120 ccgggtaaag gtctggaatg ggttagcgca attagtggct ccggcggtag cacctattac     180
gccgattctg ttaaaggtcg ttttaccatc tcacgcgaca actcgaaaaa tacgctgtat     240
ctgcagatga acagtctgcg cgcagaagat accgctgtct attactgcgc aaaaacgcgg     300
aggactacta tgttcgacta ctggggccaa ggtacgctgg ttacggttag cagc           354

<210> SEQ ID NO 92
<211> LENGTH: 118
<212> TYPE: PRT
<213> ORGANISM: Artificial Sequence
<220> FEATURE:
<223> OTHER INFORMATION: Description of the artificial sequence: amino
      acid sequence of VH of CSPG5214 excluding signal sequence

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Thr Arg Arg Thr Thr Met Phe Asp Tyr Trp Gly Gln Gly Thr
            100                 105                 110

Leu Val Thr Val Ser Ser
        115

<210> SEQ ID NO 93
<211> LENGTH: 5
<212> TYPE: PRT

```
<213> ORGANISM: Artificial Sequence
<220> FEATURE:
<223> OTHER INFORMATION: Description of the artificial sequence: amino
      acid sequence of HCDR1 of CSPG5214

<400> SEQUENCE: 93

Ser Tyr Ala Met Ser
1               5

<210> SEQ ID NO 94
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5214

<400> SEQUENCE: 94

Ala Ile Ser Gly Ser Gly Gly Ser Thr Tyr Tyr Ala Asp Ser Val Lys
1               5                  10                  15

Gly

<210> SEQ ID NO 95
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CSPG5214

<400> SEQUENCE: 95

Thr Arg Arg Thr Thr Met Phe Asp Tyr
1               5

<210> SEQ ID NO 96
<211> LENGTH: 333
<212> TYPE: DNA
<213> ORGANISM: Artificial Sequence
<220> FEATURE:
<223> OTHER INFORMATION: Description of the artificial sequence: base
      sequence of VL of CSPG5214 excluding signal sequence

<400> SEQUENCE: 96
caatcggctc tgacccaacc ggcaagtgtc tctggttctc cgggtcaatc aatcacgatc      60
tcctgtacgg gtacctctac ggatgtcaac ggctataatt acgtcagctg gtatcagcaa     120
tacgcgggta agccccgaa actgattatc tttgatgtta gtaaacgtcc gtcgggcgtt      180
agcaaccgct tcagtggctc caaatcaggt gacaccgcct ctctgacgat ttccggtctg     240
caggcagaag atgaagctga ctatcattgc agctcttaca atccgcatca ttcgggtgtc     300
ctgtttggtg gtggcacgaa actgaccgtt ctg                                  333

<210> SEQ ID NO 97
<211> LENGTH: 111
<212> TYPE: PRT
<213> ORGANISM: Artificial Sequence
<220> FEATURE:
<223> OTHER INFORMATION: Description of the artificial sequence: amino
      acid sequence of VL of CSPG5214 excluding signal sequence

<400> SEQUENCE: 97

Gln Ser Ala Leu Thr Gln Pro Ala Ser Val Ser Gly Ser Pro Gly Gln
1               5                  10                  15

Ser Ile Thr Ile Ser Cys Thr Gly Thr Ser Thr Asp Val Asn Gly Tyr
            20                  25                  30
```

```
Asn Tyr Val Ser Trp Tyr Gln Gln Tyr Ala Gly Lys Ala Pro Lys Leu
            35                  40                  45

Ile Ile Phe Asp Val Ser Lys Arg Pro Ser Gly Val Ser Asn Arg Phe
    50                  55                  60

Ser Gly Ser Lys Ser Gly Asp Thr Ala Ser Leu Thr Ile Ser Gly Leu
 65                  70                  75                  80

Gln Ala Glu Asp Glu Ala Asp Tyr His Cys Ser Ser Tyr Asn Pro His
                85                  90                  95

His Ser Gly Val Leu Phe Gly Gly Gly Thr Lys Leu Thr Val Leu
                100                 105                 110

<210> SEQ ID NO 98
<211> LENGTH: 14
<212> TYPE: PRT
<213> ORGANISM: Artificial Sequence
<220> FEATURE:
<223> OTHER INFORMATION: Description of the artificial sequence: amino
      acid sequence of LCDR1 of CSPG5214

<400> SEQUENCE: 98

Thr Gly Thr Ser Thr Asp Val Asn Gly Tyr Asn Tyr Val Ser
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5214

<400> SEQUENCE: 99

Asp Val Ser Lys Arg Pro Ser
1               5

<210> SEQ ID NO 100
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR3 of CSPG5214

<400> SEQUENCE: 100

Ser Ser Tyr Asn Pro His His Ser Gly Val Leu
1               5                   10

<210> SEQ ID NO 101
<211> LENGTH: 354
<212> TYPE: DNA
<213> ORGANISM: Artificial Sequence
<220> FEATURE:
<223> OTHER INFORMATION: Description of the artificial sequence: base
      sequence of VH of CSPG5219 excluding signal sequence

<400> SEQUENCE: 101
gaagtccaac tgctggaatc gggtggtggt ctggtgcaac gggcggctc gctgcgtctg      60 tcatgtgctg cgtcgggctt tacctttagc tcttatgcaa tgtcctgggt gcgtcaggca     120
ccgggtaaag gtctggaatg ggttagcgca attagtggct ccggcggtag cacctattac     180
gccgattctg ttaaaggtcg ttttaccatc tcacgcgaca actcgaaaaa tacgctgtat     240
ctgcagatga acagtctgcg cgcagaagat accgctgtct attactgcgc aaaaatgaat     300
```

```
tcgtggcgtg cgttcgacta ctggggccaa ggtacgctgg ttacggttag cagc          354
```

<210> SEQ ID NO 102
<211> LENGTH: 118
<212> TYPE: PRT
<213> ORGANISM: Artificial Sequence
<220> FEATURE:
<223> OTHER INFORMATION: Description of the artificial sequence: amino
      acid sequence of VH of CSPG5219 excluding signal sequence

<400> SEQUENCE: 102

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Met Asn Ser Trp Arg Ala Phe Asp Tyr Trp Gly Gln Gly Thr
            100                 105                 110

Leu Val Thr Val Ser Ser
        115

<210> SEQ ID NO 103
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5219

<400> SEQUENCE: 103

Ser Tyr Ala Met Ser
1               5

<210> SEQ ID NO 104
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5219

<400> SEQUENCE: 104

Ala Ile Ser Gly Ser Gly Gly Ser Thr Tyr Tyr Ala Asp Ser Val Lys
1               5                   10                  15

Gly

<210> SEQ ID NO 105
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CSPG5219

<400> SEQUENCE: 105

Met Asn Ser Trp Arg Ala Phe Asp Tyr

<210> SEQ ID NO 106
<211> LENGTH: 324
<212> TYPE: DNA
<213> ORGANISM: Artificial Sequence
<220> FEATURE:
<223> OTHER INFORMATION: Description of the artificial sequence: base
      sequence of VL of CSPG5219 excluding signal sequence

<400> SEQUENCE: 106

```
gaaatcgttc tgacgcaatc tccgggtacg ctgtccctga gtccgggcga acgtgcaacc      60
ctgtcctgtc gcgcttcgca atccgtgagc tctagttatc tggcatggta ccagcaaaaa     120
ccgggtcagg ctccgcgtct gctgatttat ggtgcatcct cacgtgcaac cggtatcccg     180
gatcgctttt cgggcagcgg ttctggcacg gacttcaccc tgacgatttc cgcctggaa      240 ccggaagatt ttgccgtgta ttactgtcaa caacttcgga ggaaggggtc gaccttcggt     300
cagggcagca aagtggaaat caaa                                             324
```

<210> SEQ ID NO 107
<211> LENGTH: 108
<212> TYPE: PRT
<213> ORGANISM: Artificial Sequence
<220> FEATURE:
<223> OTHER INFORMATION: Description of the artificial sequence: amino
      acid sequence of VL of CSPG5219 excluding signal sequence

<400> SEQUENCE: 107

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Arg Arg Lys Gly
                85                  90                  95

Ser Thr Phe Gly Gln Gly Ser Lys Val Glu Ile Lys
            100                 105

<210> SEQ ID NO 108
<211> LENGTH: 12
<212> TYPE: PRT
<213> ORGANISM: Artificial Sequence
<220> FEATURE:
<223> OTHER INFORMATION: Description of the artificial sequence: amino
      acid sequence of LCDR1 of CSPG5219

<400> SEQUENCE: 108

Arg Ala Ser Gln Ser Val Ser Ser Ser Tyr Leu Ala
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5219

<400> SEQUENCE: 109

Gly Ala Ser Ser Arg Ala Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CSPG5219

<400> SEQUENCE: 110

Gln Gln Leu Arg Arg Lys Gly Ser Thr
1               5

<210> SEQ ID NO 111
<211> LENGTH: 354
<212> TYPE: DNA
<213> ORGANISM: Artificial Sequence
<220> FEATURE:
<223> OTHER INFORMATION: Description of the artificial sequence: amino
      acid sequence of VH of CSPG5222 excluding signal sequence

<400> SEQUENCE: 111
gaagtccaac tgctggaatc gggtggtggt ctggtgcaac cgggcggctc gctgcgtctg      60
tcatgtgctg cgtcgggctt tacctttagc tcttatgcaa tgtcctgggt gcgtcaggca     120
ccgggtaaag gtctggaatg ggttagcgca attagtggct ccggcggtag cacctattac     180
gccgattctg ttaaaggtcg ttttaccatc tcacgcgaca actcgaaaaa tacgctgtat     240
ctgcagatga acagtctgcg cgcagaagat accgctgtct attactgcgc aaaaattaag     300
cagacggggg ctttcgacta ctgggccaa ggtacgctgg ttacggttag cagc            354

<210> SEQ ID NO 112
<211> LENGTH: 118
<212> TYPE: PRT
<213> ORGANISM: Artificial Sequence
<220> FEATURE:
<223> OTHER INFORMATION: Description of the artificial sequence: amino
      acid sequence of VH of CSPG5222 excluding signal sequence

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Lys Gln Thr Gly Ala Phe Asp Tyr Trp Gly Gln Gly Thr
            100                 105                 110

Leu Val Thr Val Ser Ser
        115

```
<210> SEQ ID NO 113
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5222

<400> SEQUENCE: 113

Ser Tyr Ala Met Ser
1               5

<210> SEQ ID NO 114
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5222

<400> SEQUENCE: 114

Ala Ile Ser Gly Ser Gly Gly Ser Thr Tyr Tyr Ala Asp Ser Val Lys
1               5                   10                  15

Gly

<210> SEQ ID NO 115
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CSPG5222

<400> SEQUENCE: 115

Ile Lys Gln Thr Gly Ala Phe Asp Tyr
1               5

<210> SEQ ID NO 116
<211> LENGTH: 339
<212> TYPE: DNA
<213> ORGANISM: Artificial Sequence
<220> FEATURE:
<223> OTHER INFORMATION: Description of the artificial sequence: base
      sequence of VL of CSPG5222 excluding signal sequence

<400> SEQUENCE: 116
gacatcgtca tgacgcaaag tccggattca ctggctgtta gtctgggcga acgtgctacg      60
atcaactgta atcctctca aagtgtgctg tatagctcta acaataaaaa ctatctggca      120
tggtaccagc aaaaaccggg tcagccgccg aaactgctga tttactgggc atctacccgt    180
gaatccggtg tcccggatcg cttttcaggc tcgggtagcg gcacggactt caccctgacg    240
atcagttccc tgcaagcgga agatgtggcc gtttattact gtcaacaact tgtgcagggg    300
ccgccgacgt tcggtcaagg caccaaagtg gaaatcaaa                            339

<210> SEQ ID NO 117
<211> LENGTH: 113
<212> TYPE: PRT
<213> ORGANISM: Artificial Sequence
<220> FEATURE:
<223> OTHER INFORMATION: Description of the artificial sequence: amino
      acid sequence of VL of CSPG5222 excluding signal sequence

<400> SEQUENCE: 117

Asp Ile Val Met Thr Gln Ser Pro Asp Ser Leu Ala Val Ser Leu Gly
1               5                   10                  15
```

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Leu Val Gln Gly Pro Pro Thr Phe Gly Gln Gly Thr Lys Val Glu Ile
            100                 105                 110

Lys

<210> SEQ ID NO 118
<211> LENGTH: 17
<212> TYPE: PRT
<213> ORGANISM: Artificial Sequence
<220> FEATURE:
<223> OTHER INFORMATION: Description of the artificial sequence: amino
      acid sequence of LCDR1 of CSPG5222

<400> SEQUENCE: 118

Lys Ser Ser Gln Ser Val Leu Tyr Ser Ser Asn Asn Lys Asn Tyr Leu
 1               5                  10                  15

Ala

<210> SEQ ID NO 119
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5222

<400> SEQUENCE: 119

Trp Ala Ser Thr Arg Glu Ser
 1               5

<210> SEQ ID NO 120
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CSPG5222

<400> SEQUENCE: 120

Gln Gln Leu Val Gln Gly Pro Pro Thr
 1               5

<210> SEQ ID NO 121
<211> LENGTH: 354
<212> TYPE: DNA
<213> ORGANISM: Artificial Sequence
<220> FEATURE:
<223> OTHER INFORMATION: Description of the artificial sequence: amino
      acid sequence of VH of CSPG5227 excluding signal sequence

<400> SEQUENCE: 121
gaagtccaac tgctggaatc gggtggtggt ctggtgcaac cgggcggctc gctgcgtctg      60
tcatgtgctg cgtcgggctt tacctttagc tcttatgcaa tgtcctgggt cgtcaggca     120

```
ccgggtaaag gtctggaatg ggttagcgca attagtggct ccggcggtag caccctattac    180 gccgattctg ttaaaggtcg ttttaccatc tcacgcgaca actcgaaaaa tacgctgtat    240
ctgcagatga acagtctgcg cgcagaagat accgctgtct attactgcgc aaaactgaag    300
cggactcagg gtttcgacta ctggggccaa ggtacgctgg ttacggttag cagc           354
```

<210> SEQ ID NO 122
<211> LENGTH: 118
<212> TYPE: PRT
<213> ORGANISM: Artificial Sequence
<220> FEATURE:
<223> OTHER INFORMATION: Description of the artificial sequence: amino
      acid sequence of VH of CSPG5227 excluding signal sequence

<400> SEQUENCE: 122

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Leu Lys Arg Thr Gln Gly Phe Asp Tyr Trp Gly Gln Gly Thr
            100                 105                 110

Leu Val Thr Val Ser Ser
        115
```

<210> SEQ ID NO 123
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5227

<400> SEQUENCE: 123

```
Ser Tyr Ala Met Ser
1               5
```

<210> SEQ ID NO 124
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5227

<400> SEQUENCE: 124

```
Ala Ile Ser Gly Ser Gly Gly Ser Thr Tyr Tyr Ala Asp Ser Val Lys
1               5                   10                  15

Gly
```

<210> SEQ ID NO 125
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CSPG5227

<400> SEQUENCE: 125

Leu Lys Arg Thr Gln Gly Phe Asp Tyr
1               5

<210> SEQ ID NO 126
<211> LENGTH: 339
<212> TYPE: DNA
<213> ORGANISM: Artificial Sequence
<220> FEATURE:
<223> OTHER INFORMATION: Description of the artificial sequence: base
      sequence of VL of CSPG5227 excluding signal sequence

<400> SEQUENCE: 126
gacatcgtca tgacgcaaag tccggattca ctggctgtta gtctgggcga acgtgctacg      60
atcaactgta atcctctca aagtgtgctg tatagctcta acaataaaaa ctatctggca     120
tggtaccagc aaaaaccggg tcagccgccg aaactgctga tttactgggc atctacccgt    180
gaatccggtg tcccggatcg cttttcaggc tcgggtagcg gcacggactt caccctgacg    240
atcagttccc tgcaagcgga agatgtggcc gtttattact gtcaacaatc gaatcgtctg    300
cctccgacgt tcggtcaagg caccaaagtg gaaatcaaa                           339

<210> SEQ ID NO 127
<211> LENGTH: 113
<212> TYPE: PRT
<213> ORGANISM: Artificial Sequence
<220> FEATURE:
<223> OTHER INFORMATION: Description of the artificial sequence: amino
      acid sequence of VL of CSPG5227 excluding signal sequence

<400> SEQUENCE: 127

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Asn Arg Leu Pro Pro Thr Phe Gly Gln Gly Thr Lys Val Glu Ile
            100                 105                 110

Lys

<210> SEQ ID NO 128
<211> LENGTH: 17
<212> TYPE: PRT
<213> ORGANISM: Artificial Sequence
<220> FEATURE:
<223> OTHER INFORMATION: Description of the artificial sequence: amino
      acid sequence of LCDR1 of CSPG5227

<400> SEQUENCE: 128

Lys Ser Ser Gln Ser Val Leu Tyr Ser Ser Asn Asn Lys Asn Tyr Leu
1               5                   10                  15

Ala

<210> SEQ ID NO 129
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5227

<400> SEQUENCE: 129

Trp Ala Ser Thr Arg Glu Ser
1               5

<210> SEQ ID NO 130
<211> LENGTH: 9
<212> TYPE: PRT
<213> ORGANISM: Artificial Sequence
<220> FEATURE:
<223> OTHER INFORMATION: Description of the artificial sequence: amino
      acid sequence of LCDR3 of CSPG5227

<400> SEQUENCE: 130

Gln Gln Ser Asn Arg Leu Pro Pro Thr
1               5

<210> SEQ ID NO 131
<211> LENGTH: 351
<212> TYPE: DNA
<213> ORGANISM: Artificial Sequence
<220> FEATURE:
<223> OTHER INFORMATION: Description of the artificial sequence: amino
      acid sequence of VH of CSPG5230 excluding signal sequence

<400> SEQUENCE: 131
gaagtccaac tgctggaatc gggtggtggt ctggtgcaac cgggcggctc gctgcgtctg      60
tcatgtgctg cgtcgggctt tacctttagc tcttatgcaa tgtcctgggt gcgtcaggca     120
ccgggtaaag gtctggaatg ggttagcgca attagtggct ccggcggtag cacctattac     180
gccgattctg ttaaaggtcg ttttaccatc tcacgcgaca actcgaaaaa tacgctgtat     240
ctgcagatga acagtctgcg cgcagaagat accgctgtct attactgcgc aaaatcgacg     300
ccggcgcggt tcgactactg gggccaaggt acgctggtta cggttagcag c              351

<210> SEQ ID NO 132
<211> LENGTH: 117
<212> TYPE: PRT
<213> ORGANISM: Artificial Sequence
<220> FEATURE:
<223> OTHER INFORMATION: Description of the artificial sequence: amino
      acid sequence of VH of CSPG5230 excluding signal sequence

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Thr Pro Ala Arg Phe Asp Tyr Trp Gly Gln Gly Thr Leu
            100                 105                 110

Val Thr Val Ser Ser
        115

<210> SEQ ID NO 133
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5230

<400> SEQUENCE: 133

Ser Tyr Ala Met Ser
1               5

<210> SEQ ID NO 134
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5230

<400> SEQUENCE: 134

Ala Ile Ser Gly Ser Gly Gly Ser Thr Tyr Tyr Ala Asp Ser Val Lys
1               5                   10                  15

Gly

<210> SEQ ID NO 135
<211> LENGTH: 8
<212> TYPE: PRT
<213> ORGANISM: Artificial Sequence
<220> FEATURE:
<223> OTHER INFORMATION: Description of the artificial sequence: amino
      acid sequence of HCDR3 of CSPG5230

<400> SEQUENCE: 135

Ser Thr Pro Ala Arg Phe Asp Tyr
1               5

<210> SEQ ID NO 136
<211> LENGTH: 333
<212> TYPE: DNA
<213> ORGANISM: Artificial Sequence
<220> FEATURE:
<223> OTHER INFORMATION: Description of the artificial sequence: base
      sequence of VL of CSPG5230 excluding signal sequence

<400> SEQUENCE: 136
caatcggctc tgacccaacc ggcaagtgtc tctggttctc cgggtcaatc aatcacgatc      60
tcctgtacgg gtacctctac ggatgtcaac ggctataatt acgtcagctg gtatcagcaa     120
tacgcgggta agcccccgaa actgattatc tttgatgtta gtaaacgtcc gtcgggcgtt     180
agcaaccgct tcagtggctc caaatcaggt gacaccgcct ctctgacgat ttccggtctg     240
caggcagaag atgaagctga ctatcattgc agctcttacc atacgcggcc tgcgactgtc     300
ctgtttggtg gtggcacgaa actgaccgtt ctg                                  333

<210> SEQ ID NO 137

```
<211> LENGTH: 111
<212> TYPE: PRT
<213> ORGANISM: Artificial Sequence
<220> FEATURE:
<223> OTHER INFORMATION: Description of the artificial sequence: amino
      acid sequence of VL of CSPG5230 excluding signal sequence

<400> SEQUENCE: 137
```

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Thr Asp Val Asn Gly Tyr
            20                  25                  30

Asn Tyr Val Ser Trp Tyr Gln Gln Tyr Ala Gly Lys Ala Pro Lys Leu
        35                  40                  45

Ile Ile Phe Asp Val Ser Lys Arg Pro Ser Gly Val Ser Asn Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr His Cys Ser Ser Tyr His Thr Arg
                85                  90                  95

Pro Ala Thr Val Leu Phe Gly Gly Gly Thr Lys Leu Thr Val Leu
            100                 105                 110

```
<210> SEQ ID NO 138
<211> LENGTH: 14
<212> TYPE: PRT
<213> ORGANISM: Artificial Sequence
<220> FEATURE:
<223> OTHER INFORMATION: Description of the artificial sequence: amino
      acid sequence of LCDR1 of CSPG5230

<400> SEQUENCE: 138
```

Thr Gly Thr Ser Thr Asp Val Asn Gly Tyr Asn Tyr Val Ser
1               5                   10

```
<210> SEQ ID NO 139
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5230

<400> SEQUENCE: 139
```

Asp Val Ser Lys Arg Pro Ser
1               5

```
<210> SEQ ID NO 140
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR3 of CSPG5230

<400> SEQUENCE: 140
```

Ser Ser Tyr His Thr Arg Pro Ala Thr Val Leu
1               5                   10

```
<210> SEQ ID NO 141
<211> LENGTH: 354
<212> TYPE: DNA
<213> ORGANISM: Artificial Sequence
<220> FEATURE:
<223> OTHER INFORMATION: Description of the artificial sequence: amino
``` acid sequence of VH of CSPG5234 excluding signal sequence

<400> SEQUENCE: 141

```
gaagtccaac tgctggaatc gggtggtggt ctggtgcaac cgggcggctc gctgcgtctg      60
tcatgtgctg cgtcgggctt tacctttagc tcttatgcaa tgtcctgggt gcgtcaggca     120
ccgggtaaag gtctggaatg ggttagcgca attagtggct ccggcggtag cacctattac     180
gccgattctg ttaaaggtcg ttttaccatc tcacgcgaca actcgaaaaa tacgctgtat     240
ctgcagatga acagtctgcg cgcagaagat accgctgtct attactgcgc aaaaaggcat     300
agttatgcgc ctttcgacta ctggggccaa ggtacgctgg ttacggttag cagc           354
```

<210> SEQ ID NO 142
<211> LENGTH: 118
<212> TYPE: PRT
<213> ORGANISM: Artificial Sequence
<220> FEATURE:
<223> OTHER INFORMATION: Description of the artificial sequence: amino
      acid sequence of VH of CSPG5234 excluding signal sequence

<400> SEQUENCE: 142

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Arg His Ser Tyr Ala Pro Phe Asp Tyr Trp Gly Gln Gly Thr
            100                 105                 110

Leu Val Thr Val Ser Ser
        115

<210> SEQ ID NO 143
<211> LENGTH: 5
<212> TYPE: PRT
<213> ORGANISM: Artificial Sequence
<220> FEATURE:
<223> OTHER INFORMATION: Description of the artificial sequence: amino
      acid sequence of HCDR1 of CSPG5234

<400> SEQUENCE: 143

Ser Tyr Ala Met Ser
1               5

<210> SEQ ID NO 144
<211> LENGTH: 17
<212> TYPE: PRT
<213> ORGANISM: Artificial Sequence
<220> FEATURE:
<223> OTHER INFORMATION: Description of the artificial sequence: amino
      acid sequence of HCDR2 of CSPG5234

<400> SEQUENCE: 144

Ala Ile Ser Gly Ser Gly Gly Ser Thr Tyr Tyr Ala Asp Ser Val Lys
1               5                   10                  15

Gly

<210> SEQ ID NO 145
<211> LENGTH: 9
<212> TYPE: PRT
<213> ORGANISM: Artificial Sequence
<220> FEATURE:
<223> OTHER INFORMATION: Description of the artificial sequence: amino
      acid sequence of HCDR3 of CSPG5234

<400> SEQUENCE: 145

Arg His Ser Tyr Ala Pro Phe Asp Tyr
1               5

<210> SEQ ID NO 146
<211> LENGTH: 333
<212> TYPE: DNA
<213> ORGANISM: Artificial Sequence
<220> FEATURE:
<223> OTHER INFORMATION: Description of the artificial sequence: base
      sequence of VL of CSPG5234 excluding signal sequence

<400> SEQUENCE: 146
caatcggctc tgacccaacc ggcaagtgtc tctggttctc cgggtcaatc aatcacgatc      60
tcctgtacgg gtacctctac ggatgtcaac ggctataatt acgtcagctg gtatcagcaa     120
tacgcgggta agccccgaa actgattatc tttgatgtta gtaaacgtcc gtcgggcgtt      180
agcaaccgct tcagtggctc caaatcaggt gacaccgcct ctctgacgat ttccggtctg     240
caggcagaag atgaagctga ctatcattgc agctcttaca ggccgaaggc taggagtgtc     300
ctgtttggtg gtggcacgaa actgaccgtt ctg                                  333

<210> SEQ ID NO 147
<211> LENGTH: 111
<212> TYPE: PRT
<213> ORGANISM: Artificial Sequence
<220> FEATURE:
<223> OTHER INFORMATION: Description of the artificial sequence: amino
      acid sequence of VL of CSPG5234 excluding signal sequence

<400> SEQUENCE: 147

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Thr Asp Val Asn Gly Tyr
            20                  25                  30

Asn Tyr Val Ser Trp Tyr Gln Gln Tyr Ala Gly Lys Ala Pro Lys Leu
        35                  40                  45

Ile Ile Phe Asp Val Ser Lys Arg Pro Ser Gly Val Ser Asn Arg Phe
    50                  55                  60

Ser Gly Ser Lys Ser Gly Asp Thr Ala Ser Leu Thr Ile Ser Gly Leu
65                  70                  75                  80

Gln Ala Glu Asp Glu Ala Asp Tyr His Cys Ser Ser Tyr Arg Pro Lys
                85                  90                  95

Ala Arg Ser Val Leu Phe Gly Gly Gly Thr Lys Leu Thr Val Leu
            100                 105                 110

<210> SEQ ID NO 148
<211> LENGTH: 14
<212> TYPE: PRT
<213> ORGANISM: Artificial Sequence
<220> FEATURE:
<223> OTHER INFORMATION: Description of the artificial sequence: amino
      acid sequence of LCDR1 of CSPG5234

<400> SEQUENCE: 148

Thr Gly Thr Ser Thr Asp Val Asn Gly Tyr Asn Tyr Val Ser
1               5                   10

<210> SEQ ID NO 149
<211> LENGTH: 7
<212> TYPE: PRT
<213> ORGANISM: Artificial Sequence
<220> FEATURE:
<223> OTHER INFORMATION: Description of the artificial sequence: amino
      acid sequence of LCDR2 of CSPG5234

<400> SEQUENCE: 149

Asp Val Ser Lys Arg Pro Ser
1               5

<210> SEQ ID NO 150
<211> LENGTH: 11
<212> TYPE: PRT
<213> ORGANISM: Artificial Sequence
<220> FEATURE:
<223> OTHER INFORMATION: Description of the artificial sequence: amino
      acid sequence of LCDR3 of CSPG5234

<400> SEQUENCE: 150

Ser Ser Tyr Arg Pro Lys Ala Arg Ser Val Leu
1               5                   10

<210> SEQ ID NO 151
<211> LENGTH: 660
<212> TYPE: DNA
<213> ORGANISM: Artificial Sequence
<220> FEATURE:
<223> OTHER INFORMATION: Description of the artificial sequence: base
      sequence of Light chain antibody sequence of pCI_CSPG5202-
      hKG4PE(R409K) excluding signal sequence

<400> SEQUENCE: 151
gacatcgtca tgacgcaaag tccggattca ctggctgtta gtctgggcga acgtgctacg      60
atcaactgta atcctctca aagtgtgctg tatagctcta caataaaaa ctatctggca     120 tggtaccagc aaaaaccggg tcagccgccg aaactgctga tttactgggc atctacccgt     180
gaatccggtg tcccggatcg cttttcaggc tcgggtagcg gcacggactt caccctgacg     240
atcagttccc tgcaagcgga agatgtggcc gtttattact gtcaacaaag tcggacgcgg     300
aggcctacgt tcggtcaagg caccaaagtg gaaatcaaac gtacggtggc tgcaccatct     360
gtcttcatct tcccgccatc tgatgagcag ttgaaatctg gaactgcctc tgttgtgtgc     420
ctgctgaata acttctatcc cagagaggcc aaagtacagt ggaaggtgga taacgccctc     480
caatcgggta actcccagga gagtgtcaca gagcaggaca gcaaggacag cacctacagc     540
ctcagcagca ccctgacgct gagcaaagca gactacgaga aacacaaagt ctacgcctgc     600
gaagtcaccc atcagggcct gagctcgccc gtcacaaaga gcttcaacag gggagagtgt     660

<210> SEQ ID NO 152
<211> LENGTH: 220
<212> TYPE: PRT
<213> ORGANISM: Artificial Sequence
<220> FEATURE:
<223> OTHER INFORMATION: Description of the artificial sequence: amino
      acid sequence of Light chain antibody sequence of pCI_CSPG5202-
      hKG4PE(R409K) excluding signal sequence

<400> SEQUENCE: 152

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Ser Arg Thr Arg Arg Pro Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
            130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
210                 215                 220
```

<210> SEQ ID NO 153
<211> LENGTH: 1335
<212> TYPE: DNA
<213> ORGANISM: Artificial Sequence
<220> FEATURE:
<223> OTHER INFORMATION: Description of the artificial sequence: base
      sequence of Heavy chain antibody sequence of pCI_CSPG5202-
      hKG4PE(R409K) excluding signal sequence

<400> SEQUENCE: 153

```
gaagtccaac tgctggaatc gggtggtggt ctggtgcaac cgggcggctc gctgcgtctg      60
tcatgtgctg cgtcgggctt tacctttagc tcttatgcaa tgtcctgggt cgtcaggca     120 ccgggtaaag gtctggaatg ggttagcgca attagtggct ccggcggtag cacctattac    180
gccgattctg ttaaaggtcg ttttaccatc tcacgcgaca actcgaaaaa tacgctgtat    240
ctgcagatga acagtctgcg cgcagaagat accgctgtct attactgcgc aaaaattagt    300
aagacgcagg ggttcgacta ctggggccaa ggtacgctgg ttacggttag cagcgctagc    360 accaagggc catccgtctt ccccctggcg ccctgctcca ggagcacctc cgagagcaca    420
gccgccctgg gctgcctggt caaggactac ttccccgaac cggtgacggt gtcgtggaac    480
tcaggcgccc tgaccagcgg cgtgcacacc ttccggctg tcctacagtc ctcaggactc    540
tactccctca gcagcgtggt gaccgtgccc tccagcagct gggcacgaa gacctacacc    600 tgcaacgtag atcacaagcc cagcaacacc aaggtggaca gagagttga gtccaaatat    660 ggtccccat gcccaccatg cccagcacct gagttcgagg ggggaccatc agtcttcctg    720
```

```
ttccccccaa acccaagga cactctcatg atctcccgga cccctgaggt cacgtgcgtg      780
gtggtggacg tgagccagga agaccccgag gtccagttca actggtacgt ggatggcgtg      840
gaggtgcata atgccaagac aaagccgcgg gaggagcagt tcaacagcac gtaccgtgtg      900
gtcagcgtcc tcaccgtcct gcaccaggac tggctgaacg gcaaggagta caagtgcaag      960
gtctccaaca aaggcctccc gtcctccatc gagaaaacca tctccaaagc caaagggcag     1020
ccccgagagc cacaggtgta caccctgccc ccatcccagg aggagatgac caagaaccag     1080
gtcagcctga cctgcctggt caaaggcttc taccccagcg acatcgccgt ggagtgggag     1140
agcaatgggc agccggagaa caactacaag accacgcctc ccgtgctgga ctccgacggc     1200
tccttcttcc tctacagcaa gctaaccgtg gacaagagca ggtggcagga ggggaatgtc     1260
ttctcatgct ccgtgatgca tgaggctctg cacaaccact acacacagaa gagcctctcc     1320
ctgtctctgg gtaaa                                                      1335
```

<210> SEQ ID NO 154
<211> LENGTH: 445
<212> TYPE: PRT
<213> ORGANISM: Artificial Sequence
<220> FEATURE:
<223> OTHER INFORMATION: Description of the artificial sequence: amino
    acid sequence of Heavy chain antibody sequence of pCI_CSPG5202-
    hKG4PE(R409K) excluding signal sequence

<400> SEQUENCE: 154

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Lys Thr Gln Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Phe Glu Gly Gly Pro Ser Val Phe Leu
225                 230                 235                 240
```

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly Lys
        435                 440                 445

<210> SEQ ID NO 155
<211> LENGTH: 648
<212> TYPE: DNA
<213> ORGANISM: Artificial Sequence
<220> FEATURE:
<223> OTHER INFORMATION: Description of the artificial sequence: base
      sequence of Light chain antibody sequence of pCI_AVM-
      hLG4PE(R409K)-CSPG5202scFv excluding signal sequence

<400> SEQUENCE: 155
cagtttgtgc tttctcagcc aaactctgtg tctacgaatc tcggaagcac agtcaaactg      60
tcttgcaagc gcagcactgg taacattgga agcaattatg tgagctggta ccagcagcat     120
gagggaagat ctcccaccac tatgatttat agggatgata agagaccaga tggagttcct     180
gacaggttct ctggctccat tgacagatct tccgactcag ccctcctgac aatcaataat     240
gtgcagactg aagatgaagc tgactacttc tgtcagtctt acagtagtgg tattaatatt     300
ttcggcggtg gaaccaagct cactgtccta ggtcagccca aggccgcccc ctcggtcact     360
ctgttcccgc cctcctctga ggagcttcaa gccaacaagg ccacactggt gtgtctcata     420
agtgacttct acccgggagc cgtgacagtg gcctggaagg cagatagcag ccccgtcaag     480
gcgggagtgg agaccaccac accctccaaa caaagcaaca caagtacgc ggccagcagc      540 tacctgagcc tgacgcctga gcagtggaag tcccacagaa gctacagctg ccaggtcacg     600
catgaaggga gcaccgtgga agacagtgt gccctacag aatgttca                    648

<210> SEQ ID NO 156
<211> LENGTH: 216
<212> TYPE: PRT
<213> ORGANISM: Artificial Sequence
<220> FEATURE:

<223> OTHER INFORMATION: Description of the artificial sequence: amino
     acid sequence of Light chain antibody sequence of pCI_AVM-
     hLG4PE(R409K)-CSPG5202scFv excluding signal sequence

<400> SEQUENCE: 156

```
Gln Phe Val Leu Ser Gln Pro Asn Ser Val Ser Thr Asn Leu Gly Ser
1               5                   10                  15

Thr Val Lys Leu Ser Cys Lys Arg Ser Thr Gly Asn Ile Gly Ser Asn
            20                  25                  30

Tyr Val Ser Trp Tyr Gln Gln His Glu Gly Arg Ser Pro Thr Thr Met
        35                  40                  45

Ile Tyr Arg Asp Asp Lys Arg Pro Asp Gly Val Pro Asp Arg Phe Ser
50                  55                  60

Gly Ser Ile Asp Arg Ser Ser Asp Ser Ala Leu Leu Thr Ile Asn Asn
65                  70                  75                  80

Val Gln Thr Glu Asp Glu Ala Asp Tyr Phe Cys Gln Ser Tyr Ser Ser
                85                  90                  95

Gly Ile Asn Ile Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215
```

<210> SEQ ID NO 157
<211> LENGTH: 2154
<212> TYPE: DNA
<213> ORGANISM: Artificial Sequence
<220> FEATURE:
<223> OTHER INFORMATION: Description of the artificial sequence: base
     sequence of Heavy chain antibody sequence of pCI_AVM-
     hLG4PE(R409K)-CSPG5202scFv excluding signal sequence

<400> SEQUENCE: 157

```
gaggtgcagc tggtggaatc tgggggaggc ttagtgcagc ctggaagatc cctgaaactc      60
tcctgtgcag cctcaggatt cactttcagt aactatgcca tggcttgggt ccgccgggct     120
ccaacgaagg gtctggagtg ggtcgcatcc attagtaatg gtggtggtaa cacttactat     180
cgcgactccg tgaagggccg attcactatc tccagagatg atgcaaaaaa caccctatac     240
ctgcaaatgg acagtctgag gtctgaggac acggccactt attactgtgc aagacacggg     300
aattatatat attatgggtc cttctttgat tactggggcc aaggagtcat ggtcacagtc     360
tcctcagcta gcaccaaggg gccatccgtc ttccccctgg cgccctgctc caggagcacc     420
tccgagagca cagccgccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacg     600
```

```
aagacctaca cctgcaacgt agatcacaag cccagcaaca ccaaggtgga caagagagtt      660
gagtccaaat atggtccccc atgcccacca tgcccagcac ctgagttcga ggggggacca      720
tcagtcttcc tgttccccccc aaacccaag acactctca tgatctcccg acccctgag       780 gtcacgtgcg tggtggtgga cgtgagccag gaagacccccg aggtccagtt caactggtac    840
gtggatggcg tggaggtgca taatgccaag acaaagccgc gggaggagca gttcaacagc     900
acgtaccgtg tggtcagcgt cctcaccgtc ctgcaccagg actggctgaa cggcaaggag     960
tacaagtgca aggtctccaa caaaggcctc ccgtcctcca tcgagaaaac catctccaaa    1020
gccaaagggc agccccgaga gccacaggtg tacaccctgc ccccatccca ggaggagatg    1080
accaagaacc aggtcagcct gacctgcctg gtcaaaggct tctacccag cgacatcgcc     1140 gtggagtggg agagcaatgg gcagccggag aacaactaca agaccacgcc tcccgtgctg    1200
gactccgacg gctccttctt cctctacagc aagctaaccg tggacaagag caggtggcag    1260 gagggggaatg tcttctcatg ctccgtgatg catgaggctc tgcacaacca ctacacacag    1320
aagagcctct ccctgtctct gggtggagga ggagggtccg gaggaggagg gtccggtgga    1380
ggtgggtccg aagtccaact gctggaatcg ggtggtggtc tggtgcaacc gggcggctcg    1440
ctgcgtctgt catgtgctgc gtcgggctt  accttagct cttatgcaat gtcctgggtg    1500
cgtcaggcac cggtaaagg tctggaatgg gttagcgcaa ttagtggctc cggcggtagc    1560
acctattacg ccgattctgt taaaggtcgt ttaccatct cacgcgacaa ctcgaaaaat     1620
acgctgtatc tgcagatgaa cagtctgcgc gcagaagata ccgctgtcta ttactgcgca    1680
aaaattagta agacgcaggg gttcgactac tggggccaag gtacgctggt tacggttagc    1740
agcgctagca ccggaggcgg tggcagcgga ggaggagggt ccggtgggg cggctcgggc      1800 ggaggtggtt cagacatcgt catgacgcaa agtccggatt cactggctgt tagtctgggc    1860
gaacgtgcta cgatcaactg taaatcctct caaagtgtgc tgtatagctc taacaataaa    1920
aactatctgg catggtacca gcaaaaaccg ggtcagccgc cgaaactgct gatttactgg    1980
gcatctaccc gtgaatccgg tgtcccggat cgcttttcag gctcgggtag cggcacggac    2040
ttcaccctga cgatcagttc cctgcaagcg gaagatgtgc ccgtttatta ctgtcaacaa    2100
agtcggacgc ggaggcctac gttcggtcaa ggcaccaaag tggaaatcaa aggt          2154
```

<210> SEQ ID NO 158
<211> LENGTH: 718
<212> TYPE: PRT
<213> ORGANISM: Artificial Sequence
<220> FEATURE:
<223> OTHER INFORMATION: Description of the artificial sequence: amino
    acid sequence of Heavy chain antibody sequence of pCI_AVM-
    hLG4PE(R409K)-CSPG5202scFv excluding signal sequence

<400> SEQUENCE: 158

```
Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asn Tyr
            20                  25                  30

Ala Met Ala Trp Val Arg Arg Ala Pro Thr Lys Gly Leu Glu Trp Val
        35                  40                  45

Ala Ser Ile Ser Asn Gly Gly Gly Asn Thr Tyr Tyr Arg Asp Ser Val
    50                  55                  60

Lys Gly Arg Phe Thr Ile Ser Arg Asp Asp Ala Lys Asn Thr Leu Tyr
65                  70                  75                  80
```

```
Leu Gln Met Asp Ser Leu Arg Ser Glu Asp Thr Ala Thr Tyr Tyr Cys
                85                  90                  95

Ala Arg His Gly Asn Tyr Ile Tyr Tyr Gly Ser Phe Phe Asp Tyr Trp
            100                 105                 110

Gly Gln Gly Val Met Val Thr Val Ser Ser Ala Ser Thr Lys Gly Pro
            115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
            195                 200                 205

His Lys Pro Ser Asn Thr Lys Val Asp Lys Arg Val Glu Ser Lys Tyr
        210                 215                 220

Gly Pro Pro Cys Pro Pro Cys Pro Ala Pro Glu Phe Glu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Gly Gly Gly Gly Ser Gly Gly Gly Ser Gly Gly Gly Ser Glu
450                 455                 460

Val Gln Leu Leu Glu Ser Gly Gly Gly Leu Val Gln Pro Gly Gly Ser
465                 470                 475                 480

Leu Arg Leu Ser Cys Ala Ala Ser Gly Phe Thr Phe Ser Ser Tyr Ala
                485                 490                 495
```

```
Met Ser Trp Val Arg Gln Ala Pro Gly Lys Gly Leu Glu Trp Val Ser
            500                 505                 510

Ala Ile Ser Gly Ser Gly Gly Ser Thr Tyr Tyr Ala Asp Ser Val Lys
        515                 520                 525

Gly Arg Phe Thr Ile Ser Arg Asp Asn Ser Lys Asn Thr Leu Tyr Leu
    530                 535                 540

Gln Met Asn Ser Leu Arg Ala Glu Asp Thr Ala Val Tyr Tyr Cys Ala
545                 550                 555                 560

Lys Ile Ser Lys Thr Gln Gly Phe Asp Tyr Trp Gly Gln Gly Thr Leu
                565                 570                 575

Val Thr Val Ser Ser Ala Ser Thr Gly Gly Gly Gly Ser Gly Gly Gly
            580                 585                 590

Gly Ser Gly Gly Gly Ser Gly Gly Gly Ser Asp Ile Val Met
            595                 600                 605

Thr Gln Ser Pro Asp Ser Leu Ala Val Ser Leu Gly Glu Arg Ala Thr
            610                 615                 620

Ile Asn Cys Lys Ser Ser Gln Ser Val Leu Tyr Ser Ser Asn Asn Lys
625                 630                 635                 640

Asn Tyr Leu Ala Trp Tyr Gln Gln Lys Pro Gly Gln Pro Pro Lys Leu
                645                 650                 655

Leu Ile Tyr Trp Ala Ser Thr Arg Glu Ser Gly Val Pro Asp Arg Phe
            660                 665                 670

Ser Gly Ser Gly Ser Gly Thr Asp Phe Thr Leu Thr Ile Ser Ser Leu
            675                 680                 685

Gln Ala Glu Asp Val Ala Val Tyr Tyr Cys Gln Gln Ser Arg Thr Arg
690                 695                 700

Arg Pro Thr Phe Gly Gln Gly Thr Lys Val Glu Ile Lys Gly
705                 710                 715

<210> SEQ ID NO 159
<211> LENGTH: 1617
<212> TYPE: DNA
<213> ORGANISM: Artificial Sequence
<220> FEATURE:
<223> OTHER INFORMATION: Description of the artificial sequence: base
      sequence of human CSPG5 including signal sequence

<400> SEQUENCE: 159
atggggcgag ccgggggcgg gggcccgggc cggggccgc cgccactgct gctgtttctg      60
ggggccgcgc tggtcctggc ctctggggcc gtgccggcgc gtgaggcggg cagcgcggtt    120
gaggccgaag agctggtgaa gggcagcccg gcgtgggagc gcctgccaa cgacacgcgg     180 gaagaagccg cccaccagc ggctgggaa gatgaggcgt cgtggacggc gcccggtggc     240
gagctggccg ggccagaaga ggtgctgcag gagtcggctg cggtgaccgg caccgcctgg    300
ctggaagctg acagcccagg cctggaggga gtgaccgcag aggcgggcag cggcgatgcc    360
caggcccttc cagctacgct ccaggctccc cacgaggtcc tcgggcagtc aatcatgccc    420
cctgccattc tgaggctac agaggccagc gggccaccct ccccaccccc ggcgacaag     480 ctgagcccag cttctgaact ccccaaggag agccccttgg aggtttggct gaacctgggg    540
ggcagcacac ccgaccctca agggccagag ctgacttacc catttcaggg caccctggag    600
ccccaaccgg catcagatat cattgacatc gactacttcg aaggactgga tggtgagggt    660
cgtggcgcag atctggggag cttcccaggg tcaccaggaa cctcagagaa ccaccctgat    720
actgagggag agacccttc ctggagcctg cttgacttat acgatgattt cacccccttc    780
```

```
gatgaatctg atttctaccc caccacatcc ttttatgatg acttggatga agaggaggag    840
gaagaggagg atgacaaaga tgcagtagga ggtggagacc tagaagatga aaatgagctt    900
ctagtgccca ctgggaagcc tggtctgggg cccgggacag gccagcccac cagtcggtgg    960
catgctgtcc ctccacagca cactctgggg tcggtccccg gcagcagcat cgccctcagg   1020
ccccgcccag gagagccagg cagggacttg gcctccagtg aaaatggcac tgagtgccgc   1080
agtggctttg tgcggcataa cggctcctgc cggtcagtgt gcgacctctt cccaagttac   1140
tgtcacaatg gcggccagtg ctacctggtg gagaacatag gggccttctg caggtgcaac   1200
acgcaggact acatctggca aaggggatg cgctgcgagt ccatcatcac cgacttccag   1260
gtgatgtgcg tggccgtggg ctcggctgcc ctcgtcctgc tcctgctctt catgatgacg   1320
gtgttctttg ccaagaagct ctacctgctc aagacggaga ataccaagct gcgtaggacc   1380
aacaaattcc ggaccccatc tgagctccac aatgataact tctccctctc caccattgcc   1440
gagggctctc acccaaatga tgatcctagt gctccccaca aaatccagga ggttctcaag   1500
tcctgcctga agaggagga gtcatttaac atccagaact ccatgtcgcc caaacttgag   1560
ggtggcaaag gtgaccaggc tgacttggat gtgaactgtc ttcagaataa tttaacc     1617
```

<210> SEQ ID NO 160
<211> LENGTH: 539
<212> TYPE: PRT
<213> ORGANISM: Artificial Sequence
<220> FEATURE:
<223> OTHER INFORMATION: Description of the artificial sequence: amino
acid sequence of human CSPG5 including signal sequence

<400> SEQUENCE: 160

```
Met Gly Arg Ala Gly Gly Gly Pro Gly Arg Gly Pro Pro Pro Leu
1               5                   10                  15

Leu Leu Phe Leu Gly Ala Ala Leu Val Leu Ala Ser Gly Ala Val Pro
                20                  25                  30

Ala Arg Glu Ala Gly Ser Ala Val Glu Ala Glu Leu Val Lys Gly
            35                  40                  45

Ser Pro Ala Trp Glu Pro Pro Ala Asn Asp Thr Arg Glu Glu Ala Gly
        50                  55                  60

Pro Pro Ala Ala Gly Glu Asp Glu Ala Ser Trp Thr Ala Pro Gly Gly
65                  70                  75                  80

Glu Leu Ala Gly Pro Glu Glu Val Leu Gln Glu Ser Ala Ala Val Thr
                85                  90                  95

Gly Thr Ala Trp Leu Glu Ala Asp Ser Pro Gly Leu Gly Gly Val Thr
            100                 105                 110

Ala Glu Ala Gly Ser Gly Asp Ala Gln Ala Leu Pro Ala Thr Leu Gln
        115                 120                 125

Ala Pro His Glu Val Leu Gly Gln Ser Ile Met Pro Pro Ala Ile Pro
    130                 135                 140

Glu Ala Thr Glu Ala Ser Gly Pro Pro Ser Pro Thr Pro Gly Asp Lys
145                 150                 155                 160

Leu Ser Pro Ala Ser Glu Leu Pro Lys Glu Ser Pro Leu Glu Val Trp
                165                 170                 175

Leu Asn Leu Gly Gly Ser Thr Pro Asp Pro Gln Gly Pro Glu Leu Thr
            180                 185                 190

Tyr Pro Phe Gln Gly Thr Leu Glu Pro Gln Pro Ala Ser Asp Ile Ile
        195                 200                 205

Asp Ile Asp Tyr Phe Glu Gly Leu Asp Gly Glu Gly Arg Gly Ala Asp
```

```
                210                 215                 220
Leu Gly Ser Phe Pro Gly Ser Pro Gly Thr Ser Glu Asn His Pro Asp
225                 230                 235                 240

Thr Glu Gly Glu Thr Pro Ser Trp Ser Leu Leu Asp Leu Tyr Asp Asp
                245                 250                 255

Phe Thr Pro Phe Asp Glu Ser Asp Phe Tyr Pro Thr Thr Ser Phe Tyr
            260                 265                 270

Asp Asp Leu Asp Glu Glu Glu Glu Glu Glu Asp Asp Lys Asp Ala
        275                 280                 285

Val Gly Gly Asp Leu Glu Asp Glu Asn Glu Leu Leu Val Pro Thr
290                 295                 300

Gly Lys Pro Gly Leu Gly Pro Gly Thr Gly Gln Pro Thr Ser Arg Trp
305                 310                 315                 320

His Ala Val Pro Pro Gln His Thr Leu Gly Ser Val Pro Gly Ser Ser
                325                 330                 335

Ile Ala Leu Arg Pro Arg Pro Gly Glu Pro Gly Arg Asp Leu Ala Ser
            340                 345                 350

Ser Glu Asn Gly Thr Glu Cys Arg Ser Gly Phe Val Arg His Asn Gly
        355                 360                 365

Ser Cys Arg Ser Val Cys Asp Leu Phe Pro Ser Tyr Cys His Asn Gly
370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415

Thr Asp Phe Gln Val Met Cys Val Ala Val Gly Ser Ala Ala Leu Val
            420                 425                 430

Leu Leu Leu Leu Phe Met Met Thr Val Phe Phe Ala Lys Lys Leu Tyr
        435                 440                 445

Leu Leu Lys Thr Glu Asn Thr Lys Leu Arg Arg Thr Asn Lys Phe Arg
450                 455                 460

Thr Pro Ser Glu Leu His Asn Asp Asn Phe Ser Leu Ser Thr Ile Ala
465                 470                 475                 480

Glu Gly Ser His Pro Asn Asp Pro Ser Ala Pro His Lys Ile Gln
                485                 490                 495

Glu Val Leu Lys Ser Cys Leu Lys Glu Glu Ser Phe Asn Ile Gln
            500                 505                 510

Asn Ser Met Ser Pro Lys Leu Glu Gly Gly Lys Gly Asp Gln Ala Asp
        515                 520                 525

Leu Asp Val Asn Cys Leu Gln Asn Asn Leu Thr
530                 535
```

<210> SEQ ID NO 161
<211> LENGTH: 1617
<212> TYPE: DNA
<213> ORGANISM: Artificial Sequence
<220> FEATURE:
<223> OTHER INFORMATION: Description of the artificial sequence: base
      sequence of mouse CSPG5 including signal sequence

<400> SEQUENCE: 161
atgggccgag ctggaggcgg gggcccggac tgggggccgc cgccagtgct gctgcttctg    60
ggggtcacgc tggtgctcac cgctggggcc gtaccggcac gggaaacagg cagtgcgatc   120
gaggctgaag agctggtgag gagcagcctg catgggagt cgcgtgccaa tgacacgcgg    180

```
gaggaagccg gcctgccagc agctggggaa gatgagacct cgtggacaga gcggggcagt     240
gagatggctg cggtgggccc tggggtcggg ccagaggagg cactagaggc atcggctgca     300
gtgactggca ctgcctggct agaggcagat ggcccaggcc tgggtggagt gactgcagag     360
gctggcagtg gcgacgccca gaccctccca gctacgctcc aggctcctga tgaggccctt     420
gggtcatcta caatgccccc tgccatccct gaggctactg aaaccagtgg acctccctcc     480
cctgctgtcc atgataagcc tagtgtaggc cctgaactcc ctaaagagat cccccttggag    540 gttcggctga acctgggagg cagcacacca gagcccactt ttccccttca gggcactctc     600
gagacccaac cagcctcaga tataattgac attgattact ttgaaggatt ggatagtgag     660
ggtcgtggtg cagacatggg cagcttcccg gggtcaccag gaacctcaga aaatcaccct     720
gataccgaag agagacccc ttcctggagc ctgcttgatt tgtatgatga cttcacccct      780
tttgatgagt ctgatttcta ccccaccaca tccttctatg atgatttgga agaggaggaa     840
gaagaggagg aggataagga tacagtagga ggtggagacc tggaagatga aaacgacctt     900
ctcctgccct ctcaaaagcc tggtgtgggg cctgggacag gacagcccac caaccggtgg    960
catgctgttc ccccacagca tactctgggg atggtacctg gcagcagcat ctctcttagg    1020
ccccgccccg gagatccagg caaggacctg gcctcaggag aaaatggcac agagtgccga    1080
gttggcttcg tcaggcacaa tggctcctgc cggtcagtct gtgacctctt tccgagttac    1140
tgtcacaacg gcggccagtg ctacctggtg gagaacatag gggctttctg caggtgtaac    1200
acccaggact acatctggca aaggggatg cgctgtgagt ccatcatcac ggacttccag     1260
gtgatgtgcg tggccgttgg ctcggctgct ctcgtgcttc tcctcctgtt catgatgact    1320
gtgttctttg ccaagaagct ctatctgctc aagactgaga ataccaagct gcggaggacc    1380
aataaattcc ggaccccatc tgagctccac aacgacaact tctccctctc caccattgcc    1440
gagggctctc atccaaatga cgaccccagc gctccccaca aaatccagga ccctctcaag    1500
tcccgcctga aggaggaaga gtcctttaac atccagaact ccatgtcacc caaacttgag    1560
ggtggcaaag gtgaccagga tgacttgggg gtgaactgtc tgcagaataa cctaacc       1617
```

<210> SEQ ID NO 162
<211> LENGTH: 539
<212> TYPE: PRT
<213> ORGANISM: Artificial Sequence
<220> FEATURE:
<223> OTHER INFORMATION: Description of the artificial sequence: amino
      acid sequence of mouse CSPG5 including signal sequence

<400> SEQUENCE: 162

```
Met Gly Arg Ala Gly Gly Gly Pro Asp Trp Gly Pro Pro Val
1               5                   10                  15

Leu Leu Leu Leu Gly Val Thr Leu Val Leu Thr Ala Gly Ala Val Pro
                20                  25                  30

Ala Arg Glu Thr Gly Ser Ala Ile Glu Ala Glu Leu Val Arg Ser
        35                  40                  45

Ser Leu Ala Trp Glu Ser Arg Ala Asn Asp Thr Arg Glu Glu Ala Gly
    50                  55                  60

Leu Pro Ala Ala Gly Glu Asp Glu Thr Ser Trp Thr Glu Arg Gly Ser
65                  70                  75                  80

Glu Met Ala Ala Val Gly Pro Gly Val Gly Pro Glu Glu Ala Leu Glu
                85                  90                  95

Ala Ser Ala Ala Val Thr Gly Thr Ala Trp Leu Glu Ala Asp Gly Pro
            100                 105                 110
```

```
Gly Leu Gly Gly Val Thr Ala Glu Ala Gly Ser Gly Asp Ala Gln Thr
        115                 120                 125

Leu Pro Ala Thr Leu Gln Ala Pro Asp Glu Ala Leu Gly Ser Ser Thr
130                 135                 140

Met Pro Pro Ala Ile Pro Glu Ala Thr Glu Thr Ser Gly Pro Pro Ser
145                 150                 155                 160

Pro Ala Val His Asp Lys Pro Ser Val Gly Pro Glu Leu Pro Lys Glu
                165                 170                 175

Ile Pro Leu Glu Val Arg Leu Asn Leu Gly Gly Ser Thr Pro Glu Pro
                180                 185                 190

Thr Phe Pro Leu Gln Gly Thr Leu Glu Thr Gln Pro Ala Ser Asp Ile
        195                 200                 205

Ile Asp Ile Asp Tyr Phe Glu Gly Leu Asp Ser Glu Gly Arg Gly Ala
210                 215                 220

Asp Met Gly Ser Phe Pro Gly Ser Pro Gly Thr Ser Glu Asn His Pro
225                 230                 235                 240

Asp Thr Glu Gly Glu Thr Pro Ser Trp Ser Leu Leu Asp Leu Tyr Asp
                245                 250                 255

Asp Phe Thr Pro Phe Asp Glu Ser Asp Phe Tyr Pro Thr Thr Ser Phe
                260                 265                 270

Tyr Asp Asp Leu Glu Glu Glu Glu Glu Glu Glu Asp Lys Asp Thr
        275                 280                 285

Val Gly Gly Asp Leu Glu Asp Glu Asn Asp Leu Leu Pro Ser
290                 295                 300

Gln Lys Pro Gly Val Gly Pro Gly Thr Gly Gln Pro Thr Asn Arg Trp
305                 310                 315                 320

His Ala Val Pro Pro Gln His Thr Leu Gly Met Val Pro Gly Ser Ser
                325                 330                 335

Ile Ser Leu Arg Pro Arg Pro Gly Asp Pro Gly Lys Asp Leu Ala Ser
                340                 345                 350

Gly Glu Asn Gly Thr Glu Cys Arg Val Gly Phe Val Arg His Asn Gly
        355                 360                 365

Ser Cys Arg Ser Val Cys Asp Leu Phe Pro Ser Tyr Cys His Asn Gly
        370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415

Thr Asp Phe Gln Val Met Cys Val Ala Val Gly Ser Ala Ala Leu Val
                420                 425                 430

Leu Leu Leu Leu Phe Met Met Thr Val Phe Phe Ala Lys Lys Leu Tyr
        435                 440                 445

Leu Leu Lys Thr Glu Asn Thr Lys Leu Arg Arg Thr Asn Lys Phe Arg
        450                 455                 460

Thr Pro Ser Glu Leu His Asn Asp Asn Phe Ser Leu Ser Thr Ile Ala
465                 470                 475                 480

Glu Gly Ser His Pro Asn Asp Asp Pro Ser Ala Pro His Lys Ile Gln
                485                 490                 495

Asp Pro Leu Lys Ser Arg Leu Lys Glu Glu Glu Ser Phe Asn Ile Gln
                500                 505                 510

Asn Ser Met Ser Pro Lys Leu Glu Gly Gly Lys Gly Asp Gln Asp Asp
        515                 520                 525
```

Leu Gly Val Asn Cys Leu Gln Asn Asn Leu Thr
    530                 535

<210> SEQ ID NO 163
<211> LENGTH: 1605
<212> TYPE: DNA
<213> ORGANISM: Artificial Sequence
<220> FEATURE:
<223> OTHER INFORMATION: Description of the artificial sequence: base
      sequence of cynomolgus monkey CSPG5 including signal sequence

<400> SEQUENCE: 163

```
atggggcgag ccggggggcgg gggcccgggc cggggggccgc cgccactgct gctgcttctg    60
ggggccgcgc tggtcctggc ctctggggcc gtgccggcgc gtgaggcggg cagcgcggtc   120
gaggccgaag agctggtgaa gggcaggccg gcgtgggagc gcgtgccaa cgacacgcga    180
gaagaagccg gcccaccagc ggctggggaa gatgaggcgt cgtggaccgc gcctggcggc   240
gagctggccg gccagagga ggtgctgcag gcgaccggca ccgcctggct ggaggctgac    300
aacccaggcc tgggaggagt gacctcagag gcgggtagtg gcgatgccca ggcccttcca   360
gctacgctcc aggctcccca cgaggtcctc gggcagtcag tcatgccccc tgccattcct   420
gaggctacag aagccagcgg gccaccctcc cccaccctg cgacaaacct gagcccagct    480
tctgaactcc ccaaggagag ccccttggag gtttggctga acctgggggg cagcacaccc   540
gaccctcaag gccagagcc gacttacccc tttcagggca ccctggagcc caaccggca    600
tcagatatca ttgacatcga ctacttccaa ggattggatg gtgagggtcg tggcgcagac   660
ctggggagct tccagggtc accaggaacc tcagagaacc accctgatac tgagggagag   720
acccccttct ggagcctgct tgacttatac gatgatttca ccccctttga tgaatctgat   780
ttctacccca ccacatcctt ttacgatgac ttggatgaag aggaggagga ggaggaggat   840
gacaaagatg cagtaggagg tggagaccta aagatgaaa atgagcttct agtgcccact   900
gggaagcccg gtctggggcc cggacaggc cagcccaaca gtcgatggca tgctgtccct   960
ccacagcaca ctctggggtc ggtccccggc agcagcatcg ccctccggcc ccgcccagga  1020
gagccaggca gggaccctggc ctccagtgaa aatggcactg agtgccgcag tggctttgtg  1080
cggcataacg gctcctgccg gtcagtgtgc gacctcttcc aagttactg tcacaatggc   1140
ggccagtgct acctggtgga gaacataggg gccttctgca ggtgcaacac acaggactac  1200
atctggcaca aggggatgcg ctgcgagtcc atcatcaccg acttccaggt gatgtgcgtg  1260
gccgtgggct cagctgccct cgtcctgctc ctgctcttca tgatgacggt gttcttcgcc  1320
aagaagctct accttctcaa gacggagaac accaagctgc gtaggaccaa caaattccgg  1380
accccagctg aactccacaa tgataacttc tcctctccca ccattgccga gggctctcac  1440
ccaaatgatg atcctagtgc tccccacaaa atccaggagg ctctcaaatc ctgcctgaaa  1500
gaggaggagt catttaacat ccagaactcc atgtcgccca aacttgaggg tggcaaaggt  1560
gaccaggctg acttggatgt gaactgtctt cagaataatt taacc               1605
```

<210> SEQ ID NO 164
<211> LENGTH: 535
<212> TYPE: PRT
<213> ORGANISM: Artificial Sequence
<220> FEATURE:
<223> OTHER INFORMATION: Description of the artificial sequence: amino
      acid sequence of cynomolgus monkey CSPG5 including signal sequence

<400> SEQUENCE: 164

```
Met Gly Arg Ala Gly Gly Gly Pro Gly Arg Pro Pro Leu
1               5                   10                  15
Leu Leu Leu Leu Gly Ala Ala Leu Val Leu Ala Ser Gly Ala Val Pro
            20                  25                  30
Ala Arg Glu Ala Gly Ser Ala Val Glu Ala Glu Leu Val Lys Gly
            35                  40                  45
Arg Pro Ala Trp Glu Pro Arg Ala Asn Asp Thr Arg Glu Ala Gly
    50                  55                  60
Pro Pro Ala Ala Gly Glu Asp Glu Ala Ser Trp Thr Ala Pro Gly Gly
65                  70                  75                  80
Glu Leu Ala Gly Pro Glu Glu Val Leu Gln Ala Thr Gly Thr Ala Trp
                85                  90                  95
Leu Glu Ala Asp Asn Pro Gly Leu Gly Gly Val Thr Ser Glu Ala Gly
                100                 105                 110
Ser Gly Asp Ala Gln Ala Leu Pro Ala Thr Leu Gln Ala Pro His Glu
            115                 120                 125
Val Leu Gly Gln Ser Val Met Pro Pro Ala Ile Pro Glu Ala Thr Glu
    130                 135                 140
Ala Ser Gly Pro Pro Ser Pro Thr Pro Gly Asp Asn Leu Ser Pro Ala
145                 150                 155                 160
Ser Glu Leu Pro Lys Glu Ser Pro Leu Glu Val Trp Leu Asn Leu Gly
                165                 170                 175
Gly Ser Thr Pro Asp Pro Gln Gly Pro Glu Pro Thr Tyr Pro Phe Gln
            180                 185                 190
Gly Thr Leu Glu Pro Gln Pro Ala Ser Asp Ile Ile Asp Ile Asp Tyr
            195                 200                 205
Phe Gln Gly Leu Asp Gly Glu Gly Arg Gly Ala Asp Leu Gly Ser Phe
    210                 215                 220
Pro Gly Ser Pro Gly Thr Ser Glu Asn His Pro Asp Thr Glu Gly Glu
225                 230                 235                 240
Thr Pro Ser Trp Ser Leu Leu Asp Leu Tyr Asp Asp Phe Thr Pro Phe
                245                 250                 255
Asp Glu Ser Asp Phe Tyr Pro Thr Thr Ser Phe Tyr Asp Asp Leu Asp
            260                 265                 270
Glu Glu Glu Glu Glu Glu Asp Asp Lys Asp Ala Val Gly Gly Gly
    275                 280                 285
Asp Leu Glu Asp Glu Asn Glu Leu Leu Val Pro Thr Gly Lys Pro Gly
    290                 295                 300
Leu Gly Pro Gly Thr Gly Gln Pro Asn Ser Arg Trp His Ala Val Pro
305                 310                 315                 320
Pro Gln His Thr Leu Gly Ser Val Pro Gly Ser Ser Ile Ala Leu Arg
            325                 330                 335
Pro Arg Pro Gly Glu Pro Gly Arg Asp Leu Ala Ser Ser Glu Asn Gly
            340                 345                 350
Thr Glu Cys Arg Ser Gly Phe Val Arg His Asn Gly Ser Cys Arg Ser
            355                 360                 365
Val Cys Asp Leu Phe Pro Ser Tyr Cys His Asn Gly Gly Gln Cys Tyr
    370                 375                 380
Leu Val Glu Asn Ile Gly Ala Phe Cys Arg Cys Asn Thr Gln Asp Tyr
385                 390                 395                 400
Ile Trp His Lys Gly Met Arg Cys Glu Ser Ile Ile Thr Asp Phe Gln
                405                 410                 415
Val Met Cys Val Ala Val Gly Ser Ala Ala Leu Val Leu Leu Leu Leu
```

```
                420             425             430
Phe Met Met Thr Val Phe Phe Ala Lys Lys Leu Tyr Leu Leu Lys Thr
            435             440             445

Glu Asn Thr Lys Leu Arg Arg Thr Asn Lys Phe Arg Thr Pro Ala Glu
        450             455             460

Leu His Asn Asp Asn Phe Ser Leu Ser Thr Ile Ala Glu Gly Ser His
465             470             475             480

Pro Asn Asp Asp Pro Ser Ala Pro His Lys Ile Gln Glu Ala Leu Lys
            485             490             495

Ser Cys Leu Lys Glu Glu Glu Ser Phe Asn Ile Gln Asn Ser Met Ser
            500             505             510

Pro Lys Leu Glu Gly Gly Lys Gly Asp Gln Ala Asp Leu Asp Val Asn
            515             520             525

Cys Leu Gln Asn Asn Leu Thr
            530         535

<210> SEQ ID NO 165
<211> LENGTH: 1977
<212> TYPE: DNA
<213> ORGANISM: Artificial Sequence
<220> FEATURE:
<223> OTHER INFORMATION: Description of the artificial sequence: base
      sequence of human CSPG5-FLAG_Fc including signal sequence

<400> SEQUENCE: 165
atggggcgag ccgggggcgg gggcccgggc cggggccgc cgccactgct gctgtttctg    60
ggggccgcgc tggtcctggc ctctggggcc gtgccggcgc gtgaggcggg cagcgcggtt   120
gaggccgaag agctggtgaa gggcagcccg gcgtgggagc cgcctgccaa cgacacgcgg   180
gaagaagccg gccaccagc ggctggggaa gatgaggcgt cgtggacggc gcccggtggc   240
gagctggccg ggccagaaga ggtgctgcag gagtcggctg cggtgaccgg caccgcctgg   300
ctggaagctg acagcccagg cctgggagga gtgaccgcag aggcgggcag cggcgatgcc   360 caggccctc cagctacgct ccaggctccc cacgaggtcc tcgggcagtc aatcatgccc   420
cctgccattc ctgaggctac agaggccagc gggccaccct cccccacccc cggcgacaag   480
ctgagcccag cttctgaact ccccaaggag agccccttgg aggtttggct gaacctgggg   540
ggcagcacac ccgaccctca agggccagag ctgacttacc catttcaggg cacctggag    600 ccccaaccgg catcagatat cattgacatc gactacttcg aaggactgga tggtgagggt   660
cgtggcgcag atctggggag cttcccaggg tcaccaggaa cctcagagaa ccaccctgat   720
actgagggag agaccccttc ctggagcctg cttgacttat acgatgattt caccccttc    780 gatgaatctg atttctaccc caccacatcc tttatgatg acttggatga agaggaggag   840
gaagaggagg atgacaaaga tgcagtagga ggtggagacc tagaagatga aaatgagctt   900
ctagtgccca ctgggaagcc tggtctgggg cccgggacag ccagcccac cagtcggtgg   960 catgctgtcc ctccacagca cactctgggg tcggtcccg gcagcagcat cgccctcagg  1020
ccccgcccag gagagccagg cagggacttg gcctccagtg aaaatggcac tgagtgccgc  1080
agtggctttg tgcggcataa cggctcctgc cggtcagtgt gcgacctctt ccaagttac   1140 tgtcacaatg gcggccagtg ctacctggtg gagaacatag ggccttctg caggtgcaac  1200 acgcaggact acatctggca caaggggatg cgctgcgagt ccatcatcac cgacttctct  1260
agagcagact acaaggacga cgatgacaag actagtgaca aaactcacac atgcccaccg  1320
tgcccagcac ctgaactcct ggggggaccg tcagtcttcc tcttcccccc aaaacccaag  1380
```

-continued

```
gacaccctca tgatctcccg gacccctgag gtcacatgcg tggtggtgga cgtgagccac   1440
gaagaccctg aggtcaagtt caactggtac gtggacggcg tggaggtgca taatgccaag   1500
acaaagccgc gggaggagca gtacaacagc acgtaccgtg tggtcagcgt cctcaccgtc   1560
ctgcaccagg actggctgaa tggcaaggag tacaagtgca aggtctccaa caaagccctc   1620
ccagccccca tcgagaaaac catctccaaa gccaagggc agccccgaga ccacaggtg    1680 tacaccctgc ccccatcccg ggatgagctg accaagaacc aggtcagcct gacctgcctg   1740
gtcaaaggct tctatcccag cgacatcgcc gtggagtggg agagcaatgg gcagccggag   1800
aacaactaca agaccacgcc tcccgtgctg gactccgacg gctccttctt cctctacagc   1860
aagctcaccg tggacaagag caggtggcag caggggaacg tcttctcatg ctccgtgatg   1920
catgaggctc tgcacaacca ctacacgcag aagagcctct ccctgtctcc gggtaaa     1977
```

<210> SEQ ID NO 166
<211> LENGTH: 659
<212> TYPE: PRT
<213> ORGANISM: Artificial Sequence
<220> FEATURE:
<223> OTHER INFORMATION: Description of the artificial sequence: amino
      acid sequence of human CSPG5 including signal sequence

<400> SEQUENCE: 166

```
Met Gly Arg Ala Gly Gly Gly Pro Gly Arg Gly Pro Pro Leu
1               5                   10                  15

Leu Leu Phe Leu Gly Ala Ala Leu Val Leu Ala Ser Gly Ala Val Pro
            20                  25                  30

Ala Arg Glu Ala Gly Ser Ala Val Glu Ala Glu Leu Val Lys Gly
        35                  40                  45

Ser Pro Ala Trp Glu Pro Ala Asn Asp Thr Arg Glu Glu Ala Gly
    50                  55                  60

Pro Pro Ala Ala Gly Glu Asp Glu Ala Ser Trp Thr Ala Pro Gly Gly
65                  70                  75                  80

Glu Leu Ala Gly Pro Glu Glu Val Leu Gln Glu Ser Ala Ala Val Thr
                85                  90                  95

Gly Thr Ala Trp Leu Glu Ala Asp Ser Pro Gly Leu Gly Gly Val Thr
            100                 105                 110

Ala Glu Ala Gly Ser Gly Asp Ala Gln Ala Leu Pro Ala Thr Leu Gln
        115                 120                 125

Ala Pro His Glu Val Leu Gly Gln Ser Ile Met Pro Pro Ala Ile Pro
    130                 135                 140

Glu Ala Thr Glu Ala Ser Gly Pro Pro Ser Pro Thr Pro Gly Asp Lys
145                 150                 155                 160

Leu Ser Pro Ala Ser Glu Leu Pro Lys Glu Ser Pro Leu Glu Val Trp
                165                 170                 175

Leu Asn Leu Gly Gly Ser Thr Pro Asp Pro Gln Gly Pro Glu Leu Thr
            180                 185                 190

Tyr Pro Phe Gln Gly Thr Leu Glu Pro Gln Pro Ala Ser Asp Ile Ile
        195                 200                 205

Asp Ile Asp Tyr Phe Glu Gly Leu Asp Gly Glu Gly Arg Gly Ala Asp
    210                 215                 220

Leu Gly Ser Phe Pro Gly Ser Pro Gly Thr Ser Glu Asn His Pro Asp
225                 230                 235                 240

Thr Glu Gly Glu Thr Pro Ser Trp Ser Leu Leu Asp Leu Tyr Asp Asp
                245                 250                 255
```

```
Phe Thr Pro Phe Asp Glu Ser Asp Phe Tyr Pro Thr Thr Ser Phe Tyr
            260                 265                 270

Asp Asp Leu Asp Glu Glu Glu Glu Glu Asp Lys Asp Ala
            275                 280                 285

Val Gly Gly Asp Leu Glu Asp Glu Asn Glu Leu Leu Val Pro Thr
290                 295                 300

Gly Lys Pro Gly Leu Gly Pro Gly Thr Gly Gln Pro Thr Ser Arg Trp
305                 310                 315                 320

His Ala Val Pro Pro Gln His Thr Leu Gly Ser Val Pro Gly Ser Ser
                325                 330                 335

Ile Ala Leu Arg Pro Arg Pro Gly Glu Pro Gly Arg Asp Leu Ala Ser
            340                 345                 350

Ser Glu Asn Gly Thr Glu Cys Arg Ser Gly Phe Val Arg His Asn Gly
            355                 360                 365

Ser Cys Arg Ser Val Cys Asp Leu Phe Pro Ser Tyr Cys His Asn Gly
            370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415

Thr Asp Phe Ser Arg Ala Asp Tyr Lys Asp Asp Asp Asp Lys Thr Ser
            420                 425                 430

Asp Lys Thr His Thr Cys Pro Pro Cys Pro Ala Pro Glu Leu Leu Gly
            435                 440                 445

Gly Pro Ser Val Phe Leu Phe Pro Pro Lys Pro Lys Asp Thr Leu Met
450                 455                 460

Ile Ser Arg Thr Pro Glu Val Thr Cys Val Val Val Asp Val Ser His
465                 470                 475                 480

Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
                500                 505                 510

Arg Val Val Ser Val Leu Thr Val Leu His Gln Asp Trp Leu Asn Gly
            515                 520                 525

Lys Glu Tyr Lys Cys Lys Val Ser Asn Lys Ala Leu Pro Ala Pro Ile
530                 535                 540

Glu Lys Thr Ile Ser Lys Ala Lys Gly Gln Pro Arg Glu Pro Gln Val
545                 550                 555                 560

Tyr Thr Leu Pro Pro Ser Arg Asp Glu Leu Thr Lys Asn Gln Val Ser
                565                 570                 575

Leu Thr Cys Leu Val Lys Gly Phe Tyr Pro Ser Asp Ile Ala Val Glu
            580                 585                 590

Trp Glu Ser Asn Gly Gln Pro Glu Asn Asn Tyr Lys Thr Thr Pro Pro
            595                 600                 605

Val Leu Asp Ser Asp Gly Ser Phe Phe Leu Tyr Ser Lys Leu Thr Val
            610                 615                 620

Asp Lys Ser Arg Trp Gln Gln Gly Asn Val Phe Ser Cys Ser Val Met
625                 630                 635                 640

His Glu Ala Leu His Asn His Tyr Thr Gln Lys Ser Leu Ser Leu Ser
                645                 650                 655

Pro Gly Lys
```

<210> SEQ ID NO 167
<211> LENGTH: 1977
<212> TYPE: DNA
<213> ORGANISM: Artificial Sequence
<220> FEATURE:
<223> OTHER INFORMATION: Description of the artificial sequence: base sequence of mouse CSPG5-FLAG_Fc including signal sequence

<400> SEQUENCE: 167

```
atgggccgag ctggaggcgg gggcccggac tggggccgc cgccagtgct gctgcttctg      60
ggggtcacgc tggtgctcac cgctggggcc gtaccggcac gggaaacagg cagtgcgatc     120
gaggctgaag agctggtgag gagcagcctg catgggagt cgcgtgccaa tgacacgcgg      180
gaggaagccg gcctgccagc agctggggaa gatgagacct cgtggacaga gcggggcagt    240
gagatggctg cggtgggccc tggggtcggg ccagaggagg cactagaggc atcggctgca    300
gtgactggca ctgcctggct agaggcagat ggcccaggcc tgggtggagt gactgcagag   360
gctggcagtg gcgacgccca gaccttcca gctacgctcc aggctcctga tgaggccctt     420
gggtcatcta caatgccccc tgccatccct gaggctactg aaaccagtgg acctccctcc    480
cctgctgtcc atgataagcc tagtgtaggc cctgaactcc ctaaagagat ccccttggag    540
gttcggctga acctgggagg cagcacacca gagcccactt tccccttca gggcactctc     600
gagacccaac cagcctcaga tataattgac attgattact ttgaaggatt ggatagtgag    660
ggtcgtggtg cagacatggg cagcttcccg gggtcaccag gaacctcaga aaatcaccct    720
gataccgaag gagagacccc ttcctggagc ctgcttgatt tgtatgatga cttcaccct     780
tttgatgagt ctgatttcta ccccaccaca tccttctatg atgatttgga agaggaggaa    840
gaagaggagg aggataagga tacagtagga ggtggagacc tggaagatga aaacgacctt   900
ctcctgccct ctcaaaagcc tggtgtgggg cctgggacag acagcccac caaccggtgg     960
catgctgttc ccccacagca tactctgggg atggtacctg gcagcagcat ctctcttagg  1020
ccccgccccg gagatccagg caaggacctg gcctcaggag aaaatggcac agagtgccga   1080
gttggcttcg tcaggcacaa tggctcctgc cggtcagtct gtgacctctt ccgagttac   1140
tgtcacaacg gcggccagtg ctacctggtg gagaacatag ggctttctg caggtgtaac  1200
acccaggact acatctggca aaggggatg cgctgtgagt ccatcatcac ggacttctct   1260
agagcagact acaaggacga cgatgacaag actagtgaca aaactcacac atgcccaccg  1320
tgcccagcac ctgaactcct gggggaccg tcagtcttcc tcttcccccc aaaacccaag   1380
gacaccctca tgatctcccg gacccctgag gtcacatgcg tggtggtgga cgtgagccac  1440
gaagaccctg aggtcaagtt caactggtac gtggacggcg tggaggtgca taatgccaag  1500
acaaagccgc gggaggagca gtacaacagc acgtaccgtg tggtcagcgt cctcaccgtc   1560
ctgcaccagg actggctgaa tggcaaggag tacaagtgca aggtctccaa caaagccctc  1620
ccagccccca tcgagaaaac catctccaaa gccaaagggc agccccgaga accacaggtg   1680
tacaccctgc cccatcccg ggatgagctg accaagaacc aggtcagcct gacctgcctg   1740
gtcaaaggct tctatcccag cgacatcgcc gtggagtggg agagcaatgg gcagccggag   1800
aacaactaca agaccacgcc tcccgtgctg gactccgacg gctccttctt cctctacagc   1860
aagctcaccg tggacaagag caggtggcag caggggaacg tcttctcatg ctccgtgatg   1920
catgaggctc tgcacaacca ctacacgcag aagagcctct ccctgtctcc gggtaaa     1977
```

<210> SEQ ID NO 168
<211> LENGTH: 659

<212> TYPE: PRT
<213> ORGANISM: Artificial Sequence
<220> FEATURE:
<223> OTHER INFORMATION: Description of the artificial sequence: amino
    acid sequence of mouse CSPG5-FLAG_Fc including signal sequence

<400> SEQUENCE: 168

| | | | | | | | | | | | | | | | |
|---|---|---|---|---|---|---|---|---|---|---|---|---|---|---|---|
| Met | Gly | Arg | Ala | Gly | Gly | Gly | Pro | Asp | Trp | Gly | Pro | Pro | Val |
| 1 | | | | 5 | | | | | 10 | | | | | 15 |
| Leu | Leu | Leu | Leu | Gly | Val | Thr | Leu | Val | Leu | Thr | Ala | Gly | Ala | Val | Pro |
| | | | 20 | | | | | 25 | | | | | 30 | | |
| Ala | Arg | Glu | Thr | Gly | Ser | Ala | Ile | Glu | Ala | Glu | Glu | Leu | Val | Arg | Ser |
| | | | 35 | | | | | 40 | | | | | 45 | | |
| Ser | Leu | Ala | Trp | Glu | Ser | Arg | Ala | Asn | Asp | Thr | Arg | Glu | Glu | Ala | Gly |
| 50 | | | | | 55 | | | | | 60 | | | | | |
| Leu | Pro | Ala | Ala | Gly | Glu | Asp | Glu | Thr | Ser | Trp | Thr | Glu | Arg | Gly | Ser |
| 65 | | | | | 70 | | | | | 75 | | | | | 80 |
| Glu | Met | Ala | Ala | Val | Gly | Pro | Gly | Val | Gly | Pro | Glu | Glu | Ala | Leu | Glu |
| | | | | 85 | | | | | 90 | | | | | 95 | |
| Ala | Ser | Ala | Ala | Val | Thr | Gly | Thr | Ala | Trp | Leu | Glu | Ala | Asp | Gly | Pro |
| | | | | 100 | | | | | 105 | | | | | 110 | |
| Gly | Leu | Gly | Gly | Val | Thr | Ala | Glu | Ala | Gly | Ser | Gly | Asp | Ala | Gln | Thr |
| | | | 115 | | | | | 120 | | | | | 125 | | |
| Leu | Pro | Ala | Thr | Leu | Gln | Ala | Pro | Asp | Glu | Ala | Leu | Gly | Ser | Ser | Thr |
| | 130 | | | | | 135 | | | | | 140 | | | | |
| Met | Pro | Pro | Ala | Ile | Pro | Glu | Ala | Thr | Glu | Thr | Ser | Gly | Pro | Pro | Ser |
| 145 | | | | | 150 | | | | | 155 | | | | | 160 |
| Pro | Ala | Val | His | Asp | Lys | Pro | Ser | Val | Gly | Pro | Glu | Leu | Pro | Lys | Glu |
| | | | | 165 | | | | | 170 | | | | | 175 | |
| Ile | Pro | Leu | Glu | Val | Arg | Leu | Asn | Leu | Gly | Gly | Ser | Thr | Pro | Glu | Pro |
| | | | 180 | | | | | 185 | | | | | 190 | | |
| Thr | Phe | Pro | Leu | Gln | Gly | Thr | Leu | Glu | Thr | Gln | Pro | Ala | Ser | Asp | Ile |
| | | | | 195 | | | | | 200 | | | | | 205 | |
| Ile | Asp | Ile | Asp | Tyr | Phe | Glu | Gly | Leu | Asp | Ser | Glu | Gly | Arg | Gly | Ala |
| | 210 | | | | | 215 | | | | | 220 | | | | |
| Asp | Met | Gly | Ser | Phe | Pro | Gly | Ser | Pro | Gly | Thr | Ser | Glu | Asn | His | Pro |
| 225 | | | | | 230 | | | | | 235 | | | | | 240 |
| Asp | Thr | Glu | Gly | Glu | Thr | Pro | Ser | Trp | Ser | Leu | Leu | Asp | Leu | Tyr | Asp |
| | | | | 245 | | | | | 250 | | | | | 255 | |
| Asp | Phe | Thr | Pro | Phe | Asp | Glu | Ser | Asp | Phe | Tyr | Pro | Thr | Thr | Ser | Phe |
| | | | 260 | | | | | 265 | | | | | 270 | | |
| Tyr | Asp | Asp | Leu | Glu | Glu | Glu | Glu | Glu | Glu | Glu | Asp | Lys | Asp | Thr |
| | 275 | | | | | 280 | | | | | 285 | | | | |
| Val | Gly | Gly | Gly | Asp | Leu | Glu | Asp | Glu | Asn | Asp | Leu | Leu | Pro | Ser |
| | 290 | | | | | 295 | | | | | 300 | | | | |
| Gln | Lys | Pro | Gly | Val | Gly | Pro | Gly | Thr | Gly | Gln | Pro | Thr | Asn | Arg | Trp |
| 305 | | | | | 310 | | | | | 315 | | | | | 320 |
| His | Ala | Val | Pro | Pro | Gln | His | Thr | Leu | Gly | Met | Val | Pro | Gly | Ser | Ser |
| | | | | 325 | | | | | 330 | | | | | 335 | |
| Ile | Ser | Leu | Arg | Pro | Arg | Pro | Gly | Asp | Pro | Gly | Lys | Asp | Leu | Ala | Ser |
| | | | 340 | | | | | 345 | | | | | 350 | | |
| Gly | Glu | Asn | Gly | Thr | Glu | Cys | Arg | Val | Gly | Phe | Val | Arg | His | Asn | Gly |
| | | | | 355 | | | | | 360 | | | | | 365 | |
| Ser | Cys | Arg | Ser | Val | Cys | Asp | Leu | Phe | Pro | Ser | Tyr | Cys | His | Asn | Gly |
| | 370 | | | | | 375 | | | | | 380 | | | | |

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
            405                 410                 415

Thr Asp Phe Ser Arg Ala Asp Tyr Lys Asp Asp Asp Lys Thr Ser
        420                 425                 430

Asp Lys Thr His Thr Cys Pro Pro Cys Pro Ala Pro Glu Leu Leu Gly
        435                 440                 445

Gly Pro Ser Val Phe Leu Phe Pro Pro Lys Pro Lys Asp Thr Leu Met
    450                 455                 460

Ile Ser Arg Thr Pro Glu Val Thr Cys Val Val Val Asp Val Ser His
465                 470                 475                 480

Glu Asp Pro Glu Val Lys Phe Asn Trp Tyr Val Asp Gly Val Glu Val
                485                 490                 495

His Asn Ala Lys Thr Lys Pro Arg Glu Glu Gln Tyr Asn Ser Thr Tyr
            500                 505                 510

Arg Val Val Ser Val Leu Thr Val Leu His Gln Asp Trp Leu Asn Gly
        515                 520                 525

Lys Glu Tyr Lys Cys Lys Val Ser Asn Lys Ala Leu Pro Ala Pro Ile
    530                 535                 540

Glu Lys Thr Ile Ser Lys Ala Lys Gly Gln Pro Arg Glu Pro Gln Val
545                 550                 555                 560

Tyr Thr Leu Pro Pro Ser Arg Asp Glu Leu Thr Lys Asn Gln Val Ser
                565                 570                 575

Leu Thr Cys Leu Val Lys Gly Phe Tyr Pro Ser Asp Ile Ala Val Glu
            580                 585                 590

Trp Glu Ser Asn Gly Gln Pro Glu Asn Asn Tyr Lys Thr Thr Pro Pro
        595                 600                 605

Val Leu Asp Ser Asp Gly Ser Phe Phe Leu Tyr Ser Lys Leu Thr Val
    610                 615                 620

Asp Lys Ser Arg Trp Gln Gln Gly Asn Val Phe Ser Cys Ser Val Met
625                 630                 635                 640

His Glu Ala Leu His Asn His Tyr Thr Gln Lys Ser Leu Ser Leu Ser
                645                 650                 655

Pro Gly Lys

<210> SEQ ID NO 169
<211> LENGTH: 1947
<212> TYPE: DNA
<213> ORGANISM: Artificial Sequence
<220> FEATURE:
<223> OTHER INFORMATION: Description of the artificial sequence: base
      sequence of human CSPG5-GST including signal sequence

<400> SEQUENCE: 169
atggggcgag ccgggggcgg gggcccgggc cggggccgc cgccactgct gctgtttctg      60
ggggccgcgc tggtcctggc ctctggggcc gtgccggcgc gtgaggcggg cagcgcggtt    120
gaggccgaag agctggtgaa gggcagcccg gcgtgggagc gcctgccaa cgacacgcgg    180 gaagaagccg ccaccagc ggctggggaa gatgaggcgt cgtggacggc gcccggtggc    240
gagctggccg ggccagaaga ggtgctgcag gagtcggctg cggtgaccgg caccgcctgg    300
ctggaagctg acagcccagg cctgggagga gtgaccgcag aggcgggcag cggcgatgcc    360
caggcccttc cagctacgct ccaggctccc cacgaggtcc tcgggcagtc aatcatgccc    420

```
cctgccattc ctgaggctac agaggccagc gggccaccct ccccacccc cggcgacaag      480 ctgagcccag cttctgaact ccccaaggag agcccttgg aggtttggct gaacctgggg      540
ggcagcacac ccgaccctca agggccagag ctgacttacc catttcaggg caccctggag    600
ccccaaccgg catcagatat cattgacatc gactacttcg aaggactgga tggtgagggt    660
cgtggcgcag atctggggag cttcccaggg tcaccaggaa cctcagagaa ccaccctgat    720
actgagggag agacccttc ctggagcctg cttgacttat acgatgattt caccccttc      780 gatgaatctg atttctaccc caccacatcc ttttatgatg acttggatga agaggaggag   840
gaagaggagg atgacaaaga tgcagtagga ggtggagacc tagaagatga aaatgagctt   900
ctagtgccca ctgggaagcc tggtctgggg cccgggacag gccagcccac cagtcggtgg   960
catgctgtcc ctccacagca cactctgggg tcggtcccg gcagcagcat cgccctcagg    1020
ccccgcccag gagagccagg cagggacttg gcctccagtg aaaatggcac tgagtgccgc   1080
agtggctttg tgcggcataa cggctcctgc cggtcagtgt gcgacctctt cccaagttac    1140
tgtcacaatg gcggccagtg ctacctggtg gagaacatag gggccttctg caggtgcaac    1200
acgcaggact acatctggca aggggatg cgctgcgagt ccatcatcac cgacttcggt      1260
accctggaag ttctgttcca ggggcccatg tcccctatac taggttattg gaaaattaag   1320
ggccttgtgc aacccactcg acttcttttg gaatatcttg aagaaaaata tgaagagcat   1380
ttgtatgagc gcgatgaagg tgataaatgg cgaaacaaaa agtttgaatt gggtttggag   1440
tttcccaatc ttccttatta tattgatggt gatgttaaat taacacagtc tatggccatc    1500
atacgttata tagctgacaa gcacaacatg ttgggtggtt gtccaaaaga gcgtgcagag   1560
atttcaatgc ttgaaggagc ggttttggat attagatacg gtgtttcgag aattgcatat    1620
agtaaagact ttgaaactct caaagttgat tttcttagca agctacctga atgctgaaa    1680 atgttcgaag atcgtttatg tcataaaaca tatttaaatg gtgatcatgt aacccatcct   1740
gacttcatgt tgtatgacgc tcttgatgtt gtttatacaa tggacccaat gtgcctggat   1800
gcgttcccaa aattagtttg ttttaaaaaa cgtattgaag ctatcccaca aattgataag   1860
tacttgaaat ccagcaagta tatagcatgg cctttgcagg gctggcaagc cacgtttggt   1920
ggtggcgacc atcctccaaa atcggat                                        1947
```

<210> SEQ ID NO 170
<211> LENGTH: 649
<212> TYPE: PRT
<213> ORGANISM: Artificial Sequence
<220> FEATURE:
<223> OTHER INFORMATION: Description of the artificial sequence: amino
      acid sequence of human CSPG5-GST including signal sequence

<400> SEQUENCE: 170

```
Met Gly Arg Ala Gly Gly Gly Pro Gly Arg Gly Pro Pro Pro Leu
1               5                   10                  15

Leu Leu Phe Leu Gly Ala Ala Leu Val Leu Ala Ser Gly Ala Val Pro
            20                  25                  30

Ala Arg Glu Ala Gly Ser Ala Val Glu Ala Glu Glu Leu Val Lys Gly
        35                  40                  45

Ser Pro Ala Trp Glu Pro Ala Asn Asp Thr Arg Glu Glu Ala Gly
    50                  55                  60

Pro Pro Ala Ala Gly Glu Asp Glu Ala Ser Trp Thr Ala Pro Gly Gly
65                  70                  75                  80

Glu Leu Ala Gly Pro Glu Glu Val Leu Gln Glu Ser Ala Ala Val Thr
```

-continued

```
                85                  90                  95
Gly Thr Ala Trp Leu Glu Ala Asp Ser Pro Gly Leu Gly Val Thr
            100                 105                 110
Ala Glu Ala Gly Ser Gly Asp Ala Gln Ala Leu Pro Ala Thr Leu Gln
            115                 120                 125
Ala Pro His Glu Val Leu Gly Gln Ser Ile Met Pro Ala Ile Pro
            130                 135                 140
Glu Ala Thr Glu Ala Ser Gly Pro Pro Ser Pro Thr Pro Gly Asp Lys
145                 150                 155                 160
Leu Ser Pro Ala Ser Glu Leu Pro Lys Glu Ser Pro Leu Glu Val Trp
                165                 170                 175
Leu Asn Leu Gly Gly Ser Thr Pro Asp Pro Gln Gly Pro Glu Leu Thr
            180                 185                 190
Tyr Pro Phe Gln Gly Thr Leu Glu Pro Gln Pro Ala Ser Asp Ile Ile
            195                 200                 205
Asp Ile Asp Tyr Phe Glu Gly Leu Asp Gly Glu Gly Arg Gly Ala Asp
        210                 215                 220
Leu Gly Ser Phe Pro Gly Ser Pro Gly Thr Ser Glu Asn His Pro Asp
225                 230                 235                 240
Thr Glu Gly Glu Thr Pro Ser Trp Ser Leu Leu Asp Leu Tyr Asp Asp
                245                 250                 255
Phe Thr Pro Phe Asp Glu Ser Asp Phe Tyr Pro Thr Thr Ser Phe Tyr
            260                 265                 270
Asp Asp Leu Asp Glu Glu Glu Glu Glu Asp Asp Lys Asp Ala
            275                 280                 285
Val Gly Gly Gly Asp Leu Glu Asp Glu Asn Glu Leu Leu Val Pro Thr
            290                 295                 300
Gly Lys Pro Gly Leu Gly Pro Gly Thr Gly Gln Pro Thr Ser Arg Trp
305                 310                 315                 320
His Ala Val Pro Pro Gln His Thr Leu Gly Ser Val Pro Gly Ser Ser
                325                 330                 335
Ile Ala Leu Arg Pro Arg Pro Gly Glu Pro Gly Arg Asp Leu Ala Ser
            340                 345                 350
Ser Glu Asn Gly Thr Glu Cys Arg Ser Gly Phe Val Arg His Asn Gly
            355                 360                 365
Ser Cys Arg Ser Val Cys Asp Leu Phe Pro Ser Tyr Cys His Asn Gly
        370                 375                 380
Gly Gln Cys Tyr Leu Val Glu Asn Ile Gly Ala Phe Cys Arg Cys Asn
385                 390                 395                 400
Thr Gln Asp Tyr Ile Trp His Lys Gly Met Arg Cys Glu Ser Ile Ile
                405                 410                 415
Thr Asp Phe Gly Thr Leu Glu Val Leu Phe Gln Gly Pro Met Ser Pro
            420                 425                 430
Ile Leu Gly Tyr Trp Lys Ile Lys Gly Leu Val Gln Pro Thr Arg Leu
            435                 440                 445
Leu Leu Glu Tyr Leu Glu Glu Lys Tyr Glu Glu His Leu Tyr Glu Arg
        450                 455                 460
Asp Glu Gly Asp Lys Trp Arg Asn Lys Lys Phe Glu Leu Gly Leu Glu
465                 470                 475                 480
Phe Pro Asn Leu Pro Tyr Tyr Ile Asp Gly Asp Val Lys Leu Thr Gln
                485                 490                 495
Ser Met Ala Ile Ile Arg Tyr Ile Ala Asp Lys His Asn Met Leu Gly
            500                 505                 510
```

-continued

```
Gly Cys Pro Lys Glu Arg Ala Glu Ile Ser Met Leu Glu Gly Ala Val
            515                 520                 525
Leu Asp Ile Arg Tyr Gly Val Ser Arg Ile Ala Tyr Ser Lys Asp Phe
        530                 535                 540
Glu Thr Leu Lys Val Asp Phe Leu Ser Lys Leu Pro Glu Met Leu Lys
545                 550                 555                 560
Met Phe Glu Asp Arg Leu Cys His Lys Thr Tyr Leu Asn Gly Asp His
                565                 570                 575
Val Thr His Pro Asp Phe Met Leu Tyr Asp Ala Leu Asp Val Val Leu
            580                 585                 590
Tyr Met Asp Pro Met Cys Leu Asp Ala Phe Pro Lys Leu Val Cys Phe
        595                 600                 605
Lys Lys Arg Ile Glu Ala Ile Pro Gln Ile Asp Lys Tyr Leu Lys Ser
    610                 615                 620
Ser Lys Tyr Ile Ala Trp Pro Leu Gln Gly Trp Gln Ala Thr Phe Gly
625                 630                 635                 640
Gly Gly Asp His Pro Pro Lys Ser Asp
                645
```

```
<210> SEQ ID NO 171
<211> LENGTH: 1947
<212> TYPE: DNA
<213> ORGANISM: Artificial Sequence
<220> FEATURE:
<223> OTHER INFORMATION: Description of the artificial sequence: base
      sequence of mouse CSPG5-GST including signal sequence

<400> SEQUENCE: 171
atgggccgag ctggaggcgg gggcccggac tggggccgc cgccagtgct gctgcttctg      60
ggggtcacgc tggtgctcac cgctggggcc gtaccggcac gggaaacagg cagtgcgatc    120
gaggctgaag agctggtgag gagcagcctg catgggagt cgcgtgccaa tgacacgcgg     180
gaggaagccg gcctgccagc agctggggaa gatgagacct cgtggacaga gcggggcagt    240
gagatggctg cggtgggccc tggggtcggg ccagaggagg cactagaggc atcggctgca    300
gtgactggca ctgcctggct agaggcagat ggcccaggcc tgggtggagt gactgcagag    360
gctggcagtg gcgacgccca gaccttcca gctacgctcc aggctcctga tgaggcctt    420 gggtcatcta caatgcccc tgccatccct gaggctactg aaaccagtgg acctccctcc    480
cctgctgtcc atgataagcc tagtgtaggc cctgaactcc ctaaagagat ccccttggag    540
gttcggctga actgggagg cagcacacca gagcccactt ttccccttca gggcactctc    600
gagacccaac cagcctcaga tataattgac attgattact ttgaaggatt ggatagtgag    660
ggtcgtggtg cagacatggg cagcttcccg gggtcaccag gaacctcaga aaatcaccct    720
gataccgaag gagagacccc ttcctggagc ctgcttgatt tgtatgatga cttcaccct    780 tttgatgagt ctgatttcta ccccaccaca tccttctatg atgatttgga agaggaggaa    840
gaagaggagg aggataagga tacagtagga ggtggagacc tggaagatga aaacgacctt    900
ctcctgccct ctcaaaagcc tggtgtgggg cctgggacag gacagcccac caaccggtgg    960
catgctgttc ccccacagca tactctgggg atggtacctg gcagcagcat ctctcttagg   1020
ccccgccccg gagatccagg caaggacctg gcctcaggag aaaatggcac agagtgccga   1080
gttggcttcg tcaggcacaa tggctcctgc cggtcagtct gtgacctctt tccgagttac   1140
tgtcacaacg gcggccagtg ctacctggtg gagaacatag gggctttctg caggtgtaac   1200
```

```
acccaggact acatctggca caaggggatg cgctgtgagt ccatcatcac ggacttcggt   1260
accctggaag ttctgttcca ggggcccatg tccectatac taggttattg gaaaattaag   1320
ggccttgtgc aacccactcg acttctttg gaatatcttg aagaaaaata tgaagagcat   1380
ttgtatgagc gcgatgaagg tgataaatgg cgaaacaaaa agtttgaatt gggtttggag   1440
tttcccaatc ttccttatta tattgatggt gatgttaaat taacacagtc tatggccatc   1500
atacgttata tagctgacaa gcacaacatg ttgggtggtt gtccaaaaga gcgtgcagag   1560
atttcaatgc ttgaaggagc ggttttggat attagatacg gtgtttcgag aattgcatat   1620
agtaaagact ttgaaactct caaagttgat tttcttagca agctacctga atgctgaaa   1680 atgttcgaag atcgtttatg tcataaaaca tatttaaatg gtgatcatgt aacccatcct   1740
gacttcatgt tgtatgacgc tcttgatgtt gttttataca tggacccaat gtgcctggat   1800
gcgttcccaa aattagttg ttttaaaaaa cgtattgaag ctatcccaca aattgataag   1860
tacttgaaat ccagcaagta tatagcatgg cctttgcagg gctggcaagc cacgtttggt   1920
ggtggcgacc atcctccaaa atcggat                                      1947

<210> SEQ ID NO 172
<211> LENGTH: 649
<212> TYPE: PRT
<213> ORGANISM: Artificial Sequence
<220> FEATURE:
<223> OTHER INFORMATION: Description of the artificial sequence: amino
      acid sequence of mouse CSPG5-GST including signal sequence

<400> SEQUENCE: 172

Met Gly Arg Ala Gly Gly Gly Gly Pro Asp Trp Gly Pro Pro Val
1               5                   10                  15

Leu Leu Leu Leu Gly Val Thr Leu Val Leu Thr Ala Gly Ala Val Pro
                20                  25                  30

Ala Arg Glu Thr Gly Ser Ala Ile Glu Ala Glu Glu Leu Val Arg Ser
            35                  40                  45

Ser Leu Ala Trp Glu Ser Arg Ala Asn Asp Thr Arg Glu Glu Ala Gly
        50                  55                  60

Leu Pro Ala Ala Gly Glu Asp Glu Thr Ser Trp Thr Glu Arg Gly Ser
65                  70                  75                  80

Glu Met Ala Ala Val Gly Pro Gly Val Gly Pro Glu Glu Ala Leu Glu
                85                  90                  95

Ala Ser Ala Ala Val Thr Gly Thr Ala Trp Leu Glu Ala Asp Gly Pro
            100                 105                 110

Gly Leu Gly Gly Val Thr Ala Glu Ala Gly Ser Gly Asp Ala Gln Thr
        115                 120                 125

Leu Pro Ala Thr Leu Gln Ala Pro Asp Glu Ala Leu Gly Ser Ser Thr
    130                 135                 140

Met Pro Pro Ala Ile Pro Glu Ala Thr Glu Thr Ser Gly Pro Pro Ser
145                 150                 155                 160

Pro Ala Val His Asp Lys Pro Ser Val Gly Pro Glu Leu Pro Lys Glu
                165                 170                 175

Ile Pro Leu Glu Val Arg Leu Asn Leu Gly Gly Ser Thr Pro Glu Pro
            180                 185                 190

Thr Phe Pro Leu Gln Gly Thr Leu Glu Thr Gln Pro Ala Ser Asp Ile
        195                 200                 205

Ile Asp Ile Asp Tyr Phe Glu Gly Leu Asp Ser Glu Gly Arg Gly Ala
    210                 215                 220
```

-continued

```
Asp Met Gly Ser Phe Pro Gly Ser Pro Gly Thr Ser Glu Asn His Pro
225                 230                 235                 240

Asp Thr Glu Gly Glu Thr Pro Ser Trp Ser Leu Leu Asp Leu Tyr Asp
                245                 250                 255

Asp Phe Thr Pro Phe Asp Glu Ser Asp Phe Tyr Pro Thr Thr Ser Phe
                260                 265                 270

Tyr Asp Asp Leu Glu Glu Glu Glu Glu Glu Glu Asp Lys Asp Thr
            275                 280                 285

Val Gly Gly Gly Asp Leu Glu Asp Glu Asn Asp Leu Leu Leu Pro Ser
290                 295                 300

Gln Lys Pro Gly Val Gly Pro Gly Thr Gly Gln Pro Thr Asn Arg Trp
305                 310                 315                 320

His Ala Val Pro Pro Gln His Thr Leu Gly Met Val Pro Gly Ser Ser
                325                 330                 335

Ile Ser Leu Arg Pro Arg Pro Gly Asp Pro Gly Lys Asp Leu Ala Ser
                340                 345                 350

Gly Glu Asn Gly Thr Glu Cys Arg Val Gly Phe Val Arg His Asn Gly
            355                 360                 365

Ser Cys Arg Ser Val Cys Asp Leu Phe Pro Ser Tyr Cys His Asn Gly
370                 375                 380

Gly Gln Cys Tyr Leu Val Glu Asn Ile Gly Ala Phe Cys Arg Cys Asn
385                 390                 395                 400

Thr Gln Asp Tyr Ile Trp His Lys Gly Met Arg Cys Glu Ser Ile Ile
                405                 410                 415

Thr Asp Phe Gly Thr Leu Glu Val Leu Phe Gln Gly Pro Met Ser Pro
                420                 425                 430

Ile Leu Gly Tyr Trp Lys Ile Lys Gly Leu Val Gln Pro Thr Arg Leu
            435                 440                 445

Leu Leu Glu Tyr Leu Glu Glu Lys Tyr Glu Glu His Leu Tyr Glu Arg
450                 455                 460

Asp Glu Gly Asp Lys Trp Arg Asn Lys Lys Phe Glu Leu Gly Leu Glu
465                 470                 475                 480

Phe Pro Asn Leu Pro Tyr Tyr Ile Asp Gly Asp Val Lys Leu Thr Gln
                485                 490                 495

Ser Met Ala Ile Ile Arg Tyr Ile Ala Asp Lys His Asn Met Leu Gly
            500                 505                 510

Gly Cys Pro Lys Glu Arg Ala Glu Ile Ser Met Leu Glu Gly Ala Val
            515                 520                 525

Leu Asp Ile Arg Tyr Gly Val Ser Arg Ile Ala Tyr Ser Lys Asp Phe
530                 535                 540

Glu Thr Leu Lys Val Asp Phe Leu Ser Lys Leu Pro Glu Met Leu Lys
545                 550                 555                 560

Met Phe Glu Asp Arg Leu Cys His Lys Thr Tyr Leu Asn Gly Asp His
                565                 570                 575

Val Thr His Pro Asp Phe Met Leu Tyr Asp Ala Leu Asp Val Val Leu
                580                 585                 590

Tyr Met Asp Pro Met Cys Leu Asp Ala Phe Pro Lys Leu Val Cys Phe
                595                 600                 605

Lys Lys Arg Ile Glu Ala Ile Pro Gln Ile Asp Lys Tyr Leu Lys Ser
610                 615                 620
```

```
Ser Lys Tyr Ile Ala Trp Pro Leu Gln Gly Trp Gln Ala Thr Phe Gly
625                 630                 635                 640

Gly Gly Asp His Pro Pro Lys Ser Asp
                645
```